(12) United States Patent
Boutaud

(10) Patent No.: US 6,703,363 B1
(45) Date of Patent: Mar. 9, 2004

(54) RECOMBINANT LAMININ 5

(75) Inventor: Ariel Boutaud, Raleigh, NC (US)

(73) Assignee: BioStratum, Inc., Durham, NC (US)

( * ) Notice: Subject to any disclaimer, the term of this patent is extended or adjusted under 35 U.S.C. 154(b) by 0 days.

(21) Appl. No.: 09/560,385

(22) Filed: Apr. 28, 2000

Related U.S. Application Data

(60) Provisional application No. 60/131,720, filed on Apr. 30, 1999, provisional application No. 60/149,738, filed on Aug. 19, 1999, and provisional application No. 60/155,945, filed on Sep. 24, 1999.

(51) Int. Cl.$^7$ ............................................... A61K 38/00
(52) U.S. Cl. ........................ 514/12; 514/12; 514/2; 435/69.1; 435/7.1; 435/6; 435/320.1; 536/23.1; 536/23.4; 530/350; 530/300
(58) Field of Search ............................ 530/300, 350; 435/6, 7.1, 320.1, 69.1; 536/23.1, 23.4; 514/2, 12

(56) References Cited

U.S. PATENT DOCUMENTS

| | | | |
|---|---|---|---|
| 5,019,087 A | 5/1991 | Nichols | 606/152 |
| 5,229,365 A | 7/1993 | Polak et al. | 514/12 |
| 5,422,264 A | 6/1995 | Quaranta et al. | 535/240.2 |
| 5,444,158 A | 8/1995 | Engvall et al. | 514/259 |
| 5,510,263 A | 4/1996 | Quaranta et al. | 435/240.243 |
| 5,541,106 A | 7/1996 | Jones | 435/240.243 |
| 5,585,267 A | 12/1996 | Jones et al. | 435/240.243 |
| 5,624,905 A | 4/1997 | Engvall et al. | 514/21 |
| 5,658,789 A | 8/1997 | Quaranta et al. | 435/375 |
| 5,672,361 A | 9/1997 | Halberstadt et al. | 424/556 |
| 5,681,587 A | 10/1997 | Halberstadt et al. | 424/562 |
| 5,770,562 A | 6/1998 | Burgeson et al. | 514/8 |
| 5,863,743 A | 1/1999 | Campbell et al. | 435/7.21 |
| 5,872,231 A | 2/1999 | Engvall et al. | 536/23.1 |

FOREIGN PATENT DOCUMENTS

| | | |
|---|---|---|
| EP | 0204302 | 12/1986 |
| WO | WO 94/05316 | 3/1994 |
| WO | WO 95/11972 | 5/1995 |
| WO | WO 95/13103 | 5/1995 |
| WO | WO 96/10646 | 4/1996 |
| WO | WO 97/12961 | 4/1997 |
| WO | WO 97/36621 | 10/1997 |
| WO | WO 97/47652 | 12/1997 |
| WO | WO 97/48415 | 12/1997 |
| WO | WO 98/11217 | 3/1998 |

OTHER PUBLICATIONS

Eble et al., Biochemistry, vol. 37, No. 31, 1998, pp. 10945–10955.*
Ueda, Direct Submission, Accession No. D 3776, 1997.*
Vailly J., et al., Gene Ther., 1998; 5: 1322–1332.
Altschul, et al., J. Mol. Biol., 215, 1990, pp. 403–410.
Altschul, et al., Nucleic Acids. Res., 25, 1997, pp. 3389–3402.

Assoain, R. K. and Marcantonio, E. E., J. Clin. Invest., 100(11), 1997, pp. S15–S18.
Aumailley, M. and Krieg, R., J. Invest. Dermatol., 106, 1996, pp. 209–214.
Aumailley et al., In The Laminins, Timpl and Ekblom, eds., Harwood Academic Publishers, Amsterdam (1996), pp. 127–158.
Bailey, S. B., et al.,J. Neurocytology, 22, 1993, pp. 176–184.
Baker et al., Exp. Cell Res., 228(2), Nov. 1, 1996, pp. 262–270.
Bates, C. A. and Meyer, R. L., Dev. Biol., 181, 1997, pp. 91–101.
Bonfil et al., Int. J. Cancer, 58, 1994, pp. 233–239.
Bowie, J. U. et al., Science, 247, 1990pp. 1306–1310.
Brown, J. C., et al., J. Cell Sci., 107, 1994, pp. 329–338.
Cheng, Y.–S., et al., J. Biol. Chem., 272(50), 1997, pp. 31525–31532.
Cleland et al., Crit. Rev. Therapeutic Drug Carrier Systems, 10, 1993, pp. 307–377.
Colognato, H., et al., J. Cell Biol., 145(3), 1999, pp. 619–631.
Cunningham and Wells, Science, 244, 1989, pp. 1081–1085.
Dobeli, et al., J. Biotechnology, 7, 1988pp. 199–216.
Donaldson, D. J. and Mahan, J. T., Cell Tissue Res., 235, 1984, pp. 221–224.
El–Ghannam, A., et al.,J. Biomed. Mater. Res., 41(4), 1998, pp. 30–40.
Ervasti and Campbell, J. Cell Biol., 122(4), 1993, pp. 809–823.
Folkman et al., Adv. Cancer Res., 43, 1985, pp. 175–203.
Gagnoux–Palacios, L., et al.,J. Biol. Chem., 271(31), 1996, pp. 18437–18444.
Galliano et al., J. Biol. Chem., 270, 1995, pp. 21820–221826.
Gayle, et al., J. Biol. Chem., 268, 1993pp. 22105–22111.
Gerecke et al.,J. Biol. Chem., 269, 1994, pp. 11073–11080.
Giannelli, G., et al., Science, 277, 1997, pp. 225–228.
Glukhova, M., et al., Dev. Biol., 157, 1993, pp. 437–447.
Goldfinger et al., J. Cell Sci., 112(Pt. 16), 1999, pp. 2615–2629.
Goldfinger, L. E., et al., J. Cell Biol., 141(1), 1998, pp. 255–265.
Gonzales et al., Mol. Biol. Cell., 10(2), Feb., 1999, pp. 259–270.

(List continued on next page.)

Primary Examiner—Karen Cochrane Carlson
Assistant Examiner—Hope A. Robinson
(74) Attorney, Agent, or Firm—McDonnell Boehnen Hulbert & Berghoff; David S. Harper

(57) ABSTRACT

The present invention provides recombinant laminin 5, methods for making recombinant laminin 5, cells that express recombinant laminin 5, and methods for using the recombinant laminin 5 to accelerate wound healing, and to promote cell attachment and migration.

8 Claims, 3 Drawing Sheets

OTHER PUBLICATIONS

Grant, D. S. and Kleinman, H. K., *Regulation of Angiogenesis*, Goldberg I.D., and Rosen, E.M., eds., Birkhauser Verlag, Basel, Switzerland, 1997, pp. 317–333.

Hedin, U., et al., *J. Cell Biol.*, 107, 1988, pp. 307–319.

Hormia, M., et al., *J. Dent. Res.*, 77(7), 1998, pp. 1479–1485.

Hormia et al., *J. Invest. Dermatol.* Oct. 1995 105(4): pp. 557–561.

Iivananinen et al., *J. Biol. Chem.*, 274, 1999, pp. 14107–14111.

Kallunki et al., *J. Cell Biol.*, 119, 1992, pp. 679–693.

Kamiguchi, H., et al., *Annu. Rev. Neurosci.*, 21, 1998, pp. 97–125.

Karlin and Altschul, Proc. Natl. Acad. Sci. USA, 87, 1990, pp. 2264–2268.

Karlin and Altschul, Proc. Natl. Acad. Sci. USA, 90, 1993, pp. 5873–5877.

Koch, M., et al., *J. Cell Biol.*, 145(2), 1999, pp. 605–617.

Lotz, M. M., et al., *Am. J. Path.*, 150(2), 1997, pp. 747–759.

Malinda, K. M. and Kleinman, H. K., *Int. J. Biochem. Cell Biol.*, 28(9), 1996, pp. 957–959.

Malinda, K. M., et al., *FASEB J.*, 13, 1999, pp. 53–62.

Matsui, C., et al., *J. Biol. Chem.*, 270(40), 1995, pp. 23496–23503.

Miner, J. H. and Patton, B. L., *Int. J. Biochem. Cell Biol.*, 31, 1999, pp. 811–816.

Mullen et al., *J. Periodontal. Res.*, 34(1), Jan., 1999, pp. 16–24.

Nicosia, R. F., et al., *Dev. Biol.*, 164, 1994, pp. 197–206.

Nomizu, M., et al., *J. Biol. Chem.*, 272(51), 1997, pp. 32198–32205.

Olsen, D., et al, *Lab. Invest.*, 60(6), 1989, pp. 772–782.

O'Toole, E. A., et al., *Exp. Cell Res.*, 233, 1997, pp. 330–339.

Patton, B. L., et al., *J. Cell Biol.*, 139(6), 1997, pp. 1506–1521.

Patton, B. L., et al., *Neuromusc. Disord.*, 9, 1999, pp. 423–433.

Pinckard et al., *Clin. Exp. Immunol.*, 2, 1967, pp. 331–340.

Ponce, M. L., et al., *Circ. Res.*, 84, 1999, pp. 688–694.

Qin and Kurpakus, *Exp. Eye Res.*, 66(5), May, 1998, pp. 569–579.

Richards, D. W., et al., *J. Dent. Res.*, 75(7), 1996, pp. 1512–1517.

Robbins et al., *Diabetes*, 36, 1987, pp. 838–845.

Ron, et al., *J. Biol. Chem.*, 268, 1993, pp. 2984–2988.

Rousselle, P., et al., *JBC*, 270(23), 1995, pp. 13766–13770.

Ryan, M., et al., *J. Cell Biol.*, 145(6), 1999, pp. 1309–1323.

Ryan, M. C. and Christiano, A. M., *Matrix Biol.*, 15, 1996, pp. 369–381.

Sato, K., et al., *Exp. Cell Res.*, 247, 1999, pp. 451–460.

Sugiyama et al., *Eur. J. Biochem.*, 228, 1995, pp. 120–128.

Takeda, A., et al., *J. Invest. Dermatology*, 113, 1999, pp. 38–42.

Thyberg, J., et al., *J. Histochem. Cytochem.*, 45(6), 1997, pp. 837–846.

Thyberg, J. and Hultgårdh–Nilsson, A., *Cell Tissue Res.*, 276, 1994, pp. 263–271.

Todorov et al., *Transplant. Proc.*, 30(2), Mar., 1998, pp. 455.

Tsunenaga et al., *Matrix Biol.* 17(8–9), 1998, pp. 603–613.

Vivinus–Nebot, M., et al., *J. Cell Biol.*, 144, 1999, pp. 563–574.

Wewer, U. M. and Engvall, E., *Neuromusc. Disord.*, 6, 1996, pp. 409–418.

Yoshiba et al., *Cell Tissue Res.*, 292(1), Apr., 1998, pp. 143–149.

Yurchenco, P. D., et al., *Proc. Natl. Acad. Sci. USA*, 94, 1997, pp. 10189–10194.

Kortesmaa, et al., Ser. No. 09/561,818; filed on Apr. 28, 2000.

* cited by examiner

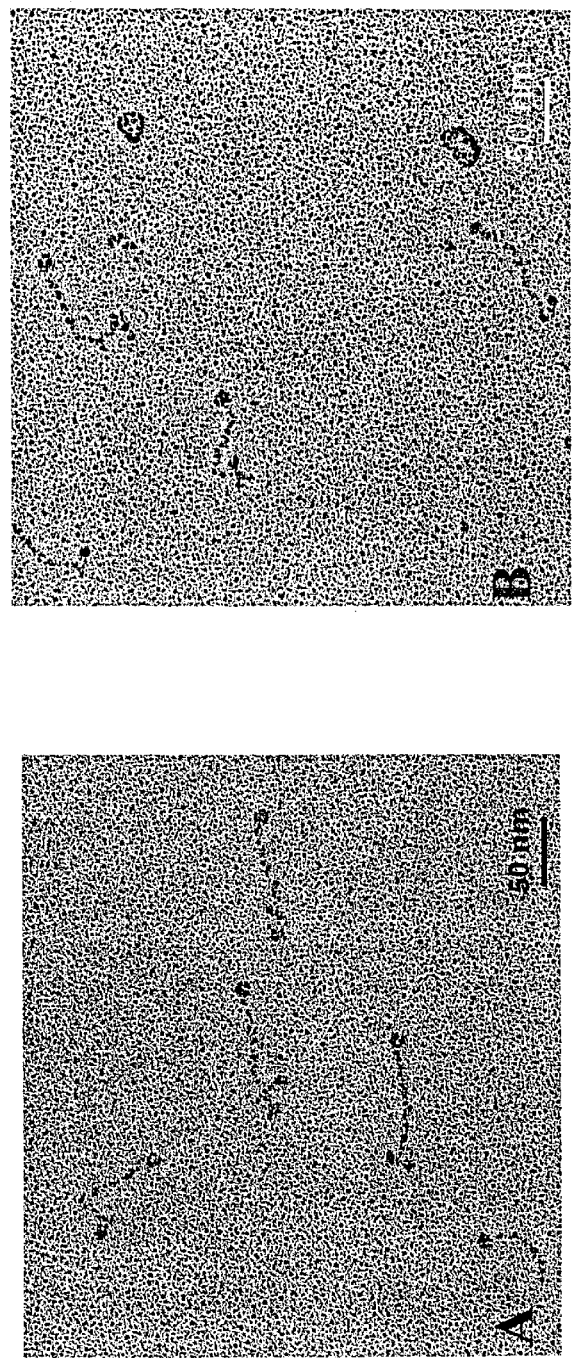
Figure 3. Rotary-shadowed electron micrographs of recombinant laminin 5 (A) and "native" laminin 5 (B).

RECOMBINANT LAMININ 5

CROSS-REFERENCE

This application claims priority to U.S. Provisional Patent Application Ser. No. 60/131,720 filed Apr. 30, 1999; Ser. No. 60/149,738 filed Aug. 19, 1999; and Ser. No. 60/155,945 filed Sep. 24, 1999, all of which are incorporated herein by reference in their entirety.

FIELD OF THE INVENTION

This application relates to recombinant laminin 5 and methods for its use.

BACKGROUND OF THE INVENTION

Basal laminae (basement membranes) are sheet-like, cell-associated extracellular matrices that play a central role in cell growth, tissue development, and tissue maintenance. They are present in virtually all tissues, and appear in the earliest stages of embryonic development.

Basal laminae are central to a variety of architectural and cell-interactive functions. (See for example, Malinda and Kleinman, Int. J. Biochem. Cell Biol. 28:957–959 (1996); Aumailley and Krieg, J. Invest. Dermatology 106:209–214 (1996)):

1. They serve as architectural supports for tissues, providing adhesive substrates for cells.

2. They create perm-selective barriers between tissue compartments that impede the migration of cells and passively regulate the exchange of macromolecules. These properties are illustrated by the kidney glomerular basement membrane, which functions as an important filtration structure, creating an effective blood-tissue barrier that is not permeable to most proteins and cells.

3. Basal laminae create highly interactive surfaces that can promote cell migration and cell elongation during embryogenesis and wound repair. Following an injury, they provide a surface upon which cells regenerate to restore normal tissue function.

4. Basal laminae present information encoded in their structure to contacting cells that is important for differentiation and tissue maintenance. This information is communicated to the cells through various receptors that include the integrins, dystroglycan, and cell surface proteoglycans. Signaling is dependent not only on the presence of matrix ligands and corresponding receptors that interact with sufficient affinities, but also on such topographical factors as ligand density in a three-dimensional matrix "landscape", and on the ability of basal lamina components to cluster receptors. Because these matrix proteins can be long-lived, basal laminae create a "surface memory" in the basal lamina for resident and transient cells.

The basal lamina is largely composed of laminin and type IV collagen heterotrimers that in turn become organized into complex polymeric structures. To date, six type IV collagen chains and at least twelve laminin chains (and twelve different heterotrimeric laminins) have been identified. These chains possess shared and unique functions and are expressed with specific temporal (developmental) and spatial (tissue-site specific) patterns.

Laminins are a family of heterotrimeric glycoproteins that reside primarily in the basal lamina. They function via binding interactions with neighboring cell receptors, and are important signaling molecules that can strongly influence cellular function. Laminins are important in both maintaining cell/tissue phenotype as well as promoting cell growth and differentiation in tissue repair and development.

Laminins are large, multi-domain proteins, with a common structural organization. The laminin molecule integrates various matrix and cell interactive functions into one molecule.

The laminin molecule is comprised of $\alpha$-, $\beta$-, and $\gamma$-chains joined together through a coiled-coil domain. Within this structure are identifiable domains that possess binding activity towards other laminin and basal lamina molecules, and membrane-bound receptors. Domains VI, IVb, and IVa form globular structures, and domains V, IIIb, and IIIa (which contain cysteine-rich EGF-like elements) form rod-like structures. (Kamiguchi et al., Ann. Rev. Neurosci. 21:97–125 (1998)) Domains I and II of the three chains participate in the formation of a triple-stranded coiled-coil structure (the long arm).

Table 1 shows the individual chains that each laminin type is composed of:

TABLE 1

| Known laminin family members | |
|---|---|
| Protein | Chains |
| Laminin-1 | $\alpha1\beta1\gamma1$ |
| Laminin-2 | $\alpha2\beta1\gamma1$ |
| Laminin-3 | $\alpha1\beta2\gamma1$ |
| Laminin-4 | $\alpha2\beta2\gamma1$ |
| Laminin-5 | $\alpha3\beta3\gamma2$ |
| Laminin-6 | $\alpha3\beta1\gamma1$ |
| Laminin-7 | $\alpha3\beta2\gamma1$ |
| Laminin-8 | $\alpha4\beta1\gamma1$ |
| Laminin-9 | $\alpha4\beta2\gamma1$ |
| Laminin-10 | $\alpha5\beta1\gamma1$ |
| Laminin-11 | $\alpha5\beta2\gamma1$ |
| Laminin-12 | $\alpha2\beta1\gamma3$ |

Four structurally-defined family groups of laminins have been identified. The first group of five identified laminin molecules all share the $\beta1$ and $\gamma1$ chains, and vary by their $\alpha$-chain composition ($\alpha1$ to $\alpha5$ chain). The second group of five identified laminin molecules all share the $\beta1$ and $\gamma1$ chain, and again vary by their $\alpha$-chain composition. The third group of identified laminin molecules has one identified member, laminin 5, with a chain composition of $\alpha3\beta3\gamma2$. The fourth group of identified laminin molecules has one identified member, laminin 12, with the newly identified $\gamma3$ chain ($\alpha2\beta1\gamma3$).

Some progress has been made in elucidating the relationship between domain structure and function. (See, for example, Wewer and Engvall, Neuromusc. Disord. 6:409–418 (1996).) The overall sequence similarity among the homologous domains in different chains varies, but it is highest in domain VI (thought to play a key role in laminin polymerization), followed by domains V (possibly involved in protein-protein interactions) and III (entactin/nidogen binding; possible cell adhesion sites), and is lowest in domains I, II (both thought to be involved in intermolecular assembly, and containing possible cell adhesion sites), and G. Not all domains are present in all 3 types of chains. The globular G domain (thought to be involved in cell receptor binding) is present only in the $\alpha$ chains. Other domains may not be present in all chains within a certain chain type. For example, domain VI is absent from $\alpha3$, $\alpha4$, and $\gamma2$ chains. (Wewer and Engvall, 1996)

As a result of their large size (>600 kD) and unique structure, the laminin molecules can be resolved in the electron microscope. (Wewer and Engvall, 1996) Typically, laminins appear as cross-shaped molecules in an EM. The three short arms of the cross represent the amino terminal portions of each of the three separate laminin chains (one short arm per chain). The long arm of the cross is composed of the C-terminal parts of the three chains, which together form a coiled coil structure. (Wewer and Engvall, 1996) The long arm ends with the globular G domain.

The coiled-coil domain of the long arm is crucial for assembly of the three chains of laminin. (Yurchenco et al., Proc. Natl. Acad. Sci. 94:10189–10194 (1997)). Disulfide bonds bridge and stabilize all three chains in the most proximal region of the long arm and join the β and γ chains in the most distal region of the long arm.

A model of laminin receptor-facilitated self-assembly, based on studies conducted with cultured skeletal myotubes and Schwann cells, predicts that laminins bind to their receptors, which freely diffuse in a fluidic membrane, when ligand-free. Receptor engagement forces these receptors into a high local two-dimensional concentration, facilitating their mass-action driven assembly into ordered surface polymers. In this process, the engaged receptors are also reorganized, accompanied by cytoskeletal rearrangements. (Colognato, J. Cell Biol. 145:619–631 (1999)) This reorganization activates the receptors, causing signal transduction with the alteration of cell expression, shape and/or behavior.

One class of laminin receptors are the integrins, which are cell surface receptors that mediate many cell-matrix and cell-cell interactions. Integrins are heterodimers, consisting of an α and β subunit. 16 α- and 8 β-subunits are known, and at least 22 combinations of α and β subunits have been identified to date. Some integrins have only one or a few known ligands, whereas others appear to be very promiscuous. Binding to integrins is generally of low affinity, and is dependent on divalent cations. Integrins, activated through binding to their ligands, transduce signals via kinase activation cascades, such as focal adhesion and mitogen-activated kinases. Several different integrins bind different laminin isoforms more or less specifically. (Aumailley et al., In The Laminins, Timpl and Ekblom, eds., Harwood Academic Publishers, Amsterdam. pp. 127–158 (1996))

Laminin-5, also referred to as kalinin, nicein, and epiligrin, plays a key role in modulating the behavior and activity of cells and tissues of epithelial origin, and is expected to have broad uses in clinical settings where increased epithelial attachment and hemidesmosome assembly are required. (Takeda et al., J. Invest. Dermatol. 1999 113(1):38–42) Laminin-5 is a principal adhesive ligand in the epidermal basal lamina, and has been shown to promote the attachment of keratinocytes and epithelial cells to the basal lamina and underlying dermis, and also promotes hemidesmosome formation. (Burgeson et al. U.S. Pat. No. 5,770,562; Quaranta and Hormia, U.S. Pat. No. 5,422,264; Jones, U.S. Pat. No. 5,541,106; Quaranta and Hornia, U.S. Pat. No. 5,658,789; Hormia et al., J. Invest. Dermatol. 1995 October 105(4):557–561).

Laminin 5 is also thought to be necessary for the healing of epithelial tissue wounds. (Goldfinger et al., J. Cell Sci. 1999; 112(Pt. 16):2615–2629) Pretreatment of human keratinocyte sheets for grafting with laminin 5 improves grafting efficiency. (Takeda et al., J. Invest. Dermatol. 1999 July; 113(1):38–42). The addition of laminin-5 accelerates the formation of a basement membrane in a skin equivalent model (Tsunenaga et al., Matrix Biol. 17(8–9):603–613, 1998). Laminin-5 also promotes epithelial cell attachment to a wide variety of biomaterials, including polymers, hydroxyapatite, and metals. (Jones et al., U.S. Pat. No. 5,585,267; El Ghannam et al., J. Biomed. Mater. Res. 1998 July; 41(1):30–40).

Laminin 5 has further been demonstrated to promote the following:

1. Epithelial cell adhesion to the internal basal lamina of teeth (Mullen et al., J. Periodontal. Res. 1999 January 34(1):16–24; Hormia et al., J. Dent. Res. 1998 July; 77(7):1479–1485). and anchorage of ameloblasts (ie: enamel-producing cells) to the enamel matrix. (Yoshiba et al., Cell Tissue Res. 1998 April; 292(1):143–149).

2. Corneal epithelial cell adhesion. (Qin and Kurpakus, Exp. Eye Res. 1998 May 66(5):569–579).

3. Intestinal epithelial restitution. (Lotz et al., Am. J. Pathol. 1997 February;150(2):747–760).

4. In vitro expansion of epithelial cells by providing an efficient adhesion substrate for primary cell cultures, thus providing the basis for a wide range of new cell therapy applications. (Gonzales et al., Mol. Biol. Cell. 1999 February; 10(2):259–270; Baker et al., Exp. Cell Res. Nov. 1, 1996; 228(2)262–270).

5. Proliferation of pancreatic beta islet cells (Todorov et al., Transplant. Proc. 1998 March; 30(2): 455; Quaranta and Jones, U.S. Pat. No. 5,510,263; Halberstadt et al, U.S. Pat. No. 5,681,587; Halberstadt et al., U.S. Pat. No. 5,672,361), and T cells (Vivinus-Nebot et al., J. Cell Biol. Feb. 8, 1999; 144(3):563–574).

Thus, laminin 5 has broad uses in clinical settings where increased epithelial attachment and hemidesmosome assembly are required. Laminin 5 can be used to promote wound healing and tissue regeneration. The application of exogenous laminin 5 has broad application for the accelerated healing of skin disorders, such as diabetic foot ulcers, venous ulcers, pressure sores, skin surgery, bums, and acute wounds. Exogenous laminin 5 may be used to directly treat a wound surface, or may be applied to a variety of medical devices and dermal grafts for skin, corneal, gastrointestinal, and periodontal epithelial wound healing. The use of laminin 5 provides enhanced biocompatibility of the device or graft, which leads to improved tissue integration and remodeling, reduced immune response, and reduced likelihood of infection. Laminin 5 is also useful for the ex vivo and in vitro proliferation of various cell types, including but not limited to epithelial cells, pancreatic beta islet cells, and T cells, and tissue equivalents. Thus, a source of laminin 5 for tissue culture media or a media supplement, as well as cell growth substrates coated with laminin 5, would be particularly useful for the cultivation of these and other cell types.

A good source and purification procedure for laminin-5 is needed to provide material for the development of the therapeutic and research applications mentioned above. Some cell lines secrete laminin-5, and procedures have been developed to purify laminin-5 from the processed cells and cell media. However, these methods are time consuming and capable of producing only small amounts of laminin 5. (Rouselle et al., J. Biol. Chem. 1995 270(23):13766–13770; Cheng et al., J. Biol. Chem. 1997, 272(50):31525–31532).

A preferred method of production, however, is the use of recombinant DNA technology to engineer a cell line of choice to produce recombinant laminin-5. A recombinant-based method of laminin-5 production has several advantages over purification from tissue or isolation from cell lines in culture:

1. The recombinant produced protein is free of pathogens. While this is also true for endogenous cell culture produced protein, protein derived from human tissue carries a risk for contamination by HIV, hepatitis, and other infectious agents.

2. Expression levels of the protein, and hence yields, can be improved through the use of genetically engineered genes/vectors that enhance the production of the encoded protein.

3. It is possible to engineer additional peptide sequences to the protein chain that provides a binding site for a commercially viable affinity purification procedure.

4. The method can provide for the modification of protein structure/function through the addition, substitution, elimination, and/or other modifications of protein domain structures. For example, it may be desirable to introduce an integrin binding site (e.g. RGD), switch integrin recognition sites, or engineer in a stable binding site to a synthetic substrate. Thus, the creation of expression vectors that express laminin chains generates enormous flexibility for future uses and creates a basis for creating second generation "designer" laminins.

Previous studies have produced cells transfected with one or two of the laminin 5 chain-encoding DNA sequences, but none have produced recombinant heterotrimeric laminin 5, nor have they produced cell lines that secrete recombinant heterotrimeric laminin 5. (Gagnoux-Palacios et al., J. Biol. Chem. 271:18437–18444 (1996); Matsui et al., J. Biol. Chem. 270:23496–23503 (1995)).

Thus, there exists a need in the art for recombinant heterotrimeric laminin 5 protein, methods for making recombinant laminin 5, and methods of using recombinant laminin 5 for wound healing and tissue regeneration, for use on a variety of medical devices and dermal grafts for skin, corneal, gastrointestinal, and periodontal epithelial wound healing, for the ex vivo and in vitro proliferation of various cell types, and for tissue culture media, media supplements, and as a component of cell growth substrates.

SUMMARY OF THE INVENTION

The present invention fulfills the need in the art for recombinant laminin 5 protein, methods for making recombinant laminin 5, and methods of using recombinant laminin 5 for the treatment of burns, for use on a variety of medical devices and dermal grafts for skin, corneal, gastrointestinal, and periodontal epithelial wound healing, for the ex vivo and in vitro proliferation of various cell types, and for tissue culture media, media supplements, and as a component of cell growth substrates.

In one aspect, the present invention provides cells that have been transfected with nucleic acid sequences encoding laminin α3, β3 and γ2 chains, wherein the cells express the individual chains, which assemble into heterotrimeric recombinant laminin-5 (hereinafter referred to as "r-laminin 5"). r-laminin 5, or processed forms thereof, are secreted by the cell.

In another aspect, the present invention provides r-laminin 5, and methods for producing substantially purified r-laminin 5, or processed forms thereof.

In a further aspect, the present invention provides pharmaceutical compositions, comprising r-laminin 5, or processed forms thereof, together with a pharmaceutically acceptable carrier. Such pharmaceutical compositions can optionally be provided with other compounds with wound healing and tissue regeneration utility, such as other extracellular matrix components.

In further aspect, the present invention provides methods and kits for using r-laminin 5 to:

a. accelerate wound healing and tissue regeneration;
b. enhance the performance of skin grafts;
c. improve the attachment of gum tissue to the tooth surface;
d. improve the biocompatibility of medical devices; and
e. accelerate cell proliferation,
by providing an amount effective of r-laminin 5 for the various methods. The invention also provides methods and kits for using laminin 5 to regulate angiogenesis. The kits comprise an amount of laminin 5 or r-laminin 5 effective for the desired effect, and instructions for the use thereof.

In a further aspect, the present invention provides improved medical devices and grafts, wherein the improvement comprises coating the devices or grafts with an amount effective of r-laminin 5 or the pharmaceutical compositions of the invention for the desired application.

In a further aspect, the invention provides improved cell culture devices for the proliferation of cells in culture, by providing an amount effective of r-laminin 5 for the attachment of cells to a cell culture device for the attachment and subsequent proliferation, differentiation, or maintenance of the cells.

In another aspect, the invention provides a cell culture growth supplement, comprising r-laminin 5. In another aspect, the invention provides an improved cell culture growth media, wherein the improvement comprises the addition of r-laminin 5.

BRIEF DESCRIPTION OF THE FIGURES

FIG. 3 is a rotary shadow analysis of r-laminin 5. Purified r-laminin 5 protein was diluted to 50 µg/ml and adjusted to 70% glycerol/30% 0.15M ammonium bicarbonate and rotary shadowed using standard techniques. An approximately 80,000×magnification field is shown of (A) r-laminin 5; (B) "native" laminin 5 (purified by BM165 monoclonal antibody affinity chromatography from SCC-25 (squamous cell carcinoma cell line) conditioned medium). The bar represents 50 nm.

DETAILED DESCRIPTION OF THE PREFERRED EMBODIMENTS

Figure 1:
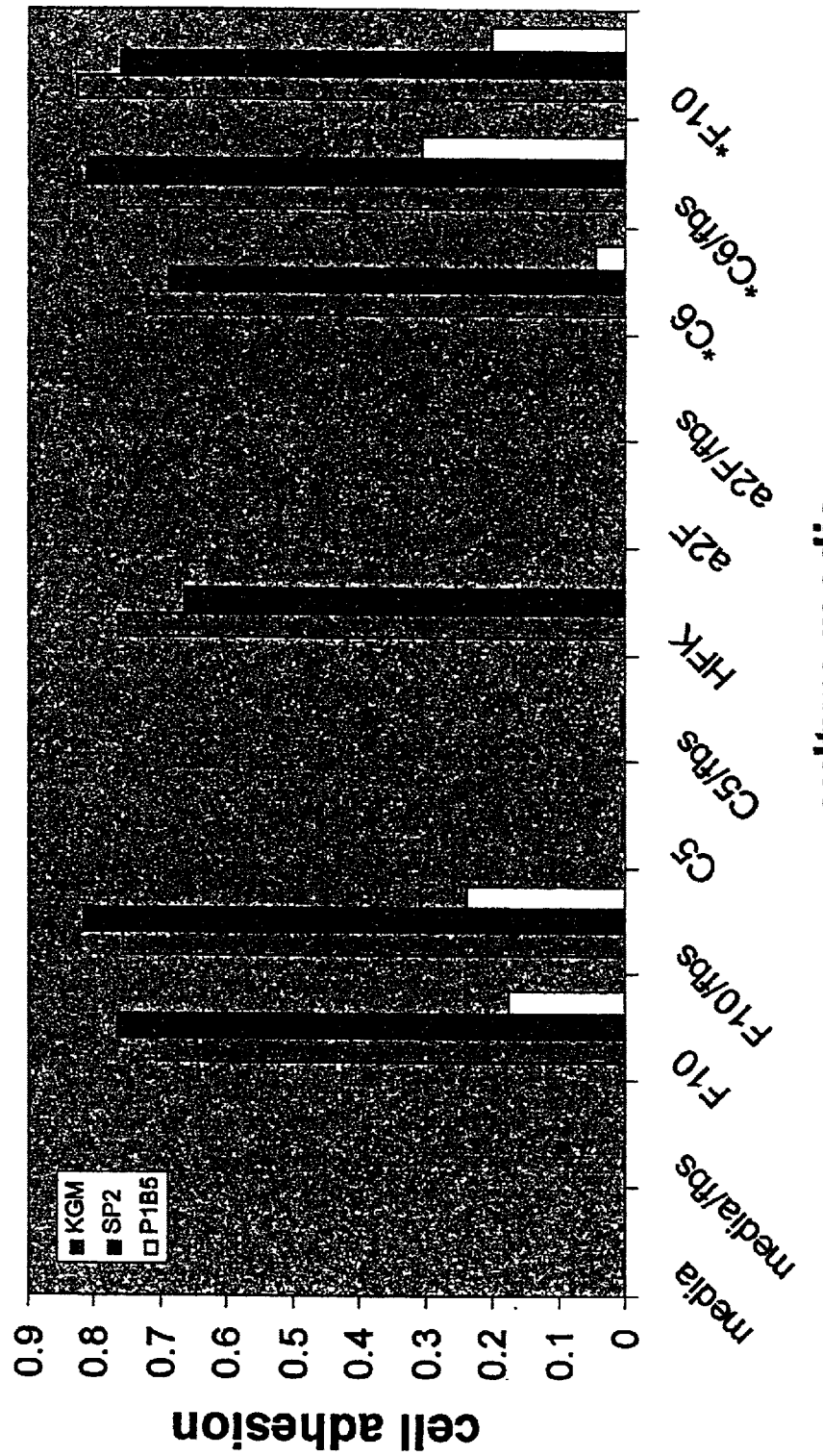
FIG. 1 is a bar graph showing the results of an HFK cell adhesion assay for r-laminin 5 activity in culture media from various clones.

All references, patents and patent applications are hereby incorporated by reference in their entirety.

Within this application, unless otherwise stated, the techniques utilized may be found in any of several well-known references such as: *Molecular Cloning: A Laboratory Manual* (Sambrook, et al., 1989, Cold Spring Harbor Laboratory Press), *Gene Expression Technology* (Methods in Enzymology, Vol. 185, edited by D. Goeddel, 1991. Academic Press, San Diego, Calif.), "Guide to Protein Purification" in *Methods in Enzymology* (M. P. Deutshcer, ed., (1990) Academic Press, Inc.); *PCR Protocols: A Guide to Methods and Applications* (Innis, et al. 1990. Academic Press, San Diego, Calif.), *Culture of Animal Cells: A Manual of Basic Technique*, 2$^{nd}$ Ed. (R. I. Freshney. 1987. Liss, Inc. New York, N.Y.), *Gene Transfer and Expression Protocols*, pp. 109–128, ed. E. J. Murray, The Humana Press Inc., Clifton, N.J.), and the Ambion 1998 Catalog (Ambion, Austin, Tex.).

As used herein "laminin 5" encompasses both r-laminin 5 and heterotrimeric laminin 5 from naturally occurring sources.

The term "r-laminin 5" refers to include recombinant heterotrimeric laminin 5 expressed by a cell that has been exogenously transfected with expression vector(s) comprising polynucleotides that encode α3, β3 and γ2 laminin polypeptide chains, or a portion of each of the chains which are capable of forming a heterotrimeric laminin 5, as well as versions thereof resulting from cellular processing events. Such r-laminin 5 can comprise α3, β3, and γ2 sequences from a single organism, or from different organisms. Laminin 5 chain DNA sequences and their encoded proteins from a variety of organisms are known in the art. (See, for example, Gerecke et al., J. Biol. Chem. 269:11073–11080 (1994); Kallunki et al., J. Cell Biol. 119:679–693 (1992); Ryan et al., J. Biol. Chem. 269:22779–22787 (1994); Iivananinen et al., J. Biol. Chem. 274:14107–14111 (1999); Galliano et al., J. Biol. Chem. 270:21820–221826 (1995); Sugiyama et al., Eur. J. Biochem. 228:120–128 (1995) all references incorporated by reference herein in their entirety).

In the present invention, r-laminin 5 is a secreted protein, which is capable of being directed to the ER, secretory vesicles, and the extracellular space as a result of a signal sequence, as well as those proteins released into the extracellular space without necessarily containing a signal sequence. If the secreted protein is released into the extracellular space, the secreted protein can undergo extracellular processing to produce a "mature" protein. Such processing event can be variable, and thus may yield different versions of the final "mature protein". The substantially purified r-laminin 5 of the present invention includes heterotrimers comprising both the full length and any such processed laminin 5 chains.

As used herein, the term "substantially purified" means that the recombinant laminin 5 so designated has been separated from its in vivo cellular environments.

As used herein, a laminin 5 polypeptide chain refers to a polypeptide chain according to one or more of the following:

(a) comprises a polypeptide structure selected from the group consisting of:
1. R1-R2-R3
2. R1-R2-R3(e)
3. R3
4. R3(e)
5. R1-R3
6. R1-R3(e)
7. R2-R3
8. R2-R3(e)

wherein R1 is a amino terminal methionine; R2 is a signal sequence that is capable of directing secretion of the polypeptide, wherein the signal sequence may be the natural signal sequence for the particular laminin chain, that of another secreted protein, an artificial sequence; R3 is a secreted laminin chain selected from the α3, β3, and γ2 chains; and R3(e) is a secreted laminin chain selected from the α3, β3, and γ2 chains that further comprises an epitope tag (such as those described below), which can be placed at any position within the laminin chain amino acid sequence; and/or (b) is encoded by a polynucleotide that is substantially similar to the disclosed laminin polynucleotide sequences or portions thereof (SEQ ID NOS: 1, 3, 5, 7, 9, 11, 13, 15, 17, 19, 21, 23, 25, 27, 29, 31, 33, 35); and/or (c) is encoded by a polynucleotide that hybridizes under high or low stringency conditions to coding regions, or portions thereof, of one or more of the recombinant laminin 5 chain DNA sequences disclosed herein (SEQ ID NOS: 1, 3, 5, 7, 9, 11, 13, 15, 17, 19, 21, 23, 25, 27, 29, 31, 33, 35), or complementary sequences thereof; and/or (d) has at least 70% identity to the disclosed laminin polypeptide claim amino acid sequences (SEQ ID NOS: 2, 4, 6, 8, 10, 12, 14, 16, 18, 20, 22, 24, 26, 28, 30, 32, 34, 36), preferably at least 80% identity, and most preferably at least about 90% identity.

The phrase "substantially similar" is used herein in reference to polynucleotide or polypeptide sequences having one or more conservative variations from the laminin 5 sequences disclosed herein, including but not limited to deletions, insertions, inversions, repeats, and substitutions, wherein the resulting laminin chain is functionally equivalent to those disclosed herein.

For example, conservative polynucleotide variants may contain alterations in the coding regions, non-coding regions, or both. Especially preferred are polynucleotide variants containing alterations which produce silent substitutions, additions, or deletions, but do not alter the properties or activities of the encoded polypeptide. Nucleotide variants produced by silent substitutions due to the degeneracy of the genetic code are preferred. Moreover, variants in which 5–10, 1–5, or 1–2 amino acids are substituted, deleted, or added in any combination are also preferred. Polynucleotide variants can be produced for a variety of reasons, including but not limited to optimizing codon expression for a particular host (change codons in the human mRNA to those preferred by a bacterial host such as E. coli).

Naturally occurring conservative variants are called "allelic variants," and refer to one of several alternate forms of a gene occupying a given locus on a chromosome of an organism. (Genes II, Lewin, B., ed., John Wiley & Sons, New York (1985).) These allelic variants can vary at either the polynucleotide and/or polypeptide level. Alternatively, non-naturally occurring conservative variants may be produced by mutagenesis techniques or by direct synthesis.

Using known methods of protein engineering and recombinant DNA technology, conservative polynucleotide variants may be generated to improve or alter the characteristics of the expressed laminin chain polypeptides. For instance, one or more amino acids can be deleted from the N-terminus or C-terminus of the secreted protein. (See, for example, Ron et al., J. Biol. Chem. 268: 2984–2988 (1993); Dobeli et al., J. Biotechnology 7:199–216 (1988)) Ample evidence demonstrates that variants often retain a biological activity similar to that of the naturally occurring protein. (See, for example, Gayle et al., J. Biol. Chem 268:22105–22111 (1993)). Furthermore, even if deleting one or more amino acids from the N-terminus or C-terminus of a polypeptide results in modification or loss of one or more biological functions, other biological activities may still be retained.

Guidance concerning how to make phenotypically silent amino acid substitutions is provided in Bowie, J. U. et al., Science 247:1306–1310 (1990), wherein the authors indicate that there are two main strategies for studying the tolerance of an amino acid sequence to change.

The first strategy exploits the tolerance of amino acid substitutions by natural selection during the process of evolution. By comparing amino acid sequences in different species, conserved amino acids can be identified. These conserved amino acids are likely important for protein function. In contrast, the amino acid positions where substitutions have been tolerated by natural selection indicates that these positions are not critical for protein function. Thus, positions tolerating amino acid substitution could be modified while still maintaining biological activity of the protein.

The second strategy uses genetic engineering to introduce amino acid changes at specific positions of a cloned gene to identify regions critical for protein function. For example, site directed mutagenesis or alanine-scanning mutagenesis (introduction of single alanine mutations at every residue in the molecule) can be used. (Cunningham and Wells, Science 244:1081–1085 (1989).) The resulting mutant molecules can then be tested for biological activity.

As the authors state, these two strategies have revealed that proteins are surprisingly tolerant of amino acid substitutions. The authors further indicate which amino acid changes are likely to be permissive at certain amino acid positions in the protein. For example, most buried (within the tertiary structure of the protein) amino acid residues require nonpolar side chains, whereas few features of surface side chains are generally conserved. Moreover, tolerated conservative amino acid substitutions involve replacement of the aliphatic or hydrophobic amino acids Ala, Val, Leu and Ile; replacement of the hydroxyl residues Ser and Thr; replacement of the acidic residues Asp and Glu; replacement of the amide residues Asn and Gln, replacement of the basic residues Lys, Arg, and His; replacement of the aromatic residues Phe, Tyr, and Trp, and replacement of the small-sized amino acids Ala, Ser, Thr, Met, and Gly.

The "substantially similar" polypeptides of the present invention also include (i) substitutions with one or more of the non-conserved amino acid residues, where the substituted amino acid residues may or may not be one encoded by the genetic code, or (ii) substitution with one or more of amino acid residues having a substituent group; (iii) fusion of the mature polypeptide with another compound, such as a compound to increase the stability and/or solubility of the polypeptide (for example, polyethylene glycol); and/or (iv) fusion of the polypeptide with additional amino acids, such as an IgG Fc fusion region peptide, or leader or secretory sequence, or a sequence facilitating purification. Such variant polypeptides are deemed to be within the scope of those skilled in the art from the teachings herein.

For example, polypeptide variants containing amino acid substitutions of charged amino acids with other charged or neutral amino acids may produce proteins with improved characteristics, such as less aggregation. Aggregation of pharmaceutical formulations both reduces activity and increases clearance due to the aggregate's immunogenic activity. (Pinckard et al., Clin. Exp. Immunol. 2:331–340 (1967); Robbins et al., Diabetes 36: 838–845 (1987); Cleland et al., Crit. Rev. Therapeutic Drug Carrier Systems 10:307–377 (1993).)

"Stringency of hybridization" is used herein to refer to conditions under which nucleic acid hybrids are stable. The invention also includes nucleic acids that hybridize under high stringency conditions (as defined herein) to all or a portion of the coding sequences of the laminin chain polynucleotides disclosed herein, or their complements. The hybridizing portion of the hybridizing nucleic acids is typically at least 50 nucleotides in length. As known to those of skill in the art, the stability of hybrids is reflected in the melting temperature ($T_M$) of the hybrids. $T_M$ decreases approximately 1–1.5° C. with every 1% decrease in sequence homology. In general, the stability of a hybrid is a function of sodium ion concentration and temperature.

Typically, the hybridization reaction is performed under conditions of lower stringency, followed by washes of varying, but higher, stringency. Reference to hybridization stringency relates to such washing conditions. Thus, as used herein, high stringency refers to an overnight incubation at 42° C. in a solution comprising 50% formamide, 5×SSC (750 mM NaCl, 75 mM sodium citrate), 50 mM sodium phosphate (pH 7.6), 5×Denhardt's solution, 10% dextran sulfate, and 20 µg/ml denatured, sheared salmon sperm DNA, followed by washing the filters in 0.1×SSC at about 65° C.

Also contemplated are laminin 5-encoding nucleic acid sequences that hybridize to the polynucleotides of the present invention at lower stringency hybridization conditions. Changes in the stringency of hybridization and signal detection are primarily accomplished through the manipulation of formamide concentration (lower percentages of formamide result in lowered stringency); salt conditions, or temperature. For example, lower stringency conditions include an overnight incubation at 37° C. in a solution comprising 6×SSPE (20×SSPE=3M NaCl; 0.2M $NaH_2PO_4$; 0.02M EDTA, pH 7.4), 0.5% SDS, 30% formamide, 100 ug/ml salmon sperm blocking DNA; followed by washes at 50° C. with 1×SSPE, 0.1% SDS. In addition, to achieve even lower stringency, washes performed following stringent hybridization can be done at higher salt concentrations (e.g. 5×SSC).

Note that variations in the above conditions may be accomplished through the inclusion and/or substitution of alternate blocking reagents used to suppress background in hybridization experiments. Typical blocking reagents include Denhardt's reagent, BLOTTO, heparin, denatured salmon sperm DNA, and commercially available proprietary formulations. The inclusion of specific blocking reagents may require modification of the hybridization conditions described above, due to problems with compatibility.

As used herein, "percent identity" of two amino acids or of two nucleic acids is determined using the algorithm of Karlin and Altshul (Proc. Natl. Acad. Sci. USA 87:2264–2268, 1990), modified as in Karlin and Altschul (Proc. Natl. Acad. Sci. USA 90:5873–5877, 1993). Such an algorithm is incorporated into the NBLAST and XBLAST programs of Altschul et al. (J. Mol. Biol. 215:403–410, 1990). BLAST nucleotide searches are performed with the NBLAST program, score=100, wordlength=12, to obtain nucleotide sequences homologous to the nucleic acid molecules of the invention. BLAST protein searches are performed with the XBLAST program, score=50, wordlength= 3, to obtain an amino acid sequence homologous to a polypeptide of the invention. To obtain gapped alignments for comparison purposes, Gapped BLAST is utilized as described in Altschul et al. (Nucleic Acids. Res. 25:3389–3402, 1997). When utilizing BLAST and Gapped BLAST programs, the default parameters of the respective programs (e.g., XBLAST and NBLAST) are used. See the web site at ncbi.nlm.nih.gov.

Further embodiments of the present invention include polynucleotides encoding laminin chain polypeptides having at least 70% identity, preferably at least 80% identity, and most preferably at least 90% identity to one or more polypeptide sequences, or fragments thereof, contained in SEQ ID NO:2, 4, 6, 8, 10, 12, 14, 16, 18, 20, 22, 24, 26, 28, 30, 32, and 34.

As used herein, "α3 polynucleotide" refers to polynucleotides encoding an α3 laminin chain of the same name. Such polynucleotides can be characterized by one or more of the following: (a) the nucleotides of said polynucleotide may encode an amino acid sequence substantially similar to one or more of the sequences set forth in SEQ ID NO: 2, 4, 6, 8, 10, 12 or fragments thereof, or fragments thereof, (b) polynucleotides that encode polypeptides which share at least 70% identity, preferably 80% identity, and most preferably at least 90% identity with one or more of the sequences set forth in SEQ ID NO: 2, 4, 6, 8, 10, 12 or fragments thereof; (c) the α3 polynucleotides hybridize under low or high stringency conditions to the coding sequence set forth in one or more of SEQ ID NO: 1, 3, 5, 7, 9, 11, fragments thereof, or complementary sequences thereof, (d) the α3 polynucleotides may encode a polypeptide with a general structure selected from (1) R1-R2-R3; (2) R1-R2-R3(e); (3) R3; (4) R3(e); (6) R1-R3(e); (7) R2-R3; and (8) R2-R3(e); wherein R1 and R2 are as described above, a and R3(e) are as described above but comprise secreted α3 chain polypeptides.

As used herein, "β3 polynucleotide" refers to polynucleotides encoding a β3 laminin chain of the same name. Such polynucleotides can be characterized by one or more of the following: (a) the nucleotides of said polynucleotide may encode an amino acid sequence substantially similar to one ore more of the sequences set forth in SEQ ID NO: 14, 16, 18, 20, 22, 24, or fragments thereof, (b) polynucleotides that encode polypeptides which share at least 70% identity, preferably at least 80%, and most preferably at least 90% identity with one or more of the sequences set forth in SEQ ID NO: 14, 16, 18, 20, 22, 24, or fragments thereof, (c) the β3 polynucleotides hybridize under low or high stringency conditions to the coding sequence of one or more of the sequences set forth SEQ ID NO: 13, 15, 17, 19, 21, 23, fragments thereof or complementary sequences thereof, (d) the β3 polynucleotides may encode a polypeptide with a general structure selected from (1) R1-R2-R3; (2) R1-R2-R3(e); (3) R3; (4) R3(e); (5) R1-R3; (6) R1-R3(e); (7) R2-R3; and (8) R2-R3(e); wherein R1 and R2 are as described above, a and R3(e) are as described above but comprise secreted β3 chain polypeptides.

As used herein, "γ2 polynucleotide" refers to polynucleotides encoding a γ2 laminin chain of the same name. Such polynucleotides can be characterized by one or more of the following: (a) the nucleotides of said polynucleotide may encode an amino acid that is substantially similar to one or more of the sequences set forth in SEQ ID NO: 26, 28, 30, 32, 34, 36 or fragments thereof, (b) polynucleotides that encode polypeptides which share at least 70% identity, preferably at least 80%, and most preferably at least 90% identity with one or more of the sequences set forth in SEQ ID NO: 26, 28, 30, 32, 34, 36 or fragments thereof, (c) the γ2 polynucleotides hybridize under low or high stringency conditions to the coding sequence set forth in one or more of SEQ ID NO: 25, 27, 29, 31, 33, 35, fragments thereof, or complementary sequences thereof, (d) the γ2 polynucleotides may encode a polypeptide with a general structure selected from (1) R1-R2-R3; (2) R1-R2-R3(e); (3) R3; (4) R3(e); (5) R1-R3; (6) R1-R3(e); (7) R2-R3; and (8) R2-R3(e); wherein R1 and R2 are as described above, and R3 and R3(e) are as described above but comprise secreted γ2 chain polypeptides.

As used herein, the term "epitope tag" refers to a polypeptide sequence that is expressed as part of a chimeric protein, where the epitope tag serves as a recognition site for binding of antibodies generated against the epitope tag, or for binding of other molecules that can be used for affinity purification of sequences containing the tag.

As used herein, the term "increased biocompatibility" refers to reduced induction of acute or chronic inflammatory response, and reduced disruption of the proper differentiation of implant-surrounding tissues for laminin 5-coated biomaterials relative to an analogous, non-coated biomaterial.

As used herein the term "graft" refers to both natural and prosthetic grafts and implants.

In one aspect, the present invention provides cells that have been systematically transfected with recombinant expression vectors comprising promoter sequences that are operatively linked to polynucleotide sequences encoding polypeptide sequences comprising α3, β3, and γ2 laminin 5 chains. After the multiple transfections, the cells express each of the recombinant laminin 5 chains, which assemble into a heterotrimer and can be purified from the cell culture medium.

In a preferred embodiment, cDNAs encoding proteins comprising the α3, β3, and γ2 laminin polypeptide chains, or fragments thereof, are subcloned into an expression vector. Alternatively, laminin 5 α3, β3, and/or γ2 gene sequences, including one or more introns, and including various 5' and 3' non-coding regions, can be used.

Any cell capable of expressing and secreting the r-laminin 5 can be used. Preferably, eukaryotic cells are used, and most preferably mammalian cells are used, including but not limited to kidney and epithelial cell lines. Especially preferred are those mammalian cells that do not endogenously express laminin 5. Carbohydrate and disulfide post-translational modifications are believed to be required for laminin 5 protein folding and function. This makes the use of eukaryotic cells preferable for producing functional r-laminin 5, although other systems are useful for obtaining, for example, antigens for antibody production.

"Recombinant expression vector" includes vectors that operatively link a nucleic acid coding region or gene to any promoter capable of effecting expression of the gene product. The promoter sequence used to drive expression of the laminin 5 individual chains may be constitutive (driven by any of a variety of promoters, including but not limited to, CMV, SV40, RSV, actin, EF) or inducible (driven by any of a number of inducible promoters including, but not limited to, tetracycline, ecdysone, steroid-responsive). The expression vector must be replicable in the host organisms either as an episome or by integration into host chromosomal DNA. In a preferred embodiment, the expression vector comprises a plasmid. However, the invention is intended to include other expression vectors that serve equivalent functions, such as viral vectors.

In one embodiment, at least one of the laminin chain polypeptide sequences, or fragments thereof, is operatively linked to a nucleic acid sequence encoding an "epitope tag", so that at least one of the chains is expressed as a fusion protein with an expressed epitope tag. The epitope tag may be expressed as the amino terminus, the carboxy terminus, or internal to the end of a r-laminin 5 chain, so long as the resulting heterotrimeric r-laminin 5 remains functional. Any epitope tag may be utilized, so long as it can be used as the basis for affinity purification of the resulting r-laminin 5 heterotrimer. Examples of such epitope tags include, but are not limited to FLAG (Sigma Chemical, St. Louis, Mo.), myc (9E10) (Invitrogen, Carlsbad, Calif.), 6-His (Invitrogen; Novagen, Madison, Wis.), and HA (Boehringer Manheim Biochemicals).

In another embodiment, one of the r-laminin 5 chains is expressed as a fusion protein with a first epitope tag, and at least one other r-laminin chain is expressed as a fusion protein with a second epitope tag. This permits multiple rounds of purification to be carried out. Alternatively, the same epitope tag can be used to create fusion proteins with more than one of the r-laminin chains.

In a further embodiment, the epitope tag can be engineered to be cleavable from the r-laminin 5 chain(s). Alternatively, no epitope tag is fused to any of the r-laminin 5 chains, and the r-laminin 5 is purified by standard chromatography techniques, including but not limited to affinity chromatography using laminin 5 specific antibodies or other laminin 5 binding molecules, ionic exchange, hydrophobic exchange, etc.

Transfection of expression vectors into the host cells can be accomplished via any technique known in the art, including but not limited to standard bacterial transformation, calcium phosphate co-precipitation, electroporation, or liposome mediated-, DEAE dextran mediated-, polycationic mediated-, or viral mediated transfection.

In a preferred embodiment, the cells are stably transfected. Any methods for stable transfection and selection of appropriate transfected cells are known in the art. In a most preferred embodiment, a CMV promoter driven expression vector is used in a human kidney embryonic 293 cell line.

Media from cells transfected with a single laminin chain are initially analyzed on Western blots using chain-specific anti-laminin-5 antibodies. The expression of single laminin chains following transfection is generally intracellular. Clones showing reactivity against individual transfected chain(s) are verified by any appropriate method, such as PCR, reverse transcription-PCR, or nucleic acid hybridization, to confirm incorporation of the transfected gene. Preferably, analysis of genomic DNA preparations from such clones is done by PCR using laminin chain-specific primer pairs. Media from transfected clones producing all three chains are further analyzed for heterotrimeric laminin 5 secretion and/or activity, by any appropriate method, including Western blot analysis and cell binding assays, such as a keratinocyte cell adhesion assay.

In another aspect, the present invention provides substantially purified r-laminin 5, comprising an α3 chain, a β3 chain, and a γ2 chain, and methods for producing substantially purified r-laminin 5. In one embodiment, the r-laminin 5 comprises a first chain comprising a polypeptide that is substantially similar to at least one of the sequences shown in SEQ ID NO:2, 4, 6, 8, 10, 12 or fragments thereof; a second chain comprising a polypeptide that is substantially similar to at least one of the sequences shown in SEQ ID NO:14, 16, 18, 20, 22, 24, or fragments thereof; and a third chain comprising a polypeptide that is substantially similar to at least one of the sequences shown in SEQ ID NO:26, 28, 30, 32, 34, 36, or fragments thereof, wherein the first, second, and third polypeptides are produced recombinantly, and wherein the first, second, and third chains assemble into a recombinant heterotrimeric laminin 5.

In another embodiment, the substantially purified r-laminin 5 comprises a first chain comprising a polypeptide that is at least about 70% identical to at least one of the sequences shown in SEQ ID NO:2, 4, 6, 8, 10, 12, or fragments thereof; a second chain comprising a polypeptide that is at least 70% identical to at least one of the sequences shown in SEQ ID NO:14, 16, 18, 20, 22, 24, or fragments thereof; and a third chain comprising a polypeptide that is at least 70% identical to at least one of the sequences shown in SEQ ID NO:26, 28, 30, 32, 34, 36, or fragments thereof, wherein the first, second, and third polypeptides assemble into a recombinant heterotrimeric laminin 5.

In a preferred embodiment, at least one of the first, second, or third chains of the substantially purified human r-laminin 5 is expressed as a fusion protein with an epitope tag.

Alternatively, the r-laminin 5 comprises a heterotrimeric polypeptide structure, wherein each individual chain comprises a general structure selected from the group consisting of: (1l) R1-R2-R3; (2) R1-R2-R3(e); (3) R3; (4) R3(e); (5) R1-R3; (6) R1-R3(e); (7) R2-R3; and (8) R2-R3(e)

wherein R1 is a amino terminal methionine; R2 is a signal sequence that is capable of directing secretion of the polypeptide, wherein the signal sequence may be the natural signal sequence for the particular laminin chain, that of another secreted protein, or an artificial sequence; R3 is a secreted α3, β3, or γ2 laminin chain; and R3(e) is a secreted laminin α3, β3, and γ2 chain that further comprises an epitope tag (such as those described above), which can be placed at any position within the laminin chain amino acid sequence.

In a preferred embodiment, purification of the r-laminin 5 is accomplished by passing media from the transfected cells through an affinity column. For example, antibodies or other binding molecules that bind to a peptide epitope expressed on at least one of the recombinant chains are attached to an affinity column, and bind r-laminin 5 that has been secreted into the media. The r-laminin 5 is removed from the column by passing excess peptide through the column. The eluted protein can subsequently be further purified, if desired.

Eluted fractions are analyzed by any appropriate method, including gel electrophoresis and Western blot analysis. In a further embodiment, the peptide epitope can be cleaved after purification. In other embodiments, two or three separate r-laminin chains are expressed as fusion proteins, each with a different epitope tag, permitting two or three rounds of purification and a doubly or triply purified r-laminin 5. The epitope tag can be engineered so as to be cleavable from the r-laminin 5 chain(s) after purification. Alternatively, no epitope tag is fused to any of the r-laminin 5 chains, and the r-laminin 5 is purified by standard techniques, including but not limited to affinity chromatography using laminin 5 specific antibodies or other laminin 5 binding molecules.

In another aspect, the present invention provides novel laminin β3 and γ2 chain nucleic acids and proteins, consisting of the nucleic acid sequences and proteins disclosed as SEQ ID NO:21–22, 23–24, 29–30, and 31–32.

The present invention further provides pharmaceutical compositions comprising r-laminin 5, as disclosed above, and a pharmaceutically acceptable carrier. According to this aspect of the invention, other agents can be included in the pharmaceutical compositions, depending on the condition being treated, including but not limited to any of the collagens, other laminin types, fibronectin, integrins, glycoproteins, proteoglycans, heparan and heparan sulfate proteoglycans, growth factors such as vascular endothelial growth factor (VEGF), platelet derived growth factor (PDGF), and keratinocyte growth factor (KGF); glycosaminoglycans, entactin, nidogen, and peptide fragments thereof.

Pharmaceutical preparations comprising r-laminin 5 can be prepared in any suitable form, and generally comprise the r-laminin 5 in combination with any of the well known pharmaceutically acceptable carriers. The carriers can be injectable carriers, topical carriers, transdermal carriers, and the like. The preparation may advantageously be in a form for topical administration, such as an ointment, gel, cream, spray, dispersion, suspension or paste. The preparations may further advantageously include preservatives, antibacterials, antifungals, antioxidants, osmotic agents, and similar materials in composition and quantity as is conventional. Suitable solutions for use in accordance with the invention are sterile, are not harmful for the proposed application, and may be subjected to conventional pharmaceutical operations such as sterilization and/or may contain conventional adjuvants, such as preservatives, stabilizers, wetting agents, emulsifiers, buffers etc. For assistance in formulating the compositions of the present invention, one may refer to Remington's Pharmaceutical Sciences, 15th Ed., Mack Publishing Co., Easton, Pa. (1975).

The dosage regimen for various treatments using the r-laminin 5 of the present invention is based on a variety of factors, including the type of injury or condition, the age, weight, sex, medical condition of the individual, the severity of the condition, and the route of administration. Thus, the dosage regimen may vary widely, but can be determined routinely by a physician using standard methods. Laminins are extremely potent molecules, and one or a few molecules per cell could produce an effect. Thus, effective doses in the pico-gram per milliliter range are possible if the delivery is optimized. Laminins are sometimes present in an insoluble form in the basement membrane and have the capability of polymerizing at concentrations ranging as low as about 50 µg/ml, depending on the laminin isoform and the conditions. Laminins can also polymerize into a gel at a concentration of 2–3 mg/ml. Dosage levels of the order of between 1 ng/ml and 10 mg/ml are thus useful for all methods disclosed herein, preferably between about 1 g/ml and about 3 mg/ml.

The treatment regime will also vary depending on the condition of the subject, based on a variety of factors, including the type of injury, the age, weight, sex, medical condition of the individual, the severity of the condition, and the route of administration. For example, r-laminin 5 can be used to coat a wound dressing, which is placed in contact with a patient's wound as frequently as the dressing needs to be changed, and for as long as the dressing is applied to the wound surface.

Similarly, the route of administration will vary depending on the condition of the subject, based on a variety of factors, including the type of injury, the age, weight, sex, medical condition of the individual, and the severity of the condition.

In further aspect, the present invention provides methods for using r-laminin 5, or the pharmaceutical compositions of the invention, to accelerate wound healing and tissue regeneration. In preferred embodiments, r-laminin 5 is used to accelerate the healing of skin in diabetic foot ulcers, venous ulcers, pressure sores, skin surgery, severe burns, and acute wounds, and enhanced performance of skin grafts (both autologous and artificial). In another aspect, the present invention provides kits for carrying out these methods, comprising an amount effective of laminin 5 or r-laminin 5 and instructions for using the laminin 5 to carry out the methods.

In one embodiment, r-laminin 5, or a pharmaceutical composition comprising r-laminin 5, is used to enhance wound healing by promoting the adhesion of transplanted cultured keratinocytes or other epithelial cells to an underlying substrate, such as a mammalian or human dermis. The substrate may comprise a wound surface, the basal surface of a confluent layer of cultured epithelial cells to be transplanted, or a substrate to be applied to the wound surface, such as a wound dressing, prior to placing the layer on a graft site. The r-laminin 5 may be supplied in a pharmaceutically acceptable carrier, preferably in amounts of between about 1 ng/ml and about 10 mg/ml.

The use of kalinin-containing (ie: laminin 5-containing) isolated cell matrices has previously been shown to enhance the adhesion of transplanted cultured keratinocytes to an underlying substrate (Burgeson et al., U.S. Pat. No. 5,770,562). This and other studies have thus demonstrated that laminin 5 stimulates epithelial cell attachment and spreading, and thus provides an appropriate surface facilitating the healing of skin and the use of skin grafts. (Quaranta and Hormia, U.S. Pat. No. 5,422,264; Jones, U.S. Pat. No. 5,541,106; Quaranta and Hormia, U.S. Pat. No. 5,658,789; Hormia et al., J. Invest. Dermatol. 1995 October 105(4):557–561; Takeda et al., J. Invest. Dermatol. 1999 July; 113(1):38–42; Goldfinger et Cell Sci. 1999; 112(Pt. 16):2615–2629).

Thus, the addition of r-laminin 5 to the appropriate injured tissue can promote cell growth, cell migration, and accelerate tissue regeneration. Accelerated healing has the added benefit of reducing inflammatory responses and scarring. This can be accomplished in some cases by simply coating the r-laminin 5 or the pharmaceutical compositions of the invention into a wound area (such as skin, periodontal epithelial cells), or in other cases, by providing a suitable substrate to which r-laminin 5 has been anchored, including but not limited to wound dressing and matrices, graft substrates, and dental abutments.

The incorporation of recombinant r-laminin 5 into wound repair dressings and matrices as well as tissue grafts will provide a natural ligand interactive surface to promote normal cell adherence, cell growth and tissue development. Many grafts are used to replace tissue that has an epithelial cell layer adherent to a basal lamina. When an inappropriate surface is provided to these cells following grafting, the graft is at risk for failure of restoration of the normal cell layer. The advantage of coating these grafts with r-laminin 5 is to create a surface that sufficiently recapitulates a normal basal lamina surface to promote cell re-population.

Skin grafts are used in cases were large surface areas of skin have been burned or injured. The application of r-laminin 5 and/or the pharmaceutical compositions of the invention will significantly promote the attachment and 'take' of skin grafts to the injured tissue, as well as promote normal skin healing processes while minimizing scar tissue formation.

Collagen-based matrices are also applied to serious skin injuries to promote the growth of the underlying dermis and improve the take of a skin graft. Coating the collagen matrices with r-laminin-5 will create a more natural ligand interactive surface to promote cell migration, cell proliferation and the regeneration of the dermis. An acceleration of the regeneration of the dermis, and take of the skin graft, will minimize scar tissue formation.

Purified laminin 5 has been demonstrated to support epithelial cell adhesion to the internal basal lamina of teeth (Mullen et al., J. Periodontal. Res. 1999 January 34(1): 16–24; Hormia et al., J. Dent. Res. 1998 July; 77(7): 1479–1485) and is believed to strengthen the anchorage of ameloblasts (ie: enamel-producing cells) to the enamel matrix. (Yoshiba et al., Cell Tissue Res. 1998 April; 292(1): 143–149). Thus, in another embodiment, the r-laminin 5 or the pharmaceutical compositions of the invention are used to stimulate epithelium cell adhesion to the internal basal lamina of teeth and of ameloblasts to the enamel matrix of teeth. Such treatments are useful for the treatment of periodontal diseases, including but not limited to oral ulcerations, gingivitis and periodontitis. For example, existing teeth may be coated with the r-laminin 5 or the pharmaceutical compositions of the present invention as a treatment for gum (junctional epithelium) diseases, including but not limited to gingivitis and periodontitis, which promote the detachment of the gum from the tooth. These disease conditions allow the accumulation of food and other foreign matter in the space between the gum and the tooth, resulting in infection. The r-laminin 5 will promote reattachment of the gum to the tooth, thus preventing entry of foreign matter and subsequent infection.

For use in treating gingivitis and other periodontal diseases and disorders, the pharmaceutical compositions of the present invention may be in the form of toothcreams, toothpastes, liquid dentifrices, tooth-powders chewing-gum, tablets and the like. The pharmaceutical compositions of the invention can also contain flavoring, coloring agents, sweeteners, preservatives, surface active agents, and the like.

Purified laminin-5 has been shown to promote the in vitro expansion of epithelial cells (Gonzales et al., Mol. Biol. Cell. 1999 February; 10(2):259–270; Baker et al., Exp. Cell Res. Nov. 1, 1996; 228(2)262–270), pancreatic beta islet cells (Todorov et al., Transplant. Proc. 1998 March; 30(2): 455; Quaranta and Jones, U.S. Pat. No. 5,510,263; Halberstadt et al, U.S. Pat. No. 5,681,587; Halberstadt et al., U.S. Pat. No. 5,672,361), and T cells (Vivinus-Nebot et al., J. Cell Biol. Feb. 8, 1999; 144(3):563–574), by providing an efficient adhesion substrate for primary cell cultures. Thus, in another aspect of the present invention, r-laminin 5 is used to enhance the adhesion of cells for proliferation, differentiation, or maintenance of cells including, but not limited to pancreatic beta islet cells, epithelial cells, or T cells, by contacting the cells with an amount effective of r-laminin 5 to provide an efficient adhesion substrate for attachment and subsequent proliferation, differentiation, or maintenance of the cells. The r-laminin 5 can be provided in the cell culture medium, as a cell culture medium supplement, or may be coated on the surface of a cell growth substrate. In each case, r-laminin 5 is preferably used at a concentration of between about 1 ng/ml and about 10 mg/ml. The cells can optionally be contacted with other compounds that promote cell adhesion, proliferation, differentiation, and/or maintenance, including but not limited to any of the collagens, other laminin types, fibronectin, integrins, glycoproteins, proteoglycans, heparan sulfate proteoglycan, glycosaminoglycans, entactin, nidogen, and peptide fragments thereof.

The cells may be primary cells or cell lines. The methods of this aspect of the invention can be used in vivo, ex vivo, or in vitro.

In a preferred embodiment, r-laminin 5 is used to coat the surface of a substrate to promote cell adhesion to the substrate, and to stimulate cell proliferation, differentiation, and/or maintenance. The substrate used herein may be any desired substrate. For laboratory use, the substrate may be as simple as glass or plastic. For use in vivo, the substrate may be any biologically compatible material capable of supporting cell growth. Suitable substrate materials include shaped articles made of or coated with such materials as collagen, regenerated collagen, polyglycolic acid, polygalactose, polylactic acid or derivatives thereof; biocompatible metals such as titanium and stainless steel; ceramic materials including prosthetic material such as hydroxylapatite; synthetic polymers including polyesters and nylons; polystyrene; polyacrylates; polytetrafluoroethylene, and virtually any other material to which biological molecules can readily adhere. The determination of the ability of a particular material to support adhesion of r-laminin 5 of the invention requires only routine experimentation by the skilled artisan.

In a further aspect, the present invention provides a method of treating Type I diabetes in a patient in need thereof comprising contacting pancreatic beta islet cells with an amount effective of r-laminin 5 to provide an efficient adhesion substrate for the cells, leading to increased proliferation of insulin-producing pancreatic beta islet cells, and administering the cells to a patient in need thereof.

Nearly two million Americans are afflicted with Type I (insulin-dependent) diabetes, in which the pancreas has lost its ability to secrete insulin due to an autoimmune disorder in which the insulin-secreting beta cells, found within the islet cells of the pancreas, are destroyed. Although insulin injections can compensate for beta cell destruction, blood sugar levels can still fluctuate dramatically. The impaired ability to take up glucose from the blood results in side reactions in which toxic products accumulate, leading to complications including blindness, kidney disease, nerve damage, and, ultimately, coma and death. (U.S. Pat. No. 5,672,361)

The pancreatic beta islet cells to be grown are plated on or applied to the matrix-coated substrate using standard tissue culture techniques, followed by expansion in standard cell growth medium (as disclosed in U.S. Pat. No. 5,672, 361) in the presence of r-laminin 5. Any medium capable of supporting the enhanced growth of adult islet cells on the matrix-coated substrate is within the scope of the invention, as discussed above.

Fetal pancreatic islet cells may be grown in vitro in the presence of r-laminin 5 for transplantation into diabetic patients. Growth of fetal pancreatic islet cells in the presence of r-laminin 5 increases the yield of islet cells for transplantation and thus solves the need to produce larger amounts of these cells. In addition, it is contemplated that the inclusion of other growth factors in the adult islet cell culture medium will further increase the yield of islet cells.

Laminins, or cell extracts containing laminins have been shown to regulate angiogenesis in a biphasic manner. (See, for example, Nicosia et al., Dev. Biol. 164:197–206 (1994); Bonfil et al., Int. J. Cancer 58:233–239 (1994)). At lower concentrations (30–300 $\mu$g/ml), a laminin-entactin complex stimulated angiogenesis in a three-dimensional culture, while at 3000 $\mu$g/ml the same complex was inhibitory to angiogenesis. Thus, in another aspect, the present invention provides methods for regulating angiogenesis, comprising contacting a tissue or culture substrate with an amount effective of laminin 5 or pharmaceutical compositions thereof to regulate angiogenesis. In one embodiments, the laminin 5 is used to promote angiogenesis by contacting a tissue or culture substrate with an amount effective of laminin 5 to promote angiogenesis. In another embodiment, the laminin 5 is used to inhibit angiogenesis, by contacting the tissue or culture substrate with an amount effective of laminin 5 to inhibit angiogenesis. An example of culture substrates to be contacted with laminin 5 to regulate angiogenesis are those used for tissue engineering purposes.

As used herein, the term "angiogenesis" refers to the formation of blood vessels. Specifically, angiogenesis is a multistep process in which endothelial cells focally degrade and invade through their own basement membrane, migrate through interstitial stroma toward an angiogenic stimulus, proliferate proximal to the migrating tip, organize into blood vessels, and reattach to newly synthesized basement membrane (see Folkman et al., Adv. Cancer Res., Vol. 43, pp. 175–203 (1985)). Compounds that promote angiogenesis can be used to promote wound healing and skin grafting, organ transplantation (including artificial organs), acceleration of endothelial cell coverage of vascular grafts to prevent graft failure due to re-occlusion, to treat ischemic conditions, and to treat inflammatory diseases.

In a further aspect, the present invention provides cell substrates comprising an amount effective of r-laminin 5 for the adhesion, growth, or maintenance of cells in culture. The substrates may comprise any of the substrates discussed above. Preferably, the r-laminin 5 is coated on the surface of the substrate using solution at a concentration of between about 1 ng/ml and about 10 mg/ml.

In another aspect of the present invention, an improved cell culture medium is provided, wherein the improvement comprises addition to the cell culture medium of an effective amount of r-laminin 5 to the cell culture medium to promote the adherence, proliferation, and/or maintenance of cells. Any cell culture media that can support the growth of cells can be used with the present invention. Such cell culture media include, but are not limited to Basal Media Eagle, Dulbecco's Modified Eagle Medium, Iscove's Modified Dulbecco's Medium, McCoy's Medium, Minimum Essential Medium, F-10 Nutrient Mixtures, Opti-MEM® Reduced-Serum Medium, RPMI Medium, and Macrophage-SFM Medium or combinations thereof.

The improved cell culture medium can be supplied in either a concentrated (ie: 10×) or non-concentrated form, and may be supplied as either a liquid, a powder, or a lyophilizate. The cell culture may be either chemically defined, or may contain a serum supplement. Culture media is commercially available from many sources, such as GIBCO BRL (Gaithersburg, Md.) and Sigma (St. Louis, Mo.). Alternatively, the r-laminin 5 is used as a cell culture supplement, and can be separately added to the cell culture medium.

Purified laminin-5 has also been shown to promote epithelial cell attachment to a wide variety of biomaterials, including polymers, hydroxyapatite, and metals, thus improving the biocompatibility of the biomaterials. (Jones et al., U.S. Pat. No. 5,585,267; El Ghannam et al., J. Biomed. Mater. Res. 1998 July; 41(1):30–40).

Thus, in a further aspect, the present invention comprises medical devices with improved biocompatibility, wherein the devices are coated with the r-laminin 5 of the invention, alone or in combination with other proteins or agents that serve to increase the biocompatibility of the device surface. The coated device stimulates cell attachment and provides for diminished inflammation and/or infection at the site of entry of the appliance. The device may also be used to stimulate gum junctional epithelium adhesion in the treatment of gingivitis and periodontitis.

Preferably, the device is a shaped article that is either an indwelling or transcutaneous catheter, polytetrafluoroethylene (PTFE), expanded PTFE (EPTFE), needle, metal pin, metal rod, colostomy tube, transcutaneous catheter, dental abutment piece or surgical mesh. In another aspect of this preferred embodiment, the device is used in vivo. Preferably, the appliance is made of or coated with a biocompatible metal that may be either stainless steel or titanium. Alternatively, the device is made of or coated with a ceramic material, or a polymer including but not limited to polyester, polyglycolic acid or a polygalactose-polyglycolic acid copolymer.

One particular use of the present invention is to increase epithelial cell adhesion to target surfaces. For example, prostheses for dental implantation may be coated with the r-laminin 5 of the invention to stimulate periodontal cell attachment. These prostheses typically comprise two separate pieces, an implant which is inserted into the bone and an abutment piece which actually contacts the junctional epithelium. Alternatively, the implant and abutment piece may be obtained as a single unit.

If the device is made of a natural or synthetic biodegradable material in the form of a mesh, sheet or fabric, the r-laminin 5 may be applied directly to the surface thereof. Epithelial cells may then be cultured on the matrix to form transplantable or implantable devices, including dental abutment pieces, needles, metal pins or rods, indwelling catheters, colostomy tubes, surgical meshes and any other appliance for which coating with the r-laminin is desirable. Alternatively, the devices may be implanted and cells may be permitted to attach in vivo. The epithelial cell-coated surgical meshes will be useful for skin allografts necessitated by compromised skin integrity.

Coupling of the r-laminin 5 may be non-covalent (such as by adsorption), or by covalent means. The device may be immersed in, incubated in, or sprayed with the r-laminin 5 of the invention. In a preferred embodiment, the concentration of r-laminin 5 for coating the device is between about 1 ng/ml and about 10 mg/ml.

The present invention also provides a method for inducing epithelial cell attachment to the device (as disclosed above), comprising coating the appliance with r-laminin 5 prior to incubation with epithelial cells.

The therapeutic application of r-laminin 5 produced in accordance with the present invention can be used for the treatment of a variety of conditions and diseases, including but not limited to Type I diabetes; skin conditions including but not limited to diabetic foot ulcers, venous ulcers, pressure sores, skin surgery, burns, acute wounds, and skin grafts; corneal ulcerations; gastro-intestinal ulcers; periodontitis; and gingivitis. The therapeutically effective amount of r-laminin 5 for use in these conditions and diseases can be readily ascertained by one of ordinary skill in the art.

The present invention may be better understood with reference to the accompanying examples that are intended for purposes of illustration only and should not be construed to limit the scope of the invention, as defined by the claims appended hereto.

EXAMPLES

Production of r-laminin-5 involved sequential transfections of a mammalian cell line with vectors containing cDNAs that encode for the chains of the laminin-5 molecule, namely α3, β3 and γ2. An additional polynucleotide sequence that encodes the 'flag' peptide (DYKDDDDK), was added to the amino terminus end of the β3 gene to facilitate affinity purification of the expressed heterotrimeric recombinant laminin-5 molecule.

IV. Materials and Methods

Expression Vector Constructs for α3

The entire coding sequence of the α3 cDNA [SEQ ID NO:1] was cloned via standard techniques into the expression vector pcDNA3.1/Zeo (Invitrogen), which contains the Zeocin resistant gene for selection. The expression vectors were used to produce stable cell lines according to the manufacturer's instructions.

In order to produce a second α3 expression vector, the full-length α3 cDNA was excised from the pZeoα3 expression construct by digestion with KpnI-NotI restriction enzymes. The double digested α3 fragment was inserted in the expression vector pTargeT (Promega; Madison, Wis.), generating pTgTα3. This expression construct carries the G418 resistant gene for selection of resistant clones. Both expression constructs have been analyzed by restriction enzyme mapping and DNA sequencing.

Construction of Full-length β3 Chain

Two cDNA fragments, Kal5-5c and Kal92-1, each cloned into separate pCR II vectors (Invitrogen), which together encode the entire β3 chain of laminin-5 [SEQ ID NO:19], were received from Dr. Burgeson's laboratory (4). The two fragments were cloned into a single vector to obtain the full-length β3 chain, plasmid PCRIIβ3.

Expression Vector Constructs for β3

The laminin β3 expression vector, pRCX3β3$_F$, was constructed containing the full-length β3 chain obtained for pCRIIβ3 and the FLAG epitope added to the amino terminus [SEQ ID NO:17–18]. pRCX3 is a vector derived from pRC/CMV (Invitrogen) and it contains a Geneticin resistant gene for selection with G418 sulfate, a BM 40 (SPARC) signal peptide sequence and the Flag peptide sequence in frame with convenient cloning sites.

A second β3 expression vector was constructed by excising the complete laminin β3-flag peptide coding region from pRCX3β3$_F$ plasmid and introducing it into pcDNA3.1/Zeo. This expression constructs carries the Zeocin resistant gene for selection.

Both β3-expression constructs have been analyzed by restriction enzyme mapping and DNA sequencing.

Expression Vector Constructs for γ2

The full-length γ2 cDNA [SEQ ID NO:29] was excised from pVL1393γ2 (received from Dr. Karl Tryggvason, Karolinska Institute, Sweden) by digestion with BamH I-Xba I restriction enzymes. The double digested γ2 fragment was inserted in the corresponding sites of the expression vector pcDNA3.1/Zeo (Invitrogen), generating the pZeoγ2 expression construct. This expression constructs carries the Zeocin resistant gene for selection.

Similarly, a BamH I-Not I full-length γ2 cDNA fragment was cloned into the expression vector pTargeT (Promega), generating pTgTγ2. This expression construct carries the G418 resistant gene for selection of resistant clones.

Both expression constructs have been analyzed by restriction enzyme mapping and DNA sequencing.

Sequence Analysis of Expression Constructs

The expression vector constructs have been sequenced and the reported gene sequences compared to the published sequences. Table 2 shows a summary of the amino acid mismatches for the different laminin chains.

α3 chain: the reported sequence matched the published sequence.

β3 chain: several discrepancies with the published sequence were found. Single and multiple base deletions and insertions are present along the sequence. These base changes generated some silent mutations, amino acid substitutions and insertion of amino acids. These changes do not cause early termination codons. Therefore, the β3 chain seems to be of "full-length" and the protein is being produced.

γ2 chain: This chain was reported to have 3 base changes creating 3 amino acid substitutions.

TABLE 2

Summary of amino acid differences from those reported in the literature

| Laminin chain | Amino acid change |
|---|---|
| α3 | None |
| β3 | P, insertion at position 251-2 |
|  | $A_{372}$–$P_{372}$ |
|  | $R_{408}R_{409}$–$Q_{408}G_{409}$ |

TABLE 2-continued

Summary of amino acid differences from those reported in the literature

| Laminin chain | Amino acid change |
|---|---|
|  | R, insertion at position 421 |
|  | $P_{584}$–$R_{584}$ |
|  | $A_{796}$–$G_{796}$ |
|  | $R_{894}S_{895}E_{896}$–$S_{894}E_{895}A_{896}$ |
| γ2 | $R_{168}$–$G_{168}$ |
|  | $I_{473}$–$M_{473}$ |
|  | $S_{521}$–$N_{521}$ |

Transfection of Human Kidney 293 Cells

Wild type human kidney 293 cells were transfected with the different expression constructs utilizing standard techniques. Two transfection reagents were used, LIPOFECTAMINE™ from GIBCO (Rockville, Md.) and SUPERFECT™ from Qiagen (Valencia, Calif.). Experiments (see below) suggested that the 293 cells do not express detectable endogenous laminin α3, β3, or γ2 chains.

Briefly, both methods required mixing the transfection reagent with the DNA of interest, incubating for a brief period at room temperature, and adding the mixture to the cells. The cells were split the previous day so they were at 50–80% confluency the day of the transfection. The incubation with the DNA-reagent complexes was conducted for 2–3 hours in serum free media for LIPOFECTAMINE™ transfection or complete media for SUPERFECT™ transfection. After this incubation period the media was replaced with fresh growth media and the incubation was continued until the selection process begins.

The selection process was carried out in DMEM F12/10% FBS containing either Geneticin (G418 sulfate) at 400 μg/ml for selection of G418 resistants, or Zeocin at 50 μg/ml for selection of Zeocin resistants. After splitting to selective media, the cells were fed every two days with fresh selective media, until cell foci were identified. Clones transfected with the three laminin chains and secreting r-laminin 5 into the medium were selected with media containing both antibiotics.

Results

Media from human kidney 293 cells transfected with a single laminin chain were initially analyzed on Western blots using chain-specific anti-laminin-5 antibodies. Cell fractions, as well as "whole" fractions containing cells plus any deposited "matrix-like" material obtained by scraping the cells into loading buffer, were also analyzed. Western blot analysis of wild type 293 cell cultures showed no detectable laminin α3, β3, or γ2 chain proteins.

The expression of single laminin chains following transfection is generally intracellular, except for a few β3 clones that appear to show β3 chain reactivity in the media in Western blot analyses using the anti-FLAG antibody.

All clones showing FLAG antibody reactivity were verified by PCR to confirrn the corporation of the transfected gene. Analysis of genomic DNA preparations from such clones by PCR was done using laminin chain-specific primer pairs. The amplified products were compared to positive controls where the original expression constructs were used as templates. Results are shown in Table 3. A few selected clones were analyzed by RT-PCR using the same laminin chain-specific primers and total RNA and/or mRNA preparations as templates. These results are also shown in Table 2.

Other data (not shown) demonstrated that the molecular sizes of some of the components of r-laminin 5 were different from those in purified laminin 5. Particularly, the major component of the α3 chain in purified laminin 5 was 165 kD, while the α3 band in r-laminin 5 migrated as two chains of 150 kD and 95 kD.

Identified co-transfected clones producing all three chains (as assessed by both genomic PCR and RT-PCR analysis), were further analyzed in a keratinocyte cell adhesion binding assay.

that the r-laminin 5 is binding to the cells via the α3β1 integrin.

To assist in the purification of the heterotrimer r-laminin-5 molecule, the laminin β3 chain was labeled with a 'flag' sequence at the amino terminus end. Media from clones transfected with all three chains, and shown to express all three chains, were passed through an anti-flag column and eluted with excess flag peptide. The eluted fractions were analyzed by gel electrophoresis. The data demonstrate that r-laminin 5 was produced and isolated.

TABLE 3

Summary analysis of selected r-L5 clones

| Clone | Western Blot | | | | PCR[1] | | | RT-PCR[2] | | | Adhesion Assay |
|---|---|---|---|---|---|---|---|---|---|---|---|
| | α3 | β3 | γ2 | Flag | α3 | β3 | γ2 | α3 | β3 | γ2 | |
| A2-3 | − | nd | nd | + | − | + | + | − | + | + | − |
| A4-3 | + | + | + | + | + | + | + | + | + | + | + |
| A10-3 | − | nd | + | + | − | + | − | − | + | + | − |
| B1-6 | nd | nd | nd | + | + | + | + | + | + | + | + |
| C2-3 | − | nd | + | + | − | + | + | + | + | + | − |
| C5-7 | nd | nd | nd | + | + | + | + | nd | + | + | − |
| C6-3 | + | + | + | + | + | + | + | + | + | + | + |
| C10-3 | − | nd | nd | + | − | + | + | + | + | + | − |
| E1-3 | − | nd | nd | − | − | + | − | − | + | + | − |
| E2-3 | − | nd | + | + | − | + | − | + | + | + | − |
| E7-3 | − | nd | − | + | − | + | − | − | + | + | − |
| F10-5 | nd | nd | nd | + | + | + | + | + | + | + | + | nd = Not determined
[1]PCR analysis of genomic DNA preparations were performed using laminin chain-specific primer pairs. The amplified products were compared to positive controls where the original expression constructs were used as templates.
[2]RT-PCR analyses were done similarly using total RNA and/or mRNA as templates and primers as above.

HFK cell adhesion assay for laminin-5. The method used measures laminin-5 activity present in conditioned media from various clones. Any laminin-5 present in the test media was trapped to a 96 well via an anti-laminin α3 antibody (C 25). Human foreskin keratinocytes (HFK) were labeled fluorescently, added to the treated wells, and allowed to adhere for 30 minutes. Fluorescence was measured before and after washing with PBS. The % cell adhesion is equal to fraction of fluorescence retained in the well. As controls, cells were pre-incubated with an anti-integrin α3β1 inhibitory antibody (P1B5)(α3β1 is the cell receptor for laminin 5), or non-specific control antibody (SP2) before being added to the wells. Media controls (Keratinocyte growth media ("KGM"); or DMEM F12 culture media ("medium")) were also used. The "a2$_F$" notation denotes culture medium from 293 cells transfected to express an unrelated FLAG-containing protein.

Figure 2:
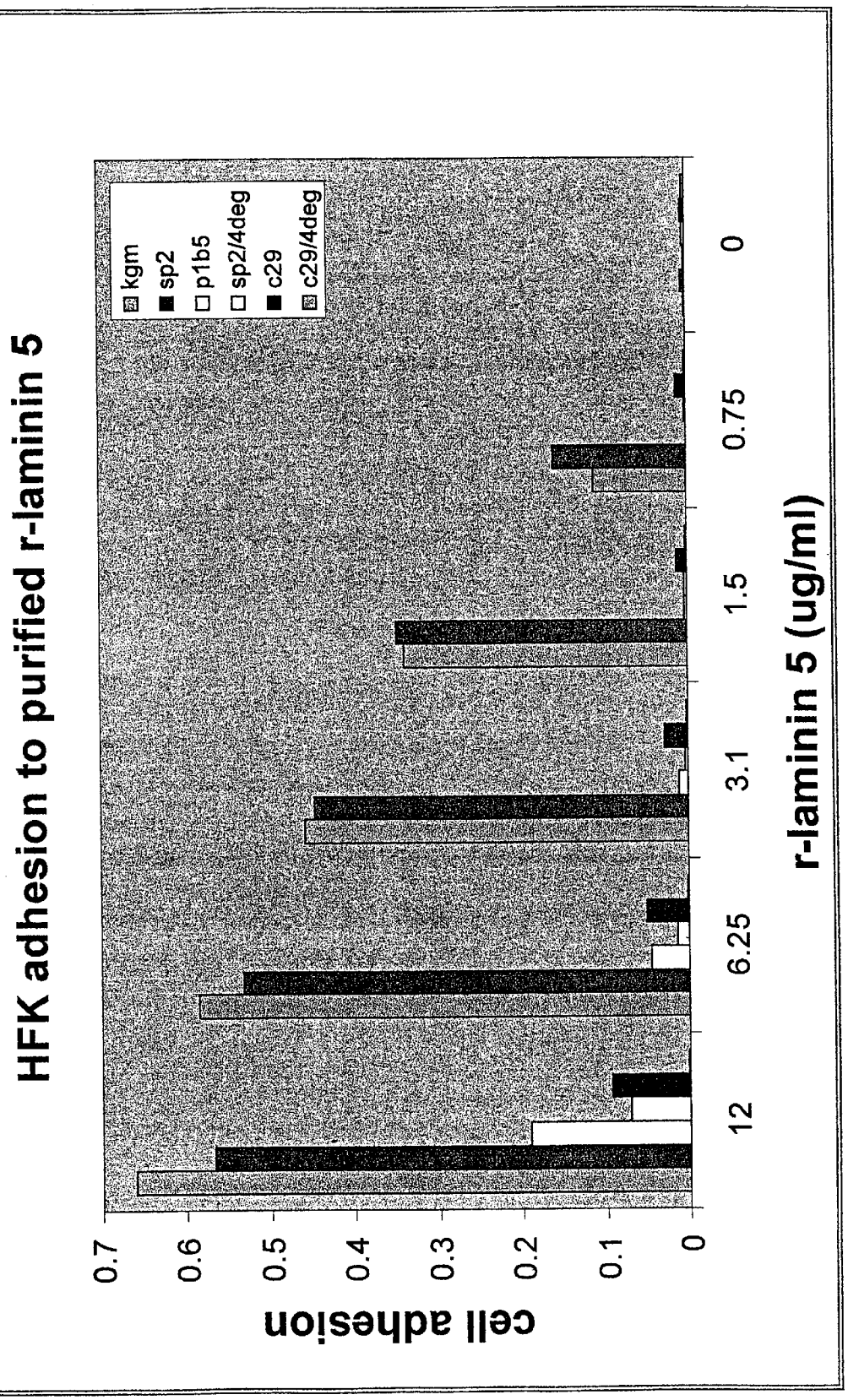
FIG. 2 is a bar graph showing a cell adhesion assay in which r-laminin 5 was coated directly onto the plate. p1b5= anti-integrin α3β1 antibody; sp2=control IgG, non-specific; C29: anti-laminin 5 antibody

The results, shown in Table 2 (last column) and in FIG. 1. The figure is labeled as follows: C5 and F10: conditioned culture media from r-laminin-5 producing clones C5 and F10; *C6 and *F10: conditioned culture media collected earlier and kept refrigerated. These data demonstrated that media from several clones produced positive results in the cell adhesion assay, indicating the r-laminin-5 produced by these clones is biologically active. The activity was inhibited in the presence of an integrin α3β1 antibody, demonstrating Several of the above clones were selected for further analysis. A 1 liter culture from clone F10-5 was prepared, and r-laminin 5 was purified using the methods described above. The r-laminin 5 was used in an HFK cell adhesion assay exactly as described above, except that r-laminin 5 was coated directly onto the plate. The results are presented in FIG. 2 and demonstrate that r-laminin 5 markedly increases adhesion of HFK cells at all concentrations tested.

Electron Micrograph Analysis

Purified r-laminin 5 protein was diluted to 50 μg/ml and adjusted to 70% glycerol/30% 0.15M ammonium bicarbonate and rotary shadowed using standard techniques. FIG. 3 shows an 80,000×magnification field of (A) r-laminin 5; and (B) "native" laminin 5 (purified by BM165 monoclonal antibody affinity chromatography from SCC-25 (squamous cell carcinoma cell line) conditioned medium). The bar represents 50 nm. These results demonstrated that both the r-laminin 5 and the "native" purified laminin 5 formed similar cross-shaped structures typical of laminins.

The present invention is not limited by the aforementioned particular preferred embodiments. It will occur to those ordinarily skilled in the art that various modifications may be made to the disclosed preferred embodiments without diverting from the concept of the invention. All such modifications are intended to be within the scope of the present invention.

I claim:

1. Recombinant laminin 5-expressing host cells, wherein the host cells have been transfected with nucleic acid sequences encoding first, second and third polypeptide chains, wherein the first, second and third polypeptide chains each comprise a polypeptide chain selected from the group consisting of: (1) R1-R2-R3; (2) R1-R2-R3(e); (3)R3; (4)R3(e); (5)R1-R3; (6)R1-R3(e); (7) R2-R3; and (8) R2–E3(e)

wherein R1 is an amino terminal methionine, R2 is a signal sequence; R3 is a secreted α3 laminin chain for the first polypeptide chain, a secreted β3 laminin chain for the second polypeptide chain, and a secreted γ2 laminin chain for the third polypeptide chain, and R3(e) is identical to R3; but further comprises an epitope tag, wherein said host cells do not express endogenous laminin-5.

2. The recombinant laminin 5-expressing host cells of claim 1, wherein the host cells do not express detectable levels of endogenous laminin α3, β3, or γ2 chains prior to transfection with the one or more recombinant expression vectors.

3. The recombinant laminin 5-expressing host cells of claim 1, wherein at least one of the first, second and third polypeptide chains comprise a polypeptide chain selected from the group consisting of: (1) R1-R2-R3(e); (2) R3(e); (3) R1-R3(e); and (4) R2-E3(e).

4. The recombinant laminin 5-expressing host cells of claim 1, wherein at least two of the first, second and third polypeptide chains comprise a polypeptide chain selected from the group consisting of: (1) R1-R2-R3(e); (2) R3(e); (3) R1-R3(e); and (4) R2–E3(e).

5. The recombinant laminin 5-expressing host cells of claim 3 or 4, wherein the host cells do not express detectable levels of endogenous laminin α3, β3, or γ2 chains prior to transfection with the one or more recombinant expression vectors.

6. A method of purifying recombinant laminin 5, comprising:
   a. providing the recombinant laminin 5-expressing host cells of any one of claim 3–5;
   b. growing the cells in cell culture medium under conditions to stimulate expression of the first, second and third polypeptide chains;
   c. passing the cell culture medium through an affinity chromatography column, wherein the column contains a compound that specifically binds to the epitope tag;
   d. washing the affinity column to remove unbound materials; and
   e. eluting the bound recombinant laminin 5 from the column.

7. A pharmaceutical composition comprising:
   a. the purified recombinant laminin 5 purified according to the method of claim 6; and
   b. a pharmaceutically acceptable carrier.

8. An isolated polynucleotide set forth in SEQ ID NO:21.

* * * * *

SEQUENCE LISTING

<160> NUMBER OF SEQ ID NOS: 36

<210> SEQ ID NO 1
<211> LENGTH: 5280
<212> TYPE: DNA
<213> ORGANISM: Homo sapiens
<220> FEATURE:
<221> NAME/KEY: CDS
<222> LOCATION: (18)..(5189)
<221> NAME/KEY: sig_peptide
<222> LOCATION: (18)..(110)

<400> SEQUENCE: 1

```
taattaactg gttccgg atg cct cca gca gtg agg cgg tca gcc tgc agc         50
                   Met Pro Pro Ala Val Arg Arg Ser Ala Cys Ser
                    1               5                  10 atg gga tgg ctg tgg atc ttt ggg gca gcc ctg ggg cag tgt ctg ggc        98
Met Gly Trp Leu Trp Ile Phe Gly Ala Ala Leu Gly Gln Cys Leu Gly
            15                  20                  25 tac agt tca cag cag caa agg gtg cca ttt ctt cag cct ccc ggt caa       146
Tyr Ser Ser Gln Gln Gln Arg Val Pro Phe Leu Gln Pro Pro Gly Gln
    30                  35                  40 agt caa ctg caa gcg agt tat gtg gag ttt aga ccc agc cag ggt tgt       194
Ser Gln Leu Gln Ala Ser Tyr Val Glu Phe Arg Pro Ser Gln Gly Cys
45                  50                  55 agc cct gga tac tat cgg gat cat aaa ggc ttg tat acc gga cgg tgt       242
Ser Pro Gly Tyr Tyr Arg Asp His Lys Gly Leu Tyr Thr Gly Arg Cys
 60                  65                  70                  75 gtt ccc tgc aat tgc aac gga cat tca aat caa tgc cag gat ggc tca       290
Val Pro Cys Asn Cys Asn Gly His Ser Asn Gln Cys Gln Asp Gly Ser
                80                  85                  90 ggc ata tgt gtt aac tgt cag cac aac acc gcg gga gag cac tgt gaa       338
Gly Ile Cys Val Asn Cys Gln His Asn Thr Ala Gly Glu His Cys Glu
            95                  100                 105 cgc tgc cag gag ggc tac tat ggc aac gcc gtc cac gga tcc tgc agg       386
Arg Cys Gln Glu Gly Tyr Tyr Gly Asn Ala Val His Gly Ser Cys Arg
        110                 115                 120 gcc tgc cca tgt cct cac act aac agc ttt gcc act ggc tgt gtg gtg       434
Ala Cys Pro Cys Pro His Thr Asn Ser Phe Ala Thr Gly Cys Val Val
    125                 130                 135 aat ggg gga gac gtg cgg tgc tcc tgc aaa gct ggg tac aca gga aca       482
Asn Gly Gly Asp Val Arg Cys Ser Cys Lys Ala Gly Tyr Thr Gly Thr
140                 145                 150                 155 cag tgt gaa agg tgt gca ccg gga tat ttc ggg aat ccc cag aaa ttc       530
Gln Cys Glu Arg Cys Ala Pro Gly Tyr Phe Gly Asn Pro Gln Lys Phe
                160                 165                 170 gga ggt agc tgc caa cca tgc agt tgt aac agc aat ggc cag ctg ggc       578
Gly Gly Ser Cys Gln Pro Cys Ser Cys Asn Ser Asn Gly Gln Leu Gly
            175                 180                 185 agc tgt cat ccc ctg act gga gac tgc ata aac caa gaa ccc aaa gat       626
Ser Cys His Pro Leu Thr Gly Asp Cys Ile Asn Gln Glu Pro Lys Asp
        190                 195                 200 agc agc cct gca gaa gaa tgt gat gat tgc gac agc tgt gtg atg acc       674
Ser Ser Pro Ala Glu Glu Cys Asp Asp Cys Asp Ser Cys Val Met Thr
    205                 210                 215 ctc ctg aac gac ctg gcc acc atg ggc gag cag ctc cgc ctg gtc aag       722
Leu Leu Asn Asp Leu Ala Thr Met Gly Glu Gln Leu Arg Leu Val Lys
220                 225                 230                 235 tct cag ctg cag ggc ctg agt gcc agc gca ggg ctt ctg gag cag atg       770
Ser Gln Leu Gln Gly Leu Ser Ala Ser Ala Gly Leu Leu Glu Gln Met
```

-continued

```
                    240                 245                 250
agg cac atg gag acc cag gcc aag gac ctg agg aat cag ttg ctc aac       818
Arg His Met Glu Thr Gln Ala Lys Asp Leu Arg Asn Gln Leu Leu Asn
                    255                 260                 265 tac cgt tct gcc att tca aat cat gga tca aaa ata gaa ggc ctg gaa       866
Tyr Arg Ser Ala Ile Ser Asn His Gly Ser Lys Ile Glu Gly Leu Glu
            270                 275                 280 aga gaa ctg act gat ttg aat caa gaa ttt gag act tta caa gaa aag       914
Arg Glu Leu Thr Asp Leu Asn Gln Glu Phe Glu Thr Leu Gln Glu Lys
        285                 290                 295 gct caa gta aat tcc aga aaa gca caa aca tta aac aac aat gtt aat       962
Ala Gln Val Asn Ser Arg Lys Ala Gln Thr Leu Asn Asn Asn Val Asn
300                 305                 310                 315 cgg gca aca caa agc gca aaa gaa cta gat gtg aag att aaa aat gtc      1010
Arg Ala Thr Gln Ser Ala Lys Glu Leu Asp Val Lys Ile Lys Asn Val
                320                 325                 330 atc cgg aat gtg cac att ctt tta aag cag atc tct ggg aca gat gga      1058
Ile Arg Asn Val His Ile Leu Leu Lys Gln Ile Ser Gly Thr Asp Gly
            335                 340                 345 gag gga aac aac gtg cct tca ggt gac ttt tcc aga gag tgg gct gaa      1106
Glu Gly Asn Asn Val Pro Ser Gly Asp Phe Ser Arg Glu Trp Ala Glu
        350                 355                 360 gcc cag cgc atg atg agg gaa ctg cgg aac agg aac ttt gga aag cac      1154
Ala Gln Arg Met Met Arg Glu Leu Arg Asn Arg Asn Phe Gly Lys His
365                 370                 375 ctc aga gaa gca gaa gct gat aaa agg gag tcg cag ctc ttg ctg aac      1202
Leu Arg Glu Ala Glu Ala Asp Lys Arg Glu Ser Gln Leu Leu Leu Asn
380                 385                 390                 395 cgg ata agg acc tgg cag aaa acc cac cag ggg gag aac aat ggg ctt      1250
Arg Ile Arg Thr Trp Gln Lys Thr His Gln Gly Glu Asn Asn Gly Leu
                400                 405                 410 gct aac agt atc cgg gat tct tta aat gaa tac gaa gcc aaa ctc agt      1298
Ala Asn Ser Ile Arg Asp Ser Leu Asn Glu Tyr Glu Ala Lys Leu Ser
            415                 420                 425 gac ctt cgt gct cgg ctg cag gag gca gct gcc caa gcc aag cag gca      1346
Asp Leu Arg Ala Arg Leu Gln Glu Ala Ala Ala Gln Ala Lys Gln Ala
        430                 435                 440 aat ggc ttg aac caa gaa aac gag aga gct ttg gga gcc att cag aga      1394
Asn Gly Leu Asn Gln Glu Asn Glu Arg Ala Leu Gly Ala Ile Gln Arg
445                 450                 455 caa gtg aaa gaa ata aat tcc ctg cag agt gat ttc acc aag tat cta      1442
Gln Val Lys Glu Ile Asn Ser Leu Gln Ser Asp Phe Thr Lys Tyr Leu
460                 465                 470                 475 acc act gca gac tca tct ttg ttg caa acc aac att gcg ctg cag ctg      1490
Thr Thr Ala Asp Ser Ser Leu Leu Gln Thr Asn Ile Ala Leu Gln Leu
                480                 485                 490 atg gag aaa agc cag aag gaa tat gaa aaa tta gcc gcc agt tta aat      1538
Met Glu Lys Ser Gln Lys Glu Tyr Glu Lys Leu Ala Ala Ser Leu Asn
            495                 500                 505 gaa gca aga caa gaa cta agt gac aaa gta aga gaa ctt tcc aga tct      1586
Glu Ala Arg Gln Glu Leu Ser Asp Lys Val Arg Glu Leu Ser Arg Ser
        510                 515                 520 gct ggc aaa aca tcc ctt gtg gag gag gca gaa aag cac gcg cgg tcc      1634
Ala Gly Lys Thr Ser Leu Val Glu Glu Ala Glu Lys His Ala Arg Ser
525                 530                 535 tta caa gag ctg gca aag cag ctg gaa gag atc aag aga aac gcc agc      1682
Leu Gln Glu Leu Ala Lys Gln Leu Glu Glu Ile Lys Arg Asn Ala Ser
540                 545                 550                 555 ggg gat gag ctg gtg cgc tgt gct gtg gat gcc gcc acc gcc tac gag      1730
```

-continued

```
                    Gly Asp Glu Leu Val Arg Cys Ala Val Asp Ala Ala Thr Ala Tyr Glu
                                    560                 565                 570 aac atc ctc aat gcc atc aaa gcg gcc gag gac gca gcc aac agg gct              1778
Asn Ile Leu Asn Ala Ile Lys Ala Ala Glu Asp Ala Ala Asn Arg Ala
                575                 580                 585 gcc agt gca tct gaa tct gcc ctc cag aca gtg ata aag gaa gat ctg              1826
Ala Ser Ala Ser Glu Ser Ala Leu Gln Thr Val Ile Lys Glu Asp Leu
            590                 595                 600 cca aga aaa gct aaa acc ctg agt tcc aac agt gat aaa ctg tta aat              1874
Pro Arg Lys Ala Lys Thr Leu Ser Ser Asn Ser Asp Lys Leu Leu Asn
        605                 610                 615 gaa gcc aag atg aca caa aag aag cta aag caa gaa gtc agt cca gct              1922
Glu Ala Lys Met Thr Gln Lys Lys Leu Lys Gln Glu Val Ser Pro Ala
620                 625                 630                 635 ctc aac aac cta cag caa acc ctg aat att gtg aca gtt cag aaa gaa              1970
Leu Asn Asn Leu Gln Gln Thr Leu Asn Ile Val Thr Val Gln Lys Glu
                640                 645                 650 gtg ata gac acc aat ctc aca act ctc cga gat ggt ctt cat ggg ata              2018
Val Ile Asp Thr Asn Leu Thr Thr Leu Arg Asp Gly Leu His Gly Ile
                655                 660                 665 cag aga ggt gat att gat gct atg atc agt agt gca aag agc atg gtc              2066
Gln Arg Gly Asp Ile Asp Ala Met Ile Ser Ser Ala Lys Ser Met Val
            670                 675                 680 aga aag gcc aac gac atc aca gat gag gtt ctg gat ggg ctc aac ccc              2114
Arg Lys Ala Asn Asp Ile Thr Asp Glu Val Leu Asp Gly Leu Asn Pro
        685                 690                 695 atc cag aca gat gtg gaa aga att aag gac acc tat ggg agg aca cag              2162
Ile Gln Thr Asp Val Glu Arg Ile Lys Asp Thr Tyr Gly Arg Thr Gln
700                 705                 710                 715 aac gaa gac ttc aaa aag gct ctg act gat gca gat aac tcg gtg aat              2210
Asn Glu Asp Phe Lys Lys Ala Leu Thr Asp Ala Asp Asn Ser Val Asn
                720                 725                 730 aag tta acc aac aaa cta cct gat ctt tgg cgc aag att gaa agt atc              2258
Lys Leu Thr Asn Lys Leu Pro Asp Leu Trp Arg Lys Ile Glu Ser Ile
                735                 740                 745 aac caa cag ctg ttg ccc ttg gga aac atc tct gac aac atg gac aga              2306
Asn Gln Gln Leu Leu Pro Leu Gly Asn Ile Ser Asp Asn Met Asp Arg
            750                 755                 760 ata cga gaa cta att cag cag gcc aga gat gct gcc agt aag gtt gct              2354
Ile Arg Glu Leu Ile Gln Gln Ala Arg Asp Ala Ala Ser Lys Val Ala
        765                 770                 775 gtc ccc atg agg ttc aat ggt aaa tct gga gtc gaa gtc cga ctg cca              2402
Val Pro Met Arg Phe Asn Gly Lys Ser Gly Val Glu Val Arg Leu Pro
780                 785                 790                 795 aat gac ctg gaa gat ttg aaa gga tat aca tct ctg tcc ttg ttt ctc              2450
Asn Asp Leu Glu Asp Leu Lys Gly Tyr Thr Ser Leu Ser Leu Phe Leu
                800                 805                 810 caa agg ccc aac tca aga gaa aat ggg ggt act gag aat atg ttt gtg              2498
Gln Arg Pro Asn Ser Arg Glu Asn Gly Gly Thr Glu Asn Met Phe Val
                815                 820                 825 atg tac ctt gga aat aaa gat gcc tcc cgg gac tac atc ggc atg gca              2546
Met Tyr Leu Gly Asn Lys Asp Ala Ser Arg Asp Tyr Ile Gly Met Ala
            830                 835                 840 gtt gtg gat ggc cag ctc acc tgt gtc tac aac ctg ggg gac cgt gag              2594
Val Val Asp Gly Gln Leu Thr Cys Val Tyr Asn Leu Gly Asp Arg Glu
        845                 850                 855 gct gaa ctc caa gtg gac cag atc ttg acc aag agt gag act aag gag              2642
Ala Glu Leu Gln Val Asp Gln Ile Leu Thr Lys Ser Glu Thr Lys Glu
860                 865                 870                 875
```

-continued

```
gca gtt atg gat cgg gtg aaa ttt cag aga att tat cag ttt gca agg      2690
Ala Val Met Asp Arg Val Lys Phe Gln Arg Ile Tyr Gln Phe Ala Arg
            880                 885                 890 ctt aat tac acc aaa gga gcc aca tcc agt aaa cca gaa aca ccc gga      2738
Leu Asn Tyr Thr Lys Gly Ala Thr Ser Ser Lys Pro Glu Thr Pro Gly
        895                 900                 905 gtc tat gac atg gat ggt aga aat agc aat aca ctc ctt aat ttg gat      2786
Val Tyr Asp Met Asp Gly Arg Asn Ser Asn Thr Leu Leu Asn Leu Asp
    910                 915                 920 cct gaa aat gtt gta ttt tat gtt gga ggt tac cca cct gat ttt aaa      2834
Pro Glu Asn Val Val Phe Tyr Val Gly Gly Tyr Pro Pro Asp Phe Lys
925                 930                 935 ctt ccc agt cga cta agt ttc cct cca tac aaa ggt tgt att gaa tta      2882
Leu Pro Ser Arg Leu Ser Phe Pro Pro Tyr Lys Gly Cys Ile Glu Leu
940                 945                 950                 955 gat gac ctc aat gaa aat gtt ctg agc ttg tac aac ttc aaa aaa aca      2930
Asp Asp Leu Asn Glu Asn Val Leu Ser Leu Tyr Asn Phe Lys Lys Thr
                960                 965                 970 ttc aat ctc aac aca act gaa gtg gag cct tgt aga agg agg aag gaa      2978
Phe Asn Leu Asn Thr Thr Glu Val Glu Pro Cys Arg Arg Arg Lys Glu
            975                 980                 985 gag tca gac aaa aat tat ttt gaa ggt acg ggc tat gct cga gtt cca      3026
Glu Ser Asp Lys Asn Tyr Phe Glu Gly Thr Gly Tyr Ala Arg Val Pro
        990                 995                 1000 act caa cca cat gct ccc atc cca acc ttt gga cag aca att cag acc      3074
Thr Gln Pro His Ala Pro Ile Pro Thr Phe Gly Gln Thr Ile Gln Thr
    1005                1010                1015 acc gtg gat aga ggc ttg ctg ttc ttt gca gaa aac ggg gat cgc ttc      3122
Thr Val Asp Arg Gly Leu Leu Phe Phe Ala Glu Asn Gly Asp Arg Phe
1020                1025                1030                1035 ata tct cta aat ata gaa gat ggc aag ctc atg gtg aga tac aaa ctg      3170
Ile Ser Leu Asn Ile Glu Asp Gly Lys Leu Met Val Arg Tyr Lys Leu
                1040                1045                1050 aat tca gag cta cca aaa gag aga gga gtt gga gac gcc ata aac aac      3218
Asn Ser Glu Leu Pro Lys Glu Arg Gly Val Gly Asp Ala Ile Asn Asn
            1055                1060                1065 ggc aga gac cat tcg att cag atc aaa att gga aaa ctc caa aag cgt      3266
Gly Arg Asp His Ser Ile Gln Ile Lys Ile Gly Lys Leu Gln Lys Arg
        1070                1075                1080 atg tgg ata aat gtg gac gtt caa aac act ata att gat ggt gaa gta      3314
Met Trp Ile Asn Val Asp Val Gln Asn Thr Ile Ile Asp Gly Glu Val
    1085                1090                1095 ttt gat ttc agc aca tat tat ctg gga gga att cca att gca atc agg      3362
Phe Asp Phe Ser Thr Tyr Tyr Leu Gly Gly Ile Pro Ile Ala Ile Arg
1100                1105                1110                1115 gaa aga ttt aac att tct acg cct gct ttc cga ggc tgc atg aaa aat      3410
Glu Arg Phe Asn Ile Ser Thr Pro Ala Phe Arg Gly Cys Met Lys Asn
                1120                1125                1130 ttg aag aaa acc agt ggt gtc gtt aga ttg aat gat act gtg gga gta      3458
Leu Lys Lys Thr Ser Gly Val Val Arg Leu Asn Asp Thr Val Gly Val
            1135                1140                1145 acc aaa aag tgc tcg gaa gac tgg aag ctt gtg cga tct gcc tca ttc      3506
Thr Lys Lys Cys Ser Glu Asp Trp Lys Leu Val Arg Ser Ala Ser Phe
        1150                1155                1160 tcc aga gga gga caa ttg agt ttc act gat ttg ggc tta cca cct act      3554
Ser Arg Gly Gly Gln Leu Ser Phe Thr Asp Leu Gly Leu Pro Pro Thr
    1165                1170                1175 gac cac ctc cag gcc tca ttt gga ttt cag acc ttt caa ccc agt ggc      3602
Asp His Leu Gln Ala Ser Phe Gly Phe Gln Thr Phe Gln Pro Ser Gly
1180                1185                1190                1195
```

```
ata tta tta gat cat cag aca tgg aca agg aac ctg cag gtc act ctg      3650
Ile Leu Leu Asp His Gln Thr Trp Thr Arg Asn Leu Gln Val Thr Leu
            1200                1205                1210 gaa gat ggt tac att gaa ttg agc acc agc gat agc ggc ggc cca att      3698
Glu Asp Gly Tyr Ile Glu Leu Ser Thr Ser Asp Ser Gly Gly Pro Ile
        1215                1220                1225 ttt aaa tct cca cag acg tat atg gat ggt tta ctg cat tat gta tct      3746
Phe Lys Ser Pro Gln Thr Tyr Met Asp Gly Leu Leu His Tyr Val Ser
    1230                1235                1240 gta ata agc gac aac tct gga cta cgg ctt ctc atc gat gac cag ctt      3794
Val Ile Ser Asp Asn Ser Gly Leu Arg Leu Leu Ile Asp Asp Gln Leu
1245                1250                1255 ctg aga aat agc aaa agg cta aaa cac att tca agt tcc cgg cag tct      3842
Leu Arg Asn Ser Lys Arg Leu Lys His Ile Ser Ser Ser Arg Gln Ser
1260                1265                1270                1275 ctg cgt ctg ggc ggg agc aat ttt gag ggt tgt att agc aat gtt ttt      3890
Leu Arg Leu Gly Gly Ser Asn Phe Glu Gly Cys Ile Ser Asn Val Phe
            1280                1285                1290 gtc cag agg tta tca ctg agt cct gaa gtc cta gat ttg acc agt aac      3938
Val Gln Arg Leu Ser Leu Ser Pro Glu Val Leu Asp Leu Thr Ser Asn
        1295                1300                1305 tct ctc aag aga gat gtg tcc ctg gga ggc tgc agt tta aac aaa cca      3986
Ser Leu Lys Arg Asp Val Ser Leu Gly Gly Cys Ser Leu Asn Lys Pro
    1310                1315                1320 cct ttt cta atg ttg ctt aaa ggt tct acc agg ttt aac aag acc aag      4034
Pro Phe Leu Met Leu Leu Lys Gly Ser Thr Arg Phe Asn Lys Thr Lys
1325                1330                1335 act ttt cgt atc aac cag ctg ttg cag gac aca cca gtg gcc tcc cca      4082
Thr Phe Arg Ile Asn Gln Leu Leu Gln Asp Thr Pro Val Ala Ser Pro
1340                1345                1350                1355 agg agc gtg aag gtg tgg caa gat gct tgc tca cca ctt ccc aag acc      4130
Arg Ser Val Lys Val Trp Gln Asp Ala Cys Ser Pro Leu Pro Lys Thr
            1360                1365                1370 cag gcc aat cat gga gcc ctc cag ttt ggg gac att ccc acc agc cac      4178
Gln Ala Asn His Gly Ala Leu Gln Phe Gly Asp Ile Pro Thr Ser His
        1375                1380                1385 ttg cta ttc aag ctt cct cag gag ctg ctg aaa ccc agg tca cag ttt      4226
Leu Leu Phe Lys Leu Pro Gln Glu Leu Leu Lys Pro Arg Ser Gln Phe
    1390                1395                1400 gct gtg gac atg cag aca aca tcc tcc aga gga ctg gtg ttt cac acg      4274
Ala Val Asp Met Gln Thr Thr Ser Ser Arg Gly Leu Val Phe His Thr
1405                1410                1415 ggc act aag aac tcc ttt atg gct ctt tat ctt tca aaa gga cgt ctg      4322
Gly Thr Lys Asn Ser Phe Met Ala Leu Tyr Leu Ser Lys Gly Arg Leu
1420                1425                1430                1435 gtc ttt gca ctg ggg aca gat ggg aaa aaa ttg agg atc aaa agc aag      4370
Val Phe Ala Leu Gly Thr Asp Gly Lys Lys Leu Arg Ile Lys Ser Lys
            1440                1445                1450 gag aaa tgc aat gat ggg aaa tgg cac acg gtg gtg ttt ggc cat gat      4418
Glu Lys Cys Asn Asp Gly Lys Trp His Thr Val Val Phe Gly His Asp
        1455                1460                1465 ggg gaa aag ggg cgc ttg gtt gtg gat gga ctg agg gcc cgg gag gga      4466
Gly Glu Lys Gly Arg Leu Val Val Asp Gly Leu Arg Ala Arg Glu Gly
    1470                1475                1480 agt ttg cct gga aac tcc acc atc agc atc aga gcg cca gtt tac ctg      4514
Ser Leu Pro Gly Asn Ser Thr Ile Ser Ile Arg Ala Pro Val Tyr Leu
1485                1490                1495 gga tca cct cca tca ggg aaa cca aag agc ctc ccc aca aac agc ttt      4562
Gly Ser Pro Pro Ser Gly Lys Pro Lys Ser Leu Pro Thr Asn Ser Phe
```

```
                                                     -continued 1500             1505             1510             1515 gtg gga tgc ctg aag aac ttt cag ctg gat tca aaa ccc ttg tat acc     4610
Val Gly Cys Leu Lys Asn Phe Gln Leu Asp Ser Lys Pro Leu Tyr Thr
                1520             1525             1530 cct tct tca agc ttc ggg gtg tct tcc tgc ttg ggt ggt cct ttg gag     4658
Pro Ser Ser Ser Phe Gly Val Ser Ser Cys Leu Gly Gly Pro Leu Glu
            1535             1540             1545 aaa ggc att tat ttc tct gaa gaa gga ggt cat gtc gtc ttg gct cac     4706
Lys Gly Ile Tyr Phe Ser Glu Glu Gly Gly His Val Val Leu Ala His
        1550             1555             1560 tct gta ttg ttg ggg cca gaa ttt aag ctt gtt ttc agc atc cgc cca     4754
Ser Val Leu Leu Gly Pro Glu Phe Lys Leu Val Phe Ser Ile Arg Pro
    1565             1570             1575 aga agt ctc act ggg atc cta ata cac atc gga agt cag ccc ggg aag     4802
Arg Ser Leu Thr Gly Ile Leu Ile His Ile Gly Ser Gln Pro Gly Lys
1580             1585             1590             1595 cac tta tgt gtt tac ctg gag gca gga aag gtc acg gcc tct atg gac     4850
His Leu Cys Val Tyr Leu Glu Ala Gly Lys Val Thr Ala Ser Met Asp
                1600             1605             1610 agt ggg gca ggt ggg acc tca acg tcg gtc aca cca aag cag tct ctg     4898
Ser Gly Ala Gly Gly Thr Ser Thr Ser Val Thr Pro Lys Gln Ser Leu
            1615             1620             1625 tgt gat gga cag tgg cac tcg gtg gca gtc acc ata aaa caa cac atc     4946
Cys Asp Gly Gln Trp His Ser Val Ala Val Thr Ile Lys Gln His Ile
        1630             1635             1640 ctg cac ctg gaa ctg gac aca gac agt agc tac aca gct gga cag atc     4994
Leu His Leu Glu Leu Asp Thr Asp Ser Ser Tyr Thr Ala Gly Gln Ile
    1645             1650             1655 ccc ttc cca cct gcc agc act caa gag cca cta cac ctt gga ggt gct     5042
Pro Phe Pro Pro Ala Ser Thr Gln Glu Pro Leu His Leu Gly Gly Ala
1660             1665             1670             1675 cca gcc aat ttg acg aca ctg agg atc cct gtg tgg aaa tca ttc ttt     5090
Pro Ala Asn Leu Thr Thr Leu Arg Ile Pro Val Trp Lys Ser Phe Phe
                1680             1685             1690 ggc tgt ctg agg aat att cat gtc aat cac atc cct gtc cct gtc act     5138
Gly Cys Leu Arg Asn Ile His Val Asn His Ile Pro Val Pro Val Thr
            1695             1700             1705 gaa gcc ttg gaa gtc cag ggg cct gtc agt ctg aat ggt tgt cct gac     5186
Glu Ala Leu Glu Val Gln Gly Pro Val Ser Leu Asn Gly Cys Pro Asp
        1710             1715             1720 cag taacccaagc ctatttcaca gcaaggaaat tcaccttcaa aagcactgat          5239
Gln tacccaatgc acctccctcc ccagctcgag atcattcttc a                      5280

<210> SEQ ID NO 2
<211> LENGTH: 1724
<212> TYPE: PRT
<213> ORGANISM: Homo sapiens

<400> SEQUENCE: 2

Met Pro Pro Ala Val Arg Arg Ser Ala Cys Ser Met Gly Trp Leu Trp
 1               5                  10                  15

Ile Phe Gly Ala Ala Leu Gly Gln Cys Leu Gly Tyr Ser Ser Gln Gln
            20                  25                  30

Gln Arg Val Pro Phe Leu Gln Pro Pro Gly Gln Ser Gln Leu Gln Ala
        35                  40                  45

Ser Tyr Val Glu Phe Arg Pro Ser Gln Gly Cys Ser Pro Gly Tyr Tyr
    50                  55                  60
```

-continued

```
Arg Asp His Lys Gly Leu Tyr Thr Gly Arg Cys Val Pro Cys Asn Cys
 65                  70                  75                  80

Asn Gly His Ser Asn Gln Cys Gln Asp Gly Ser Gly Ile Cys Val Asn
                 85                  90                  95

Cys Gln His Asn Thr Ala Gly Glu His Cys Glu Arg Cys Gln Glu Gly
            100                 105                 110

Tyr Tyr Gly Asn Ala Val His Gly Ser Cys Arg Ala Cys Pro Cys Pro
            115                 120                 125

His Thr Asn Ser Phe Ala Thr Gly Cys Val Val Asn Gly Gly Asp Val
    130                 135                 140

Arg Cys Ser Cys Lys Ala Gly Tyr Thr Gly Thr Gln Cys Glu Arg Cys
145                 150                 155                 160

Ala Pro Gly Tyr Phe Gly Asn Pro Gln Lys Phe Gly Ser Cys Gln
                165                 170                 175

Pro Cys Ser Cys Asn Ser Asn Gly Gln Leu Gly Ser Cys His Pro Leu
            180                 185                 190

Thr Gly Asp Cys Ile Asn Gln Glu Pro Lys Asp Ser Ser Pro Ala Glu
            195                 200                 205

Glu Cys Asp Asp Cys Asp Ser Cys Val Met Thr Leu Leu Asn Asp Leu
    210                 215                 220

Ala Thr Met Gly Glu Gln Leu Arg Leu Val Lys Ser Gln Leu Gln Gly
225                 230                 235                 240

Leu Ser Ala Ser Ala Gly Leu Leu Glu Gln Met Arg His Met Glu Thr
                245                 250                 255

Gln Ala Lys Asp Leu Arg Asn Gln Leu Leu Asn Tyr Arg Ser Ala Ile
            260                 265                 270

Ser Asn His Gly Ser Lys Ile Glu Gly Leu Glu Arg Glu Leu Thr Asp
    275                 280                 285

Leu Asn Gln Glu Phe Glu Thr Leu Gln Glu Lys Ala Gln Val Asn Ser
    290                 295                 300

Arg Lys Ala Gln Thr Leu Asn Asn Asn Val Asn Arg Ala Thr Gln Ser
305                 310                 315                 320

Ala Lys Glu Leu Asp Val Lys Ile Lys Asn Val Ile Arg Asn Val His
            325                 330                 335

Ile Leu Leu Lys Gln Ile Ser Gly Thr Asp Gly Glu Gly Asn Asn Val
            340                 345                 350

Pro Ser Gly Asp Phe Ser Arg Glu Trp Ala Glu Ala Gln Arg Met Met
            355                 360                 365

Arg Glu Leu Arg Asn Arg Asn Phe Gly Lys His Leu Arg Glu Ala Glu
    370                 375                 380

Ala Asp Lys Arg Glu Ser Gln Leu Leu Leu Asn Arg Ile Arg Thr Trp
385                 390                 395                 400

Gln Lys Thr His Gln Gly Glu Asn Asn Gly Leu Ala Asn Ser Ile Arg
            405                 410                 415

Asp Ser Leu Asn Glu Tyr Glu Ala Lys Leu Ser Asp Leu Arg Ala Arg
            420                 425                 430

Leu Gln Glu Ala Ala Ala Gln Ala Lys Gln Ala Asn Gly Leu Asn Gln
        435                 440                 445

Glu Asn Glu Arg Ala Leu Gly Ala Ile Gln Arg Gln Val Lys Glu Ile
    450                 455                 460

Asn Ser Leu Gln Ser Asp Phe Thr Lys Tyr Leu Thr Thr Ala Asp Ser
465                 470                 475                 480

Ser Leu Leu Gln Thr Asn Ile Ala Leu Gln Leu Met Glu Lys Ser Gln
```

```
                    485                 490                 495

Lys Glu Tyr Glu Lys Leu Ala Ala Ser Leu Asn Glu Ala Arg Gln Glu
                500                 505                 510

Leu Ser Asp Lys Val Arg Glu Leu Ser Arg Ser Ala Gly Lys Thr Ser
                515                 520                 525

Leu Val Glu Glu Ala Glu Lys His Ala Arg Ser Leu Gln Glu Leu Ala
            530                 535                 540

Lys Gln Leu Glu Glu Ile Lys Arg Asn Ala Ser Gly Asp Glu Leu Val
545                 550                 555                 560

Arg Cys Ala Val Asp Ala Ala Thr Ala Tyr Glu Asn Ile Leu Asn Ala
                565                 570                 575

Ile Lys Ala Ala Glu Asp Ala Ala Asn Arg Ala Ala Ser Ala Ser Glu
                580                 585                 590

Ser Ala Leu Gln Thr Val Ile Lys Glu Asp Leu Pro Arg Lys Ala Lys
            595                 600                 605

Thr Leu Ser Ser Asn Ser Asp Lys Leu Leu Asn Glu Ala Lys Met Thr
            610                 615                 620

Gln Lys Lys Leu Lys Gln Glu Val Ser Pro Ala Leu Asn Asn Leu Gln
625                 630                 635                 640

Gln Thr Leu Asn Ile Val Thr Val Gln Lys Glu Val Ile Asp Thr Asn
                645                 650                 655

Leu Thr Thr Leu Arg Asp Gly Leu His Gly Ile Gln Arg Gly Asp Ile
                660                 665                 670

Asp Ala Met Ile Ser Ser Ala Lys Ser Met Val Arg Lys Ala Asn Asp
            675                 680                 685

Ile Thr Asp Glu Val Leu Asp Gly Leu Asn Pro Ile Gln Thr Asp Val
            690                 695                 700

Glu Arg Ile Lys Asp Thr Tyr Gly Arg Thr Gln Asn Glu Asp Phe Lys
705                 710                 715                 720

Lys Ala Leu Thr Asp Ala Asp Asn Ser Val Asn Lys Leu Thr Asn Lys
                725                 730                 735

Leu Pro Asp Leu Trp Arg Lys Ile Glu Ser Ile Asn Gln Gln Leu Leu
                740                 745                 750

Pro Leu Gly Asn Ile Ser Asp Asn Met Asp Arg Ile Arg Glu Leu Ile
            755                 760                 765

Gln Gln Ala Arg Asp Ala Ala Ser Lys Val Ala Val Pro Met Arg Phe
770                 775                 780

Asn Gly Lys Ser Gly Val Glu Val Arg Leu Pro Asn Asp Leu Glu Asp
785                 790                 795                 800

Leu Lys Gly Tyr Thr Ser Leu Ser Leu Phe Leu Gln Arg Pro Asn Ser
                805                 810                 815

Arg Glu Asn Gly Gly Thr Glu Asn Met Phe Val Met Tyr Leu Gly Asn
            820                 825                 830

Lys Asp Ala Ser Arg Asp Tyr Ile Gly Met Ala Val Val Asp Gly Gln
            835                 840                 845

Leu Thr Cys Val Tyr Asn Leu Gly Asp Arg Glu Ala Glu Leu Gln Val
            850                 855                 860

Asp Gln Ile Leu Thr Lys Ser Glu Thr Lys Glu Ala Val Met Asp Arg
865                 870                 875                 880

Val Lys Phe Gln Arg Ile Tyr Gln Phe Ala Arg Leu Asn Tyr Thr Lys
                885                 890                 895

Gly Ala Thr Ser Ser Lys Pro Glu Thr Pro Gly Val Tyr Asp Met Asp
            900                 905                 910
```

-continued

Gly Arg Asn Ser Asn Thr Leu Leu Asn Leu Asp Pro Glu Asn Val Val
            915                 920                 925

Phe Tyr Val Gly Gly Tyr Pro Pro Asp Phe Lys Leu Pro Ser Arg Leu
        930                 935                 940

Ser Phe Pro Pro Tyr Lys Gly Cys Ile Glu Leu Asp Asp Leu Asn Glu
945                 950                 955                 960

Asn Val Leu Ser Leu Tyr Asn Phe Lys Lys Thr Phe Asn Leu Asn Thr
                965                 970                 975

Thr Glu Val Glu Pro Cys Arg Arg Arg Lys Glu Glu Ser Asp Lys Asn
            980                 985                 990

Tyr Phe Glu Gly Thr Gly Tyr Ala Arg Val Pro Thr Gln Pro His Ala
        995                 1000                1005

Pro Ile Pro Thr Phe Gly Gln Thr Ile Gln Thr Thr Val Asp Arg Gly
    1010                1015                1020

Leu Leu Phe Phe Ala Glu Asn Gly Asp Arg Phe Ile Ser Leu Asn Ile
1025                1030                1035                1040

Glu Asp Gly Lys Leu Met Val Arg Tyr Lys Leu Asn Ser Glu Leu Pro
            1045                1050                1055

Lys Glu Arg Gly Val Gly Asp Ala Ile Asn Asn Gly Arg Asp His Ser
        1060                1065                1070

Ile Gln Ile Lys Ile Gly Lys Leu Gln Lys Arg Met Trp Ile Asn Val
    1075                1080                1085

Asp Val Gln Asn Thr Ile Ile Asp Gly Glu Val Phe Asp Phe Ser Thr
            1090                1095                1100

Tyr Tyr Leu Gly Gly Ile Pro Ile Ala Ile Arg Glu Arg Phe Asn Ile
1105                1110                1115                1120

Ser Thr Pro Ala Phe Arg Gly Cys Met Lys Asn Leu Lys Lys Thr Ser
            1125                1130                1135

Gly Val Val Arg Leu Asn Asp Thr Val Gly Val Thr Lys Lys Cys Ser
        1140                1145                1150

Glu Asp Trp Lys Leu Val Arg Ser Ala Ser Phe Ser Arg Gly Gly Gln
    1155                1160                1165

Leu Ser Phe Thr Asp Leu Gly Leu Pro Pro Thr Asp His Leu Gln Ala
    1170                1175                1180

Ser Phe Gly Phe Gln Thr Phe Gln Pro Ser Gly Ile Leu Leu Asp His
1185                1190                1195                1200

Gln Thr Trp Thr Arg Asn Leu Gln Val Thr Leu Glu Asp Gly Tyr Ile
            1205                1210                1215

Glu Leu Ser Thr Ser Asp Ser Gly Gly Pro Ile Phe Lys Ser Pro Gln
        1220                1225                1230

Thr Tyr Met Asp Gly Leu Leu His Tyr Val Ser Val Ile Ser Asp Asn
            1235                1240                1245

Ser Gly Leu Arg Leu Leu Ile Asp Asp Gln Leu Leu Arg Asn Ser Lys
1250                1255                1260

Arg Leu Lys His Ile Ser Ser Arg Gln Ser Leu Arg Leu Gly Gly
1265                1270                1275                1280

Ser Asn Phe Glu Gly Cys Ile Ser Asn Val Phe Val Gln Arg Leu Ser
            1285                1290                1295

Leu Ser Pro Glu Val Leu Asp Leu Thr Ser Asn Ser Leu Lys Arg Asp
        1300                1305                1310

Val Ser Leu Gly Gly Cys Ser Leu Asn Lys Pro Pro Phe Leu Met Leu
    1315                1320                1325

```
Leu Lys Gly Ser Thr Arg Phe Asn Lys Thr Lys Thr Phe Arg Ile Asn
    1330                1335                1340

Gln Leu Leu Gln Asp Thr Pro Val Ala Ser Pro Arg Ser Val Lys Val
1345                1350                1355                1360

Trp Gln Asp Ala Cys Ser Pro Leu Pro Lys Thr Gln Ala Asn His Gly
            1365                1370                1375

Ala Leu Gln Phe Gly Asp Ile Pro Thr Ser His Leu Leu Phe Lys Leu
        1380                1385                1390

Pro Gln Glu Leu Leu Lys Pro Arg Ser Gln Phe Ala Val Asp Met Gln
    1395                1400                1405

Thr Thr Ser Ser Arg Gly Leu Val Phe His Thr Gly Thr Lys Asn Ser
1410                1415                1420

Phe Met Ala Leu Tyr Leu Ser Lys Gly Arg Leu Val Phe Ala Leu Gly
1425                1430                1435                1440

Thr Asp Gly Lys Lys Leu Arg Ile Lys Ser Lys Glu Lys Cys Asn Asp
            1445                1450                1455

Gly Lys Trp His Thr Val Val Phe Gly His Asp Gly Glu Lys Gly Arg
        1460                1465                1470

Leu Val Val Asp Gly Leu Arg Ala Arg Glu Gly Ser Leu Pro Gly Asn
    1475                1480                1485

Ser Thr Ile Ser Ile Arg Ala Pro Val Tyr Leu Gly Ser Pro Pro Ser
1490                1495                1500

Gly Lys Pro Lys Ser Leu Pro Thr Asn Ser Phe Val Gly Cys Leu Lys
1505                1510                1515                1520

Asn Phe Gln Leu Asp Ser Lys Pro Leu Tyr Thr Pro Ser Ser Ser Phe
            1525                1530                1535

Gly Val Ser Ser Cys Leu Gly Gly Pro Leu Glu Lys Gly Ile Tyr Phe
        1540                1545                1550

Ser Glu Glu Gly Gly His Val Val Leu Ala His Ser Val Leu Leu Gly
    1555                1560                1565

Pro Glu Phe Lys Leu Val Phe Ser Ile Arg Pro Arg Ser Leu Thr Gly
1570                1575                1580

Ile Leu Ile His Ile Gly Ser Gln Pro Gly Lys His Leu Cys Val Tyr
1585                1590                1595                1600

Leu Glu Ala Gly Lys Val Thr Ala Ser Met Asp Ser Gly Ala Gly Gly
            1605                1610                1615

Thr Ser Thr Ser Val Thr Pro Lys Gln Ser Leu Cys Asp Gly Gln Trp
        1620                1625                1630

His Ser Val Ala Val Thr Ile Lys Gln His Ile Leu His Leu Glu Leu
    1635                1640                1645

Asp Thr Asp Ser Ser Tyr Thr Ala Gly Gln Ile Pro Phe Pro Pro Ala
1650                1655                1660

Ser Thr Gln Glu Pro Leu His Leu Gly Gly Ala Pro Ala Asn Leu Thr
1665                1670                1675                1680

Thr Leu Arg Ile Pro Val Trp Lys Ser Phe Phe Gly Cys Leu Arg Asn
            1685                1690                1695

Ile His Val Asn His Ile Pro Val Pro Val Thr Glu Ala Leu Glu Val
        1700                1705                1710

Gln Gly Pro Val Ser Leu Asn Gly Cys Pro Asp Gln
    1715                1720

<210> SEQ ID NO 3
<211> LENGTH: 5170
<212> TYPE: DNA
```

-continued

```
<213> ORGANISM: Homo sapiens
<220> FEATURE:
<221> NAME/KEY: CDS
<222> LOCATION: (1)..(5079)

<400> SEQUENCE: 3 cag caa agg gtg cca ttt ctt cag cct ccc ggt caa agt caa ctg caa        48
Gln Gln Arg Val Pro Phe Leu Gln Pro Pro Gly Gln Ser Gln Leu Gln
  1               5                  10                  15 gcg agt tat gtg gag ttt aga ccc agc cag ggt tgt agc cct gga tac        96
Ala Ser Tyr Val Glu Phe Arg Pro Ser Gln Gly Cys Ser Pro Gly Tyr
                 20                  25                  30 tat cgg gat cat aaa ggc ttg tat acc gga cgg tgt gtt ccc tgc aat       144
Tyr Arg Asp His Lys Gly Leu Tyr Thr Gly Arg Cys Val Pro Cys Asn
             35                  40                  45 tgc aac gga cat tca aat caa tgc cag gat ggc tca ggc ata tgt gtt       192
Cys Asn Gly His Ser Asn Gln Cys Gln Asp Gly Ser Gly Ile Cys Val
         50                  55                  60 aac tgt cag cac aac acc gcg gga gag cac tgt gaa cgc tgc cag gag       240
Asn Cys Gln His Asn Thr Ala Gly Glu His Cys Glu Arg Cys Gln Glu
 65                  70                  75                  80 ggc tac tat ggc aac gcc gtc cac gga tcc tgc agg gcc tgc cca tgt       288
Gly Tyr Tyr Gly Asn Ala Val His Gly Ser Cys Arg Ala Cys Pro Cys
                 85                  90                  95 cct cac act aac agc ttt gcc act ggc tgt gtg gtg aat ggg gga gac       336
Pro His Thr Asn Ser Phe Ala Thr Gly Cys Val Val Asn Gly Gly Asp
                100                 105                 110 gtg cgg tgc tcc tgc aaa gct ggg tac aca gga aca cag tgt gaa agg       384
Val Arg Cys Ser Cys Lys Ala Gly Tyr Thr Gly Thr Gln Cys Glu Arg
            115                 120                 125 tgt gca ccg gga tat ttc ggg aat ccc cag aaa ttc gga ggt agc tgc       432
Cys Ala Pro Gly Tyr Phe Gly Asn Pro Gln Lys Phe Gly Gly Ser Cys
        130                 135                 140 caa cca tgc agt tgt aac agc aat ggc cag ctg ggc agc tgt cat ccc       480
Gln Pro Cys Ser Cys Asn Ser Asn Gly Gln Leu Gly Ser Cys His Pro
145                 150                 155                 160 ctg act gga gac tgc ata aac caa gaa ccc aaa gat agc agc cct gca       528
Leu Thr Gly Asp Cys Ile Asn Gln Glu Pro Lys Asp Ser Ser Pro Ala
                165                 170                 175 gaa gaa tgt gat gat tgc gac agc tgt gtg atg acc ctc ctg aac gac       576
Glu Glu Cys Asp Asp Cys Asp Ser Cys Val Met Thr Leu Leu Asn Asp
            180                 185                 190 ctg gcc acc atg ggc gag cag ctc cgc ctg gtc aag tct cag ctg cag       624
Leu Ala Thr Met Gly Glu Gln Leu Arg Leu Val Lys Ser Gln Leu Gln
        195                 200                 205 ggc ctg agt gcc agc gca ggg ctt ctg gag cag atg agg cac atg gag       672
Gly Leu Ser Ala Ser Ala Gly Leu Leu Glu Gln Met Arg His Met Glu
210                 215                 220 acc cag gcc aag gac ctg agg aat cag ttg ctc aac tac cgt tct gcc       720
Thr Gln Ala Lys Asp Leu Arg Asn Gln Leu Leu Asn Tyr Arg Ser Ala
225                 230                 235                 240 att tca aat cat gga tca aaa ata gaa ggc ctg gaa aga gaa ctg act       768
Ile Ser Asn His Gly Ser Lys Ile Glu Gly Leu Glu Arg Glu Leu Thr
                245                 250                 255 gat ttg aat caa gaa ttt gag act tta caa gaa aag gct caa gta aat       816
Asp Leu Asn Gln Glu Phe Glu Thr Leu Gln Glu Lys Ala Gln Val Asn
            260                 265                 270 tcc aga aaa gca caa aca tta aac aac aat gtt aat cgg gca aca caa       864
Ser Arg Lys Ala Gln Thr Leu Asn Asn Asn Val Asn Arg Ala Thr Gln
        275                 280                 285
```

```
agc gca aaa gaa cta gat gtg aag att aaa aat gtc atc cgg aat gtg       912
Ser Ala Lys Glu Leu Asp Val Lys Ile Lys Asn Val Ile Arg Asn Val
    290                 295                 300 cac att ctt tta aag cag atc tct ggg aca gat gga gag gga aac aac       960
His Ile Leu Leu Lys Gln Ile Ser Gly Thr Asp Gly Glu Gly Asn Asn
305                 310                 315                 320 gtg cct tca ggt gac ttt tcc aga gag tgg gct gaa gcc cag cgc atg      1008
Val Pro Ser Gly Asp Phe Ser Arg Glu Trp Ala Glu Ala Gln Arg Met
                325                 330                 335 atg agg gaa ctg cgg aac agg aac ttt gga aag cac ctc aga gaa gca      1056
Met Arg Glu Leu Arg Asn Arg Asn Phe Gly Lys His Leu Arg Glu Ala
            340                 345                 350 gaa gct gat aaa agg gag tcg cag ctc ttg ctg aac cgg ata agg acc      1104
Glu Ala Asp Lys Arg Glu Ser Gln Leu Leu Leu Asn Arg Ile Arg Thr
        355                 360                 365 tgg cag aaa acc cac cag ggg gag aac aat ggg ctt gct aac agt atc      1152
Trp Gln Lys Thr His Gln Gly Glu Asn Asn Gly Leu Ala Asn Ser Ile
    370                 375                 380 cgg gat tct tta aat gaa tac gaa gcc aaa ctc agt gac ctt cgt gct      1200
Arg Asp Ser Leu Asn Glu Tyr Glu Ala Lys Leu Ser Asp Leu Arg Ala
385                 390                 395                 400 cgg ctg cag gag gca gct gcc caa gcc aag cag gca aat ggc ttg aac      1248
Arg Leu Gln Glu Ala Ala Ala Gln Ala Lys Gln Ala Asn Gly Leu Asn
                405                 410                 415 caa gaa aac gag aga gct ttg gga gcc att cag aga caa gtg aaa gaa      1296
Gln Glu Asn Glu Arg Ala Leu Gly Ala Ile Gln Arg Gln Val Lys Glu
            420                 425                 430 ata aat tcc ctg cag agt gat ttc acc aag tat cta acc act gca gac      1344
Ile Asn Ser Leu Gln Ser Asp Phe Thr Lys Tyr Leu Thr Thr Ala Asp
        435                 440                 445 tca tct ttg ttg caa acc aac att gcg ctg cag ctg atg gag aaa agc      1392
Ser Ser Leu Leu Gln Thr Asn Ile Ala Leu Gln Leu Met Glu Lys Ser
    450                 455                 460 cag aag gaa tat gaa aaa tta gct gcc agt tta aat gaa gca aga caa      1440
Gln Lys Glu Tyr Glu Lys Leu Ala Ala Ser Leu Asn Glu Ala Arg Gln
465                 470                 475                 480 gaa cta agt gac aaa gta aga gaa ctt tcc aga tct gct ggc aaa aca      1488
Glu Leu Ser Asp Lys Val Arg Glu Leu Ser Arg Ser Ala Gly Lys Thr
                485                 490                 495 tcc ctt gtg gag gag gca gaa aag cac gcg cgg tcc tta caa gag ctg      1536
Ser Leu Val Glu Glu Ala Glu Lys His Ala Arg Ser Leu Gln Glu Leu
            500                 505                 510 gca aag cag ctg gaa gag atc aag aga aac gcc agc ggg gat gag ctg      1584
Ala Lys Gln Leu Glu Glu Ile Lys Arg Asn Ala Ser Gly Asp Glu Leu
        515                 520                 525 gtg cgc tgt gct gtg gat gcc gcc acc gcc tac gag aac atc ctc aat      1632
Val Arg Cys Ala Val Asp Ala Ala Thr Ala Tyr Glu Asn Ile Leu Asn
    530                 535                 540 gcc atc aaa gcg gcc gag gac gca gcc aac agg gct gcc agt gca tct      1680
Ala Ile Lys Ala Ala Glu Asp Ala Ala Asn Arg Ala Ala Ser Ala Ser
545                 550                 555                 560 gaa tct gcc ctc cag aca gtg ata aag gaa gat ctg cca aga aaa gct      1728
Glu Ser Ala Leu Gln Thr Val Ile Lys Glu Asp Leu Pro Arg Lys Ala
                565                 570                 575 aaa acc ctg agt tcc aac agt gat aaa ctg tta aat gaa gcc aag atg      1776
Lys Thr Leu Ser Ser Asn Ser Asp Lys Leu Leu Asn Glu Ala Lys Met
            580                 585                 590 aca caa aag aag cta aag caa gaa gtc agt cca gct ctc aac aac cta      1824
Thr Gln Lys Lys Leu Lys Gln Glu Val Ser Pro Ala Leu Asn Asn Leu
        595                 600                 605
```

```
cag caa acc ctg aat att gtg aca gtt cag aaa gaa gtg ata gac acc      1872
Gln Gln Thr Leu Asn Ile Val Thr Val Gln Lys Glu Val Ile Asp Thr
            610                 615                 620 aat ctc aca act ctc cga gat ggt ctt cat ggg ata cag aga ggt gat      1920
Asn Leu Thr Thr Leu Arg Asp Gly Leu His Gly Ile Gln Arg Gly Asp
625                 630                 635                 640 att gat gct atg atc agt agt gca aag agc atg gtc aga aag gcc aac      1968
Ile Asp Ala Met Ile Ser Ser Ala Lys Ser Met Val Arg Lys Ala Asn
                645                 650                 655 gac atc aca gat gag gtt ctg gat ggg ctc aac ccc atc cag aca gat      2016
Asp Ile Thr Asp Glu Val Leu Asp Gly Leu Asn Pro Ile Gln Thr Asp
            660                 665                 670 gtg gaa aga att aag gac acc tat ggg agg aca cag aac gaa gac ttc      2064
Val Glu Arg Ile Lys Asp Thr Tyr Gly Arg Thr Gln Asn Glu Asp Phe
        675                 680                 685 aaa aag gct ctg act gat gca gat aac tcg gtg aat aag tta acc aac      2112
Lys Lys Ala Leu Thr Asp Ala Asp Asn Ser Val Asn Lys Leu Thr Asn
690                 695                 700 aaa cta cct gat ctt tgg cgc aag att gaa agt atc aac caa cag ctg      2160
Lys Leu Pro Asp Leu Trp Arg Lys Ile Glu Ser Ile Asn Gln Gln Leu
705                 710                 715                 720 ttg ccc ttg gga aac atc tct gac aac atg gac aga ata cga gaa cta      2208
Leu Pro Leu Gly Asn Ile Ser Asp Asn Met Asp Arg Ile Arg Glu Leu
                725                 730                 735 att cag cag gcc aga gat gct gcc agt aag gtt gct gtc ccc atg agg      2256
Ile Gln Gln Ala Arg Asp Ala Ala Ser Lys Val Ala Val Pro Met Arg
            740                 745                 750 ttc aat ggt aaa tct gga gtc gaa gtc cga ctg cca aat gac ctg gaa      2304
Phe Asn Gly Lys Ser Gly Val Glu Val Arg Leu Pro Asn Asp Leu Glu
        755                 760                 765 gat ttg aaa gga tat aca tct ctg tcc ttg ttt ctc caa agg ccc aac      2352
Asp Leu Lys Gly Tyr Thr Ser Leu Ser Leu Phe Leu Gln Arg Pro Asn
770                 775                 780 tca aga gaa aat ggg ggt act gag aat atg ttt gtg atg tac ctt gga      2400
Ser Arg Glu Asn Gly Gly Thr Glu Asn Met Phe Val Met Tyr Leu Gly
785                 790                 795                 800 aat aaa gat gcc tcc cgg gac tac atc ggc atg gca gtt gtg gat ggc      2448
Asn Lys Asp Ala Ser Arg Asp Tyr Ile Gly Met Ala Val Val Asp Gly
                805                 810                 815 cag ctc acc tgt gtc tac aac ctg ggg gac cgt gag gct gaa ctc caa      2496
Gln Leu Thr Cys Val Tyr Asn Leu Gly Asp Arg Glu Ala Glu Leu Gln
            820                 825                 830 gtg gac cag atc ttg acc aag agt gag act aag gag gca gtt atg gat      2544
Val Asp Gln Ile Leu Thr Lys Ser Glu Thr Lys Glu Ala Val Met Asp
        835                 840                 845 cgg gtg aaa ttt cag aga att tat cag ttt gca agg ctt aat tac acc      2592
Arg Val Lys Phe Gln Arg Ile Tyr Gln Phe Ala Arg Leu Asn Tyr Thr
850                 855                 860 aaa gga gcc aca tcc agt aaa cca gaa aca ccc gga gtc tat gac atg      2640
Lys Gly Ala Thr Ser Ser Lys Pro Glu Thr Pro Gly Val Tyr Asp Met
865                 870                 875                 880 gat ggt aga aat agc aat aca ctc ctt aat ttg gat cct gaa aat gtt      2688
Asp Gly Arg Asn Ser Asn Thr Leu Leu Asn Leu Asp Pro Glu Asn Val
                885                 890                 895 gta ttt tat gtt gga ggt tac cca cct gat ttt aaa ctt ccc agt cga      2736
Val Phe Tyr Val Gly Gly Tyr Pro Pro Asp Phe Lys Leu Pro Ser Arg
            900                 905                 910 cta agt ttc cct cca tac aaa ggt tgt att gaa tta gat gac ctc aat      2784
Leu Ser Phe Pro Pro Tyr Lys Gly Cys Ile Glu Leu Asp Asp Leu Asn
```

|   |   |
|---|---|
| gaa aat gtt ctg agc ttg tac aac ttc aaa aaa aca ttc aat ctc aac<br>Glu Asn Val Leu Ser Leu Tyr Asn Phe Lys Lys Thr Phe Asn Leu Asn<br>930           935          940 | 2832 |
| aca act gaa gtg gag cct tgt aga agg agg aag gaa gag tca gac aaa<br>Thr Thr Glu Val Glu Pro Cys Arg Arg Arg Lys Glu Glu Ser Asp Lys<br>945          950         955          960 | 2880 |
| aat tat ttt gaa ggt acg ggc tat gct cga gtt cca act caa cca cat<br>Asn Tyr Phe Glu Gly Thr Gly Tyr Ala Arg Val Pro Thr Gln Pro His<br>          965         970          975 | 2928 |
| gct ccc atc cca acc ttt gga cag aca att cag acc acc gtg gat aga<br>Ala Pro Ile Pro Thr Phe Gly Gln Thr Ile Gln Thr Thr Val Asp Arg<br>    980         985          990 | 2976 |
| ggc ttg ctg ttc ttt gca gaa aac ggg gat cgc ttc ata tct cta aat<br>Gly Leu Leu Phe Phe Ala Glu Asn Gly Asp Arg Phe Ile Ser Leu Asn<br>995         1000         1005 | 3024 |
| ata gaa gat ggc aag ctc atg gtg aga tac aaa ctg aat tca gag cta<br>Ile Glu Asp Gly Lys Leu Met Val Arg Tyr Lys Leu Asn Ser Glu Leu<br>1010         1015         1020 | 3072 |
| cca aaa gag aga gga gtt gga gac gcc ata aac aac ggc aga gac cat<br>Pro Lys Glu Arg Gly Val Gly Asp Ala Ile Asn Asn Gly Arg Asp His<br>1025         1030         1035         1040 | 3120 |
| tcg att cag atc aaa att gga aaa ctc caa aag cgt atg tgg ata aat<br>Ser Ile Gln Ile Lys Ile Gly Lys Leu Gln Lys Arg Met Trp Ile Asn<br>         1045         1050         1055 | 3168 |
| gtg gac gtt caa aac act ata att gat ggt gaa gta ttt gat ttc agc<br>Val Asp Val Gln Asn Thr Ile Ile Asp Gly Glu Val Phe Asp Phe Ser<br>    1060         1065         1070 | 3216 |
| aca tat tat ctg gga gga att cca att gca atc agg gaa aga ttt aac<br>Thr Tyr Tyr Leu Gly Gly Ile Pro Ile Ala Ile Arg Glu Arg Phe Asn<br>1075         1080         1085 | 3264 |
| att tct acg cct gct ttc cga ggc tgc atg aaa aat ttg aag aaa acc<br>Ile Ser Thr Pro Ala Phe Arg Gly Cys Met Lys Asn Leu Lys Lys Thr<br>1090         1095         1100 | 3312 |
| agt ggt gtc gtt aga ttg aat gat act gtg gga gta acc aaa aag tgc<br>Ser Gly Val Val Arg Leu Asn Asp Thr Val Gly Val Thr Lys Lys Cys<br>1105         1110         1115         1120 | 3360 |
| tcg gaa gac tgg aag ctt gtg cga tct gcc tca ttc tcc aga gga gga<br>Ser Glu Asp Trp Lys Leu Val Arg Ser Ala Ser Phe Ser Arg Gly Gly<br>         1125         1130         1135 | 3408 |
| caa ttg agt ttc act gat ttg ggc tta cca cct act gac cac ctc cag<br>Gln Leu Ser Phe Thr Asp Leu Gly Leu Pro Pro Thr Asp His Leu Gln<br>    1140         1145         1150 | 3456 |
| gcc tca ttt gga ttt cag acc ttt caa ccc agt ggc ata tta tta gat<br>Ala Ser Phe Gly Phe Gln Thr Phe Gln Pro Ser Gly Ile Leu Leu Asp<br>1155         1160         1165 | 3504 |
| cat cag aca tgg aca agg aac ctg cag gtc act ctg gaa gat ggt tac<br>His Gln Thr Trp Thr Arg Asn Leu Gln Val Thr Leu Glu Asp Gly Tyr<br>1170         1175         1180 | 3552 |
| att gaa ttg agc acc agc gat agc ggc ggc cca att ttt aaa tct cca<br>Ile Glu Leu Ser Thr Ser Asp Ser Gly Gly Pro Ile Phe Lys Ser Pro<br>1185         1190         1195         1200 | 3600 |
| cag acg tat atg gat ggt tta ctg cat tat gta tct gta ata agc gac<br>Gln Thr Tyr Met Asp Gly Leu Leu His Tyr Val Ser Val Ile Ser Asp<br>         1205         1210         1215 | 3648 |
| aac tct gga cta cgg ctt ctc atc gat gac cag ctt ctg aga aat agc<br>Asn Ser Gly Leu Arg Leu Leu Ile Asp Asp Gln Leu Leu Arg Asn Ser<br>    1220         1225         1230 | 3696 |
| aaa agg cta aaa cac att tca agt tcc cgg cag tct ctg cgt ctg ggc | 3744 |

```
Lys Arg Leu Lys His Ile Ser Ser Ser Arg Gln Ser Leu Arg Leu Gly
        1235                1240                1245 ggg agc aat ttt gag ggt tgt att agc aat gtt ttt gtc cag agg tta        3792
Gly Ser Asn Phe Glu Gly Cys Ile Ser Asn Val Phe Val Gln Arg Leu
1250                1255                1260 tca ctg agt cct gaa gtc cta gat ttg acc agt aac tct ctc aag aga        3840
Ser Leu Ser Pro Glu Val Leu Asp Leu Thr Ser Asn Ser Leu Lys Arg
1265                1270                1275                1280 gat gtg tcc ctg gga ggc tgc agt tta aac aaa cca cct ttt cta atg        3888
Asp Val Ser Leu Gly Gly Cys Ser Leu Asn Lys Pro Pro Phe Leu Met
                1285                1290                1295 ttg ctt aaa ggt tct acc agg ttt aac aag acc aag act ttt cgt atc        3936
Leu Leu Lys Gly Ser Thr Arg Phe Asn Lys Thr Lys Thr Phe Arg Ile
            1300                1305                1310 aac cag ctg ttg cag gac aca cca gtg gcc tcc cca agg agc gtg aag        3984
Asn Gln Leu Leu Gln Asp Thr Pro Val Ala Ser Pro Arg Ser Val Lys
        1315                1320                1325 gtg tgg caa gat gct tgc tca cca ctt ccc aag acc cag gcc aat cat        4032
Val Trp Gln Asp Ala Cys Ser Pro Leu Pro Lys Thr Gln Ala Asn His
    1330                1335                1340 gga gcc ctc cag ttt ggg gac att ccc acc agc cac ttg cta ttc aag        4080
Gly Ala Leu Gln Phe Gly Asp Ile Pro Thr Ser His Leu Leu Phe Lys
1345                1350                1355                1360 ctt cct cag gag ctg ctg aaa ccc agg tca cag ttt gct gtg gac atg        4128
Leu Pro Gln Glu Leu Leu Lys Pro Arg Ser Gln Phe Ala Val Asp Met
                1365                1370                1375 cag aca aca tcc tcc aga gga ctg gtg ttt cac acg ggc act aag aac        4176
Gln Thr Thr Ser Ser Arg Gly Leu Val Phe His Thr Gly Thr Lys Asn
            1380                1385                1390 tcc ttt atg gct ctt tat ctt tca aaa gga cgt ctg gtc ttt gca ctg        4224
Ser Phe Met Ala Leu Tyr Leu Ser Lys Gly Arg Leu Val Phe Ala Leu
        1395                1400                1405 ggg aca gat ggg aaa aaa ttg agg atc aaa agc aag gag aaa tgc aat        4272
Gly Thr Asp Gly Lys Lys Leu Arg Ile Lys Ser Lys Glu Lys Cys Asn
    1410                1415                1420 gat ggg aaa tgg cac acg gtg gtg ttt ggc cat gat ggg gaa aag ggg        4320
Asp Gly Lys Trp His Thr Val Val Phe Gly His Asp Gly Glu Lys Gly
1425                1430                1435                1440 cgc ttg gtt gtg gat gga ctg agg gcc cgg gag gga agt ttg cct gga        4368
Arg Leu Val Val Asp Gly Leu Arg Ala Arg Glu Gly Ser Leu Pro Gly
                1445                1450                1455 aac tcc acc atc agc atc aga gcg cca gtt tac ctg gga tca cct cca        4416
Asn Ser Thr Ile Ser Ile Arg Ala Pro Val Tyr Leu Gly Ser Pro Pro
            1460                1465                1470 tca ggg aaa cca aag agc ctc ccc aca aac agc ttt gtg gga tgc ctg        4464
Ser Gly Lys Pro Lys Ser Leu Pro Thr Asn Ser Phe Val Gly Cys Leu
        1475                1480                1485 aag aac ttt cag ctg gat tca aaa ccc ttg tat acc cct tct tca agc        4512
Lys Asn Phe Gln Leu Asp Ser Lys Pro Leu Tyr Thr Pro Ser Ser Ser
    1490                1495                1500 ttc ggg gtg tct tcc tgc ttg ggt ggt cct ttg gag aaa ggc att tat        4560
Phe Gly Val Ser Ser Cys Leu Gly Gly Pro Leu Glu Lys Gly Ile Tyr
1505                1510                1515                1520 ttc tct gaa gaa gga ggt cat gtc gtc ttg gct cac tct gta ttg ttg        4608
Phe Ser Glu Glu Gly Gly His Val Val Leu Ala His Ser Val Leu Leu
                1525                1530                1535 ggg cca gaa ttt aag ctt gtt ttc agc atc cgc cca aga agt ctc act        4656
Gly Pro Glu Phe Lys Leu Val Phe Ser Ile Arg Pro Arg Ser Leu Thr
            1540                1545                1550
```

-continued

| | | |
|---|---|---|
| ggg atc cta ata cac atc gga agt cag ccc ggg aag cac tta tgt gtt<br>Gly Ile Leu Ile His Ile Gly Ser Gln Pro Gly Lys His Leu Cys Val<br>       1555                  1560                1565 | 4704 |
| tac ctg gag gca gga aag gtc acg gcc tct atg gac agt ggg gca ggt<br>Tyr Leu Glu Ala Gly Lys Val Thr Ala Ser Met Asp Ser Gly Ala Gly<br>1570                  1575                1580 | 4752 |
| ggg acc tca acg tcg gtc aca cca aag cag tct ctg tgt gat gga cag<br>Gly Thr Ser Thr Ser Val Thr Pro Lys Gln Ser Leu Cys Asp Gly Gln<br>1585                1590                1595              1600 | 4800 |
| tgg cac tcg gtg gca gtc acc ata aaa caa cac atc ctg cac ctg gaa<br>Trp His Ser Val Ala Val Thr Ile Lys Gln His Ile Leu His Leu Glu<br>       1605                  1610                1615 | 4848 |
| ctg gac aca gac agt agc tac aca gct gga cag atc ccc ttc cca cct<br>Leu Asp Thr Asp Ser Ser Tyr Thr Ala Gly Gln Ile Pro Phe Pro Pro<br>       1620                  1625                1630 | 4896 |
| gcc agc act caa gag cca cta cac ctt gga ggt gct cca gcc aat ttg<br>Ala Ser Thr Gln Glu Pro Leu His Leu Gly Gly Ala Pro Ala Asn Leu<br>       1635                  1640                1645 | 4944 |
| acg aca ctg agg atc cct gtg tgg aaa tca ttc ttt ggc tgt ctg agg<br>Thr Thr Leu Arg Ile Pro Val Trp Lys Ser Phe Phe Gly Cys Leu Arg<br>   1650                  1655                1660 | 4992 |
| aat att cat gtc aat cac atc cct gtc cct gtc act gaa gcc ttg gaa<br>Asn Ile His Val Asn His Ile Pro Val Pro Val Thr Glu Ala Leu Glu<br>1665                1670                1675              1680 | 5040 |
| gtc cag ggg cct gtc agt ctg aat ggt tgt cct gac cag taacccaagc<br>Val Gln Gly Pro Val Ser Leu Asn Gly Cys Pro Asp Gln<br>                 1685                1690 | 5089 |
| ctatttcaca gcaaggaaat tcaccttcaa aagcactgat tacccaatgc acctccctcc | 5149 |
| ccagctcgag atcattcttc a | 5170 |

<210> SEQ ID NO 4
<211> LENGTH: 1693
<212> TYPE: PRT
<213> ORGANISM: Homo sapiens

<400> SEQUENCE: 4

Gln Gln Arg Val Pro Phe Leu Gln Pro Pro Gly Gln Ser Gln Leu Gln
 1               5                  10                  15

Ala Ser Tyr Val Glu Phe Arg Pro Ser Gln Gly Cys Ser Pro Gly Tyr
            20                  25                  30

Tyr Arg Asp His Lys Gly Leu Tyr Thr Gly Arg Cys Val Pro Cys Asn
        35                  40                  45

Cys Asn Gly His Ser Asn Gln Cys Gln Asp Gly Ser Gly Ile Cys Val
    50                  55                  60

Asn Cys Gln His Asn Thr Ala Gly Glu His Cys Glu Arg Cys Gln Glu
65                  70                  75                  80

Gly Tyr Tyr Gly Asn Ala Val His Gly Ser Cys Arg Ala Cys Pro Cys
                85                  90                  95

Pro His Thr Asn Ser Phe Ala Thr Gly Cys Val Val Asn Gly Gly Asp
            100                 105                 110

Val Arg Cys Ser Cys Lys Ala Gly Tyr Thr Gly Thr Gln Cys Glu Arg
        115                 120                 125

Cys Ala Pro Gly Tyr Phe Gly Asn Pro Gln Lys Phe Gly Gly Ser Cys
    130                 135                 140

Gln Pro Cys Ser Cys Asn Ser Asn Gly Gln Leu Gly Ser Cys His Pro
145                 150                 155                 160

Leu Thr Gly Asp Cys Ile Asn Gln Glu Pro Lys Asp Ser Ser Pro Ala

-continued

```
                    165                 170                 175
Glu Glu Cys Asp Asp Cys Asp Ser Cys Val Met Thr Leu Leu Asn Asp
                180                 185                 190

Leu Ala Thr Met Gly Glu Gln Leu Arg Leu Val Lys Ser Gln Leu Gln
            195                 200                 205

Gly Leu Ser Ala Ser Ala Gly Leu Leu Glu Gln Met Arg His Met Glu
        210                 215                 220

Thr Gln Ala Lys Asp Leu Arg Asn Gln Leu Leu Asn Tyr Arg Ser Ala
225                 230                 235                 240

Ile Ser Asn His Gly Ser Lys Ile Glu Gly Leu Glu Arg Glu Leu Thr
                245                 250                 255

Asp Leu Asn Gln Glu Phe Glu Thr Leu Gln Glu Lys Ala Gln Val Asn
                260                 265                 270

Ser Arg Lys Ala Gln Thr Leu Asn Asn Asn Val Asn Arg Ala Thr Gln
            275                 280                 285

Ser Ala Lys Glu Leu Asp Val Lys Ile Lys Asn Val Ile Arg Asn Val
        290                 295                 300

His Ile Leu Leu Lys Gln Ile Ser Gly Thr Asp Gly Glu Gly Asn Asn
305                 310                 315                 320

Val Pro Ser Gly Asp Phe Ser Arg Glu Trp Ala Glu Ala Gln Arg Met
                325                 330                 335

Met Arg Glu Leu Arg Asn Arg Asn Phe Gly Lys His Leu Arg Glu Ala
                340                 345                 350

Glu Ala Asp Lys Arg Glu Ser Gln Leu Leu Leu Asn Arg Ile Arg Thr
            355                 360                 365

Trp Gln Lys Thr His Gln Gly Glu Asn Asn Gly Leu Ala Asn Ser Ile
        370                 375                 380

Arg Asp Ser Leu Asn Glu Tyr Glu Ala Lys Leu Ser Asp Leu Arg Ala
385                 390                 395                 400

Arg Leu Gln Glu Ala Ala Gln Ala Lys Gln Ala Asn Gly Leu Asn
                405                 410                 415

Gln Glu Asn Glu Arg Ala Leu Gly Ala Ile Gln Arg Gln Val Lys Glu
            420                 425                 430

Ile Asn Ser Leu Gln Ser Asp Phe Thr Lys Tyr Leu Thr Thr Ala Asp
        435                 440                 445

Ser Ser Leu Leu Gln Thr Asn Ile Ala Leu Gln Leu Met Glu Lys Ser
450                 455                 460

Gln Lys Glu Tyr Glu Lys Leu Ala Ala Ser Leu Asn Glu Ala Arg Gln
465                 470                 475                 480

Glu Leu Ser Asp Lys Val Arg Glu Leu Ser Arg Ser Ala Gly Lys Thr
                485                 490                 495

Ser Leu Val Glu Glu Ala Glu Lys His Ala Arg Ser Leu Gln Glu Leu
            500                 505                 510

Ala Lys Gln Leu Glu Glu Ile Lys Arg Asn Ala Ser Gly Asp Glu Leu
        515                 520                 525

Val Arg Cys Ala Val Asp Ala Thr Ala Tyr Glu Asn Ile Leu Asn
                530                 535                 540

Ala Ile Lys Ala Ala Glu Asp Ala Ala Asn Arg Ala Ala Ser Ala Ser
545                 550                 555                 560

Glu Ser Ala Leu Gln Thr Val Ile Lys Glu Asp Leu Pro Arg Lys Ala
                565                 570                 575

Lys Thr Leu Ser Ser Asn Ser Asp Lys Leu Leu Asn Glu Ala Lys Met
            580                 585                 590
```

-continued

```
Thr Gln Lys Lys Leu Lys Gln Glu Val Ser Pro Ala Leu Asn Asn Leu
        595                 600                 605
Gln Gln Thr Leu Asn Ile Val Thr Val Gln Lys Glu Val Ile Asp Thr
        610                 615                 620
Asn Leu Thr Thr Leu Arg Asp Gly Leu His Gly Ile Gln Arg Gly Asp
625                 630                 635                 640
Ile Asp Ala Met Ile Ser Ser Ala Lys Ser Met Val Arg Lys Ala Asn
                    645                 650                 655
Asp Ile Thr Asp Glu Val Leu Asp Gly Leu Asn Pro Ile Gln Thr Asp
            660                 665                 670
Val Glu Arg Ile Lys Asp Thr Tyr Gly Arg Thr Gln Asn Glu Asp Phe
        675                 680                 685
Lys Lys Ala Leu Thr Asp Ala Asp Asn Ser Val Asn Lys Leu Thr Asn
        690                 695                 700
Lys Leu Pro Asp Leu Trp Arg Lys Ile Glu Ser Ile Asn Gln Gln Leu
705                 710                 715                 720
Leu Pro Leu Gly Asn Ile Ser Asp Asn Met Asp Arg Ile Arg Glu Leu
                    725                 730                 735
Ile Gln Gln Ala Arg Asp Ala Ala Ser Lys Val Ala Val Pro Met Arg
            740                 745                 750
Phe Asn Gly Lys Ser Gly Val Glu Val Arg Leu Pro Asn Asp Leu Glu
        755                 760                 765
Asp Leu Lys Gly Tyr Thr Ser Leu Ser Leu Phe Leu Gln Arg Pro Asn
        770                 775                 780
Ser Arg Glu Asn Gly Gly Thr Glu Asn Met Phe Val Met Tyr Leu Gly
785                 790                 795                 800
Asn Lys Asp Ala Ser Arg Asp Tyr Ile Gly Met Ala Val Val Asp Gly
                    805                 810                 815
Gln Leu Thr Cys Val Tyr Asn Leu Gly Asp Arg Glu Ala Glu Leu Gln
            820                 825                 830
Val Asp Gln Ile Leu Thr Lys Ser Glu Thr Lys Glu Ala Val Met Asp
        835                 840                 845
Arg Val Lys Phe Gln Arg Ile Tyr Gln Phe Ala Arg Leu Asn Tyr Thr
        850                 855                 860
Lys Gly Ala Thr Ser Ser Lys Pro Glu Thr Pro Gly Val Tyr Asp Met
865                 870                 875                 880
Asp Gly Arg Asn Ser Asn Thr Leu Leu Asn Leu Asp Pro Glu Asn Val
                    885                 890                 895
Val Phe Tyr Val Gly Gly Tyr Pro Pro Asp Phe Lys Leu Pro Ser Arg
            900                 905                 910
Leu Ser Phe Pro Pro Tyr Lys Gly Cys Ile Glu Leu Asp Asp Leu Asn
        915                 920                 925
Glu Asn Val Leu Ser Leu Tyr Asn Phe Lys Lys Thr Phe Asn Leu Asn
        930                 935                 940
Thr Thr Glu Val Glu Pro Cys Arg Arg Lys Glu Glu Ser Asp Lys
945                 950                 955                 960
Asn Tyr Phe Glu Gly Thr Gly Tyr Ala Arg Val Pro Thr Gln Pro His
                    965                 970                 975
Ala Pro Ile Pro Thr Phe Gly Gln Thr Ile Gln Thr Thr Val Asp Arg
            980                 985                 990
Gly Leu Leu Phe Phe Ala Glu Asn Gly Asp Arg Phe Ile Ser Leu Asn
        995                 1000                1005
```

```
Ile Glu Asp Gly Lys Leu Met Val Arg Tyr Lys Leu Asn Ser Glu Leu
    1010                1015                1020

Pro Lys Glu Arg Gly Val Gly Asp Ala Ile Asn Asn Gly Arg Asp His
1025                1030                1035                1040

Ser Ile Gln Ile Lys Ile Gly Lys Leu Gln Lys Arg Met Trp Ile Asn
                1045                1050                1055

Val Asp Val Gln Asn Thr Ile Ile Asp Gly Glu Val Phe Asp Phe Ser
            1060                1065                1070

Thr Tyr Tyr Leu Gly Gly Ile Pro Ile Ala Ile Arg Glu Arg Phe Asn
        1075                1080                1085

Ile Ser Thr Pro Ala Phe Arg Gly Cys Met Lys Asn Leu Lys Lys Thr
    1090                1095                1100

Ser Gly Val Val Arg Leu Asn Asp Thr Val Gly Val Thr Lys Lys Cys
1105                1110                1115                1120

Ser Glu Asp Trp Lys Leu Val Arg Ser Ala Ser Phe Ser Arg Gly Gly
                1125                1130                1135

Gln Leu Ser Phe Thr Asp Leu Gly Leu Pro Pro Thr Asp His Leu Gln
            1140                1145                1150

Ala Ser Phe Gly Phe Gln Thr Phe Gln Pro Ser Gly Ile Leu Leu Asp
        1155                1160                1165

His Gln Thr Trp Thr Arg Asn Leu Gln Val Thr Leu Glu Asp Gly Tyr
    1170                1175                1180

Ile Glu Leu Ser Thr Ser Asp Ser Gly Gly Pro Ile Phe Lys Ser Pro
1185                1190                1195                1200

Gln Thr Tyr Met Asp Gly Leu Leu His Tyr Val Ser Val Ile Ser Asp
                1205                1210                1215

Asn Ser Gly Leu Arg Leu Leu Ile Asp Asp Gln Leu Leu Arg Asn Ser
            1220                1225                1230

Lys Arg Leu Lys His Ile Ser Ser Ser Arg Gln Ser Leu Arg Leu Gly
        1235                1240                1245

Gly Ser Asn Phe Glu Gly Cys Ile Ser Asn Val Phe Val Gln Arg Leu
    1250                1255                1260

Ser Leu Ser Pro Glu Val Leu Asp Leu Thr Ser Asn Ser Leu Lys Arg
1265                1270                1275                1280

Asp Val Ser Leu Gly Gly Cys Ser Leu Asn Lys Pro Pro Phe Leu Met
                1285                1290                1295

Leu Leu Lys Gly Ser Thr Arg Phe Asn Lys Thr Lys Thr Phe Arg Ile
            1300                1305                1310

Asn Gln Leu Leu Gln Asp Thr Pro Val Ala Ser Pro Arg Ser Val Lys
        1315                1320                1325

Val Trp Gln Asp Ala Cys Ser Pro Leu Pro Lys Thr Gln Ala Asn His
    1330                1335                1340

Gly Ala Leu Gln Phe Gly Asp Ile Pro Thr Ser His Leu Leu Phe Lys
1345                1350                1355                1360

Leu Pro Gln Glu Leu Leu Lys Pro Arg Ser Gln Phe Ala Val Asp Met
                1365                1370                1375

Gln Thr Thr Ser Ser Arg Gly Leu Val Phe His Thr Gly Thr Lys Asn
            1380                1385                1390

Ser Phe Met Ala Leu Tyr Leu Ser Lys Gly Arg Leu Val Phe Ala Leu
        1395                1400                1405

Gly Thr Asp Gly Lys Lys Leu Arg Ile Lys Ser Lys Glu Lys Cys Asn
    1410                1415                1420

Asp Gly Lys Trp His Thr Val Val Phe Gly His Asp Gly Glu Lys Gly
```

```
1425                1430                1435                1440
```

Arg Leu Val Val Asp Gly Leu Arg Ala Arg Glu Gly Ser Leu Pro Gly
             1445                1450                1455

Asn Ser Thr Ile Ser Ile Arg Ala Pro Val Tyr Leu Gly Ser Pro Pro
         1460                1465                1470

Ser Gly Lys Pro Lys Ser Leu Pro Thr Asn Ser Phe Val Gly Cys Leu
     1475                1480                1485

Lys Asn Phe Gln Leu Asp Ser Lys Pro Leu Tyr Thr Pro Ser Ser Ser
 1490                1495                1500

Phe Gly Val Ser Ser Cys Leu Gly Gly Pro Leu Glu Lys Gly Ile Tyr
1505                1510                1515                1520

Phe Ser Glu Glu Gly Gly His Val Val Leu Ala His Ser Val Leu Leu
             1525                1530                1535

Gly Pro Glu Phe Lys Leu Val Phe Ser Ile Arg Pro Arg Ser Leu Thr
         1540                1545                1550

Gly Ile Leu Ile His Ile Gly Ser Gln Pro Gly Lys His Leu Cys Val
     1555                1560                1565

Tyr Leu Glu Ala Gly Lys Val Thr Ala Ser Met Asp Ser Gly Ala Gly
 1570                1575                1580

Gly Thr Ser Thr Ser Val Thr Pro Lys Gln Ser Leu Cys Asp Gly Gln
1585                1590                1595                1600

Trp His Ser Val Ala Val Thr Ile Lys Gln His Ile Leu His Leu Glu
             1605                1610                1615

Leu Asp Thr Asp Ser Ser Tyr Thr Ala Gly Gln Ile Pro Phe Pro Pro
         1620                1625                1630

Ala Ser Thr Gln Glu Pro Leu His Leu Gly Gly Ala Pro Ala Asn Leu
     1635                1640                1645

Thr Thr Leu Arg Ile Pro Val Trp Lys Ser Phe Phe Gly Cys Leu Arg
 1650                1655                1660

Asn Ile His Val Asn His Ile Pro Val Pro Val Thr Glu Ala Leu Glu
1665                1670                1675                1680

Val Gln Gly Pro Val Ser Leu Asn Gly Cys Pro Asp Gln
             1685                1690

<210> SEQ ID NO 5
<211> LENGTH: 5433
<212> TYPE: DNA
<213> ORGANISM: Homo sapiens
<220> FEATURE:
<221> NAME/KEY: CDS
<222> LOCATION: (1)..(5139)
<221> NAME/KEY: sig_peptide
<222> LOCATION: (1)..(60)

<400> SEQUENCE: 5

```
atg gga tgg ctg tgg atc ttt ggg gca gcc ctg ggg cag tgt ctg ggc      48
Met Gly Trp Leu Trp Ile Phe Gly Ala Ala Leu Gly Gln Cys Leu Gly
 1               5                  10                  15 tac agt tca cag cag caa agg gtg cca ttt ctt cag cct ccc ggt caa      96
Tyr Ser Ser Gln Gln Gln Arg Val Pro Phe Leu Gln Pro Pro Gly Gln
             20                  25                  30 agt caa ctg caa gcg agt tat gtg gag ttt aga ccc agc cag ggt tgt     144
Ser Gln Leu Gln Ala Ser Tyr Val Glu Phe Arg Pro Ser Gln Gly Cys
         35                  40                  45 agc cct gga tac tat cgg gat cat aaa ggc ttg tat acc gga cgg tgt     192
Ser Pro Gly Tyr Tyr Arg Asp His Lys Gly Leu Tyr Thr Gly Arg Cys
     50                  55                  60
```

```
gtt ccc tgc aat tgc aac gga cat tca aat caa tgc cag gat ggc tca      240
Val Pro Cys Asn Cys Asn Gly His Ser Asn Gln Cys Gln Asp Gly Ser
 65                  70                  75                  80 ggc ata tgt gtt aac tgt cag cac aac acc gcg gga gag cac tgt gaa      288
Gly Ile Cys Val Asn Cys Gln His Asn Thr Ala Gly Glu His Cys Glu
                 85                  90                  95 cgc tgc cag gag ggc tac tat ggc aac gcc gtc cac gga tcc tgc agg      336
Arg Cys Gln Glu Gly Tyr Tyr Gly Asn Ala Val His Gly Ser Cys Arg
            100                 105                 110 gcc tgc cca tgt cct cac act aac agc ttt gcc act ggc tgt gtg gtg      384
Ala Cys Pro Cys Pro His Thr Asn Ser Phe Ala Thr Gly Cys Val Val
        115                 120                 125 aat ggg gga gac gtg cgg tgc tcc tgc aaa gct ggg tac aca gga aca      432
Asn Gly Gly Asp Val Arg Cys Ser Cys Lys Ala Gly Tyr Thr Gly Thr
    130                 135                 140 cag tgt gaa agg tgt gca ccg gga tat ttc ggg aat ccc cag aaa ttc      480
Gln Cys Glu Arg Cys Ala Pro Gly Tyr Phe Gly Asn Pro Gln Lys Phe
145                 150                 155                 160 gga ggt agc tgc caa cca tgc agt tgt aac agc aat ggc cag ctg ggc      528
Gly Gly Ser Cys Gln Pro Cys Ser Cys Asn Ser Asn Gly Gln Leu Gly
                165                 170                 175 agc tgt cat ccc ctg act gga gac tgc ata aac caa gaa ccc aaa gat      576
Ser Cys His Pro Leu Thr Gly Asp Cys Ile Asn Gln Glu Pro Lys Asp
            180                 185                 190 agc agc cct gca gaa gaa tgt gat gat tgc gac agc tgt gtg atg acc      624
Ser Ser Pro Ala Glu Glu Cys Asp Asp Cys Asp Ser Cys Val Met Thr
        195                 200                 205 ctc ctg aac gac ctg gcc acc atg ggc gag cag ctc cgc ctg gtc aag      672
Leu Leu Asn Asp Leu Ala Thr Met Gly Glu Gln Leu Arg Leu Val Lys
    210                 215                 220 tct cag ctg cag ggc ctg agt gcc agc gca ggg ctt ctg gag cag atg      720
Ser Gln Leu Gln Gly Leu Ser Ala Ser Ala Gly Leu Leu Glu Gln Met
225                 230                 235                 240 agg cac atg gag acc cag gcc aag gac ctg agg aat cag ttg ctc aac      768
Arg His Met Glu Thr Gln Ala Lys Asp Leu Arg Asn Gln Leu Leu Asn
                245                 250                 255 tac cgt tct gcc att tca aat cat gga tca aaa ata gaa ggc ctg gaa      816
Tyr Arg Ser Ala Ile Ser Asn His Gly Ser Lys Ile Glu Gly Leu Glu
            260                 265                 270 aga gaa ctg act gat ttg aat caa gaa ttt gag act ttg caa gaa aag      864
Arg Glu Leu Thr Asp Leu Asn Gln Glu Phe Glu Thr Leu Gln Glu Lys
        275                 280                 285 gct caa gta aat tcc aga aaa gca caa aca tta aac aac aat gtt aat      912
Ala Gln Val Asn Ser Arg Lys Ala Gln Thr Leu Asn Asn Asn Val Asn
    290                 295                 300 cgg gca aca caa agc gca aaa gaa ctg gat gtg aag att aaa aat gtc      960
Arg Ala Thr Gln Ser Ala Lys Glu Leu Asp Val Lys Ile Lys Asn Val
305                 310                 315                 320 atc cgg aat gtg cac att ctt tta aag cag atc tct ggg aca gat gga     1008
Ile Arg Asn Val His Ile Leu Leu Lys Gln Ile Ser Gly Thr Asp Gly
                325                 330                 335 gag gga aac aac gtg cct tca ggt gac ttt ccc aga gag tgg gct gaa     1056
Glu Gly Asn Asn Val Pro Ser Gly Asp Phe Ser Arg Glu Trp Ala Glu
            340                 345                 350 gcc cag cgc atg atg agg gaa ctg cgg aac agg aac ttt gga aag cac     1104
Ala Gln Arg Met Met Arg Glu Leu Arg Asn Arg Asn Phe Gly Lys His
        355                 360                 365 ctc aga gaa gca gaa gct gat aaa agg gag tcg cag ctc ttg ctg aac     1152
Leu Arg Glu Ala Glu Ala Asp Lys Arg Glu Ser Gln Leu Leu Leu Asn
    370                 375                 380
```

```
cgg ata agg acc tgg cag aaa acc cac cag ggg gag aac aat ggg ctt      1200
Arg Ile Arg Thr Trp Gln Lys Thr His Gln Gly Glu Asn Asn Gly Leu
385                 390                 395                 400 gct aac agt atc cgg gat tct tta aat gaa tac gaa gcc aaa ctc agt      1248
Ala Asn Ser Ile Arg Asp Ser Leu Asn Glu Tyr Glu Ala Lys Leu Ser
                405                 410                 415 gac ctt cgt gct cgg ctg cag gag gca gct gcc caa gcc aag cag gca      1296
Asp Leu Arg Ala Arg Leu Gln Glu Ala Ala Ala Gln Ala Lys Gln Ala
            420                 425                 430 aat ggc ttg aac caa gaa aac gag aga gct ttg gga gcc att cag aga      1344
Asn Gly Leu Asn Gln Glu Asn Glu Arg Ala Leu Gly Ala Ile Gln Arg
        435                 440                 445 caa gtg aaa gaa ata aat tcc ctg cag agt gat ttc acc aag tat cta      1392
Gln Val Lys Glu Ile Asn Ser Leu Gln Ser Asp Phe Thr Lys Tyr Leu
    450                 455                 460 acc act gca gac tca tct ttg ttg caa acc aac att gcg ctg cag ctg      1440
Thr Thr Ala Asp Ser Ser Leu Leu Gln Thr Asn Ile Ala Leu Gln Leu
465                 470                 475                 480 atg gag aaa agc cag aag gaa tat gaa aaa tta gct gcc agt tta aat      1488
Met Glu Lys Ser Gln Lys Glu Tyr Glu Lys Leu Ala Ala Ser Leu Asn
                485                 490                 495 gaa gca aga caa gaa cta agt gac aaa gta aga gaa ctt tcc aga tct      1536
Glu Ala Arg Gln Glu Leu Ser Asp Lys Val Arg Glu Leu Ser Arg Ser
            500                 505                 510 gct ggc aaa aca tcc ctt gtg gag gag gca gaa aag cac gcg cgg tcc      1584
Ala Gly Lys Thr Ser Leu Val Glu Glu Ala Glu Lys His Ala Arg Ser
        515                 520                 525 tta caa gag ctg gca aag cag ctg gaa gag atc aag aga aac gcc agc      1632
Leu Gln Glu Leu Ala Lys Gln Leu Glu Glu Ile Lys Arg Asn Ala Ser
    530                 535                 540 ggg gat gag ctg gtg cgc tgt gct gtg gat gcc gcc acc gcc tac gag      1680
Gly Asp Glu Leu Val Arg Cys Ala Val Asp Ala Ala Thr Ala Tyr Glu
545                 550                 555                 560 aac atc ctc aat gcc atc aaa gcg gcc gag gac gca gcc aac agg gct      1728
Asn Ile Leu Asn Ala Ile Lys Ala Ala Glu Asp Ala Ala Asn Arg Ala
                565                 570                 575 gcc agt gca tct gaa tct gcc ctc cag aca gtg ata aag gaa gat ctg      1776
Ala Ser Ala Ser Glu Ser Ala Leu Gln Thr Val Ile Lys Glu Asp Leu
            580                 585                 590 cca aga aaa gct aaa acc ctg agt tcc aac agt gat aaa ctg tta aat      1824
Pro Arg Lys Ala Lys Thr Leu Ser Ser Asn Ser Asp Lys Leu Leu Asn
        595                 600                 605 gaa gcc aag atg aca caa aag aag cta aag caa gaa gtc agt cca gct      1872
Glu Ala Lys Met Thr Gln Lys Lys Leu Lys Gln Glu Val Ser Pro Ala
    610                 615                 620 ctc aac aac cta cag caa acc ctg aat att gtg aca gtt cag aaa gaa      1920
Leu Asn Asn Leu Gln Gln Thr Leu Asn Ile Val Thr Val Gln Lys Glu
625                 630                 635                 640 gtg ata gac acc aat ctc aca act ctc cga gat ggt ctt cat ggg ata      1968
Val Ile Asp Thr Asn Leu Thr Thr Leu Arg Asp Gly Leu His Gly Ile
                645                 650                 655 cag aga ggt gat att gat gct atg atc agt agt gca aag agc atg gtc      2016
Gln Arg Gly Asp Ile Asp Ala Met Ile Ser Ser Ala Lys Ser Met Val
            660                 665                 670 aga aag gcc aac gac atc aca gat gag gtt ctg gat ggg ctc aac ccc      2064
Arg Lys Ala Asn Asp Ile Thr Asp Glu Val Leu Asp Gly Leu Asn Pro
        675                 680                 685 atc cag aca gat gtg gaa aga att aag gac acc tat ggg agg aca cag      2112
Ile Gln Thr Asp Val Glu Arg Ile Lys Asp Thr Tyr Gly Arg Thr Gln
```

|     |     |     |     |     |     |     |     |     |     |     |     |     |     |     |     |     |
|---|---|---|---|---|---|---|---|---|---|---|---|---|---|---|---|---|
|     | 690 |     |     |     | 695 |     |     |     | 700 |     |     |     |     |     |     |     |
| aac | gaa | gac | ttc | aaa | aag | gct | ctg | act | gat | gca | gat | aac | tcg | gtg | aat | 2160 |
| Asn | Glu | Asp | Phe | Lys | Lys | Ala | Leu | Thr | Asp | Ala | Asp | Asn | Ser | Val | Asn |     |
| 705 |     |     |     | 710 |     |     |     | 715 |     |     |     | 720 |     |     |     |     |
| aag | tta | acc | aac | aaa | cta | cct | gat | ctt | tgg | cgc | aag | att | gaa | agt | atc | 2208 |
| Lys | Leu | Thr | Asn | Lys | Leu | Pro | Asp | Leu | Trp | Arg | Lys | Ile | Glu | Ser | Ile |     |
|     |     |     |     | 725 |     |     |     | 730 |     |     |     | 735 |     |     |     |     |
| aac | caa | cag | ctg | ttg | ccc | ttg | gga | aac | atc | tct | gac | aac | atg | gac | aga | 2256 |
| Asn | Gln | Gln | Leu | Leu | Pro | Leu | Gly | Asn | Ile | Ser | Asp | Asn | Met | Asp | Arg |     |
|     |     |     | 740 |     |     |     | 745 |     |     |     | 750 |     |     |     |     |     |
| ata | cga | gaa | cta | att | cag | cag | gcc | aga | gat | gct | gcc | agt | aag | gtt | gct | 2304 |
| Ile | Arg | Glu | Leu | Ile | Gln | Gln | Ala | Arg | Asp | Ala | Ala | Ser | Lys | Val | Ala |     |
|     |     | 755 |     |     |     | 760 |     |     |     | 765 |     |     |     |     |     |     |
| gtc | ccc | atg | agg | ttc | aat | ggt | aaa | tct | gga | gtc | gaa | gtc | cga | ctg | cca | 2352 |
| Val | Pro | Met | Arg | Phe | Asn | Gly | Lys | Ser | Gly | Val | Glu | Val | Arg | Leu | Pro |     |
|     | 770 |     |     |     | 775 |     |     |     | 780 |     |     |     |     |     |     |     |
| aat | gac | ctg | gaa | gat | ttg | aaa | gga | tat | aca | tct | ctg | tcc | ttg | ttt | ctc | 2400 |
| Asn | Asp | Leu | Glu | Asp | Leu | Lys | Gly | Tyr | Thr | Ser | Leu | Ser | Leu | Phe | Leu |     |
| 785 |     |     |     | 790 |     |     |     | 795 |     |     |     | 800 |     |     |     |     |
| caa | agg | ccc | aac | tca | aga | gaa | aat | ggg | ggt | act | gag | aat | atg | ttt | gtg | 2448 |
| Gln | Arg | Pro | Asn | Ser | Arg | Glu | Asn | Gly | Gly | Thr | Glu | Asn | Met | Phe | Val |     |
|     |     |     | 805 |     |     |     | 810 |     |     |     | 815 |     |     |     |     |     |
| atg | tac | ctt | gga | aat | aaa | gat | gcc | tcc | cgg | gac | tac | atc | ggc | atg | gca | 2496 |
| Met | Tyr | Leu | Gly | Asn | Lys | Asp | Ala | Ser | Arg | Asp | Tyr | Ile | Gly | Met | Ala |     |
|     |     | 820 |     |     |     | 825 |     |     |     | 830 |     |     |     |     |     |     |
| gtt | gtg | gat | ggc | cag | ctc | acc | tgt | gtc | tac | aac | ctg | ggg | gac | cgt | gag | 2544 |
| Val | Val | Asp | Gly | Gln | Leu | Thr | Cys | Val | Tyr | Asn | Leu | Gly | Asp | Arg | Glu |     |
|     | 835 |     |     |     | 840 |     |     |     | 845 |     |     |     |     |     |     |     |
| gct | gaa | ctc | caa | gtg | gac | cag | atc | ttg | acc | aag | agt | gag | act | aag | gag | 2592 |
| Ala | Glu | Leu | Gln | Val | Asp | Gln | Ile | Leu | Thr | Lys | Ser | Glu | Thr | Lys | Glu |     |
| 850 |     |     |     | 855 |     |     |     | 860 |     |     |     |     |     |     |     |     |
| gca | gtt | atg | gat | cgg | gtg | aaa | ttt | cag | aga | att | tat | cag | ttt | gca | agg | 2640 |
| Ala | Val | Met | Asp | Arg | Val | Lys | Phe | Gln | Arg | Ile | Tyr | Gln | Phe | Ala | Arg |     |
| 865 |     |     | 870 |     |     |     | 875 |     |     |     | 880 |     |     |     |     |     |
| ctt | aat | tac | acc | aaa | gga | gcc | aca | tcc | agt | aaa | cca | gaa | aca | ccc | gga | 2688 |
| Leu | Asn | Tyr | Thr | Lys | Gly | Ala | Thr | Ser | Ser | Lys | Pro | Glu | Thr | Pro | Gly |     |
|     |     |     | 885 |     |     |     | 890 |     |     |     | 895 |     |     |     |     |     |
| gtc | tat | gac | atg | gat | ggt | aga | aat | agc | aat | aca | ctc | ctt | aat | ttg | gat | 2736 |
| Val | Tyr | Asp | Met | Asp | Gly | Arg | Asn | Ser | Asn | Thr | Leu | Leu | Asn | Leu | Asp |     |
|     |     | 900 |     |     |     | 905 |     |     |     | 910 |     |     |     |     |     |     |
| cct | gaa | aat | gtt | gta | ttt | tat | gtt | gga | ggt | tac | cca | cct | gat | ttt | aaa | 2784 |
| Pro | Glu | Asn | Val | Val | Phe | Tyr | Val | Gly | Gly | Tyr | Pro | Pro | Asp | Phe | Lys |     |
|     | 915 |     |     |     | 920 |     |     |     | 925 |     |     |     |     |     |     |     |
| ctt | ccc | agt | cga | cta | agt | ttc | cct | cca | tac | aaa | ggt | tgt | att | gaa | tta | 2832 |
| Leu | Pro | Ser | Arg | Leu | Ser | Phe | Pro | Pro | Tyr | Lys | Gly | Cys | Ile | Glu | Leu |     |
| 930 |     |     |     | 935 |     |     |     | 940 |     |     |     |     |     |     |     |     |
| gat | gac | ctc | aat | gaa | aat | gtt | ctg | agc | ttg | tac | aac | ttc | aaa | aaa | aca | 2880 |
| Asp | Asp | Leu | Asn | Glu | Asn | Val | Leu | Ser | Leu | Tyr | Asn | Phe | Lys | Lys | Thr |     |
| 945 |     |     |     | 950 |     |     |     | 955 |     |     |     | 960 |     |     |     |     |
| ttc | aat | ctc | aac | aca | act | gaa | gtg | gag | cct | tgt | aga | agg | agg | aag | gaa | 2928 |
| Phe | Asn | Leu | Asn | Thr | Thr | Glu | Val | Glu | Pro | Cys | Arg | Arg | Arg | Lys | Glu |     |
|     |     |     | 965 |     |     |     | 970 |     |     |     | 975 |     |     |     |     |     |
| gag | tca | gac | aaa | aat | tat | ttt | gaa | ggt | acg | ggc | tat | gct | cga | gtt | cca | 2976 |
| Glu | Ser | Asp | Lys | Asn | Tyr | Phe | Glu | Gly | Thr | Gly | Tyr | Ala | Arg | Val | Pro |     |
|     |     | 980 |     |     |     | 985 |     |     |     | 990 |     |     |     |     |     |     |
| act | caa | cca | cat | gct | ccc | atc | cca | acc | ttt | gga | cag | aca | att | cag | acc | 3024 |
| Thr | Gln | Pro | His | Ala | Pro | Ile | Pro | Thr | Phe | Gly | Gln | Thr | Ile | Gln | Thr |     |
|     | 995 |     |     |     | 1000 |     |     |     | 1005 |     |     |     |     |     |     |     |
| acc | gtg | gat | aga | ggc | ttg | ctg | ttc | ttt | gca | gaa | aac | ggg | gat | cgc | ttc | 3072 |

```
Thr Val Asp Arg Gly Leu Leu Phe Phe Ala Glu Asn Gly Asp Arg Phe
    1010                1015                1020 ata tct cta aat ata gaa gat ggc aag ctc atg gtg aga tac aaa ctg      3120
Ile Ser Leu Asn Ile Glu Asp Gly Lys Leu Met Val Arg Tyr Lys Leu
1025            1030                1035                1040 aat tca gag cta cca aaa gag aga gga gtt gga gac gcc ata aac aac      3168
Asn Ser Glu Leu Pro Lys Glu Arg Gly Val Gly Asp Ala Ile Asn Asn
            1045                1050                1055 ggc aga gac cat tcg att cag atc aaa att gga aaa ctc caa aag cgt      3216
Gly Arg Asp His Ser Ile Gln Ile Lys Ile Gly Lys Leu Gln Lys Arg
        1060                1065                1070 atg tgg ata aat gtg gac gtt caa aac act ata att gat ggt gaa gta      3264
Met Trp Ile Asn Val Asp Val Gln Asn Thr Ile Ile Asp Gly Glu Val
    1075                1080                1085 ttt gat ttc agc aca tat tat ctg gga gga att cca att gca atc agg      3312
Phe Asp Phe Ser Thr Tyr Tyr Leu Gly Gly Ile Pro Ile Ala Ile Arg
1090                1095                1100 gaa aga ttt aac att tct acg cct gct ttc cga ggc tgc atg aaa aat      3360
Glu Arg Phe Asn Ile Ser Thr Pro Ala Phe Arg Gly Cys Met Lys Asn
1105                1110                1115                1120 ttg aag aaa acc agt ggt gtc gtt aga ttg aat gat act gtg gga gta      3408
Leu Lys Lys Thr Ser Gly Val Val Arg Leu Asn Asp Thr Val Gly Val
            1125                1130                1135 acc aaa aag tgc tcg gaa gac tgg aag ctt gtg cga tct gcc tca ttc      3456
Thr Lys Lys Cys Ser Glu Asp Trp Lys Leu Val Arg Ser Ala Ser Phe
        1140                1145                1150 tcc aga gga gga caa ttg agt ttc act gat ttg ggc tta cca cct act      3504
Ser Arg Gly Gly Gln Leu Ser Phe Thr Asp Leu Gly Leu Pro Pro Thr
    1155                1160                1165 gac cac ctc cag gcc tca ttt gga ttt cag acc ttt caa ccc agt ggc      3552
Asp His Leu Gln Ala Ser Phe Gly Phe Gln Thr Phe Gln Pro Ser Gly
1170                1175                1180 ata tta tta gat cat cag aca tgg aca agg aac ctg cag gtc act ctg      3600
Ile Leu Leu Asp His Gln Thr Trp Thr Arg Asn Leu Gln Val Thr Leu
1185                1190                1195                1200 gaa gat ggt tac att gaa ttg agc acc agc gat agc ggc ggc cca att      3648
Glu Asp Gly Tyr Ile Glu Leu Ser Thr Ser Asp Ser Gly Gly Pro Ile
            1205                1210                1215 ttt aaa tct cca cag acg tat atg gat ggt tta ctg cat tat gta tct      3696
Phe Lys Ser Pro Gln Thr Tyr Met Asp Gly Leu Leu His Tyr Val Ser
        1220                1225                1230 gta ata agc gac aac tct gga cta cgg ctt ctc atc gat gac cag ctt      3744
Val Ile Ser Asp Asn Ser Gly Leu Arg Leu Leu Ile Asp Asp Gln Leu
    1235                1240                1245 ctg aga aat agc aaa agg cta aaa cac att tca agt tcc cgg cag tct      3792
Leu Arg Asn Ser Lys Arg Leu Lys His Ile Ser Ser Ser Arg Gln Ser
1250                1255                1260 ctg cgt ctg ggc ggg agc aat ttt gag ggt tgt att agc aat gtt ttt      3840
Leu Arg Leu Gly Gly Ser Asn Phe Glu Gly Cys Ile Ser Asn Val Phe
1265                1270                1275                1280 gtc cag agg tta tca ctg agt cct gaa gtc cta gat ttg acc agt aac      3888
Val Gln Arg Leu Ser Leu Ser Pro Glu Val Leu Asp Leu Thr Ser Asn
            1285                1290                1295 tct ctc aag aga gat gtg tcc ctg gga ggc tgc agt tta aac aaa cca      3936
Ser Leu Lys Arg Asp Val Ser Leu Gly Gly Cys Ser Leu Asn Lys Pro
        1300                1305                1310 cct ttt cta atg ttg ctt aaa ggt tct acc agg ttt aac aag acc aag      3984
Pro Phe Leu Met Leu Leu Lys Gly Ser Thr Arg Phe Asn Lys Thr Lys
    1315                1320                1325
```

-continued

| | |
|---|---|
| act ttt cgt atc aac cag ctg ttg cag gac aca cca gtg gcc tcc cca<br>Thr Phe Arg Ile Asn Gln Leu Leu Gln Asp Thr Pro Val Ala Ser Pro<br>    1330                       1335                1340 | 4032 |
| agg agc gtg aag gtg tgg caa gat gct tgc tca cca ctt ccc aag acc<br>Arg Ser Val Lys Val Trp Gln Asp Ala Cys Ser Pro Leu Pro Lys Thr<br>1345                  1350                1355                1360 | 4080 |
| cag gcc aat cat gga gcc ctc cag ttt ggg gac att ccc acc agc cac<br>Gln Ala Asn His Gly Ala Leu Gln Phe Gly Asp Ile Pro Thr Ser His<br>                1365                1370                1375 | 4128 |
| ttg cta ttc aag ctt cct cag gag ctg ctg aaa ccc agg tca cag ttt<br>Leu Leu Phe Lys Leu Pro Gln Glu Leu Leu Lys Pro Arg Ser Gln Phe<br>    1380                       1385                1390 | 4176 |
| gct gtg gac atg cag aca aca tcc tcc aga gga ctg gtg ttt cac acg<br>Ala Val Asp Met Gln Thr Thr Ser Ser Arg Gly Leu Val Phe His Thr<br>                1395                1400                1405 | 4224 |
| ggc act aag aac tcc ttt atg gct ctt tat ctt tca aaa gga cgt ctg<br>Gly Thr Lys Asn Ser Phe Met Ala Leu Tyr Leu Ser Lys Gly Arg Leu<br>        1410                       1415                1420 | 4272 |
| gtc ttt gca ctg ggg aca gat ggg aaa aaa ttg agg atc aaa agc aag<br>Val Phe Ala Leu Gly Thr Asp Gly Lys Lys Leu Arg Ile Lys Ser Lys<br>1425                  1430                1435                1440 | 4320 |
| gag aaa tgc aat gat ggg aaa tgg cac acg gtg gtg ttt ggc cat gat<br>Glu Lys Cys Asn Asp Gly Lys Trp His Thr Val Val Phe Gly His Asp<br>                1445                1450                1455 | 4368 |
| ggg gaa aag ggg cgc ttg gtt gtg gat gga ctg agg gcc cgg gag gga<br>Gly Glu Lys Gly Arg Leu Val Val Asp Gly Leu Arg Ala Arg Glu Gly<br>    1460                       1465                1470 | 4416 |
| agt ttg cct gga aac tcc acc atc agc atc aga gcg cca gtt tac ctg<br>Ser Leu Pro Gly Asn Ser Thr Ile Ser Ile Arg Ala Pro Val Tyr Leu<br>                1475                1480                1485 | 4464 |
| gga tca cct cca tca ggg aaa cca aag agc ctc ccc aca aac agc ttt<br>Gly Ser Pro Pro Ser Gly Lys Pro Lys Ser Leu Pro Thr Asn Ser Phe<br>    1490                       1495                1500 | 4512 |
| gtg gga tgc ctg aag aac ttt cag ctg gat tca aaa ccc ttg tat acc<br>Val Gly Cys Leu Lys Asn Phe Gln Leu Asp Ser Lys Pro Leu Tyr Thr<br>1505                  1510                1515                1520 | 4560 |
| cct tct tca agc ttc ggg gtg tct tcc tgc ttg ggt ggt cct ttg gag<br>Pro Ser Ser Ser Phe Gly Val Ser Ser Cys Leu Gly Gly Pro Leu Glu<br>                1525                1530                1535 | 4608 |
| aaa ggc att tat ttc tct gaa gaa gga ggt cat gtc gtc ttg gct cac<br>Lys Gly Ile Tyr Phe Ser Glu Glu Gly Gly His Val Val Leu Ala His<br>    1540                       1545                1550 | 4656 |
| tct gta ttg ttg ggg cca gaa ttt aag ctt gtt ttc agc atc cgc cca<br>Ser Val Leu Leu Gly Pro Glu Phe Lys Leu Val Phe Ser Ile Arg Pro<br>                1555                1560                1565 | 4704 |
| aga agt ctc act ggg atc cta ata cac atc gga agt cag ccc ggg aag<br>Arg Ser Leu Thr Gly Ile Leu Ile His Ile Gly Ser Gln Pro Gly Lys<br>    1570                       1575                1580 | 4752 |
| cac tta tgt gtt tac ctg gag gca gga aag gtc acg gcc tct atg gac<br>His Leu Cys Val Tyr Leu Glu Ala Gly Lys Val Thr Ala Ser Met Asp<br>1585                  1590                1595                1600 | 4800 |
| agt ggg gca ggt ggg acc tca acg tcg gtc aca cca aag cag tct ctg<br>Ser Gly Ala Gly Gly Thr Ser Thr Ser Val Thr Pro Lys Gln Ser Leu<br>                1605                1610                1615 | 4848 |
| tgt gat gga cag tgg cac tcg gtg gca gtc acc ata aaa caa cac atc<br>Cys Asp Gly Gln Trp His Ser Val Ala Val Thr Ile Lys Gln His Ile<br>    1620                       1625                1630 | 4896 |
| ctg cac ctg gaa ctg gac aca gac agt agc tac aca gct gga cag atc<br>Leu His Leu Glu Leu Asp Thr Asp Ser Ser Tyr Thr Ala Gly Gln Ile<br>1635                  1640                1645 | 4944 |

```
ccc ttc cca cct gcc agc act caa gag cca cta cac ctt gga ggt gct        4992
Pro Phe Pro Pro Ala Ser Thr Gln Glu Pro Leu His Leu Gly Gly Ala
    1650                1655                1660 cca gcc aat ttg acg aca ctg agg atc cct gtg tgg aaa tca ttc ttt        5040
Pro Ala Asn Leu Thr Thr Leu Arg Ile Pro Val Trp Lys Ser Phe Phe
1665                1670                1675                1680 ggc tgt ctg agg aat att cat gtc aat cac atc cct gtc cct gtc act        5088
Gly Cys Leu Arg Asn Ile His Val Asn His Ile Pro Val Pro Val Thr
            1685                1690                1695 gaa gcc ttg gaa gtc cag ggg cct gtc agt ctg aat ggt tgt cct gac        5136
Glu Ala Leu Glu Val Gln Gly Pro Val Ser Leu Asn Gly Cys Pro Asp
        1700                1705                1710 cag taacccaagc ctatttcaca gcaaggaaat tcaccttcaa aagcactgat             5189
Gln tacccaatgc acctccctcc ccagctcgag atcattcttc aattaggaca caaaccagac      5249
aggtttaata gcgaatctaa ttttgaattc tgaccatgga tacccatcac tttggcattc      5309
agtgctacat gtgtatttta tataaaaatc ccatttcttg aagataaaaa aattgttatt      5369
caaattgtta tgcacagaat gtttttggta atattaattt ccactaaaaa attaaatgtc      5429
tttt                                                                   5433

<210> SEQ ID NO 6
<211> LENGTH: 1713
<212> TYPE: PRT
<213> ORGANISM: Homo sapiens

<400> SEQUENCE: 6

Met Gly Trp Leu Trp Ile Phe Gly Ala Ala Leu Gly Gln Cys Leu Gly
1               5                   10                  15

Tyr Ser Ser Gln Gln Gln Arg Val Pro Phe Leu Gln Pro Pro Gly Gln
            20                  25                  30

Ser Gln Leu Gln Ala Ser Tyr Val Glu Phe Arg Pro Ser Gln Gly Cys
        35                  40                  45

Ser Pro Gly Tyr Tyr Arg Asp His Lys Gly Leu Tyr Thr Gly Arg Cys
    50                  55                  60

Val Pro Cys Asn Cys Asn Gly His Ser Asn Gln Cys Gln Asp Gly Ser
65                  70                  75                  80

Gly Ile Cys Val Asn Cys Gln His Asn Thr Ala Gly Glu His Cys Glu
                85                  90                  95

Arg Cys Gln Glu Gly Tyr Tyr Gly Asn Ala Val His Gly Ser Cys Arg
            100                 105                 110

Ala Cys Pro Cys Pro His Thr Asn Ser Phe Ala Thr Gly Cys Val Val
        115                 120                 125

Asn Gly Gly Asp Val Arg Cys Ser Cys Lys Ala Gly Tyr Thr Gly Thr
    130                 135                 140

Gln Cys Glu Arg Cys Ala Pro Gly Tyr Phe Gly Asn Pro Gln Lys Phe
145                 150                 155                 160

Gly Gly Ser Cys Gln Pro Cys Ser Cys Asn Ser Asn Gly Gln Leu Gly
                165                 170                 175

Ser Cys His Pro Leu Thr Gly Asp Cys Ile Asn Gln Glu Pro Lys Asp
            180                 185                 190

Ser Ser Pro Ala Glu Glu Cys Asp Asp Cys Asp Ser Cys Val Met Thr
        195                 200                 205

Leu Leu Asn Asp Leu Ala Thr Met Gly Glu Gln Leu Arg Leu Val Lys
    210                 215                 220
```

-continued

```
Ser Gln Leu Gln Gly Leu Ser Ala Ser Ala Gly Leu Leu Glu Gln Met
225                 230                 235                 240

Arg His Met Glu Thr Gln Ala Lys Asp Leu Arg Asn Gln Leu Leu Asn
            245                 250                 255

Tyr Arg Ser Ala Ile Ser Asn His Gly Ser Lys Ile Glu Gly Leu Glu
        260                 265                 270

Arg Glu Leu Thr Asp Leu Asn Gln Glu Phe Glu Thr Leu Gln Glu Lys
    275                 280                 285

Ala Gln Val Asn Ser Arg Lys Ala Gln Thr Leu Asn Asn Asn Val Asn
290                 295                 300

Arg Ala Thr Gln Ser Ala Lys Glu Leu Asp Val Lys Ile Lys Asn Val
305                 310                 315                 320

Ile Arg Asn Val His Ile Leu Leu Lys Gln Ile Ser Gly Thr Asp Gly
                325                 330                 335

Glu Gly Asn Asn Val Pro Ser Gly Asp Phe Ser Arg Glu Trp Ala Glu
            340                 345                 350

Ala Gln Arg Met Met Arg Glu Leu Arg Asn Arg Asn Phe Gly Lys His
        355                 360                 365

Leu Arg Glu Ala Glu Ala Asp Lys Arg Glu Ser Gln Leu Leu Leu Asn
    370                 375                 380

Arg Ile Arg Thr Trp Gln Lys Thr His Gln Gly Asn Asn Gly Leu
385                 390                 395                 400

Ala Asn Ser Ile Arg Asp Ser Leu Asn Glu Tyr Glu Ala Lys Leu Ser
                405                 410                 415

Asp Leu Arg Ala Arg Leu Gln Glu Ala Ala Gln Ala Lys Gln Ala
            420                 425                 430

Asn Gly Leu Asn Gln Glu Asn Glu Arg Ala Leu Gly Ala Ile Gln Arg
        435                 440                 445

Gln Val Lys Glu Ile Asn Ser Leu Gln Ser Asp Phe Thr Lys Tyr Leu
    450                 455                 460

Thr Thr Ala Asp Ser Ser Leu Leu Gln Thr Asn Ile Ala Leu Gln Leu
465                 470                 475                 480

Met Glu Lys Ser Gln Lys Glu Tyr Glu Lys Leu Ala Ala Ser Leu Asn
                485                 490                 495

Glu Ala Arg Gln Glu Leu Ser Asp Lys Val Arg Glu Leu Ser Arg Ser
            500                 505                 510

Ala Gly Lys Thr Ser Leu Val Glu Glu Ala Glu Lys His Ala Arg Ser
        515                 520                 525

Leu Gln Glu Leu Ala Lys Gln Leu Glu Glu Ile Lys Arg Asn Ala Ser
    530                 535                 540

Gly Asp Glu Leu Val Arg Cys Ala Val Asp Ala Ala Thr Ala Tyr Glu
545                 550                 555                 560

Asn Ile Leu Asn Ala Ile Lys Ala Ala Glu Asp Ala Ala Asn Arg Ala
                565                 570                 575

Ala Ser Ala Ser Glu Ser Ala Leu Gln Thr Val Ile Lys Glu Asp Leu
            580                 585                 590

Pro Arg Lys Ala Lys Thr Leu Ser Ser Asn Ser Asp Lys Leu Leu Asn
        595                 600                 605

Glu Ala Lys Met Thr Gln Lys Lys Leu Lys Gln Glu Val Ser Pro Ala
    610                 615                 620

Leu Asn Asn Leu Gln Gln Thr Leu Asn Ile Val Thr Val Gln Lys Glu
625                 630                 635                 640
```

-continued

```
Val Ile Asp Thr Asn Leu Thr Thr Leu Arg Asp Gly Leu His Gly Ile
            645                 650                 655

Gln Arg Gly Asp Ile Asp Ala Met Ile Ser Ser Ala Lys Ser Met Val
            660                 665                 670

Arg Lys Ala Asn Asp Ile Thr Asp Glu Val Leu Asp Gly Leu Asn Pro
            675                 680                 685

Ile Gln Thr Asp Val Glu Arg Ile Lys Asp Thr Tyr Gly Arg Thr Gln
            690                 695                 700

Asn Glu Asp Phe Lys Lys Ala Leu Thr Asp Ala Asp Asn Ser Val Asn
705                 710                 715                 720

Lys Leu Thr Asn Lys Leu Pro Asp Leu Trp Arg Lys Ile Glu Ser Ile
            725                 730                 735

Asn Gln Gln Leu Leu Pro Leu Gly Asn Ile Ser Asp Asn Met Asp Arg
            740                 745                 750

Ile Arg Glu Leu Ile Gln Gln Ala Arg Asp Ala Ala Ser Lys Val Ala
            755                 760                 765

Val Pro Met Arg Phe Asn Gly Lys Ser Gly Val Glu Val Arg Leu Pro
            770                 775                 780

Asn Asp Leu Glu Asp Leu Lys Gly Tyr Thr Ser Leu Ser Leu Phe Leu
785                 790                 795                 800

Gln Arg Pro Asn Ser Arg Glu Asn Gly Gly Thr Glu Asn Met Phe Val
            805                 810                 815

Met Tyr Leu Gly Asn Lys Asp Ala Ser Arg Asp Tyr Ile Gly Met Ala
            820                 825                 830

Val Val Asp Gly Gln Leu Thr Cys Val Tyr Asn Leu Gly Asp Arg Glu
            835                 840                 845

Ala Glu Leu Gln Val Asp Gln Ile Leu Thr Lys Ser Glu Thr Lys Glu
850                 855                 860

Ala Val Met Asp Arg Val Lys Phe Gln Arg Ile Tyr Gln Phe Ala Arg
865                 870                 875                 880

Leu Asn Tyr Thr Lys Gly Ala Thr Ser Ser Lys Pro Glu Thr Pro Gly
            885                 890                 895

Val Tyr Asp Met Asp Gly Arg Asn Ser Asn Thr Leu Leu Asn Leu Asp
            900                 905                 910

Pro Glu Asn Val Val Phe Tyr Val Gly Gly Tyr Pro Pro Asp Phe Lys
            915                 920                 925

Leu Pro Ser Arg Leu Ser Phe Pro Pro Tyr Lys Gly Cys Ile Glu Leu
            930                 935                 940

Asp Asp Leu Asn Glu Asn Val Leu Ser Leu Tyr Asn Phe Lys Lys Thr
945                 950                 955                 960

Phe Asn Leu Asn Thr Thr Glu Val Glu Pro Cys Arg Arg Lys Glu
            965                 970                 975

Glu Ser Asp Lys Asn Tyr Phe Glu Gly Thr Gly Tyr Ala Arg Val Pro
            980                 985                 990

Thr Gln Pro His Ala Pro Ile Pro Thr Phe Gly Gln Thr Ile Gln Thr
            995                 1000                1005

Thr Val Asp Arg Gly Leu Leu Phe Phe Ala Glu Asn Gly Asp Arg Phe
     1010                1015                1020

Ile Ser Leu Asn Ile Glu Asp Gly Lys Leu Met Val Arg Tyr Lys Leu
1025                1030                1035                1040

Asn Ser Glu Leu Pro Lys Glu Arg Gly Val Gly Asp Ala Ile Asn Asn
                1045                1050                1055

Gly Arg Asp His Ser Ile Gln Ile Lys Ile Gly Lys Leu Gln Lys Arg
```

-continued

```
                 1060               1065               1070
Met Trp Ile Asn Val Asp Val Gln Asn Thr Ile Ile Asp Gly Glu Val
        1075               1080               1085
Phe Asp Phe Ser Thr Tyr Tyr Leu Gly Gly Ile Pro Ile Ala Ile Arg
1090               1095               1100
Glu Arg Phe Asn Ile Ser Thr Pro Ala Phe Arg Gly Cys Met Lys Asn
1105               1110               1115               1120
Leu Lys Lys Thr Ser Gly Val Val Arg Leu Asn Asp Thr Val Gly Val
           1125               1130               1135
Thr Lys Lys Cys Ser Glu Asp Trp Lys Leu Val Arg Ser Ala Ser Phe
           1140               1145               1150
Ser Arg Gly Gly Gln Leu Ser Phe Thr Asp Leu Gly Leu Pro Pro Thr
           1155               1160               1165
Asp His Leu Gln Ala Ser Phe Gly Phe Gln Thr Phe Gln Pro Ser Gly
        1170               1175               1180
Ile Leu Leu Asp His Gln Thr Trp Thr Arg Asn Leu Gln Val Thr Leu
1185               1190               1195               1200
Glu Asp Gly Tyr Ile Glu Leu Ser Thr Ser Asp Ser Gly Gly Pro Ile
           1205               1210               1215
Phe Lys Ser Pro Gln Thr Tyr Met Asp Gly Leu Leu His Tyr Val Ser
           1220               1225               1230
Val Ile Ser Asp Asn Ser Gly Leu Arg Leu Leu Ile Asp Asp Gln Leu
        1235               1240               1245
Leu Arg Asn Ser Lys Arg Leu Lys His Ile Ser Ser Ser Arg Gln Ser
   1250               1255               1260
Leu Arg Leu Gly Gly Ser Asn Phe Glu Gly Cys Ile Ser Asn Val Phe
1265               1270               1275               1280
Val Gln Arg Leu Ser Leu Ser Pro Glu Val Leu Asp Leu Thr Ser Asn
           1285               1290               1295
Ser Leu Lys Arg Asp Val Ser Leu Gly Gly Cys Ser Leu Asn Lys Pro
           1300               1305               1310
Pro Phe Leu Met Leu Leu Lys Gly Ser Thr Arg Phe Asn Lys Thr Lys
           1315               1320               1325
Thr Phe Arg Ile Asn Gln Leu Leu Gln Asp Thr Pro Val Ala Ser Pro
   1330               1335               1340
Arg Ser Val Lys Val Trp Gln Asp Ala Cys Ser Pro Leu Pro Lys Thr
   1345               1350               1355               1360
Gln Ala Asn His Gly Ala Leu Gln Phe Gly Asp Ile Pro Thr Ser His
           1365               1370               1375
Leu Leu Phe Lys Leu Pro Gln Glu Leu Leu Lys Pro Arg Ser Gln Phe
           1380               1385               1390
Ala Val Asp Met Gln Thr Thr Ser Ser Arg Gly Leu Val Phe His Thr
        1395               1400               1405
Gly Thr Lys Asn Ser Phe Met Ala Leu Tyr Leu Ser Lys Gly Arg Leu
   1410               1415               1420
Val Phe Ala Leu Gly Thr Asp Gly Lys Lys Leu Arg Ile Lys Ser Lys
1425               1430               1435               1440
Glu Lys Cys Asn Asp Gly Lys Trp His Thr Val Val Phe Gly His Asp
           1445               1450               1455
Gly Glu Lys Gly Arg Leu Val Val Asp Gly Leu Arg Ala Arg Glu Gly
           1460               1465               1470
Ser Leu Pro Gly Asn Ser Thr Ile Ser Ile Arg Ala Pro Val Tyr Leu
   1475               1480               1485
```

```
Gly Ser Pro Pro Ser Gly Lys Pro Lys Ser Leu Pro Thr Asn Ser Phe
    1490                1495                1500

Val Gly Cys Leu Lys Asn Phe Gln Leu Asp Ser Lys Pro Leu Tyr Thr
1505                1510                1515                1520

Pro Ser Ser Ser Phe Gly Val Ser Cys Leu Gly Gly Pro Leu Glu
                1525                1530                1535

Lys Gly Ile Tyr Phe Ser Glu Glu Gly Gly His Val Leu Ala His
            1540                1545                1550

Ser Val Leu Leu Gly Pro Glu Phe Lys Leu Val Phe Ser Ile Arg Pro
        1555                1560                1565

Arg Ser Leu Thr Gly Ile Leu Ile His Ile Gly Ser Gln Pro Gly Lys
    1570                1575                1580

His Leu Cys Val Tyr Leu Glu Ala Gly Lys Val Thr Ala Ser Met Asp
1585                1590                1595                1600

Ser Gly Ala Gly Gly Thr Ser Thr Ser Val Thr Pro Lys Gln Ser Leu
                1605                1610                1615

Cys Asp Gly Gln Trp His Ser Val Ala Val Thr Ile Lys Gln His Ile
            1620                1625                1630

Leu His Leu Glu Leu Asp Thr Asp Ser Ser Tyr Thr Ala Gly Gln Ile
            1635                1640                1645

Pro Phe Pro Pro Ala Ser Thr Gln Glu Pro Leu His Leu Gly Gly Ala
    1650                1655                1660

Pro Ala Asn Leu Thr Thr Leu Arg Ile Pro Val Trp Lys Ser Phe Phe
1665                1670                1675                1680

Gly Cys Leu Arg Asn Ile His Val Asn His Ile Pro Val Pro Val Thr
                1685                1690                1695

Glu Ala Leu Glu Val Gln Gly Pro Val Ser Leu Asn Gly Cys Pro Asp
        1700                1705                1710

Gln

<210> SEQ ID NO 7
<211> LENGTH: 5373
<212> TYPE: DNA
<213> ORGANISM: Homo sapiens
<220> FEATURE:
<221> NAME/KEY: CDS
<222> LOCATION: (1)..(5079)

<400> SEQUENCE: 7 cag caa agg gtg cca ttt ctt cag cct ccc ggt caa agt caa ctg caa     48
Gln Gln Arg Val Pro Phe Leu Gln Pro Pro Gly Gln Ser Gln Leu Gln
 1               5                  10                  15 gcg agt tat gtg gag ttt aga ccc agc cag ggt tgt agc cct gga tac     96
Ala Ser Tyr Val Glu Phe Arg Pro Ser Gln Gly Cys Ser Pro Gly Tyr
            20                  25                  30 tat cgg gat cat aaa ggc ttg tat acc gga cgg tgt gtt ccc tgc aat    144
Tyr Arg Asp His Lys Gly Leu Tyr Thr Gly Arg Cys Val Pro Cys Asn
        35                  40                  45 tgc aac gga cat tca aat caa tgc cag gat ggc tca ggc ata tgt gtt    192
Cys Asn Gly His Ser Asn Gln Cys Gln Asp Gly Ser Gly Ile Cys Val
    50                  55                  60 aac tgt cag cac aac acc gcg gga gag cac tgt gaa cgc tgc cag gag    240
Asn Cys Gln His Asn Thr Ala Gly Glu His Cys Glu Arg Cys Gln Glu
65                  70                  75                  80 ggc tac tat ggc aac gcc gtc cac gga tcc tgc agg gcc tgc cca tgt    288
Gly Tyr Tyr Gly Asn Ala Val His Gly Ser Cys Arg Ala Cys Pro Cys
                85                  90                  95
```

```
cct cac act aac agc ttt gcc act ggc tgt gtg gtg aat ggg gga gac      336
Pro His Thr Asn Ser Phe Ala Thr Gly Cys Val Val Asn Gly Gly Asp
            100                 105                 110 gtg cgg tgc tcc tgc aaa gct ggg tac aca gga aca cag tgt gaa agg      384
Val Arg Cys Ser Cys Lys Ala Gly Tyr Thr Gly Thr Gln Cys Glu Arg
                115                 120                 125 tgt gca ccg gga tat ttc ggg aat ccc cag aaa ttc gga ggt agc tgc      432
Cys Ala Pro Gly Tyr Phe Gly Asn Pro Gln Lys Phe Gly Gly Ser Cys
    130                 135                 140 caa cca tgc agt tgt aac agc aat ggc cag ctg ggc agc tgt cat ccc      480
Gln Pro Cys Ser Cys Asn Ser Asn Gly Gln Leu Gly Ser Cys His Pro
145                 150                 155                 160 ctg act gga gac tgc ata aac caa gaa ccc aaa gat agc agc cct gca      528
Leu Thr Gly Asp Cys Ile Asn Gln Glu Pro Lys Asp Ser Ser Pro Ala
                165                 170                 175 gaa gaa tgt gat gat tgc gac agc tgt gtg atg acc ctc ctg aac gac      576
Glu Glu Cys Asp Asp Cys Asp Ser Cys Val Met Thr Leu Leu Asn Asp
                180                 185                 190 ctg gcc acc atg ggc gag cag ctc cgc ctg gtc aag tct cag ctg cag      624
Leu Ala Thr Met Gly Glu Gln Leu Arg Leu Val Lys Ser Gln Leu Gln
        195                 200                 205 ggc ctg agt gcc agc gca ggg ctt ctg gag cag atg agg cac atg gag      672
Gly Leu Ser Ala Ser Ala Gly Leu Leu Glu Gln Met Arg His Met Glu
210                 215                 220 acc cag gcc aag gac ctg agg aat cag ttg ctc aac tac cgt tct gcc      720
Thr Gln Ala Lys Asp Leu Arg Asn Gln Leu Leu Asn Tyr Arg Ser Ala
225                 230                 235                 240 att tca aat cat gga tca aaa ata gaa ggc ctg gaa aga gaa ctg act      768
Ile Ser Asn His Gly Ser Lys Ile Glu Gly Leu Glu Arg Glu Leu Thr
                245                 250                 255 gat ttg aat caa gaa ttt gag act ttg caa gaa aag gct caa gta aat      816
Asp Leu Asn Gln Glu Phe Glu Thr Leu Gln Glu Lys Ala Gln Val Asn
            260                 265                 270 tcc aga aaa gca caa aca tta aac aac aat gtt aat cgg gca aca caa      864
Ser Arg Lys Ala Gln Thr Leu Asn Asn Asn Val Asn Arg Ala Thr Gln
        275                 280                 285 agc gca aaa gaa ctg gat gtg aag att aaa aat gtc atc cgg aat gtg      912
Ser Ala Lys Glu Leu Asp Val Lys Ile Lys Asn Val Ile Arg Asn Val
290                 295                 300 cac att ctt tta aag cag atc tct ggg aca gat gga gag gga aac aac      960
His Ile Leu Leu Lys Gln Ile Ser Gly Thr Asp Gly Glu Gly Asn Asn
305                 310                 315                 320 gtg cct tca ggt gac ttt tcc aga gag tgg gct gaa gcc cag cgc atg     1008
Val Pro Ser Gly Asp Phe Ser Arg Glu Trp Ala Glu Ala Gln Arg Met
                325                 330                 335 atg agg gaa ctg cgg aac agg aac ttt gga aag cac ctc aga gaa gca     1056
Met Arg Glu Leu Arg Asn Arg Asn Phe Gly Lys His Leu Arg Glu Ala
            340                 345                 350 gaa gct gat aaa agg gag tcg cag ctc ttg ctg aac cgg ata agg acc     1104
Glu Ala Asp Lys Arg Glu Ser Gln Leu Leu Leu Asn Arg Ile Arg Thr
        355                 360                 365 tgg cag aaa acc cac cag ggg gag aac aat ggg ctt gct aac agt atc     1152
Trp Gln Lys Thr His Gln Gly Glu Asn Asn Gly Leu Ala Asn Ser Ile
370                 375                 380 cgg gat tct tta aat gaa tac gaa gcc aaa ctc agt gac ctt cgt gct     1200
Arg Asp Ser Leu Asn Glu Tyr Glu Ala Lys Leu Ser Asp Leu Arg Ala
385                 390                 395                 400 cgg ctg cag gag gca gct gcc caa gcc aag cag gca aat ggc ttg aac     1248
Arg Leu Gln Glu Ala Ala Ala Gln Ala Lys Gln Ala Asn Gly Leu Asn
```

-continued

```
                        405                      410                      415
caa gaa aac gag aga gct ttg gga gcc att cag aga caa gtg aaa gaa       1296
Gln Glu Asn Glu Arg Ala Leu Gly Ala Ile Gln Arg Gln Val Lys Glu
                420                      425                      430 ata aat tcc ctg cag agt gat ttc acc aag tat cta acc act gca gac       1344
Ile Asn Ser Leu Gln Ser Asp Phe Thr Lys Tyr Leu Thr Thr Ala Asp
            435                      440                      445 tca tct ttg ttg caa acc aac att gcg ctg cag ctg atg gag aaa agc       1392
Ser Ser Leu Leu Gln Thr Asn Ile Ala Leu Gln Leu Met Glu Lys Ser
        450                      455                      460 cag aag gaa tat gaa aaa tta gct gcc agt tta aat gaa gca aga caa       1440
Gln Lys Glu Tyr Glu Lys Leu Ala Ala Ser Leu Asn Glu Ala Arg Gln
465                      470                      475                      480 gaa cta agt gac aaa gta aga gaa ctt tcc aga tct gct ggc aaa aca       1488
Glu Leu Ser Asp Lys Val Arg Glu Leu Ser Arg Ser Ala Gly Lys Thr
                485                      490                      495 tcc ctt gtg gag gag gca gaa aag cac gcg cgg tcc tta caa gag ctg       1536
Ser Leu Val Glu Glu Ala Glu Lys His Ala Arg Ser Leu Gln Glu Leu
            500                      505                      510 gca aag cag ctg gaa gag atc aag aga aac gcc agc ggg gat gag ctg       1584
Ala Lys Gln Leu Glu Glu Ile Lys Arg Asn Ala Ser Gly Asp Glu Leu
        515                      520                      525 gtg cgc tgt gct gtg gat gcc gcc acc gcc tac gag aac atc ctc aat       1632
Val Arg Cys Ala Val Asp Ala Ala Thr Ala Tyr Glu Asn Ile Leu Asn
530                      535                      540 gcc atc aaa gcg gcc gag gac gca gcc aac agg gct gcc agt gca tct       1680
Ala Ile Lys Ala Ala Glu Asp Ala Ala Asn Arg Ala Ala Ser Ala Ser
545                      550                      555                      560 gaa tct gcc ctc cag aca gtg ata aag gaa gat ctg cca aga aaa gct       1728
Glu Ser Ala Leu Gln Thr Val Ile Lys Glu Asp Leu Pro Arg Lys Ala
                565                      570                      575 aaa acc ctg agt tcc aac agt gat aaa ctg tta aat gaa gcc aag atg       1776
Lys Thr Leu Ser Ser Asn Ser Asp Lys Leu Leu Asn Glu Ala Lys Met
            580                      585                      590 aca caa aag aag cta aag caa gaa gtc agt cca gct ctc aac aac cta       1824
Thr Gln Lys Lys Leu Lys Gln Glu Val Ser Pro Ala Leu Asn Asn Leu
        595                      600                      605 cag caa acc ctg aat att gtg aca gtt cag aaa gaa gtg ata gac acc       1872
Gln Gln Thr Leu Asn Ile Val Thr Val Gln Lys Glu Val Ile Asp Thr
    610                      615                      620 aat ctc aca act ctc cga gat ggt ctt cat ggg ata cag aga ggt gat       1920
Asn Leu Thr Thr Leu Arg Asp Gly Leu His Gly Ile Gln Arg Gly Asp
625                      630                      635                      640 att gat gct atg atc agt agt gca aag agc atg gtc aga aag gcc aac       1968
Ile Asp Ala Met Ile Ser Ser Ala Lys Ser Met Val Arg Lys Ala Asn
                645                      650                      655 gac atc aca gat gag gtt ctg gat ggg ctc aac ccc atc cag aca gat       2016
Asp Ile Thr Asp Glu Val Leu Asp Gly Leu Asn Pro Ile Gln Thr Asp
            660                      665                      670 gtg gaa aga att aag gac acc tat ggg agg aca cag aac gaa gac ttc       2064
Val Glu Arg Ile Lys Asp Thr Tyr Gly Arg Thr Gln Asn Glu Asp Phe
        675                      680                      685 aaa aag gct ctg act gat gca gat aac tcg gtg aat aag tta acc aac       2112
Lys Lys Ala Leu Thr Asp Ala Asp Asn Ser Val Asn Lys Leu Thr Asn
    690                      695                      700 aaa cta cct gat ctt tgg cgc aag att gaa agt atc aac caa cag ctg       2160
Lys Leu Pro Asp Leu Trp Arg Lys Ile Glu Ser Ile Asn Gln Gln Leu
705                      710                      715                      720 ttg ccc ttg gga aac atc tct gac aac atg gac aga ata cga gaa cta       2208
```

-continued

```
                Leu Pro Leu Gly Asn Ile Ser Asp Asn Met Asp Arg Ile Arg Glu Leu
                                725                 730                 735 att cag cag gcc aga gat gct gcc agt aag gtt gct gtc ccc atg agg       2256
Ile Gln Gln Ala Arg Asp Ala Ala Ser Lys Val Ala Val Pro Met Arg
            740                 745                 750 ttc aat ggt aaa tct gga gtc gaa gtc cga ctg cca aat gac ctg gaa       2304
Phe Asn Gly Lys Ser Gly Val Glu Val Arg Leu Pro Asn Asp Leu Glu
            755                 760                 765 gat ttg aaa gga tat aca tct ctg tcc ttg ttt ctc caa agg ccc aac       2352
Asp Leu Lys Gly Tyr Thr Ser Leu Ser Leu Phe Leu Gln Arg Pro Asn
770                 775                 780 tca aga gaa aat ggg ggt act gag aat atg ttt gtg atg tac ctt gga       2400
Ser Arg Glu Asn Gly Gly Thr Glu Asn Met Phe Val Met Tyr Leu Gly
785                 790                 795                 800 aat aaa gat gcc tcc cgg gac tac atc ggc atg gca gtt gtg gat ggc       2448
Asn Lys Asp Ala Ser Arg Asp Tyr Ile Gly Met Ala Val Val Asp Gly
                805                 810                 815 cag ctc acc tgt gtc tac aac ctg ggg gac cgt gag gct gaa ctc caa       2496
Gln Leu Thr Cys Val Tyr Asn Leu Gly Asp Arg Glu Ala Glu Leu Gln
            820                 825                 830 gtg gac cag atc ttg acc aag agt gag act aag gag gca gtt atg gat       2544
Val Asp Gln Ile Leu Thr Lys Ser Glu Thr Lys Glu Ala Val Met Asp
            835                 840                 845 cgg gtg aaa ttt cag aga att tat cag ttt gca agg ctt aat tac acc       2592
Arg Val Lys Phe Gln Arg Ile Tyr Gln Phe Ala Arg Leu Asn Tyr Thr
850                 855                 860 aaa gga gcc aca tcc agt aaa cca gaa aca ccc gga gtc tat gac atg       2640
Lys Gly Ala Thr Ser Ser Lys Pro Glu Thr Pro Gly Val Tyr Asp Met
865                 870                 875                 880 gat ggt aga aat agc aat aca ctc ctt aat ttg gat cct gaa aat gtt       2688
Asp Gly Arg Asn Ser Asn Thr Leu Leu Asn Leu Asp Pro Glu Asn Val
                885                 890                 895 gta ttt tat gtt gga ggt tac cca cct gat ttt aaa ctt ccc agt cga       2736
Val Phe Tyr Val Gly Gly Tyr Pro Pro Asp Phe Lys Leu Pro Ser Arg
            900                 905                 910 cta agt ttc cct cca tac aaa ggt tgt att gaa tta gat gac ctc aat       2784
Leu Ser Phe Pro Pro Tyr Lys Gly Cys Ile Glu Leu Asp Asp Leu Asn
            915                 920                 925 gaa aat gtt ctg agc ttg tac aac ttc aaa aaa aca ttc aat ctc aac       2832
Glu Asn Val Leu Ser Leu Tyr Asn Phe Lys Lys Thr Phe Asn Leu Asn
930                 935                 940 aca act gaa gtg gag cct tgt aga agg agg aag gaa gag tca gac aaa       2880
Thr Thr Glu Val Glu Pro Cys Arg Arg Arg Lys Glu Glu Ser Asp Lys
945                 950                 955                 960 aat tat ttt gaa ggt acg ggc tat gct cga gtt cca act caa cca cat       2928
Asn Tyr Phe Glu Gly Thr Gly Tyr Ala Arg Val Pro Thr Gln Pro His
                965                 970                 975 gct ccc atc cca acc ttt gga cag aca att cag acc acc gtg gat aga       2976
Ala Pro Ile Pro Thr Phe Gly Gln Thr Ile Gln Thr Thr Val Asp Arg
            980                 985                 990 ggc ttg ctg ttc ttt gca gaa aac ggg gat cgc ttc ata tct cta aat       3024
Gly Leu Leu Phe Phe Ala Glu Asn Gly Asp Arg Phe Ile Ser Leu Asn
            995                 1000                1005 ata gaa gat ggc aag ctc atg gtg aga tac aaa ctg aat tca gag cta       3072
Ile Glu Asp Gly Lys Leu Met Val Arg Tyr Lys Leu Asn Ser Glu Leu
        1010                1015                1020 cca aaa gag aga gga gtt gga gac gcc ata aac aac ggc aga gac cat       3120
Pro Lys Glu Arg Gly Val Gly Asp Ala Ile Asn Asn Gly Arg Asp His
1025                1030                1035                1040
```

```
tcg att cag atc aaa att gga aaa ctc caa aag cgt atg tgg ata aat    3168
Ser Ile Gln Ile Lys Ile Gly Lys Leu Gln Lys Arg Met Trp Ile Asn
        1045                1050                1055 gtg gac gtt caa aac act ata att gat ggt gaa gta ttt gat ttc agc    3216
Val Asp Val Gln Asn Thr Ile Ile Asp Gly Glu Val Phe Asp Phe Ser
    1060                1065                1070 aca tat tat ctg gga gga att cca att gca atc agg gaa aga ttt aac    3264
Thr Tyr Tyr Leu Gly Gly Ile Pro Ile Ala Ile Arg Glu Arg Phe Asn
        1075                1080                1085 att tct acg cct gct ttc cga ggc tgc atg aaa aat ttg aag aaa acc    3312
Ile Ser Thr Pro Ala Phe Arg Gly Cys Met Lys Asn Leu Lys Lys Thr
    1090                1095                1100 agt ggt gtc gtt aga ttg aat gat act gtg gga gta acc aaa aag tgc    3360
Ser Gly Val Val Arg Leu Asn Asp Thr Val Gly Val Thr Lys Lys Cys
1105                1110                1115                1120 tcg gaa gac tgg aag ctt gtg cga tct gcc tca ttc tcc aga gga gga    3408
Ser Glu Asp Trp Lys Leu Val Arg Ser Ala Ser Phe Ser Arg Gly Gly
        1125                1130                1135 caa ttg agt ttc act gat ttg ggc tta cca cct act gac cac ctc cag    3456
Gln Leu Ser Phe Thr Asp Leu Gly Leu Pro Pro Thr Asp His Leu Gln
    1140                1145                1150 gcc tca ttt gga ttt cag acc ttt caa ccc agt ggc ata tta tta gat    3504
Ala Ser Phe Gly Phe Gln Thr Phe Gln Pro Ser Gly Ile Leu Leu Asp
        1155                1160                1165 cat cag aca tgg aca agg aac ctg cag gtc act ctg gaa gat ggt tac    3552
His Gln Thr Trp Thr Arg Asn Leu Gln Val Thr Leu Glu Asp Gly Tyr
    1170                1175                1180 att gaa ttg agc acc agc gat agc ggc ggc cca att ttt aaa tct cca    3600
Ile Glu Leu Ser Thr Ser Asp Ser Gly Gly Pro Ile Phe Lys Ser Pro
1185                1190                1195                1200 cag acg tat atg gat ggt tta ctg cat tat gta tct gta ata agc gac    3648
Gln Thr Tyr Met Asp Gly Leu Leu His Tyr Val Ser Val Ile Ser Asp
        1205                1210                1215 aac tct gga cta cgg ctt ctc atc gat gac cag ctt ctg aga aat agc    3696
Asn Ser Gly Leu Arg Leu Leu Ile Asp Asp Gln Leu Leu Arg Asn Ser
    1220                1225                1230 aaa agg cta aaa cac att tca agt tcc cgg cag tct ctg cgt ctg ggc    3744
Lys Arg Leu Lys His Ile Ser Ser Ser Arg Gln Ser Leu Arg Leu Gly
        1235                1240                1245 ggg agc aat ttt gag ggt tgt att agc aat gtt ttt gtc cag agg tta    3792
Gly Ser Asn Phe Glu Gly Cys Ile Ser Asn Val Phe Val Gln Arg Leu
    1250                1255                1260 tca ctg agt cct gaa gtc cta gat ttg acc agt aac tct ctc aag aga    3840
Ser Leu Ser Pro Glu Val Leu Asp Leu Thr Ser Asn Ser Leu Lys Arg
1265                1270                1275                1280 gat gtg tcc ctg gga ggc tgc agt tta aac aaa cca cct ttt cta atg    3888
Asp Val Ser Leu Gly Gly Cys Ser Leu Asn Lys Pro Pro Phe Leu Met
        1285                1290                1295 ttg ctt aaa ggt tct acc agg ttt aac aag acc aag act ttt cgt atc    3936
Leu Leu Lys Gly Ser Thr Arg Phe Asn Lys Thr Lys Thr Phe Arg Ile
        1300                1305                1310 aac cag ctg ttg cag gac aca cca gtg gcc tcc cca agg agc gtg aag    3984
Asn Gln Leu Leu Gln Asp Thr Pro Val Ala Ser Pro Arg Ser Val Lys
    1315                1320                1325 gtg tgg caa gat gct tgc tca cca ctt ccc aag acc cag gcc aat cat    4032
Val Trp Gln Asp Ala Cys Ser Pro Leu Pro Lys Thr Gln Ala Asn His
1330                1335                1340 gga gcc ctc cag ttt ggg gac att ccc acc agc cac ttg cta ttc aag    4080
Gly Ala Leu Gln Phe Gly Asp Ile Pro Thr Ser His Leu Leu Phe Lys
1345                1350                1355                1360
```

-continued

```
ctt cct cag gag ctg ctg aaa ccc agg tca cag ttt gct gtg gac atg      4128
Leu Pro Gln Glu Leu Leu Lys Pro Arg Ser Gln Phe Ala Val Asp Met
            1365                1370                1375 cag aca aca tcc tcc aga gga ctg gtg ttt cac acg ggc act aag aac      4176
Gln Thr Thr Ser Ser Arg Gly Leu Val Phe His Thr Gly Thr Lys Asn
        1380                1385                1390 tcc ttt atg gct ctt tat ctt tca aaa gga cgt ctg gtc ttt gca ctg      4224
Ser Phe Met Ala Leu Tyr Leu Ser Lys Gly Arg Leu Val Phe Ala Leu
    1395                1400                1405 ggg aca gat ggg aaa aaa ttg agg atc aaa agc aag gag aaa tgc aat      4272
Gly Thr Asp Gly Lys Lys Leu Arg Ile Lys Ser Lys Glu Lys Cys Asn
1410                1415                1420 gat ggg aaa tgg cac acg gtg gtg ttt ggc cat gat ggg gaa aag ggg      4320
Asp Gly Lys Trp His Thr Val Val Phe Gly His Asp Gly Glu Lys Gly
1425                1430                1435                1440 cgc ttg gtt gtg gat gga ctg agg gcc cgg gag gga agt ttg cct gga      4368
Arg Leu Val Val Asp Gly Leu Arg Ala Arg Glu Gly Ser Leu Pro Gly
                1445                1450                1455 aac tcc acc atc agc atc aga gcg cca gtt tac ctg gga tca cct cca      4416
Asn Ser Thr Ile Ser Ile Arg Ala Pro Val Tyr Leu Gly Ser Pro Pro
            1460                1465                1470 tca ggg aaa cca aag agc ctc ccc aca aac agc ttt gtg gga tgc ctg      4464
Ser Gly Lys Pro Lys Ser Leu Pro Thr Asn Ser Phe Val Gly Cys Leu
        1475                1480                1485 aag aac ttt cag ctg gat tca aaa ccc ttg tat acc cct tct tca agc      4512
Lys Asn Phe Gln Leu Asp Ser Lys Pro Leu Tyr Thr Pro Ser Ser Ser
    1490                1495                1500 ttc ggg gtg tct tcc tgc ttg ggt ggt cct ttg gag aaa ggc att tat      4560
Phe Gly Val Ser Ser Cys Leu Gly Gly Pro Leu Glu Lys Gly Ile Tyr
1505                1510                1515                1520 ttc tct gaa gaa gga ggt cat gtc gtc ttg gct cac tct gta ttg ttg      4608
Phe Ser Glu Glu Gly Gly His Val Val Leu Ala His Ser Val Leu Leu
                1525                1530                1535 ggg cca gaa ttt aag ctt gtt ttc agc atc cgc cca aga agt ctc act      4656
Gly Pro Glu Phe Lys Leu Val Phe Ser Ile Arg Pro Arg Ser Leu Thr
            1540                1545                1550 ggg atc cta ata cac atc gga agt cag ccc ggg aag cac tta tgt gtt      4704
Gly Ile Leu Ile His Ile Gly Ser Gln Pro Gly Lys His Leu Cys Val
        1555                1560                1565 tac ctg gag gca gga aag gtc acg gcc tct atg gac agt ggg gca ggt      4752
Tyr Leu Glu Ala Gly Lys Val Thr Ala Ser Met Asp Ser Gly Ala Gly
    1570                1575                1580 ggg acc tca acg tcg gtc aca cca aag cag tct ctg tgt gat gga cag      4800
Gly Thr Ser Thr Ser Val Thr Pro Lys Gln Ser Leu Cys Asp Gly Gln
1585                1590                1595                1600 tgg cac tcg gtg gca gtc acc ata aaa caa cac atc ctg cac ctg gaa      4848
Trp His Ser Val Ala Val Thr Ile Lys Gln His Ile Leu His Leu Glu
                1605                1610                1615 ctg gac aca gac agt agc tac aca gct gga cag atc ccc ttc cca cct      4896
Leu Asp Thr Asp Ser Ser Tyr Thr Ala Gly Gln Ile Pro Phe Pro Pro
            1620                1625                1630 gcc agc act caa gag cca cta cac ctt gga ggt gct cca gcc aat ttg      4944
Ala Ser Thr Gln Glu Pro Leu His Leu Gly Gly Ala Pro Ala Asn Leu
        1635                1640                1645 acg aca ctg agg atc cct gtg tgg aaa tca ttc ttt ggc tgt ctg agg      4992
Thr Thr Leu Arg Ile Pro Val Trp Lys Ser Phe Phe Gly Cys Leu Arg
    1650                1655                1660 aat att cat gtc aat cac atc cct gtc cct gtc act gaa gcc ttg gaa      5040
Asn Ile His Val Asn His Ile Pro Val Pro Val Thr Glu Ala Leu Glu
```

```
                    1665            1670           1675           1680
gtc cag ggg cct gtc agt ctg aat ggt tgt cct gac cag taacccaagc                5089
Val Gln Gly Pro Val Ser Leu Asn Gly Cys Pro Asp Gln
                1685           1690 ctatttcaca gcaaggaaat tcaccttcaa agcactgat  tacccaatgc acctccctcc            5149
ccagctcgag atcattcttc aattaggaca caaaccagag aggtttaata gcgaatctaa            5209
ttttgaattc tgaccatgga tacccatcac tttggcattc agtgctacat gtgtattta             5269 tataaaaatc ccatttcttg aagataaaaa aattgttatt caaattgtta tgcacagaat            5329 gttttggta atattaattt ccactaaaaa attaaatgtc tttt                              5373
```

<210> SEQ ID NO 8
<211> LENGTH: 1693
<212> TYPE: PRT
<213> ORGANISM: Homo sapiens

<400> SEQUENCE: 8

```
Gln Gln Arg Val Pro Phe Leu Gln Pro Pro Gly Gln Ser Gln Leu Gln
  1               5                  10                  15

Ala Ser Tyr Val Glu Phe Arg Pro Ser Gln Gly Cys Ser Pro Gly Tyr
             20                  25                  30

Tyr Arg Asp His Lys Gly Leu Tyr Thr Gly Arg Cys Val Pro Cys Asn
         35                  40                  45

Cys Asn Gly His Ser Asn Gln Cys Gln Asp Gly Ser Gly Ile Cys Val
     50                  55                  60

Asn Cys Gln His Asn Thr Ala Gly Glu His Cys Glu Arg Cys Gln Glu
 65                  70                  75                  80

Gly Tyr Tyr Gly Asn Ala Val His Gly Ser Cys Arg Ala Cys Pro Cys
                 85                  90                  95

Pro His Thr Asn Ser Phe Ala Thr Gly Cys Val Val Asn Gly Gly Asp
            100                 105                 110

Val Arg Cys Ser Cys Lys Ala Gly Tyr Thr Gly Thr Gln Cys Glu Arg
        115                 120                 125

Cys Ala Pro Gly Tyr Phe Gly Asn Pro Gln Lys Phe Gly Gly Ser Cys
    130                 135                 140

Gln Pro Cys Ser Cys Asn Ser Asn Gly Gln Leu Gly Ser Cys His Pro
145                 150                 155                 160

Leu Thr Gly Asp Cys Ile Asn Gln Glu Pro Lys Asp Ser Ser Pro Ala
                165                 170                 175

Glu Glu Cys Asp Asp Cys Asp Ser Cys Val Met Thr Leu Leu Asn Asp
            180                 185                 190

Leu Ala Thr Met Gly Glu Gln Leu Arg Leu Val Lys Ser Gln Leu Gln
        195                 200                 205

Gly Leu Ser Ala Ser Ala Gly Leu Leu Glu Gln Met Arg His Met Glu
    210                 215                 220

Thr Gln Ala Lys Asp Leu Arg Asn Gln Leu Leu Asn Tyr Arg Ser Ala
225                 230                 235                 240

Ile Ser Asn His Gly Ser Lys Ile Glu Gly Leu Glu Arg Glu Leu Thr
                245                 250                 255

Asp Leu Asn Gln Glu Phe Glu Thr Leu Gln Glu Lys Ala Gln Val Asn
            260                 265                 270

Ser Arg Lys Ala Gln Thr Leu Asn Asn Asn Val Asn Arg Ala Thr Gln
        275                 280                 285

Ser Ala Lys Glu Leu Asp Val Lys Ile Lys Asn Val Ile Arg Asn Val
```

```
            290                 295                 300
His Ile Leu Leu Lys Gln Ile Ser Gly Thr Asp Gly Glu Gly Asn Asn
305                 310                 315                 320
Val Pro Ser Gly Asp Phe Ser Arg Glu Trp Ala Glu Ala Gln Arg Met
                    325                 330                 335
Met Arg Glu Leu Arg Asn Arg Asn Phe Gly Lys His Leu Arg Glu Ala
                340                 345                 350
Glu Ala Asp Lys Arg Glu Ser Gln Leu Leu Leu Asn Arg Ile Arg Thr
            355                 360                 365
Trp Gln Lys Thr His Gln Gly Glu Asn Asn Gly Leu Ala Asn Ser Ile
        370                 375                 380
Arg Asp Ser Leu Asn Glu Tyr Glu Ala Lys Leu Ser Asp Leu Arg Ala
385                 390                 395                 400
Arg Leu Gln Glu Ala Ala Gln Ala Lys Gln Ala Asn Gly Leu Asn
                    405                 410                 415
Gln Glu Asn Glu Arg Ala Leu Gly Ala Ile Gln Arg Gln Val Lys Glu
                420                 425                 430
Ile Asn Ser Leu Gln Ser Asp Phe Thr Lys Tyr Leu Thr Thr Ala Asp
            435                 440                 445
Ser Ser Leu Leu Gln Thr Asn Ile Ala Leu Gln Leu Met Glu Lys Ser
        450                 455                 460
Gln Lys Glu Tyr Glu Lys Leu Ala Ala Ser Leu Asn Glu Ala Arg Gln
465                 470                 475                 480
Glu Leu Ser Asp Lys Val Arg Glu Leu Ser Arg Ser Ala Gly Lys Thr
                    485                 490                 495
Ser Leu Val Glu Glu Ala Glu Lys His Ala Arg Ser Leu Gln Glu Leu
                500                 505                 510
Ala Lys Gln Leu Glu Glu Ile Lys Arg Asn Ala Ser Gly Asp Glu Leu
            515                 520                 525
Val Arg Cys Ala Val Asp Ala Thr Ala Tyr Glu Asn Ile Leu Asn
        530                 535                 540
Ala Ile Lys Ala Ala Glu Asp Ala Ala Asn Arg Ala Ala Ser Ala Ser
545                 550                 555                 560
Glu Ser Ala Leu Gln Thr Val Ile Lys Glu Asp Leu Pro Arg Lys Ala
                    565                 570                 575
Lys Thr Leu Ser Ser Asn Ser Asp Lys Leu Leu Asn Glu Ala Lys Met
                580                 585                 590
Thr Gln Lys Lys Leu Lys Gln Glu Val Ser Pro Ala Leu Asn Asn Leu
            595                 600                 605
Gln Gln Thr Leu Asn Ile Val Thr Val Gln Lys Glu Val Ile Asp Thr
        610                 615                 620
Asn Leu Thr Thr Leu Arg Asp Gly Leu His Gly Ile Gln Arg Gly Asp
625                 630                 635                 640
Ile Asp Ala Met Ile Ser Ser Ala Lys Ser Met Val Arg Lys Ala Asn
                    645                 650                 655
Asp Ile Thr Asp Glu Val Leu Asp Gly Leu Asn Pro Ile Gln Thr Asp
                660                 665                 670
Val Glu Arg Ile Lys Asp Thr Tyr Gly Arg Thr Gln Asn Glu Asp Phe
            675                 680                 685
Lys Lys Ala Leu Thr Asp Ala Asp Asn Ser Val Asn Lys Leu Thr Asn
        690                 695                 700
Lys Leu Pro Asp Leu Trp Arg Lys Ile Glu Ser Ile Asn Gln Gln Leu
705                 710                 715                 720
```

-continued

```
Leu Pro Leu Gly Asn Ile Ser Asp Asn Met Asp Arg Ile Arg Glu Leu
            725                 730                 735
Ile Gln Gln Ala Arg Asp Ala Ala Ser Lys Val Ala Val Pro Met Arg
        740                 745                 750
Phe Asn Gly Lys Ser Gly Val Glu Val Arg Leu Pro Asn Asp Leu Glu
    755                 760                 765
Asp Leu Lys Gly Tyr Thr Ser Leu Ser Leu Phe Leu Gln Arg Pro Asn
770                 775                 780
Ser Arg Glu Asn Gly Gly Thr Glu Asn Met Phe Val Met Tyr Leu Gly
785                 790                 795                 800
Asn Lys Asp Ala Ser Arg Asp Tyr Ile Gly Met Ala Val Val Asp Gly
                805                 810                 815
Gln Leu Thr Cys Val Tyr Asn Leu Gly Asp Arg Glu Ala Glu Leu Gln
            820                 825                 830
Val Asp Gln Ile Leu Thr Lys Ser Glu Thr Lys Glu Ala Val Met Asp
        835                 840                 845
Arg Val Lys Phe Gln Arg Ile Tyr Gln Phe Ala Arg Leu Asn Tyr Thr
    850                 855                 860
Lys Gly Ala Thr Ser Ser Lys Pro Glu Thr Pro Gly Val Tyr Asp Met
865                 870                 875                 880
Asp Gly Arg Asn Ser Asn Thr Leu Leu Asn Leu Asp Pro Glu Asn Val
                885                 890                 895
Val Phe Tyr Val Gly Gly Tyr Pro Pro Asp Phe Lys Leu Pro Ser Arg
            900                 905                 910
Leu Ser Phe Pro Pro Tyr Lys Gly Cys Ile Glu Leu Asp Asp Leu Asn
        915                 920                 925
Glu Asn Val Leu Ser Leu Tyr Asn Phe Lys Lys Thr Phe Asn Leu Asn
    930                 935                 940
Thr Thr Glu Val Glu Pro Cys Arg Arg Lys Glu Glu Ser Asp Lys
945                 950                 955                 960
Asn Tyr Phe Glu Gly Thr Gly Tyr Ala Arg Val Pro Thr Gln Pro His
                965                 970                 975
Ala Pro Ile Pro Thr Phe Gly Gln Thr Ile Gln Thr Thr Val Asp Arg
            980                 985                 990
Gly Leu Leu Phe Phe Ala Glu Asn Gly Asp Arg Phe Ile Ser Leu Asn
        995                 1000                1005
Ile Glu Asp Gly Lys Leu Met Val Arg Tyr Lys Leu Asn Ser Glu Leu
    1010                1015                1020
Pro Lys Glu Arg Gly Val Gly Asp Ala Ile Asn Asn Gly Arg Asp His
1025                1030                1035                1040
Ser Ile Gln Ile Lys Ile Gly Lys Leu Gln Lys Arg Met Trp Ile Asn
                1045                1050                1055
Val Asp Val Gln Asn Thr Ile Ile Asp Gly Glu Val Phe Asp Phe Ser
            1060                1065                1070
Thr Tyr Tyr Leu Gly Gly Ile Pro Ile Ala Ile Arg Glu Arg Phe Asn
        1075                1080                1085
Ile Ser Thr Pro Ala Phe Arg Gly Cys Met Lys Asn Leu Lys Lys Thr
    1090                1095                1100
Ser Gly Val Val Arg Leu Asn Asp Thr Val Gly Val Thr Lys Lys Cys
1105                1110                1115                1120
Ser Glu Asp Trp Lys Leu Val Arg Ser Ala Ser Phe Ser Arg Gly Gly
                1125                1130                1135
```

-continued

```
Gln Leu Ser Phe Thr Asp Leu Gly Leu Pro Pro Thr Asp His Leu Gln
        1140                1145                1150
Ala Ser Phe Gly Phe Gln Thr Phe Gln Pro Ser Gly Ile Leu Leu Asp
    1155                1160                1165
His Gln Thr Trp Thr Arg Asn Leu Gln Val Thr Leu Glu Asp Gly Tyr
1170                1175                1180
Ile Glu Leu Ser Thr Ser Asp Ser Gly Gly Pro Ile Phe Lys Ser Pro
1185                1190                1195                1200
Gln Thr Tyr Met Asp Gly Leu Leu His Tyr Val Ser Val Ile Ser Asp
            1205                1210                1215
Asn Ser Gly Leu Arg Leu Leu Ile Asp Asp Gln Leu Leu Arg Asn Ser
        1220                1225                1230
Lys Arg Leu Lys His Ile Ser Ser Ser Arg Gln Ser Leu Arg Leu Gly
    1235                1240                1245
Gly Ser Asn Phe Glu Gly Cys Ile Ser Asn Val Phe Val Gln Arg Leu
1250                1255                1260
Ser Leu Ser Pro Glu Val Leu Asp Leu Thr Ser Asn Ser Leu Lys Arg
1265                1270                1275                1280
Asp Val Ser Leu Gly Gly Cys Ser Leu Asn Lys Pro Pro Phe Leu Met
            1285                1290                1295
Leu Leu Lys Gly Ser Thr Arg Phe Asn Lys Thr Lys Thr Phe Arg Ile
        1300                1305                1310
Asn Gln Leu Leu Gln Asp Thr Pro Val Ala Ser Pro Arg Ser Val Lys
    1315                1320                1325
Val Trp Gln Asp Ala Cys Ser Pro Leu Pro Lys Thr Gln Ala Asn His
1330                1335                1340
Gly Ala Leu Gln Phe Gly Asp Ile Pro Thr Ser His Leu Leu Phe Lys
1345                1350                1355                1360
Leu Pro Gln Glu Leu Leu Lys Pro Arg Ser Gln Phe Ala Val Asp Met
            1365                1370                1375
Gln Thr Thr Ser Ser Arg Gly Leu Val Phe His Thr Gly Thr Lys Asn
        1380                1385                1390
Ser Phe Met Ala Leu Tyr Leu Ser Lys Gly Arg Leu Val Phe Ala Leu
    1395                1400                1405
Gly Thr Asp Gly Lys Lys Leu Arg Ile Lys Ser Lys Glu Lys Cys Asn
1410                1415                1420
Asp Gly Lys Trp His Thr Val Val Phe Gly His Asp Gly Glu Lys Gly
1425                1430                1435                1440
Arg Leu Val Val Asp Gly Leu Arg Ala Arg Glu Gly Ser Leu Pro Gly
            1445                1450                1455
Asn Ser Thr Ile Ser Ile Arg Ala Pro Val Tyr Leu Gly Ser Pro Pro
        1460                1465                1470
Ser Gly Lys Pro Lys Ser Leu Pro Thr Asn Ser Phe Val Gly Cys Leu
    1475                1480                1485
Lys Asn Phe Gln Leu Asp Ser Lys Pro Leu Tyr Thr Pro Ser Ser Ser
    1490                1495                1500
Phe Gly Val Ser Ser Cys Leu Gly Gly Pro Leu Glu Lys Gly Ile Tyr
1505                1510                1515                1520
Phe Ser Glu Glu Gly Gly His Val Val Leu Ala His Ser Val Leu Leu
            1525                1530                1535
Gly Pro Glu Phe Lys Leu Val Phe Ser Ile Arg Pro Arg Ser Leu Thr
        1540                1545                1550
Gly Ile Leu Ile His Ile Gly Ser Gln Pro Gly Lys His Leu Cys Val
```

-continued

```
              1555                1560                1565
Tyr Leu Glu Ala Gly Lys Val Thr Ala Ser Met Asp Ser Gly Ala Gly
    1570                1575                1580

Gly Thr Ser Thr Ser Val Thr Pro Lys Gln Ser Leu Cys Asp Gly Gln
1585                1590                1595                1600

Trp His Ser Val Ala Val Thr Ile Lys Gln His Ile Leu His Leu Glu
                1605                1610                1615

Leu Asp Thr Asp Ser Ser Tyr Thr Ala Gly Gln Ile Pro Phe Pro Pro
            1620                1625                1630

Ala Ser Thr Gln Glu Pro Leu His Leu Gly Gly Ala Pro Ala Asn Leu
        1635                1640                1645

Thr Thr Leu Arg Ile Pro Val Trp Lys Ser Phe Phe Gly Cys Leu Arg
    1650                1655                1660

Asn Ile His Val Asn His Ile Pro Val Pro Val Thr Glu Ala Leu Glu
1665                1670                1675                1680

Val Gln Gly Pro Val Ser Leu Asn Gly Cys Pro Asp Gln
                1685                1690
```

<210> SEQ ID NO 9
<211> LENGTH: 5264
<212> TYPE: DNA
<213> ORGANISM: Rattus norvegicus
<220> FEATURE:
<221> NAME/KEY: CDS
<222> LOCATION: (59)..(5233)
<221> NAME/KEY: sig_peptide
<222> LOCATION: (59)..(151)

<400> SEQUENCE: 9

```
gtataagagg aagaacacaa aggtttgcag cagccaggca gaacaccaag ggatcaag         58 atg ccg cct aca gtg agg tgg tca gcc tgg tgc aca gga tgg ctg tgg       106
Met Pro Pro Thr Val Arg Trp Ser Ala Trp Cys Thr Gly Trp Leu Trp
  1               5                  10                  15 atc ttt ggg gca gct ctg ggc cag tgc ctg ggg tat ggc tca gag cag       154
Ile Phe Gly Ala Ala Leu Gly Gln Cys Leu Gly Tyr Gly Ser Glu Gln
             20                  25                  30 caa agg gta gca ttt ctt cag cat cca ggg caa aac cat ctg caa gca       202
Gln Arg Val Ala Phe Leu Gln His Pro Gly Gln Asn His Leu Gln Ala
         35                  40                  45 agt tat atg gag ctt aga ccc agc cag ggc tgt cgc cca gga tac tat       250
Ser Tyr Met Glu Leu Arg Pro Ser Gln Gly Cys Arg Pro Gly Tyr Tyr
     50                  55                  60 cga gac atc aaa agc ttc cct gcg gga agg tct gtt ccc tgc aat tgc       298
Arg Asp Ile Lys Ser Phe Pro Ala Gly Arg Ser Val Pro Cys Asn Cys
 65                  70                  75                  80 aac gga cat tca aat aga tgc caa gac ggc tcg gga gtg tgc att aac       346
Asn Gly His Ser Asn Arg Cys Gln Asp Gly Ser Gly Val Cys Ile Asn
                 85                  90                  95 tgt cag cac aac aca gct ggg gag cac tgt gag cgt tgc aag agg ggt       394
Cys Gln His Asn Thr Ala Gly Glu His Cys Glu Arg Cys Lys Arg Gly
            100                 105                 110 tac tat gga agc gcc atc cat gga tcc tgc agg gtt tgc ccc tgt cct       442
Tyr Tyr Gly Ser Ala Ile His Gly Ser Cys Arg Val Cys Pro Cys Pro
        115                 120                 125 cac acc aac agc ttt gcc act ggc tgt gct gtg gat gga gga gct gtg       490
His Thr Asn Ser Phe Ala Thr Gly Cys Ala Val Asp Gly Gly Ala Val
    130                 135                 140 agg tgt gcc tgc aaa ccc gga tac aca gga gca cag tgt gag agg tgt       538
Arg Cys Ala Cys Lys Pro Gly Tyr Thr Gly Ala Gln Cys Glu Arg Cys
```

```
                  145                 150                 155                 160
gca cca gga tat ttt ggg aac ccc cag aaa ttt gga ggt agc tgc caa                586
Ala Pro Gly Tyr Phe Gly Asn Pro Gln Lys Phe Gly Gly Ser Cys Gln
                165                 170                 175 cca tgc aat tgc aac agt aat ggc cag ttt ggc act tgt gat ccc cta                634
Pro Cys Asn Cys Asn Ser Asn Gly Gln Phe Gly Thr Cys Asp Pro Leu
                180                 185                 190 act gga gac tgt gta agc caa gaa ccc aaa gat ggc agc cct gca gaa                682
Thr Gly Asp Cys Val Ser Gln Glu Pro Lys Asp Gly Ser Pro Ala Glu
            195                 200                 205 gaa tgt gat gac tgt gac agc tgt gtg atg act ctc cta aat gac ttg                730
Glu Cys Asp Asp Cys Asp Ser Cys Val Met Thr Leu Leu Asn Asp Leu
        210                 215                 220 gtc ccc atg ggt gag gaa ctc gcc ctg gtg aaa tca aaa ctt cag ggg                778
Val Pro Met Gly Glu Glu Leu Ala Leu Val Lys Ser Lys Leu Gln Gly
225                 230                 235                 240 ctg agt gtg aac act ggt tct ctg gaa cag atc cgg cat gtg gag atg                826
Leu Ser Val Asn Thr Gly Ser Leu Glu Gln Ile Arg His Val Glu Met
                245                 250                 255 cag gcc aag gac ctg agg aac cag ctg ctt ggc ttc cgt tcc gcc atc                874
Gln Ala Lys Asp Leu Arg Asn Gln Leu Leu Gly Phe Arg Ser Ala Ile
            260                 265                 270 tcc agt cac ggg tcc caa atg gac ggc ctg gaa aaa gaa ctc agt cat                922
Ser Ser His Gly Ser Gln Met Asp Gly Leu Glu Lys Glu Leu Ser His
        275                 280                 285 ttg tac cag gaa ttc gaa act ttg caa gaa aag gcg cag gtc aat tcc                970
Leu Tyr Gln Glu Phe Glu Thr Leu Gln Glu Lys Ala Gln Val Asn Ser
    290                 295                 300 aga aaa gca caa aca tta tat aac aac atc gat acg aca atc caa aac               1018
Arg Lys Ala Gln Thr Leu Tyr Asn Asn Ile Asp Thr Thr Ile Gln Asn
305                 310                 315                 320 gcc aaa gag ttg gac atg aag att aaa aac ata ctt acg aat gtg cac               1066
Ala Lys Glu Leu Asp Met Lys Ile Lys Asn Ile Leu Thr Asn Val His
                325                 330                 335 att ctc ctg aag cag atc gct cgg cca ggt gga gaa gga atg gac ttg               1114
Ile Leu Leu Lys Gln Ile Ala Arg Pro Gly Gly Glu Gly Met Asp Leu
            340                 345                 350 ccg gtg ggc gac tgg tcc agg gag tcg gcg gaa gct cag cgc atg ttg               1162
Pro Val Gly Asp Trp Ser Arg Glu Ser Ala Glu Ala Gln Arg Met Leu
        355                 360                 365 cgg gag ctg cga ggc cga gac ttt aaa aag cac ctc caa gaa gca gag               1210
Arg Glu Leu Arg Gly Arg Asp Phe Lys Lys His Leu Gln Glu Ala Glu
    370                 375                 380 gcc cag aaa atg gaa gcc cag ctc tta ctg aac cga atc agg acc tgg               1258
Ala Gln Lys Met Glu Ala Gln Leu Leu Leu Asn Arg Ile Arg Thr Trp
385                 390                 395                 400 ctg gaa tcc cac cag gtg gag aac aat gga ctg cta aag aat att cgg               1306
Leu Glu Ser His Gln Val Glu Asn Asn Gly Leu Leu Lys Asn Ile Arg
                405                 410                 415 gat tca tta aat gat tat gaa gcc aaa ctt cag gac ctg cgt tcc gtg               1354
Asp Ser Leu Asn Asp Tyr Glu Ala Lys Leu Gln Asp Leu Arg Ser Val
            420                 425                 430 ctt cag gag gcg gca gcc cag gga aag cag gct aca ggc ctc aac cac               1402
Leu Gln Glu Ala Ala Ala Gln Gly Lys Gln Ala Thr Gly Leu Asn His
        435                 440                 445 gaa aat gag ggg gtc cta gga gcc atc cag aga caa atg aag gaa atg               1450
Glu Asn Glu Gly Val Leu Gly Ala Ile Gln Arg Gln Met Lys Glu Met
    450                 455                 460 gat tcc ctg aag aag tac ctc acc gag cac ctg gcc aca gca gac gct               1498
```

```
Asp Ser Leu Lys Lys Tyr Leu Thr Glu His Leu Ala Thr Ala Asp Ala
465                 470                 475                 480 tcc ctg ctg caa acc aac agt cta ctg cag cgg atg gac acg agc cag     1546
Ser Leu Leu Gln Thr Asn Ser Leu Leu Gln Arg Met Asp Thr Ser Gln
                    485                 490                 495 aag gag tat gaa agc tta gct gct gct tta aac gga gca aga cag gaa     1594
Lys Glu Tyr Glu Ser Leu Ala Ala Ala Leu Asn Gly Ala Arg Gln Glu
                500                 505                 510 ctg aat gac caa gtg cgg gaa ctc tcc aga tcc gga ggc aaa gca ccc     1642
Leu Asn Asp Gln Val Arg Glu Leu Ser Arg Ser Gly Lys Ala Pro
            515                 520                 525 ctg gtg gct gag gcc gag aag cac gct cag tct tta cag gag ctg gca     1690
Leu Val Ala Glu Ala Glu Lys His Ala Gln Ser Leu Gln Glu Leu Ala
        530                 535                 540 aag cag ctg gaa gag ata aag aga aac acc agt ggg gat gag tcg gtg     1738
Lys Gln Leu Glu Glu Ile Lys Arg Asn Thr Ser Gly Asp Glu Ser Val
545                 550                 555                 560 cgc tgt gtc gtg gac gct gcc act gcc tat gag agc atc ctc aac gcc     1786
Arg Cys Val Val Asp Ala Ala Thr Ala Tyr Glu Ser Ile Leu Asn Ala
                565                 570                 575 atc cga gca gca gag gat gca gcc ggc aag gcc gac agt gcc tca gag     1834
Ile Arg Ala Ala Glu Asp Ala Ala Gly Lys Ala Asp Ser Ala Ser Glu
            580                 585                 590 tcc gcc ttc cag aca gtg ata aag gaa gat ctt ccg aga aga gcc aaa     1882
Ser Ala Phe Gln Thr Val Ile Lys Glu Asp Leu Pro Arg Arg Ala Lys
        595                 600                 605 acc ctg agt tct gac agc gag gaa ctg tta aac gag gcc aag atg aca     1930
Thr Leu Ser Ser Asp Ser Glu Glu Leu Leu Asn Glu Ala Lys Met Thr
610                 615                 620 cgg aaa agg cta cag caa gaa atc aat cca gct ctc aac agc cta cag     1978
Arg Lys Arg Leu Gln Gln Glu Ile Asn Pro Ala Leu Asn Ser Leu Gln
625                 630                 635                 640 caa acc ctg aag act gta tca gtt cag aag gac ctg cta gat gcc aat     2026
Gln Thr Leu Lys Thr Val Ser Val Gln Lys Asp Leu Leu Asp Ala Asn
                645                 650                 655 gtc act gct gtc cgt aat gac ctt cgt ggg atc cag aga ggt gat att     2074
Val Thr Ala Val Arg Asn Asp Leu Arg Gly Ile Gln Arg Gly Asp Ile
            660                 665                 670 gac agt gtg gtg agt gga gcg aag agc atg gtc agg aaa gcc aat ggg     2122
Asp Ser Val Val Ser Gly Ala Lys Ser Met Val Arg Lys Ala Asn Gly
        675                 680                 685 ata acg agc gag gtc ctg gac ggg ctc agc ccc atc cag acg gat ttg     2170
Ile Thr Ser Glu Val Leu Asp Gly Leu Ser Pro Ile Gln Thr Asp Leu
690                 695                 700 gga agg att aag gac agc tac ggg agc aca cgg cat gag gac ttc aac     2218
Gly Arg Ile Lys Asp Ser Tyr Gly Ser Thr Arg His Glu Asp Phe Asn
705                 710                 715                 720 aaa gct ctg att gac gcc aat aac tca gta aag aaa tta acc aag aag     2266
Lys Ala Leu Ile Asp Ala Asn Asn Ser Val Lys Lys Leu Thr Lys Lys
                725                 730                 735 ttg cct gat ctt ttt gtc aag att gaa agc atc aat caa cag ttg ctg     2314
Leu Pro Asp Leu Phe Val Lys Ile Glu Ser Ile Asn Gln Gln Leu Leu
            740                 745                 750 ccc ctg gga aac atc tct gac aat gta gac cga atc cga gag ctc att     2362
Pro Leu Gly Asn Ile Ser Asp Asn Val Asp Arg Ile Arg Glu Leu Ile
        755                 760                 765 acg cag gcc aga gat gct gcg aac aag gtt gca att ccc atg agg ttc     2410
Thr Gln Ala Arg Asp Ala Ala Asn Lys Val Ala Ile Pro Met Arg Phe
770                 775                 780
```

```
aat ggt aaa tct ggt gtt gaa gtc cgt ctg cca aat gac cta gaa gac      2458
Asn Gly Lys Ser Gly Val Glu Val Arg Leu Pro Asn Asp Leu Glu Asp
785                 790                 795                 800 ttg aag gga tac acg tct ctg tct ttg ttc ctc caa aga cca gac tta      2506
Leu Lys Gly Tyr Thr Ser Leu Ser Leu Phe Leu Gln Arg Pro Asp Leu
                805                 810                 815 aga gag aat gga ggc act gag gac atg ttt gta atg tac ctt gga aac      2554
Arg Glu Asn Gly Gly Thr Glu Asp Met Phe Val Met Tyr Leu Gly Asn
            820                 825                 830 aag gat gcc tcc aag gac tac atc ggc atg gcg gtt gta gat ggc cag      2602
Lys Asp Ala Ser Lys Asp Tyr Ile Gly Met Ala Val Val Asp Gly Gln
        835                 840                 845 ctg acg tgt gtc tac aac ctg ggg gac cga gaa gct gaa gtt cag atc      2650
Leu Thr Cys Val Tyr Asn Leu Gly Asp Arg Glu Ala Glu Val Gln Ile
    850                 855                 860 gat cag gtc ctg acg gag agt gag tct cag gag gca gtt atg gac cgg      2698
Asp Gln Val Leu Thr Glu Ser Glu Ser Gln Glu Ala Val Met Asp Arg
865                 870                 875                 880 gtg aag ttc cag aga ata tat caa ttt gcc aag ctt aat tac acc aaa      2746
Val Lys Phe Gln Arg Ile Tyr Gln Phe Ala Lys Leu Asn Tyr Thr Lys
                885                 890                 895 gaa gcc acg tcc aat aaa ccc aaa gct ccc gcg gtc tac gac ctg gag      2794
Glu Ala Thr Ser Asn Lys Pro Lys Ala Pro Ala Val Tyr Asp Leu Glu
            900                 905                 910 ggt ggc agt agc aac acg ctc ctt aat ttg gat ccc gag gac gct gtg      2842
Gly Gly Ser Ser Asn Thr Leu Leu Asn Leu Asp Pro Glu Asp Ala Val
        915                 920                 925 ttt tat gtc gga ggt tac cca ccg gat ttt gaa ctt cct agc aga ctg      2890
Phe Tyr Val Gly Gly Tyr Pro Pro Asp Phe Glu Leu Pro Ser Arg Leu
    930                 935                 940 cgg ttc cct cca tac aaa ggc tgt atc gaa cta gat gac ctc aat gaa      2938
Arg Phe Pro Pro Tyr Lys Gly Cys Ile Glu Leu Asp Asp Leu Asn Glu
945                 950                 955                 960 aac gtt cta agc ttg tac aat ttc aag aca act ttc aat ctc aac acc      2986
Asn Val Leu Ser Leu Tyr Asn Phe Lys Thr Thr Phe Asn Leu Asn Thr
                965                 970                 975 acg gag gtg gag cct tgt agg agg aga aag gaa gag tca gac aaa aat      3034
Thr Glu Val Glu Pro Cys Arg Arg Arg Lys Glu Glu Ser Asp Lys Asn
            980                 985                 990 tac ttt gaa ggt aca ggc tat gct cgc atc cct act caa cca aat gct      3082
Tyr Phe Glu Gly Thr Gly Tyr Ala Arg Ile Pro Thr Gln Pro Asn Ala
        995                 1000                1005 ccc ttc cca aac ttc ata cag acc atc cag act act gtg gac aga ggt      3130
Pro Phe Pro Asn Phe Ile Gln Thr Ile Gln Thr Thr Val Asp Arg Gly
    1010                1015                1020 tta ctg ttc ttc gca gaa aac cag gat aac ttc ata tct ctg aac ata      3178
Leu Leu Phe Phe Ala Glu Asn Gln Asp Asn Phe Ile Ser Leu Asn Ile
1025                1030                1035                1040 gaa gat ggc aat ctc atg gtg aga tac aaa cta aat tca gag cca ccc      3226
Glu Asp Gly Asn Leu Met Val Arg Tyr Lys Leu Asn Ser Glu Pro Pro
                1045                1050                1055 aaa gag aag gga att cga gac acc atc aac gat ggg aaa gat cat tcg      3274
Lys Glu Lys Gly Ile Arg Asp Thr Ile Asn Asp Gly Lys Asp His Ser
            1060                1065                1070 atc tta atc aca att gga aaa cta caa aaa cgc atg tgg ata aat gtg      3322
Ile Leu Ile Thr Ile Gly Lys Leu Gln Lys Arg Met Trp Ile Asn Val
        1075                1080                1085 aac gaa cgc agt gta cga atc gaa ggg gaa ata ttt gat ttc agc aca      3370
Asn Glu Arg Ser Val Arg Ile Glu Gly Glu Ile Phe Asp Phe Ser Thr
    1090                1095                1100
```

```
                                                    -continued tat tat ttg ggc gga att cca att gca atc aga gaa agg ttt aac atc      3418
Tyr Tyr Leu Gly Gly Ile Pro Ile Ala Ile Arg Glu Arg Phe Asn Ile
1105                1110                1115                1120 tca acg cct gct ttc caa ggc tgc atg aag aat ctg aag aaa acc agt      3466
Ser Thr Pro Ala Phe Gln Gly Cys Met Lys Asn Leu Lys Lys Thr Ser
                1125                1130                1135 ggg gtt gtc agg ttg aat gat act gtg ggt gta acc aag aag tgc tca      3514
Gly Val Val Arg Leu Asn Asp Thr Val Gly Val Thr Lys Lys Cys Ser
        1140                1145                1150 gaa gac tgg aag ctt gtg cga acc gcc tcg ttc tcc aga gga ggg cag      3562
Glu Asp Trp Lys Leu Val Arg Thr Ala Ser Phe Ser Arg Gly Gly Gln
    1155                1160                1165 atg agc ttt aca aac ttg gac gtg ccc tcg act gac cgc ttc cag ctc      3610
Met Ser Phe Thr Asn Leu Asp Val Pro Ser Thr Asp Arg Phe Gln Leu
    1170                1175                1180 tcc ttt ggg ttt cag acc ttt caa ccc agt ggc aca ctg ctc aat cat      3658
Ser Phe Gly Phe Gln Thr Phe Gln Pro Ser Gly Thr Leu Leu Asn His
1185                1190                1195                1200 cag acg cgg aca agc agc ctg ctg gtc acc ctg gaa gat ggg cac att      3706
Gln Thr Arg Thr Ser Ser Leu Leu Val Thr Leu Glu Asp Gly His Ile
                1205                1210                1215 gag ttg agc act agg gac agc aac atc cca att ttc aag tct cca ggg      3754
Glu Leu Ser Thr Arg Asp Ser Asn Ile Pro Ile Phe Lys Ser Pro Gly
        1220                1225                1230 acc tac atg gac ggt tta ctg cat cat gta tct gta ata agt gac acc      3802
Thr Tyr Met Asp Gly Leu Leu His His Val Ser Val Ile Ser Asp Thr
    1235                1240                1245 tca ggt ctc cgc ctt ctc atc gat gac cag gtc ctg aga agg aac cag      3850
Ser Gly Leu Arg Leu Leu Ile Asp Asp Gln Val Leu Arg Arg Asn Gln
    1250                1255                1260 agg ctt cct agc ttc tct aac gcc cag cag tcg ctc cgc ctt gga gga      3898
Arg Leu Pro Ser Phe Ser Asn Ala Gln Gln Ser Leu Arg Leu Gly Gly
1265                1270                1275                1280 ggt cat ttc gag ggt tgt atc agc aat gtt tta gtc caa agg ttt tca      3946
Gly His Phe Glu Gly Cys Ile Ser Asn Val Leu Val Gln Arg Phe Ser
                1285                1290                1295 cag agt cca gaa gtc ctg gat ctg gcc agt aaa tct acc aag aag gat      3994
Gln Ser Pro Glu Val Leu Asp Leu Ala Ser Lys Ser Thr Lys Lys Asp
        1300                1305                1310 gca tcc cta gga ggc tgc agt tta aac aag cca cct ttt ctt atg ttg      4042
Ala Ser Leu Gly Gly Cys Ser Leu Asn Lys Pro Pro Phe Leu Met Leu
    1315                1320                1325 ttt aaa agt ccc aag aga ttt aac aag ggc cgg att ttc aat gtt aat      4090
Phe Lys Ser Pro Lys Arg Phe Asn Lys Gly Arg Ile Phe Asn Val Asn
    1330                1335                1340 cag ctg atg caa gat gca cct cag gcc aca agg agc aca gag gct tgg      4138
Gln Leu Met Gln Asp Ala Pro Gln Ala Thr Arg Ser Thr Glu Ala Trp
1345                1350                1355                1360 caa gat ggg agg tcc tgc cta cca cct ctg aac acc aag gcc tct cac      4186
Gln Asp Gly Arg Ser Cys Leu Pro Pro Leu Asn Thr Lys Ala Ser His
                1365                1370                1375 aga gcc ctg cag ttt gga gac agc ccc acc agc cac ttg cta ctc aag      4234
Arg Ala Leu Gln Phe Gly Asp Ser Pro Thr Ser His Leu Leu Leu Lys
        1380                1385                1390 ctt ccc cag gaa ctg ctg aaa cct agg tca cag ttt tct tta gac ata      4282
Leu Pro Gln Glu Leu Leu Lys Pro Arg Ser Gln Phe Ser Leu Asp Ile
    1395                1400                1405 cag aca act tcc ccc aaa gga ctg gtg ttt tac gca ggc acc aag gac      4330
Gln Thr Thr Ser Pro Lys Gly Leu Val Phe Tyr Ala Gly Thr Lys Asp
```

```
                1410            1415            1420
tcc ttc ctg gct ctt tat gtc gca gat ggc cgt gtt gtc ttt gct ttg      4378
Ser Phe Leu Ala Leu Tyr Val Ala Asp Gly Arg Val Val Phe Ala Leu
1425            1430            1435            1440 ggg gca gga ggg aag aaa ctg aga ctc agg agc aag gag aga tac cat      4426
Gly Ala Gly Gly Lys Lys Leu Arg Leu Arg Ser Lys Glu Arg Tyr His
            1445            1450            1455 gac ggg aag tgg cac acg gtg gtg ttc gga cta aat gga gga aag gca      4474
Asp Gly Lys Trp His Thr Val Val Phe Gly Leu Asn Gly Gly Lys Ala
    1460            1465            1470 cgc ctg gtt gtg gat ggg cta agg gcc cag gaa ggc agt ttg cct gga      4522
Arg Leu Val Val Asp Gly Leu Arg Ala Gln Glu Gly Ser Leu Pro Gly
1475            1480            1485 aat tct acc atc agc ccc aga gaa cag gtt tac cta ggg ttg ccg cta      4570
Asn Ser Thr Ile Ser Pro Arg Glu Gln Val Tyr Leu Gly Leu Pro Leu
    1490            1495            1500 tca aga aag cca aag agc cta ccc cag cac agt ttt gtg ggg tgc ctg      4618
Ser Arg Lys Pro Lys Ser Leu Pro Gln His Ser Phe Val Gly Cys Leu
1505            1510            1515            1520 aga gat ttc cag ttg aac tcg aaa ccc ctg gat tct cct tct gcg agg      4666
Arg Asp Phe Gln Leu Asn Ser Lys Pro Leu Asp Ser Pro Ser Ala Arg
            1525            1530            1535 ttt ggg gta tct ccc tgc ttg ggt ggc tct tta gag aaa ggc att tat      4714
Phe Gly Val Ser Pro Cys Leu Gly Gly Ser Leu Glu Lys Gly Ile Tyr
    1540            1545            1550 ttc tcc caa gga gga ggc cat gtg atc cta gcc aat tct gtg tcc ttg      4762
Phe Ser Gln Gly Gly Gly His Val Ile Leu Ala Asn Ser Val Ser Leu
1555            1560            1565 ggg cca gag ctt aag ctc act ttc agc att cgc cca cgg agt ctc act      4810
Gly Pro Glu Leu Lys Leu Thr Phe Ser Ile Arg Pro Arg Ser Leu Thr
    1570            1575            1580 ggg gtc tta ata cac gtc gga agt caa tct gga cag cgc tta agt gtg      4858
Gly Val Leu Ile His Val Gly Ser Gln Ser Gly Gln Arg Leu Ser Val
1585            1590            1595            1600 tac atg gag gca gga aag gtc aca acc tct gtg agc agt gat gca gga      4906
Tyr Met Glu Ala Gly Lys Val Thr Thr Ser Val Ser Ser Asp Ala Gly
            1605            1610            1615 gga agt gtg aca tca att aca ccg aag cag tct ctg tgt gat gga cag      4954
Gly Ser Val Thr Ser Ile Thr Pro Lys Gln Ser Leu Cys Asp Gly Gln
    1620            1625            1630 tgg cac tcg gtg gca gtc tcc att aaa cag cgc atc ctg cat cta gaa      5002
Trp His Ser Val Ala Val Ser Ile Lys Gln Arg Ile Leu His Leu Glu
1635            1640            1645 ctg gat aca gac agt agc tac aca gtc gca cca ctt tcc ttc tca cca      5050
Leu Asp Thr Asp Ser Ser Tyr Thr Val Ala Pro Leu Ser Phe Ser Pro
    1650            1655            1660 aac agc acc cga ggg tca ctg cac gtc gga ggt gtc cca gac aaa ttg      5098
Asn Ser Thr Arg Gly Ser Leu His Val Gly Gly Val Pro Asp Lys Leu
1665            1670            1675            1680 aaa atg ctt aca ctc cct gtg tgg aac tca ttt ttt ggc tgt ctg aag      5146
Lys Met Leu Thr Leu Pro Val Trp Asn Ser Phe Phe Gly Cys Leu Lys
            1685            1690            1695 aat att caa gtc aac cat gtc cct gtc ccc atc aca gaa gcc aca gaa      5194
Asn Ile Gln Val Asn His Val Pro Val Pro Ile Thr Glu Ala Thr Glu
    1700            1705            1710 gtc caa ggt tct gtc agc ctg aat ggc tgc cct gac cac taaccctaca      5243
Val Gln Gly Ser Val Ser Leu Asn Gly Cys Pro Asp His
1715            1720            1725 cagcaagatt caccttgga g                                                5264
```

<210> SEQ ID NO 10
<211> LENGTH: 1725
<212> TYPE: PRT
<213> ORGANISM: Rattus norvegicus

<400> SEQUENCE: 10

```
Met Pro Pro Thr Val Arg Trp Ser Ala Trp Cys Thr Gly Trp Leu Trp
  1               5                  10                  15
Ile Phe Gly Ala Ala Leu Gly Gln Cys Leu Gly Tyr Gly Ser Glu Gln
             20                  25                  30
Gln Arg Val Ala Phe Leu Gln His Pro Gly Gln Asn His Leu Gln Ala
         35                  40                  45
Ser Tyr Met Glu Leu Arg Pro Ser Gln Gly Cys Arg Pro Gly Tyr Tyr
     50                  55                  60
Arg Asp Ile Lys Ser Phe Pro Ala Gly Arg Ser Val Pro Cys Asn Cys
 65                  70                  75                  80
Asn Gly His Ser Asn Arg Cys Gln Asp Gly Ser Gly Val Cys Ile Asn
                 85                  90                  95
Cys Gln His Asn Thr Ala Gly Glu His Cys Glu Arg Cys Lys Arg Gly
            100                 105                 110
Tyr Tyr Gly Ser Ala Ile His Gly Ser Cys Arg Val Cys Pro Cys Pro
        115                 120                 125
His Thr Asn Ser Phe Ala Thr Gly Cys Ala Val Asp Gly Gly Ala Val
    130                 135                 140
Arg Cys Ala Cys Lys Pro Gly Tyr Thr Gly Ala Gln Cys Glu Arg Cys
145                 150                 155                 160
Ala Pro Gly Tyr Phe Gly Asn Pro Gln Lys Phe Gly Gly Ser Cys Gln
                165                 170                 175
Pro Cys Asn Cys Asn Ser Asn Gly Gln Phe Gly Thr Cys Asp Pro Leu
            180                 185                 190
Thr Gly Asp Cys Val Ser Gln Glu Pro Lys Asp Gly Ser Pro Ala Glu
        195                 200                 205
Glu Cys Asp Asp Cys Asp Ser Cys Val Met Thr Leu Leu Asn Asp Leu
    210                 215                 220
Val Pro Met Gly Glu Leu Ala Leu Val Lys Ser Lys Leu Gln Gly
225                 230                 235                 240
Leu Ser Val Asn Thr Gly Ser Leu Glu Gln Ile Arg His Val Glu Met
                245                 250                 255
Gln Ala Lys Asp Leu Arg Asn Gln Leu Leu Gly Phe Arg Ser Ala Ile
            260                 265                 270
Ser Ser His Gly Ser Gln Met Asp Gly Leu Glu Lys Glu Leu Ser His
        275                 280                 285
Leu Tyr Gln Glu Phe Glu Thr Leu Gln Glu Lys Ala Gln Val Asn Ser
    290                 295                 300
Arg Lys Ala Gln Thr Leu Tyr Asn Asn Ile Asp Thr Thr Ile Gln Asn
305                 310                 315                 320
Ala Lys Glu Leu Asp Met Lys Ile Lys Asn Ile Leu Thr Asn Val His
                325                 330                 335
Ile Leu Leu Lys Gln Ile Ala Arg Pro Gly Gly Glu Gly Met Asp Leu
            340                 345                 350
Pro Val Gly Asp Trp Ser Arg Glu Ser Ala Glu Ala Gln Arg Met Leu
        355                 360                 365
Arg Glu Leu Arg Gly Arg Asp Phe Lys Lys His Leu Gln Glu Ala Glu
```

```
            370             375             380
Ala Gln Lys Met Glu Ala Gln Leu Leu Asn Arg Ile Arg Thr Trp
385             390             395             400
Leu Glu Ser His Gln Val Glu Asn Asn Gly Leu Leu Lys Asn Ile Arg
            405             410             415
Asp Ser Leu Asn Asp Tyr Glu Ala Lys Leu Gln Asp Leu Arg Ser Val
            420             425             430
Leu Gln Glu Ala Ala Ala Gln Gly Lys Gln Ala Thr Gly Leu Asn His
            435             440             445
Glu Asn Glu Gly Val Leu Gly Ala Ile Gln Arg Gln Met Lys Glu Met
450             455             460
Asp Ser Leu Lys Lys Tyr Leu Thr Glu His Leu Ala Thr Ala Asp Ala
465             470             475             480
Ser Leu Leu Gln Thr Asn Ser Leu Leu Gln Arg Met Asp Thr Ser Gln
            485             490             495
Lys Glu Tyr Glu Ser Leu Ala Ala Ala Leu Asn Gly Ala Arg Gln Glu
            500             505             510
Leu Asn Asp Gln Val Arg Glu Leu Ser Arg Ser Gly Gly Lys Ala Pro
            515             520             525
Leu Val Ala Glu Ala Glu Lys His Ala Gln Ser Leu Gln Glu Leu Ala
            530             535             540
Lys Gln Leu Glu Glu Ile Lys Arg Asn Thr Ser Gly Asp Glu Ser Val
545             550             555             560
Arg Cys Val Val Asp Ala Ala Thr Ala Tyr Glu Ser Ile Leu Asn Ala
            565             570             575
Ile Arg Ala Ala Glu Asp Ala Ala Gly Lys Ala Asp Ser Ala Ser Glu
            580             585             590
Ser Ala Phe Gln Thr Val Ile Lys Glu Asp Leu Pro Arg Arg Ala Lys
            595             600             605
Thr Leu Ser Ser Asp Ser Glu Glu Leu Leu Asn Glu Ala Lys Met Thr
610             615             620
Arg Lys Arg Leu Gln Gln Glu Ile Asn Pro Ala Leu Asn Ser Leu Gln
625             630             635             640
Gln Thr Leu Lys Thr Val Ser Val Gln Lys Asp Leu Leu Asp Ala Asn
            645             650             655
Val Thr Ala Val Arg Asn Asp Leu Arg Gly Ile Gln Arg Gly Asp Ile
            660             665             670
Asp Ser Val Val Ser Gly Ala Lys Ser Met Val Arg Lys Ala Asn Gly
            675             680             685
Ile Thr Ser Glu Val Leu Asp Gly Leu Ser Pro Ile Gln Thr Asp Leu
            690             695             700
Gly Arg Ile Lys Asp Ser Tyr Gly Ser Thr Arg His Glu Asp Phe Asn
705             710             715             720
Lys Ala Leu Ile Asp Ala Asn Asn Ser Val Lys Lys Leu Thr Lys Lys
            725             730             735
Leu Pro Asp Leu Phe Val Lys Ile Glu Ser Ile Asn Gln Gln Leu Leu
            740             745             750
Pro Leu Gly Asn Ile Ser Asp Asn Val Asp Arg Ile Arg Glu Leu Ile
            755             760             765
Thr Gln Ala Arg Asp Ala Ala Asn Lys Val Ala Ile Pro Met Arg Phe
            770             775             780
Asn Gly Lys Ser Gly Val Glu Val Arg Leu Pro Asn Asp Leu Glu Asp
785             790             795             800
```

-continued

```
Leu Lys Gly Tyr Thr Ser Leu Ser Leu Phe Leu Gln Arg Pro Asp Leu
            805                 810                 815

Arg Glu Asn Gly Gly Thr Glu Asp Met Phe Val Met Tyr Leu Gly Asn
        820                 825                 830

Lys Asp Ala Ser Lys Asp Tyr Ile Gly Met Ala Val Val Asp Gly Gln
        835                 840                 845

Leu Thr Cys Val Tyr Asn Leu Gly Asp Arg Glu Ala Glu Val Gln Ile
    850                 855                 860

Asp Gln Val Leu Thr Glu Ser Glu Ser Gln Glu Ala Val Met Asp Arg
865                 870                 875                 880

Val Lys Phe Gln Arg Ile Tyr Gln Phe Ala Lys Leu Asn Tyr Thr Lys
            885                 890                 895

Glu Ala Thr Ser Asn Lys Pro Lys Ala Pro Ala Val Tyr Asp Leu Glu
        900                 905                 910

Gly Gly Ser Ser Asn Thr Leu Leu Asn Leu Asp Pro Glu Asp Ala Val
        915                 920                 925

Phe Tyr Val Gly Gly Tyr Pro Pro Asp Phe Glu Leu Pro Ser Arg Leu
    930                 935                 940

Arg Phe Pro Pro Tyr Lys Gly Cys Ile Glu Leu Asp Asp Leu Asn Glu
945                 950                 955                 960

Asn Val Leu Ser Leu Tyr Asn Phe Lys Thr Thr Phe Asn Leu Asn Thr
            965                 970                 975

Thr Glu Val Glu Pro Cys Arg Arg Arg Lys Glu Ser Asp Lys Asn
        980                 985                 990

Tyr Phe Glu Gly Thr Gly Tyr Ala Arg Ile Pro Thr Gln Pro Asn Ala
        995                1000                1005

Pro Phe Pro Asn Phe Ile Gln Thr Ile Gln Thr Thr Val Asp Arg Gly
    1010                1015                1020

Leu Leu Phe Phe Ala Glu Asn Gln Asp Asn Phe Ile Ser Leu Asn Ile
1025                1030                1035                1040

Glu Asp Gly Asn Leu Met Val Arg Tyr Lys Leu Asn Ser Glu Pro Pro
            1045                1050                1055

Lys Glu Lys Gly Ile Arg Asp Thr Ile Asn Asp Gly Lys Asp His Ser
        1060                1065                1070

Ile Leu Ile Thr Ile Gly Lys Leu Gln Lys Arg Met Trp Ile Asn Val
    1075                1080                1085

Asn Glu Arg Ser Val Arg Ile Glu Gly Glu Ile Phe Asp Phe Ser Thr
    1090                1095                1100

Tyr Tyr Leu Gly Gly Ile Pro Ile Ala Ile Arg Glu Arg Phe Asn Ile
1105                1110                1115                1120

Ser Thr Pro Ala Phe Gln Gly Cys Met Lys Asn Leu Lys Lys Thr Ser
            1125                1130                1135

Gly Val Val Arg Leu Asn Asp Thr Val Gly Val Thr Lys Lys Cys Ser
        1140                1145                1150

Glu Asp Trp Lys Leu Val Arg Thr Ala Ser Phe Ser Arg Gly Gly Gln
        1155                1160                1165

Met Ser Phe Thr Asn Leu Asp Val Pro Ser Thr Asp Arg Phe Gln Leu
    1170                1175                1180

Ser Phe Gly Phe Gln Thr Phe Gln Pro Ser Gly Thr Leu Leu Asn His
1185                1190                1195                1200

Gln Thr Arg Thr Ser Ser Leu Leu Val Thr Leu Glu Asp Gly His Ile
            1205                1210                1215
```

-continued

```
Glu Leu Ser Thr Arg Asp Ser Asn Ile Pro Ile Phe Lys Ser Pro Gly
        1220                1225                1230

Thr Tyr Met Asp Gly Leu Leu His His Val Ser Val Ile Ser Asp Thr
        1235                1240                1245

Ser Gly Leu Arg Leu Leu Ile Asp Asp Gln Val Leu Arg Arg Asn Gln
1250                1255                1260

Arg Leu Pro Ser Phe Ser Asn Ala Gln Gln Ser Leu Arg Leu Gly Gly
1265                1270                1275                1280

Gly His Phe Glu Gly Cys Ile Ser Asn Val Leu Val Gln Arg Phe Ser
                1285                1290                1295

Gln Ser Pro Glu Val Leu Asp Leu Ala Ser Lys Ser Thr Lys Lys Asp
                1300                1305                1310

Ala Ser Leu Gly Gly Cys Ser Leu Asn Lys Pro Pro Phe Leu Met Leu
                1315                1320                1325

Phe Lys Ser Pro Lys Arg Phe Asn Lys Gly Arg Ile Phe Asn Val Asn
        1330                1335                1340

Gln Leu Met Gln Asp Ala Pro Gln Ala Thr Arg Ser Thr Glu Ala Trp
1345                1350                1355                1360

Gln Asp Gly Arg Ser Cys Leu Pro Pro Leu Asn Thr Lys Ala Ser His
                1365                1370                1375

Arg Ala Leu Gln Phe Gly Asp Ser Pro Thr Ser His Leu Leu Leu Lys
                1380                1385                1390

Leu Pro Gln Glu Leu Leu Lys Pro Arg Ser Gln Phe Ser Leu Asp Ile
        1395                1400                1405

Gln Thr Thr Ser Pro Lys Gly Leu Val Phe Tyr Ala Gly Thr Lys Asp
        1410                1415                1420

Ser Phe Leu Ala Leu Tyr Val Ala Asp Gly Arg Val Val Phe Ala Leu
1425                1430                1435                1440

Gly Ala Gly Gly Lys Lys Leu Arg Leu Arg Ser Lys Glu Arg Tyr His
                1445                1450                1455

Asp Gly Lys Trp His Thr Val Val Phe Gly Leu Asn Gly Gly Lys Ala
                1460                1465                1470

Arg Leu Val Val Asp Gly Leu Arg Ala Gln Glu Gly Ser Leu Pro Gly
        1475                1480                1485

Asn Ser Thr Ile Ser Pro Arg Glu Gln Val Tyr Leu Gly Leu Pro Leu
        1490                1495                1500

Ser Arg Lys Pro Lys Ser Leu Pro Gln His Ser Phe Val Gly Cys Leu
1505                1510                1515                1520

Arg Asp Phe Gln Leu Asn Ser Lys Pro Leu Asp Ser Pro Ser Ala Arg
                1525                1530                1535

Phe Gly Val Ser Pro Cys Leu Gly Gly Ser Leu Glu Lys Gly Ile Tyr
                1540                1545                1550

Phe Ser Gln Gly Gly Gly His Val Ile Leu Ala Asn Ser Val Ser Leu
        1555                1560                1565

Gly Pro Glu Leu Lys Leu Thr Phe Ser Ile Arg Pro Arg Ser Leu Thr
        1570                1575                1580

Gly Val Leu Ile His Val Gly Ser Gln Ser Gly Gln Arg Leu Ser Val
1585                1590                1595                1600

Tyr Met Glu Ala Gly Lys Val Thr Thr Ser Val Ser Ser Asp Ala Gly
                1605                1610                1615

Gly Ser Val Thr Ser Ile Thr Pro Lys Gln Ser Leu Cys Asp Gly Gln
        1620                1625                1630

Trp His Ser Val Ala Val Ser Ile Lys Gln Arg Ile Leu His Leu Glu
```

-continued

```
               1635                1640                1645

Leu Asp Thr Asp Ser Ser Tyr Thr Val Ala Pro Leu Ser Phe Ser Pro
    1650                1655                1660

Asn Ser Thr Arg Gly Ser Leu His Val Gly Val Pro Asp Lys Leu
1665                1670                1675                1680

Lys Met Leu Thr Leu Pro Val Trp Asn Ser Phe Phe Gly Cys Leu Lys
                1685                1690                1695

Asn Ile Gln Val Asn His Val Pro Val Pro Ile Thr Glu Ala Thr Glu
            1700                1705                1710

Val Gln Gly Ser Val Ser Leu Asn Gly Cys Pro Asp His
        1715                1720                1725

<210> SEQ ID NO 11
<211> LENGTH: 5113
<212> TYPE: DNA
<213> ORGANISM: Rattus norvegicus
<220> FEATURE:
<221> NAME/KEY: CDS
<222> LOCATION: (1)..(5082)

<400> SEQUENCE: 11 cag caa agg gta gca ttt ctt cag cat cca ggg caa aac cat ctg caa        48
Gln Gln Arg Val Ala Phe Leu Gln His Pro Gly Gln Asn His Leu Gln
  1               5                  10                  15 gca agt tat atg gag ctt aga ccc agc cag ggc tgt cgc cca gga tac        96
Ala Ser Tyr Met Glu Leu Arg Pro Ser Gln Gly Cys Arg Pro Gly Tyr
             20                  25                  30 tat cga gac atc aaa agc ttc cct gcg gga agg tct gtt ccc tgc aat       144
Tyr Arg Asp Ile Lys Ser Phe Pro Ala Gly Arg Ser Val Pro Cys Asn
         35                  40                  45 tgc aac gga cat tca aat aga tgc caa gac ggc tcg gga gtg tgc att       192
Cys Asn Gly His Ser Asn Arg Cys Gln Asp Gly Ser Gly Val Cys Ile
     50                  55                  60 aac tgt cag cac aac aca gct ggg gag cac tgt gag cgt tgc aag agg       240
Asn Cys Gln His Asn Thr Ala Gly Glu His Cys Glu Arg Cys Lys Arg
 65                  70                  75                  80 ggt tac tat gga agc gcc atc cat gga tcc tgc agg gtt tgc ccc tgt       288
Gly Tyr Tyr Gly Ser Ala Ile His Gly Ser Cys Arg Val Cys Pro Cys
                 85                  90                  95 cct cac acc aac agc ttt gcc act ggc tgt gct gtg gat gga gga gct       336
Pro His Thr Asn Ser Phe Ala Thr Gly Cys Ala Val Asp Gly Gly Ala
            100                 105                 110 gtg agg tgt gcc tgc aaa ccc gga tac aca gga gca cag tgt gag agg       384
Val Arg Cys Ala Cys Lys Pro Gly Tyr Thr Gly Ala Gln Cys Glu Arg
        115                 120                 125 tgt gca cca gga tat ttt ggg aac ccc cag aaa ttt gga ggt agc tgc       432
Cys Ala Pro Gly Tyr Phe Gly Asn Pro Gln Lys Phe Gly Gly Ser Cys
    130                 135                 140 caa cca tgc aat tgc aac agt aat ggc cag ttt ggc act tgt gat ccc       480
Gln Pro Cys Asn Cys Asn Ser Asn Gly Gln Phe Gly Thr Cys Asp Pro
145                 150                 155                 160 cta act gga gac tgt gta agc caa gaa ccc aaa gat ggc agc cct gca       528
Leu Thr Gly Asp Cys Val Ser Gln Glu Pro Lys Asp Gly Ser Pro Ala
                165                 170                 175 gaa gaa tgt gat gac tgt gac agc tgt gtg atg act ctc cta aat gac       576
Glu Glu Cys Asp Asp Cys Asp Ser Cys Val Met Thr Leu Leu Asn Asp
            180                 185                 190 ttg gtc ccc atg ggt gag gaa ctc gcc ctg gtg aaa tca aaa ctt cag       624
Leu Val Pro Met Gly Glu Glu Leu Ala Leu Val Lys Ser Lys Leu Gln
        195                 200                 205
```

```
ggg ctg agt gtg aac act ggt tct ctg gaa cag atc cgg cat gtg gag    672
Gly Leu Ser Val Asn Thr Gly Ser Leu Glu Gln Ile Arg His Val Glu
    210                 215                 220 atg cag gcc aag gac ctg agg aac cag ctg ctt ggc ttc cgt tcc gcc    720
Met Gln Ala Lys Asp Leu Arg Asn Gln Leu Leu Gly Phe Arg Ser Ala
225                 230                 235                 240 atc tcc agt cac ggg tcc caa atg gac ggc ctg gaa aaa gaa ctc agt    768
Ile Ser Ser His Gly Ser Gln Met Asp Gly Leu Glu Lys Glu Leu Ser
                245                 250                 255 cat ttg tac cag gaa ttc gaa act ttg caa gaa aag gcg cag gtc aat    816
His Leu Tyr Gln Glu Phe Glu Thr Leu Gln Glu Lys Ala Gln Val Asn
            260                 265                 270 tcc aga aaa gca caa aca tta tat aac aac atc gat acg aca atc caa    864
Ser Arg Lys Ala Gln Thr Leu Tyr Asn Asn Ile Asp Thr Thr Ile Gln
        275                 280                 285 aac gcc aaa gag ttg gac atg aag att aaa aac ata ctt acg aat gtg    912
Asn Ala Lys Glu Leu Asp Met Lys Ile Lys Asn Ile Leu Thr Asn Val
    290                 295                 300 cac att ctc ctg aag cag atc gct cgg cca ggt gga gaa gga atg gac    960
His Ile Leu Leu Lys Gln Ile Ala Arg Pro Gly Gly Glu Gly Met Asp
305                 310                 315                 320 ttg ccg gtg ggc gac tgg tcc agg gag tcg gcg gaa gct cag cgc atg   1008
Leu Pro Val Gly Asp Trp Ser Arg Glu Ser Ala Glu Ala Gln Arg Met
                325                 330                 335 ttg cgg gag ctg cga ggc cga gac ttt aaa aag cac ctc caa gaa gca   1056
Leu Arg Glu Leu Arg Gly Arg Asp Phe Lys Lys His Leu Gln Glu Ala
            340                 345                 350 gag gcc cag aaa atg gaa gcc cag ctc tta ctg aac cga atc agg acc   1104
Glu Ala Gln Lys Met Glu Ala Gln Leu Leu Leu Asn Arg Ile Arg Thr
        355                 360                 365 tgg ctg gaa tcc cac cag gtg gag aac aat gga ctg cta aag aat att   1152
Trp Leu Glu Ser His Gln Val Glu Asn Asn Gly Leu Leu Lys Asn Ile
    370                 375                 380 cgg gat tca tta aat gat tat gaa gcc aaa ctt cag gac ctg cgt tcc   1200
Arg Asp Ser Leu Asn Asp Tyr Glu Ala Lys Leu Gln Asp Leu Arg Ser
385                 390                 395                 400 gtg ctt cag gag gcg gca gcc cag gga aag cag gct aca ggc ctc aac   1248
Val Leu Gln Glu Ala Ala Ala Gln Gly Lys Gln Ala Thr Gly Leu Asn
                405                 410                 415 cac gaa aat gag ggg gtc cta gga gcc atc cag aga caa atg aag gaa   1296
His Glu Asn Glu Gly Val Leu Gly Ala Ile Gln Arg Gln Met Lys Glu
            420                 425                 430 atg gat tcc ctg aag aag tac ctc acc gag cac ctg gcc aca gca gac   1344
Met Asp Ser Leu Lys Lys Tyr Leu Thr Glu His Leu Ala Thr Ala Asp
        435                 440                 445 gct tcc ctg ctg caa acc aac agt cta ctg cag cgg atg gac acg agc   1392
Ala Ser Leu Leu Gln Thr Asn Ser Leu Leu Gln Arg Met Asp Thr Ser
    450                 455                 460 cag aag gag tat gaa agc tta gct gct gct tta aac gga gca aga cag   1440
Gln Lys Glu Tyr Glu Ser Leu Ala Ala Ala Leu Asn Gly Ala Arg Gln
465                 470                 475                 480 gaa ctg aat gac caa gtg cgg gaa ctc tcc aga tcc gga ggc aaa gca   1488
Glu Leu Asn Asp Gln Val Arg Glu Leu Ser Arg Ser Gly Gly Lys Ala
                485                 490                 495 ccc ctg gtg gct gag gcc gag aag cac gct cag tct tta cag gag ctg   1536
Pro Leu Val Ala Glu Ala Glu Lys His Ala Gln Ser Leu Gln Glu Leu
            500                 505                 510 gca aag cag ctg gaa gag ata aag aga aac acc agt ggg gat gag tcg   1584
Ala Lys Gln Leu Glu Glu Ile Lys Arg Asn Thr Ser Gly Asp Glu Ser
```

-continued

|  |  | 515 |  |  |  | 520 |  |  |  | 525 |  |  |  |  |
|---|---|---|---|---|---|---|---|---|---|---|---|---|---|---|
| gtg | cgc | tgt | gtc | gtg | gac | gct | gcc | act | gcc | tat | gag | agc | atc ctc aac | 1632 |
| Val | Arg | Cys | Val | Val | Asp | Ala | Ala | Thr | Ala | Tyr | Glu | Ser | Ile Leu Asn |  |
|  | 530 |  |  |  | 535 |  |  |  | 540 |  |  |  |  |  |
| gcc | atc | cga | gca | gca | gag | gat | gca | gcc | ggc | aag | gcc | gac | agt gcc tca | 1680 |
| Ala | Ile | Arg | Ala | Ala | Glu | Asp | Ala | Ala | Gly | Lys | Ala | Asp | Ser Ala Ser |  |
| 545 |  |  |  | 550 |  |  |  | 555 |  |  |  | 560 |  |  |
| gag | tcc | gcc | ttc | cag | aca | gtg | ata | aag | gaa | gat | ctt | ccg | aga aga gcc | 1728 |
| Glu | Ser | Ala | Phe | Gln | Thr | Val | Ile | Lys | Glu | Asp | Leu | Pro | Arg Arg Ala |  |
|  |  |  | 565 |  |  |  | 570 |  |  |  | 575 |  |  |  |
| aaa | acc | ctg | agt | tct | gac | agc | gag | gaa | ctg | tta | aac | gag | gcc aag atg | 1776 |
| Lys | Thr | Leu | Ser | Ser | Asp | Ser | Glu | Glu | Leu | Leu | Asn | Glu | Ala Lys Met |  |
|  |  |  | 580 |  |  |  | 585 |  |  |  | 590 |  |  |  |
| aca | cgg | aaa | agg | cta | cag | caa | gaa | atc | aat | cca | gct | ctc | aac agc cta | 1824 |
| Thr | Arg | Lys | Arg | Leu | Gln | Gln | Glu | Ile | Asn | Pro | Ala | Leu | Asn Ser Leu |  |
|  |  | 595 |  |  |  | 600 |  |  |  | 605 |  |  |  |  |
| cag | caa | acc | ctg | aag | act | gta | tca | gtt | cag | aag | gac | ctg | cta gat gcc | 1872 |
| Gln | Gln | Thr | Leu | Lys | Thr | Val | Ser | Val | Gln | Lys | Asp | Leu | Leu Asp Ala |  |
|  | 610 |  |  |  | 615 |  |  |  | 620 |  |  |  |  |  |
| aat | gtc | act | gct | gtc | cgt | aat | gac | ctt | cgt | ggg | atc | cag | aga ggt gat | 1920 |
| Asn | Val | Thr | Ala | Val | Arg | Asn | Asp | Leu | Arg | Gly | Ile | Gln | Arg Gly Asp |  |
| 625 |  |  |  | 630 |  |  |  | 635 |  |  |  | 640 |  |  |
| att | gac | agt | gtg | gtg | agt | gga | gcg | aag | agc | atg | gtc | agg | aaa gcc aat | 1968 |
| Ile | Asp | Ser | Val | Val | Ser | Gly | Ala | Lys | Ser | Met | Val | Arg | Lys Ala Asn |  |
|  |  |  | 645 |  |  |  | 650 |  |  |  | 655 |  |  |  |
| ggg | ata | acg | agc | gag | gtc | ctg | gac | ggg | ctc | agc | ccc | atc | cag acg gat | 2016 |
| Gly | Ile | Thr | Ser | Glu | Val | Leu | Asp | Gly | Leu | Ser | Pro | Ile | Gln Thr Asp |  |
|  |  |  | 660 |  |  |  | 665 |  |  |  | 670 |  |  |  |
| ttg | gga | agg | att | aag | gac | agc | tac | ggg | agc | aca | cgg | cat | gag gac ttc | 2064 |
| Leu | Gly | Arg | Ile | Lys | Asp | Ser | Tyr | Gly | Ser | Thr | Arg | His | Glu Asp Phe |  |
|  |  | 675 |  |  |  | 680 |  |  |  | 685 |  |  |  |  |
| aac | aaa | gct | ctg | att | gac | gcc | aat | aac | tca | gta | aag | aaa | tta acc aag | 2112 |
| Asn | Lys | Ala | Leu | Ile | Asp | Ala | Asn | Asn | Ser | Val | Lys | Lys | Leu Thr Lys |  |
|  | 690 |  |  |  | 695 |  |  |  | 700 |  |  |  |  |  |
| aag | ttg | cct | gat | ctt | ttt | gtc | aag | att | gaa | agc | atc | aat | caa cag ttg | 2160 |
| Lys | Leu | Pro | Asp | Leu | Phe | Val | Lys | Ile | Glu | Ser | Ile | Asn | Gln Gln Leu |  |
| 705 |  |  |  | 710 |  |  |  | 715 |  |  |  | 720 |  |  |
| ctg | ccc | ctg | gga | aac | atc | tct | gac | aat | gta | gac | cga | atc | cga gag ctc | 2208 |
| Leu | Pro | Leu | Gly | Asn | Ile | Ser | Asp | Asn | Val | Asp | Arg | Ile | Arg Glu Leu |  |
|  |  |  | 725 |  |  |  | 730 |  |  |  | 735 |  |  |  |
| att | acg | cag | gcc | aga | gat | gct | gcg | aac | aag | gtt | gca | att | ccc atg agg | 2256 |
| Ile | Thr | Gln | Ala | Arg | Asp | Ala | Ala | Asn | Lys | Val | Ala | Ile | Pro Met Arg |  |
|  |  | 740 |  |  |  | 745 |  |  |  | 750 |  |  |  |  |
| ttc | aat | ggt | aaa | tct | ggt | gtt | gaa | gtc | cgt | ctg | cca | aat | gac cta gaa | 2304 |
| Phe | Asn | Gly | Lys | Ser | Gly | Val | Glu | Val | Arg | Leu | Pro | Asn | Asp Leu Glu |  |
|  | 755 |  |  |  | 760 |  |  |  | 765 |  |  |  |  |  |
| gac | ttg | aag | gga | tac | acg | tct | ctg | tct | ttg | ttc | ctc | caa | aga cca gac | 2352 |
| Asp | Leu | Lys | Gly | Tyr | Thr | Ser | Leu | Ser | Leu | Phe | Leu | Gln | Arg Pro Asp |  |
|  | 770 |  |  |  | 775 |  |  |  | 780 |  |  |  |  |  |
| tta | aga | gag | aat | gga | ggc | act | gag | gac | atg | ttt | gta | atg | tac ctt gga | 2400 |
| Leu | Arg | Glu | Asn | Gly | Gly | Thr | Glu | Asp | Met | Phe | Val | Met | Tyr Leu Gly |  |
| 785 |  |  |  | 790 |  |  |  | 795 |  |  |  | 800 |  |  |
| aac | aag | gat | gcc | tcc | aag | gac | tac | atc | ggc | atg | gcg | gtt | gta gat ggc | 2448 |
| Asn | Lys | Asp | Ala | Ser | Lys | Asp | Tyr | Ile | Gly | Met | Ala | Val | Val Asp Gly |  |
|  |  |  | 805 |  |  |  | 810 |  |  |  | 815 |  |  |  |
| cag | ctg | acg | tgt | gtc | tac | aac | ctg | ggg | gac | cga | gaa | gct | gaa gtt cag | 2496 |
| Gln | Leu | Thr | Cys | Val | Tyr | Asn | Leu | Gly | Asp | Arg | Glu | Ala | Glu Val Gln |  |
|  | 820 |  |  |  | 825 |  |  |  | 830 |  |  |  |  |  |
| atc | gat | cag | gtc | ctg | acg | gag | agt | gag | tct | cag | gag | gca | gtt atg gac | 2544 |

```
Ile Asp Gln Val Leu Thr Glu Ser Glu Ser Gln Glu Ala Val Met Asp
        835                 840                 845 cgg gtg aag ttc cag aga ata tat caa ttt gcc aag ctt aat tac acc    2592
Arg Val Lys Phe Gln Arg Ile Tyr Gln Phe Ala Lys Leu Asn Tyr Thr
850                 855                 860 aaa gaa gcc acg tcc aat aaa ccc aaa gct ccc gcg gtc tac gac ctg    2640
Lys Glu Ala Thr Ser Asn Lys Pro Lys Ala Pro Ala Val Tyr Asp Leu
865                 870                 875                 880 gag ggt ggc agt agc aac acg ctc ctt aat ttg gat ccc gag gac gct    2688
Glu Gly Gly Ser Ser Asn Thr Leu Leu Asn Leu Asp Pro Glu Asp Ala
                885                 890                 895 gtg ttt tat gtc gga ggt tac cca ccg gat ttt gaa ctt cct agc aga    2736
Val Phe Tyr Val Gly Gly Tyr Pro Pro Asp Phe Glu Leu Pro Ser Arg
        900                 905                 910 ctg cgg ttc cct cca tac aaa ggc tgt atc gaa cta gat gac ctc aat    2784
Leu Arg Phe Pro Pro Tyr Lys Gly Cys Ile Glu Leu Asp Asp Leu Asn
        915                 920                 925 gaa aac gtt cta agc ttg tac aat ttc aag aca act ttc aat ctc aac    2832
Glu Asn Val Leu Ser Leu Tyr Asn Phe Lys Thr Thr Phe Asn Leu Asn
930                 935                 940 acc acg gag gtg gag cct tgt agg agg aga aag gaa gag tca gac aaa    2880
Thr Thr Glu Val Glu Pro Cys Arg Arg Arg Lys Glu Glu Ser Asp Lys
945                 950                 955                 960 aat tac ttt gaa ggt aca ggc tat gct cgc atc cct act caa cca aat    2928
Asn Tyr Phe Glu Gly Thr Gly Tyr Ala Arg Ile Pro Thr Gln Pro Asn
                965                 970                 975 gct ccc ttc cca aac ttc ata cag acc atc cag act act gtg gac aga    2976
Ala Pro Phe Pro Asn Phe Ile Gln Thr Ile Gln Thr Thr Val Asp Arg
        980                 985                 990 ggt tta ctg ttc ttc gca gaa aac cag gat aac ttc ata tct ctg aac    3024
Gly Leu Leu Phe Phe Ala Glu Asn Gln Asp Asn Phe Ile Ser Leu Asn
        995                 1000                1005 ata gaa gat ggc aat ctc atg gtg aga tac aaa cta aat tca gag cca    3072
Ile Glu Asp Gly Asn Leu Met Val Arg Tyr Lys Leu Asn Ser Glu Pro
   1010                1015                1020 ccc aaa gag aag gga att cga gac acc atc aac gat ggg aaa gat cat    3120
Pro Lys Glu Lys Gly Ile Arg Asp Thr Ile Asn Asp Gly Lys Asp His
1025                1030                1035                1040 tcg atc tta atc aca att gga aaa cta caa aaa cgc atg tgg ata aat    3168
Ser Ile Leu Ile Thr Ile Gly Lys Leu Gln Lys Arg Met Trp Ile Asn
                1045                1050                1055 gtg aac gaa cgc agt gta cga atc gaa ggg gaa ata ttt gat ttc agc    3216
Val Asn Glu Arg Ser Val Arg Ile Glu Gly Glu Ile Phe Asp Phe Ser
        1060                1065                1070 aca tat tat ttg ggc gga att cca att gca atc aga gaa agg ttt aac    3264
Thr Tyr Tyr Leu Gly Gly Ile Pro Ile Ala Ile Arg Glu Arg Phe Asn
        1075                1080                1085 atc tca acg cct gct ttc caa ggc tgc atg aag aat ctg aag aaa acc    3312
Ile Ser Thr Pro Ala Phe Gln Gly Cys Met Lys Asn Leu Lys Lys Thr
        1090                1095                1100 agt ggg gtt gtc agg ttg aat gat act gtg ggt gta acc aag aag tgc    3360
Ser Gly Val Val Arg Leu Asn Asp Thr Val Gly Val Thr Lys Lys Cys
1105                1110                1115                1120 tca gaa gac tgg aag ctt gtg cga acc gcc tcg ttc tcc aga gga ggg    3408
Ser Glu Asp Trp Lys Leu Val Arg Thr Ala Ser Phe Ser Arg Gly Gly
                1125                1130                1135 cag atg agc ttt aca aac ttg gac gtg ccc tcg act gac cgc ttc cag    3456
Gln Met Ser Phe Thr Asn Leu Asp Val Pro Ser Thr Asp Arg Phe Gln
        1140                1145                1150
```

```
ctc tcc ttt ggg ttt cag acc ttt caa ccc agt ggc aca ctg ctc aat    3504
Leu Ser Phe Gly Phe Gln Thr Phe Gln Pro Ser Gly Thr Leu Leu Asn
        1155                1160                1165 cat cag acg cgg aca agc agc ctg ctg gtc acc ctg gaa gat ggg cac    3552
His Gln Thr Arg Thr Ser Ser Leu Leu Val Thr Leu Glu Asp Gly His
    1170                1175                1180 att gag ttg agc act agg gac agc aac atc cca att ttc aag tct cca    3600
Ile Glu Leu Ser Thr Arg Asp Ser Asn Ile Pro Ile Phe Lys Ser Pro
1185                1190                1195                1200 ggg acc tac atg gac ggt tta ctg cat cat gta tct gta ata agt gac    3648
Gly Thr Tyr Met Asp Gly Leu Leu His His Val Ser Val Ile Ser Asp
            1205                1210                1215 acc tca ggt ctc cgc ctt ctc atc gat gac cag gtc ctg aga agg aac    3696
Thr Ser Gly Leu Arg Leu Leu Ile Asp Asp Gln Val Leu Arg Arg Asn
        1220                1225                1230 cag agg ctt cct agc ttc tct aac gcc cag cag tcg ctc cgc ctt gga    3744
Gln Arg Leu Pro Ser Phe Ser Asn Ala Gln Gln Ser Leu Arg Leu Gly
    1235                1240                1245 gga ggt cat ttc gag ggt tgt atc agc aat gtt tta gtc caa agg ttt    3792
Gly Gly His Phe Glu Gly Cys Ile Ser Asn Val Leu Val Gln Arg Phe
1250                1255                1260 tca cag agt cca gaa gtc ctg gat ctg gcc agt aaa tct acc aag aag    3840
Ser Gln Ser Pro Glu Val Leu Asp Leu Ala Ser Lys Ser Thr Lys Lys
1265                1270                1275                1280 gat gca tcc cta gga ggc tgc agt tta aac aag cca cct ttt ctt atg    3888
Asp Ala Ser Leu Gly Gly Cys Ser Leu Asn Lys Pro Pro Phe Leu Met
            1285                1290                1295 ttg ttt aaa agt ccc aag aga ttt aac aag ggc cgg att ttc aat gtt    3936
Leu Phe Lys Ser Pro Lys Arg Phe Asn Lys Gly Arg Ile Phe Asn Val
        1300                1305                1310 aat cag ctg atg caa gat gca cct cag gcc aca agg agc aca gag gct    3984
Asn Gln Leu Met Gln Asp Ala Pro Gln Ala Thr Arg Ser Thr Glu Ala
    1315                1320                1325 tgg caa gat ggg agg tcc tgc cta cca cct ctg aac acc aag gcc tct    4032
Trp Gln Asp Gly Arg Ser Cys Leu Pro Pro Leu Asn Thr Lys Ala Ser
1330                1335                1340 cac aga gcc ctg cag ttt gga gac agc ccc acc agc cac ttg cta ctc    4080
His Arg Ala Leu Gln Phe Gly Asp Ser Pro Thr Ser His Leu Leu Leu
1345                1350                1355                1360 aag ctt ccc cag gaa ctg ctg aaa cct agg tca cag ttt tct tta gac    4128
Lys Leu Pro Gln Glu Leu Leu Lys Pro Arg Ser Gln Phe Ser Leu Asp
            1365                1370                1375 ata cag aca act tcc ccc aaa gga ctg gtg ttt tac gca ggc acc aag    4176
Ile Gln Thr Thr Ser Pro Lys Gly Leu Val Phe Tyr Ala Gly Thr Lys
        1380                1385                1390 gac tcc ttc ctg gct ctt tat gtc gca gat ggc cgt gtt gtc ttt gct    4224
Asp Ser Phe Leu Ala Leu Tyr Val Ala Asp Gly Arg Val Val Phe Ala
    1395                1400                1405 ttg ggg gca gga ggg aag aaa ctg aga ctc agg agc aag gag aga tac    4272
Leu Gly Ala Gly Gly Lys Lys Leu Arg Leu Arg Ser Lys Glu Arg Tyr
1410                1415                1420 cat gac ggg aag tgg cac acg gtg gtg ttc gga cta aat gga gga aag    4320
His Asp Gly Lys Trp His Thr Val Val Phe Gly Leu Asn Gly Gly Lys
1425                1430                1435                1440 gca cgc ctg gtt gtg gat ggg cta agg gcc cag gaa ggc agt ttg cct    4368
Ala Arg Leu Val Val Asp Gly Leu Arg Ala Gln Glu Gly Ser Leu Pro
            1445                1450                1455 gga aat tct acc atc agc ccc aga gaa cag gtt tac cta ggg ttg ccg    4416
Gly Asn Ser Thr Ile Ser Pro Arg Glu Gln Val Tyr Leu Gly Leu Pro
        1460                1465                1470
```

```
cta tca aga aag cca aag agc cta ccc cag cac agt ttt gtg ggg tgc      4464
Leu Ser Arg Lys Pro Lys Ser Leu Pro Gln His Ser Phe Val Gly Cys
        1475                1480                1485 ctg aga gat ttc cag ttg aac tcg aaa ccc ctg gat tct cct tct gcg      4512
Leu Arg Asp Phe Gln Leu Asn Ser Lys Pro Leu Asp Ser Pro Ser Ala
    1490                1495                1500 agg ttt ggg gta tct ccc tgc ttg ggt ggc tct tta gag aaa ggc att      4560
Arg Phe Gly Val Ser Pro Cys Leu Gly Gly Ser Leu Glu Lys Gly Ile
1505                1510                1515                1520 tat ttc tcc caa gga gga ggc cat gtg atc cta gcc aat tct gtg tcc      4608
Tyr Phe Ser Gln Gly Gly Gly His Val Ile Leu Ala Asn Ser Val Ser
                1525                1530                1535 ttg ggg cca gag ctt aag ctc act ttc agc att cgc cca cgg agt ctc      4656
Leu Gly Pro Glu Leu Lys Leu Thr Phe Ser Ile Arg Pro Arg Ser Leu
            1540                1545                1550 act ggg gtc tta ata cac gtc gga agt caa tct gga cag cgc tta agt      4704
Thr Gly Val Leu Ile His Val Gly Ser Gln Ser Gly Gln Arg Leu Ser
        1555                1560                1565 gtg tac atg gag gca gga aag gtc aca acc tct gtg agc agt gat gca      4752
Val Tyr Met Glu Ala Gly Lys Val Thr Thr Ser Val Ser Ser Asp Ala
    1570                1575                1580 gga gga agt gtg aca tca att aca ccg aag cag tct ctg tgt gat gga      4800
Gly Gly Ser Val Thr Ser Ile Thr Pro Lys Gln Ser Leu Cys Asp Gly
1585                1590                1595                1600 cag tgg cac tcg gtg gca gtc tcc att aaa cag cgc atc ctg cat cta      4848
Gln Trp His Ser Val Ala Val Ser Ile Lys Gln Arg Ile Leu His Leu
                1605                1610                1615 gaa ctg gat aca gac agt agc tac aca gtc gca cca ctt tcc ttc tca      4896
Glu Leu Asp Thr Asp Ser Ser Tyr Thr Val Ala Pro Leu Ser Phe Ser
            1620                1625                1630 cca aac agc acc cga ggg tca ctg cac gtc gga ggt gtc cca gac aaa      4944
Pro Asn Ser Thr Arg Gly Ser Leu His Val Gly Gly Val Pro Asp Lys
        1635                1640                1645 ttg aaa atg ctt aca ctc cct gtg tgg aac tca ttt ttt ggc tgt ctg      4992
Leu Lys Met Leu Thr Leu Pro Val Trp Asn Ser Phe Phe Gly Cys Leu
    1650                1655                1660 aag aat att caa gtc aac cat gtc cct gtc ccc atc aca gaa gcc aca      5040
Lys Asn Ile Gln Val Asn His Val Pro Val Pro Ile Thr Glu Ala Thr
1665                1670                1675                1680 gaa gtc caa ggt tct gtc agc ctg aat ggc tgc cct gac cac               5082
Glu Val Gln Gly Ser Val Ser Leu Asn Gly Cys Pro Asp His
                1685                1690 taaccctaca cagcaagatt cacctttgga g                                   5113

<210> SEQ ID NO 12
<211> LENGTH: 1694
<212> TYPE: PRT
<213> ORGANISM: Rattus norvegicus

<400> SEQUENCE: 12

Gln Gln Arg Val Ala Phe Leu Gln His Pro Gly Gln Asn His Leu Gln
 1               5                   10                  15

Ala Ser Tyr Met Glu Leu Arg Pro Ser Gln Gly Cys Arg Pro Gly Tyr
                20                  25                  30

Tyr Arg Asp Ile Lys Ser Phe Pro Ala Gly Arg Ser Val Pro Cys Asn
            35                  40                  45

Cys Asn Gly His Ser Asn Arg Cys Gln Asp Gly Ser Gly Val Cys Ile
        50                  55                  60
```

-continued

```
Asn Cys Gln His Asn Thr Ala Gly Glu His Cys Glu Arg Cys Lys Arg
 65                  70                  75                  80

Gly Tyr Tyr Gly Ser Ala Ile His Gly Ser Cys Arg Val Cys Pro Cys
                 85                  90                  95

Pro His Thr Asn Ser Phe Ala Thr Gly Cys Ala Val Asp Gly Gly Ala
                100                 105                 110

Val Arg Cys Ala Cys Lys Pro Gly Tyr Thr Gly Ala Gln Cys Glu Arg
            115                 120                 125

Cys Ala Pro Gly Tyr Phe Gly Asn Pro Gln Lys Phe Gly Gly Ser Cys
130                 135                 140

Gln Pro Cys Asn Cys Asn Ser Asn Gly Gln Phe Gly Thr Cys Asp Pro
145                 150                 155                 160

Leu Thr Gly Asp Cys Val Ser Gln Glu Pro Lys Asp Gly Ser Pro Ala
                165                 170                 175

Glu Glu Cys Asp Asp Cys Asp Ser Cys Val Met Thr Leu Leu Asn Asp
            180                 185                 190

Leu Val Pro Met Gly Glu Glu Leu Ala Leu Val Lys Ser Lys Leu Gln
            195                 200                 205

Gly Leu Ser Val Asn Thr Gly Ser Leu Glu Gln Ile Arg His Val Glu
        210                 215                 220

Met Gln Ala Lys Asp Leu Arg Asn Gln Leu Leu Gly Phe Arg Ser Ala
225                 230                 235                 240

Ile Ser Ser His Gly Ser Gln Met Asp Gly Leu Glu Lys Glu Leu Ser
                245                 250                 255

His Leu Tyr Gln Glu Phe Glu Thr Leu Gln Glu Lys Ala Gln Val Asn
            260                 265                 270

Ser Arg Lys Ala Gln Thr Leu Tyr Asn Asn Ile Asp Thr Thr Ile Gln
        275                 280                 285

Asn Ala Lys Glu Leu Asp Met Lys Ile Lys Asn Ile Leu Thr Asn Val
        290                 295                 300

His Ile Leu Leu Lys Gln Ile Ala Arg Pro Gly Gly Glu Gly Met Asp
305                 310                 315                 320

Leu Pro Val Gly Asp Trp Ser Arg Glu Ser Ala Glu Ala Gln Arg Met
                325                 330                 335

Leu Arg Glu Leu Arg Gly Arg Asp Phe Lys Lys His Leu Gln Glu Ala
            340                 345                 350

Glu Ala Gln Lys Met Glu Ala Gln Leu Leu Leu Asn Arg Ile Arg Thr
        355                 360                 365

Trp Leu Glu Ser His Gln Val Glu Asn Asn Gly Leu Leu Lys Asn Ile
370                 375                 380

Arg Asp Ser Leu Asn Asp Tyr Glu Ala Lys Leu Gln Asp Leu Arg Ser
385                 390                 395                 400

Val Leu Gln Glu Ala Ala Gln Gly Lys Gln Ala Thr Gly Leu Asn
                405                 410                 415

His Glu Asn Glu Gly Val Leu Gly Ala Ile Gln Arg Gln Met Lys Glu
            420                 425                 430

Met Asp Ser Leu Lys Lys Tyr Leu Thr Glu His Leu Ala Thr Ala Asp
        435                 440                 445

Ala Ser Leu Leu Gln Thr Asn Ser Leu Leu Gln Arg Met Asp Thr Ser
        450                 455                 460

Gln Lys Glu Tyr Glu Ser Leu Ala Ala Ala Leu Asn Gly Ala Arg Gln
465                 470                 475                 480

Glu Leu Asn Asp Gln Val Arg Glu Leu Ser Arg Ser Gly Gly Lys Ala
```

-continued

```
                485                 490                 495
Pro Leu Val Ala Glu Ala Glu Lys His Ala Gln Ser Leu Gln Glu Leu
                500                 505                 510

Ala Lys Gln Leu Glu Glu Ile Lys Arg Asn Thr Ser Gly Asp Glu Ser
                515                 520                 525

Val Arg Cys Val Val Asp Ala Ala Thr Ala Tyr Glu Ser Ile Leu Asn
                530                 535                 540

Ala Ile Arg Ala Ala Glu Asp Ala Ala Gly Lys Ala Asp Ser Ala Ser
545                 550                 555                 560

Glu Ser Ala Phe Gln Thr Val Ile Lys Glu Asp Leu Pro Arg Arg Ala
                565                 570                 575

Lys Thr Leu Ser Ser Asp Ser Glu Glu Leu Leu Asn Glu Ala Lys Met
                580                 585                 590

Thr Arg Lys Arg Leu Gln Gln Glu Ile Asn Pro Ala Leu Asn Ser Leu
                595                 600                 605

Gln Gln Thr Leu Lys Thr Val Ser Val Gln Lys Asp Leu Leu Asp Ala
                610                 615                 620

Asn Val Thr Ala Val Arg Asn Asp Leu Arg Gly Ile Gln Arg Gly Asp
625                 630                 635                 640

Ile Asp Ser Val Val Ser Gly Ala Lys Ser Met Val Arg Lys Ala Asn
                645                 650                 655

Gly Ile Thr Ser Glu Val Leu Asp Gly Leu Ser Pro Ile Gln Thr Asp
                660                 665                 670

Leu Gly Arg Ile Lys Asp Ser Tyr Gly Ser Thr Arg His Glu Asp Phe
                675                 680                 685

Asn Lys Ala Leu Ile Asp Ala Asn Asn Ser Val Lys Lys Leu Thr Lys
                690                 695                 700

Lys Leu Pro Asp Leu Phe Val Lys Ile Glu Ser Ile Asn Gln Gln Leu
705                 710                 715                 720

Leu Pro Leu Gly Asn Ile Ser Asp Asn Val Asp Arg Ile Arg Glu Leu
                725                 730                 735

Ile Thr Gln Ala Arg Asp Ala Ala Asn Lys Val Ala Ile Pro Met Arg
                740                 745                 750

Phe Asn Gly Lys Ser Gly Val Glu Val Arg Leu Pro Asn Asp Leu Glu
                755                 760                 765

Asp Leu Lys Gly Tyr Thr Ser Leu Ser Leu Phe Leu Gln Arg Pro Asp
770                 775                 780

Leu Arg Glu Asn Gly Gly Thr Glu Asp Met Phe Val Met Tyr Leu Gly
785                 790                 795                 800

Asn Lys Asp Ala Ser Lys Asp Tyr Ile Gly Met Ala Val Val Asp Gly
                805                 810                 815

Gln Leu Thr Cys Val Tyr Asn Leu Gly Asp Arg Glu Ala Glu Val Gln
                820                 825                 830

Ile Asp Gln Val Leu Thr Glu Ser Glu Ser Gln Glu Ala Val Met Asp
                835                 840                 845

Arg Val Lys Phe Gln Arg Ile Tyr Gln Phe Ala Lys Leu Asn Tyr Thr
                850                 855                 860

Lys Glu Ala Thr Ser Asn Lys Pro Lys Ala Pro Ala Val Tyr Asp Leu
865                 870                 875                 880

Glu Gly Gly Ser Ser Asn Thr Leu Leu Asn Leu Asp Pro Glu Asp Ala
                885                 890                 895

Val Phe Tyr Val Gly Gly Tyr Pro Pro Asp Phe Glu Leu Pro Ser Arg
                900                 905                 910
```

-continued

```
Leu Arg Phe Pro Pro Tyr Lys Gly Cys Ile Glu Leu Asp Asp Leu Asn
            915                 920                 925
Glu Asn Val Leu Ser Leu Tyr Asn Phe Lys Thr Thr Phe Asn Leu Asn
        930                 935                 940
Thr Thr Glu Val Glu Pro Cys Arg Arg Arg Lys Glu Glu Ser Asp Lys
945                 950                 955                 960
Asn Tyr Phe Glu Gly Thr Gly Tyr Ala Arg Ile Pro Thr Gln Pro Asn
                965                 970                 975
Ala Pro Phe Pro Asn Phe Ile Gln Thr Ile Gln Thr Thr Val Asp Arg
            980                 985                 990
Gly Leu Leu Phe Phe Ala Glu Asn Gln Asp Asn Phe Ile Ser Leu Asn
        995                 1000                1005
Ile Glu Asp Gly Asn Leu Met Val Arg Tyr Lys Leu Asn Ser Glu Pro
    1010                1015                1020
Pro Lys Glu Lys Gly Ile Arg Asp Thr Ile Asn Asp Gly Lys Asp His
1025                1030                1035                1040
Ser Ile Leu Ile Thr Ile Gly Lys Leu Gln Lys Arg Met Trp Ile Asn
                1045                1050                1055
Val Asn Glu Arg Ser Val Arg Ile Glu Gly Glu Ile Phe Asp Phe Ser
            1060                1065                1070
Thr Tyr Tyr Leu Gly Gly Ile Pro Ile Ala Ile Arg Glu Arg Phe Asn
        1075                1080                1085
Ile Ser Thr Pro Ala Phe Gln Gly Cys Met Lys Asn Leu Lys Lys Thr
    1090                1095                1100
Ser Gly Val Val Arg Leu Asn Asp Thr Val Gly Val Thr Lys Lys Cys
1105                1110                1115                1120
Ser Glu Asp Trp Lys Leu Val Arg Thr Ala Ser Phe Ser Arg Gly Gly
                1125                1130                1135
Gln Met Ser Phe Thr Asn Leu Asp Val Pro Ser Thr Asp Arg Phe Gln
            1140                1145                1150
Leu Ser Phe Gly Phe Gln Thr Phe Gln Pro Ser Gly Thr Leu Leu Asn
        1155                1160                1165
His Gln Thr Arg Thr Ser Ser Leu Leu Val Thr Leu Glu Asp Gly His
    1170                1175                1180
Ile Glu Leu Ser Thr Arg Asp Ser Asn Ile Pro Ile Phe Lys Ser Pro
1185                1190                1195                1200
Gly Thr Tyr Met Asp Gly Leu Leu His His Val Ser Val Ile Ser Asp
                1205                1210                1215
Thr Ser Gly Leu Arg Leu Leu Ile Asp Asp Gln Val Leu Arg Arg Asn
            1220                1225                1230
Gln Arg Leu Pro Ser Phe Ser Asn Ala Gln Gln Ser Leu Arg Leu Gly
        1235                1240                1245
Gly Gly His Phe Glu Gly Cys Ile Ser Asn Val Leu Val Gln Arg Phe
    1250                1255                1260
Ser Gln Ser Pro Glu Val Leu Asp Leu Ala Ser Lys Ser Thr Lys Lys
1265                1270                1275                1280
Asp Ala Ser Leu Gly Gly Cys Ser Leu Asn Lys Pro Pro Phe Leu Met
                1285                1290                1295
Leu Phe Lys Ser Pro Lys Arg Phe Asn Lys Gly Arg Ile Phe Asn Val
            1300                1305                1310
Asn Gln Leu Met Gln Asp Ala Pro Gln Ala Thr Arg Ser Thr Glu Ala
        1315                1320                1325
```

```
Trp Gln Asp Gly Arg Ser Cys Leu Pro Pro Leu Asn Thr Lys Ala Ser
    1330                1335                1340

His Arg Ala Leu Gln Phe Gly Asp Ser Pro Thr Ser His Leu Leu Leu
1345                1350                1355                1360

Lys Leu Pro Gln Glu Leu Leu Lys Pro Arg Ser Gln Phe Ser Leu Asp
            1365                1370                1375

Ile Gln Thr Thr Ser Pro Lys Gly Leu Val Phe Tyr Ala Gly Thr Lys
        1380                1385                1390

Asp Ser Phe Leu Ala Leu Tyr Val Ala Asp Gly Arg Val Val Phe Ala
        1395                1400                1405

Leu Gly Ala Gly Gly Lys Lys Leu Arg Leu Arg Ser Lys Glu Arg Tyr
    1410                1415                1420

His Asp Gly Lys Trp His Thr Val Val Phe Gly Leu Asn Gly Gly Lys
1425                1430                1435                1440

Ala Arg Leu Val Val Asp Gly Leu Arg Ala Gln Glu Gly Ser Leu Pro
            1445                1450                1455

Gly Asn Ser Thr Ile Ser Pro Arg Glu Gln Val Tyr Leu Gly Leu Pro
        1460                1465                1470

Leu Ser Arg Lys Pro Lys Ser Leu Pro Gln His Ser Phe Val Gly Cys
        1475                1480                1485

Leu Arg Asp Phe Gln Leu Asn Ser Lys Pro Leu Asp Ser Pro Ser Ala
    1490                1495                1500

Arg Phe Gly Val Ser Pro Cys Leu Gly Gly Ser Leu Glu Lys Gly Ile
1505                1510                1515                1520

Tyr Phe Ser Gln Gly Gly Gly His Val Ile Leu Ala Asn Ser Val Ser
            1525                1530                1535

Leu Gly Pro Glu Leu Lys Leu Thr Phe Ser Ile Arg Pro Arg Ser Leu
        1540                1545                1550

Thr Gly Val Leu Ile His Val Gly Ser Gln Ser Gly Gln Arg Leu Ser
        1555                1560                1565

Val Tyr Met Glu Ala Gly Lys Val Thr Thr Ser Val Ser Ser Asp Ala
    1570                1575                1580

Gly Gly Ser Val Thr Ser Ile Thr Pro Lys Gln Ser Leu Cys Asp Gly
1585                1590                1595                1600

Gln Trp His Ser Val Ala Val Ser Ile Lys Gln Arg Ile Leu His Leu
            1605                1610                1615

Glu Leu Asp Thr Asp Ser Ser Tyr Thr Val Ala Pro Leu Ser Phe Ser
        1620                1625                1630

Pro Asn Ser Thr Arg Gly Ser Leu His Val Gly Gly Val Pro Asp Lys
        1635                1640                1645

Leu Lys Met Leu Thr Leu Pro Val Trp Asn Ser Phe Phe Gly Cys Leu
    1650                1655                1660

Lys Asn Ile Gln Val Asn His Val Pro Val Pro Ile Thr Glu Ala Thr
1665                1670                1675                1680

Glu Val Gln Gly Ser Val Ser Leu Asn Gly Cys Pro Asp His
            1685                1690

<210> SEQ ID NO 13
<211> LENGTH: 3930
<212> TYPE: DNA
<213> ORGANISM: Homo sapiens
<220> FEATURE:
<221> NAME/KEY: CDS
<222> LOCATION: (121)..(3630)
<221> NAME/KEY: sig_peptide
<222> LOCATION: (121)..(171)
```

```
<400> SEQUENCE: 13
gggcgggagg aggactgtat ctctggatgc ctggggcctg gtttcagggc ctgatttatt      60
cctcttcctg ggagctcact caggaaaggt cctttctggg gatcacccca ttggctgaag     120 atg aga cca ttc ttc ctc ttg tgt ttt gcc ctg cct ggc ctc ctg cat      168
Met Arg Pro Phe Phe Leu Leu Cys Phe Ala Leu Pro Gly Leu Leu His
  1               5                  10                  15 gcc caa caa gcc tgc tcc cgt ggg gcc tgc tat cca cct gtt ggg gac      216
Ala Gln Gln Ala Cys Ser Arg Gly Ala Cys Tyr Pro Pro Val Gly Asp
             20                  25                  30 ctg ctt gtt ggg agg acc cgg ttt ctc cga gct tca tct acc tgt gga      264
Leu Leu Val Gly Arg Thr Arg Phe Leu Arg Ala Ser Ser Thr Cys Gly
         35                  40                  45 ctg acc aag cct gag acc tac tgc acc cag tat ggc gag tgg cag atg      312
Leu Thr Lys Pro Glu Thr Tyr Cys Thr Gln Tyr Gly Glu Trp Gln Met
 50                  55                  60 aaa tgc tgc aag tgt gac tcc agg cag cct cac aac tac tac agt cac      360
Lys Cys Cys Lys Cys Asp Ser Arg Gln Pro His Asn Tyr Tyr Ser His
 65                  70                  75                  80 cga gta gag aat gtg gct tca tcc tcc ggc ccc atg cgc tgg tgg cag      408
Arg Val Glu Asn Val Ala Ser Ser Ser Gly Pro Met Arg Trp Trp Gln
                 85                  90                  95 tcc cag aat gat gtg aac cct gtc tct ctg cag ctg gac ctg gac agg      456
Ser Gln Asn Asp Val Asn Pro Val Ser Leu Gln Leu Asp Leu Asp Arg
            100                 105                 110 aga ttc cag ctt caa gaa gtc atg atg gag ttc cga ggg ccc atg cct      504
Arg Phe Gln Leu Gln Glu Val Met Met Glu Phe Arg Gly Pro Met Pro
        115                 120                 125 gcc ggc atg ctg att gag cgc tcc tca gac ttc ggt aag acc tgg cga      552
Ala Gly Met Leu Ile Glu Arg Ser Ser Asp Phe Gly Lys Thr Trp Arg
130                 135                 140 gtg tac cag tac ctg gct gcc gac tgc acc tcc acc ttc cct cgg gtc      600
Val Tyr Gln Tyr Leu Ala Ala Asp Cys Thr Ser Thr Phe Pro Arg Val
145                 150                 155                 160 cgc cag ggt cgg cct cag agc tgg cag gat gtt cgg tgc cag tcc ctg      648
Arg Gln Gly Arg Pro Gln Ser Trp Gln Asp Val Arg Cys Gln Ser Leu
                165                 170                 175 cct cag agg cct aat gca cgc cta aat ggg ggg aag gtc caa ctt aac      696
Pro Gln Arg Pro Asn Ala Arg Leu Asn Gly Gly Lys Val Gln Leu Asn
            180                 185                 190 ctt atg gat tta gtg tct ggg att cca gca act caa agt caa aaa att      744
Leu Met Asp Leu Val Ser Gly Ile Pro Ala Thr Gln Ser Gln Lys Ile
        195                 200                 205 caa gag gtg ggg gag atc aca aac ttg aga gtc aat ttc acc agg ctg      792
Gln Glu Val Gly Glu Ile Thr Asn Leu Arg Val Asn Phe Thr Arg Leu
210                 215                 220 gcc cct gtg ccc caa agg ggc tac cac cct ccc agc gcc tac tat gct      840
Ala Pro Val Pro Gln Arg Gly Tyr His Pro Pro Ser Ala Tyr Tyr Ala
225                 230                 235                 240 gtg tcc cag ctc cgt ctg cag ggg agc tgc ttc tgt cac ggc cat gct      888
Val Ser Gln Leu Arg Leu Gln Gly Ser Cys Phe Cys His Gly His Ala
                245                 250                 255 gat cgc tgc gca ccc aag cct ggg gcc tct gca ggc tcc acc gct gtg      936
Asp Arg Cys Ala Pro Lys Pro Gly Ala Ser Ala Gly Ser Thr Ala Val
            260                 265                 270 cag gtc cac gat gtc tgc gtc tgc cag cac aac act gcc ggc cca aat      984
Gln Val His Asp Val Cys Val Cys Gln His Asn Thr Ala Gly Pro Asn
        275                 280                 285
```

```
                                                                -continued tgt gag cgc tgt gca ccc ttc tac aac aac cgg ccc tgg aga ccg gcg        1032
Cys Glu Arg Cys Ala Pro Phe Tyr Asn Asn Arg Pro Trp Arg Pro Ala
290                 295                 300 gag ggc cag gac gcc cat gaa tgc caa agg tgc gac tgc aat ggg cac        1080
Glu Gly Gln Asp Ala His Glu Cys Gln Arg Cys Asp Cys Asn Gly His
305                 310                 315                 320 tca gag aca tgt cac ttt gac ccc gct gtg ttt gcc gcc agc cag ggg        1128
Ser Glu Thr Cys His Phe Asp Pro Ala Val Phe Ala Ala Ser Gln Gly
            325                 330                 335 gca tat gga ggt gtg tgt gac aat tgc cgg gac cac acc gaa ggc aag        1176
Ala Tyr Gly Gly Val Cys Asp Asn Cys Arg Asp His Thr Glu Gly Lys
        340                 345                 350 aac tgt gag cgg tgt cag ctg cac tat ttc cgg aac cgg cgc ccg gga        1224
Asn Cys Glu Arg Cys Gln Leu His Tyr Phe Arg Asn Arg Arg Pro Gly
    355                 360                 365 gct tcc att cag gag acc tgc atc tcc tgc gag tgt gat ccg gat ggg        1272
Ala Ser Ile Gln Glu Thr Cys Ile Ser Cys Glu Cys Asp Pro Asp Gly
370                 375                 380 gca gtc gca ggg gct ccc tgt gac cca gtg acc ggg cag tgt gtg tgc        1320
Ala Val Ala Gly Ala Pro Cys Asp Pro Val Thr Gly Gln Cys Val Cys
385                 390                 395                 400 aag gag cat gtg cag gga gag cgc tgt gac cta tgc aag ccg ggc ttc        1368
Lys Glu His Val Gln Gly Glu Arg Cys Asp Leu Cys Lys Pro Gly Phe
            405                 410                 415 act gga ctc acc tac gcc aac ccg cga cgg tgc cac cgc tgt gac tgc        1416
Thr Gly Leu Thr Tyr Ala Asn Pro Arg Arg Cys His Arg Cys Asp Cys
        420                 425                 430 aac atc ctg ggg tcc cgg gag atg ccg tgt gac gag gag agt ggg cgc        1464
Asn Ile Leu Gly Ser Arg Glu Met Pro Cys Asp Glu Glu Ser Gly Arg
    435                 440                 445 tgc ctt tgt ctg ccc aac gtg gtg ggt ccc aaa tgt gac cag tgt gct        1512
Cys Leu Cys Leu Pro Asn Val Val Gly Pro Lys Cys Asp Gln Cys Ala
450                 455                 460 ccc tac cac tgg aag ctg gcc agt ggc cag ggc tgt gaa ccg tgt gcc        1560
Pro Tyr His Trp Lys Leu Ala Ser Gly Gln Gly Cys Glu Pro Cys Ala
465                 470                 475                 480 tgc gac ccg cac aac tcc ctc agc cca cag tgc aac cag ttc aca ggg        1608
Cys Asp Pro His Asn Ser Leu Ser Pro Gln Cys Asn Gln Phe Thr Gly
            485                 490                 495 cag tgc ccc tgt cgg gaa ggc ttt ggt ggc ctg atg tgc agc gct gca        1656
Gln Cys Pro Cys Arg Glu Gly Phe Gly Gly Leu Met Cys Ser Ala Ala
        500                 505                 510 gcc atc cgc cag tgt cca gac cgg acc tat gga gac gtg gcc aca gga        1704
Ala Ile Arg Gln Cys Pro Asp Arg Thr Tyr Gly Asp Val Ala Thr Gly
    515                 520                 525 tgc cga gcc tgt gac tgt gat ttc cgg gga aca gag ggc ccg ggc tgc        1752
Cys Arg Ala Cys Asp Cys Asp Phe Arg Gly Thr Glu Gly Pro Gly Cys
530                 535                 540 gac aag gca tca ggc cgc tgc ctc tgc cgc cct ggc ttg acc ggg ccc        1800
Asp Lys Ala Ser Gly Arg Cys Leu Cys Arg Pro Gly Leu Thr Gly Pro
545                 550                 555                 560 cgc tgt gac cag tgc cag cga ggc tac tgc aat cgc tac ccg gtg tgc        1848
Arg Cys Asp Gln Cys Gln Arg Gly Tyr Cys Asn Arg Tyr Pro Val Cys
            565                 570                 575 gtg gcc tgc cac cct tgc ttc cag acc tat gat gcg gac ctc cgg gag        1896
Val Ala Cys His Pro Cys Phe Gln Thr Tyr Asp Ala Asp Leu Arg Glu
        580                 585                 590 cag gcc ctg cgc ttt ggt aga ctc ccg aat gcc acc gcc agc ctg tgg        1944
Gln Ala Leu Arg Phe Gly Arg Leu Pro Asn Ala Thr Ala Ser Leu Trp
    595                 600                 605
```

-continued

| | | | | | | | | | | | | | | | | |
|---|---|---|---|---|---|---|---|---|---|---|---|---|---|---|---|---|
| tca | ggg | cct | ggg | ctg | gag | gac | cgt | ggc | ctg | gcc | tcc | cgg | atc | cta | gat | 1992 |
| Ser | Gly | Pro | Gly | Leu | Glu | Asp | Arg | Gly | Leu | Ala | Ser | Arg | Ile | Leu | Asp | |
| | 610 | | | | | 615 | | | | | 620 | | | | | |
| gca | aag | agt | aag | att | gag | cag | atc | cga | gca | gtt | ctc | agc | agc | ccc | gca | 2040 |
| Ala | Lys | Ser | Lys | Ile | Glu | Gln | Ile | Arg | Ala | Val | Leu | Ser | Ser | Pro | Ala | |
| 625 | | | | | 630 | | | | | 635 | | | | | 640 | |
| gtc | aca | gag | cag | gag | gtg | gct | cag | gtg | gcc | agt | gcc | atc | ctc | tcc | ctc | 2088 |
| Val | Thr | Glu | Gln | Glu | Val | Ala | Gln | Val | Ala | Ser | Ala | Ile | Leu | Ser | Leu | |
| | | | | 645 | | | | | 650 | | | | | 655 | | |
| agg | cga | act | ctc | cag | ggc | ctg | cag | ctg | gat | ctg | ccc | ctg | gag | gag | gag | 2136 |
| Arg | Arg | Thr | Leu | Gln | Gly | Leu | Gln | Leu | Asp | Leu | Pro | Leu | Glu | Glu | Glu | |
| | | | 660 | | | | | 665 | | | | | 670 | | | |
| acg | ttg | tcc | ctt | ccg | aga | gac | ctg | gag | agt | ctt | gac | aga | agc | ttc | aat | 2184 |
| Thr | Leu | Ser | Leu | Pro | Arg | Asp | Leu | Glu | Ser | Leu | Asp | Arg | Ser | Phe | Asn | |
| | | 675 | | | | | 680 | | | | | 685 | | | | |
| ggt | ctc | ctt | act | atg | tat | cag | agg | aag | agg | gag | cag | ttt | gaa | aaa | ata | 2232 |
| Gly | Leu | Leu | Thr | Met | Tyr | Gln | Arg | Lys | Arg | Glu | Gln | Phe | Glu | Lys | Ile | |
| | 690 | | | | | 695 | | | | | 700 | | | | | |
| agc | agt | gct | gat | cct | tca | gga | gcc | ttc | cgg | atg | ctg | agc | aca | gcc | tac | 2280 |
| Ser | Ser | Ala | Asp | Pro | Ser | Gly | Ala | Phe | Arg | Met | Leu | Ser | Thr | Ala | Tyr | |
| 705 | | | | | 710 | | | | | 715 | | | | | 720 | |
| gag | cag | tca | gcc | cag | gct | gct | cag | cag | gtc | tcc | gac | agc | tcg | cgc | ctt | 2328 |
| Glu | Gln | Ser | Ala | Gln | Ala | Ala | Gln | Gln | Val | Ser | Asp | Ser | Ser | Arg | Leu | |
| | | | | 725 | | | | | 730 | | | | | 735 | | |
| ttg | gac | cag | ctc | agg | gac | agc | cgg | aga | gag | gca | gag | agg | ctg | gtg | cgg | 2376 |
| Leu | Asp | Gln | Leu | Arg | Asp | Ser | Arg | Arg | Glu | Ala | Glu | Arg | Leu | Val | Arg | |
| | | | 740 | | | | | 745 | | | | | 750 | | | |
| cag | gcg | gga | gga | gga | gga | ggc | acc | ggc | agc | ccc | aag | ctt | gtg | gcc | ctg | 2424 |
| Gln | Ala | Gly | Gly | Gly | Gly | Gly | Thr | Gly | Ser | Pro | Lys | Leu | Val | Ala | Leu | |
| | | 755 | | | | | 760 | | | | | 765 | | | | |
| agg | ttg | gag | atg | tct | tcg | ttg | cct | gac | ctg | aca | ccc | acc | ttc | aac | aag | 2472 |
| Arg | Leu | Glu | Met | Ser | Ser | Leu | Pro | Asp | Leu | Thr | Pro | Thr | Phe | Asn | Lys | |
| | 770 | | | | | 775 | | | | | 780 | | | | | |
| ctc | tgt | ggc | aac | tcc | agg | cag | atg | gct | tgc | acc | cca | ata | tca | tgc | cct | 2520 |
| Leu | Cys | Gly | Asn | Ser | Arg | Gln | Met | Ala | Cys | Thr | Pro | Ile | Ser | Cys | Pro | |
| 785 | | | | | 790 | | | | | 795 | | | | | 800 | |
| ggt | gag | cta | tgt | ccc | caa | gac | aat | ggc | aca | gcc | tgt | gcg | tcc | cgc | tgc | 2568 |
| Gly | Glu | Leu | Cys | Pro | Gln | Asp | Asn | Gly | Thr | Ala | Cys | Ala | Ser | Arg | Cys | |
| | | | | 805 | | | | | 810 | | | | | 815 | | |
| agg | ggt | gtc | ctt | ccc | agg | gcc | ggt | ggg | gcc | ttc | ttg | atg | gcg | ggg | cag | 2616 |
| Arg | Gly | Val | Leu | Pro | Arg | Ala | Gly | Gly | Ala | Phe | Leu | Met | Ala | Gly | Gln | |
| | | | 820 | | | | | 825 | | | | | 830 | | | |
| gtg | gct | gag | cag | ctg | cgg | ggc | ttc | aat | gcc | cag | ctc | cag | cgg | acc | agg | 2664 |
| Val | Ala | Glu | Gln | Leu | Arg | Gly | Phe | Asn | Ala | Gln | Leu | Gln | Arg | Thr | Arg | |
| | | 835 | | | | | 840 | | | | | 845 | | | | |
| cag | atg | att | agg | gca | gcc | gag | gaa | tct | gcc | tca | cag | att | caa | tcc | agt | 2712 |
| Gln | Met | Ile | Arg | Ala | Ala | Glu | Glu | Ser | Ala | Ser | Gln | Ile | Gln | Ser | Ser | |
| | 850 | | | | | 855 | | | | | 860 | | | | | |
| gcc | cag | cgc | ttg | gag | acc | cag | gtg | agc | gcc | agc | cgc | tcc | cag | atg | gag | 2760 |
| Ala | Gln | Arg | Leu | Glu | Thr | Gln | Val | Ser | Ala | Ser | Arg | Ser | Gln | Met | Glu | |
| 865 | | | | | 870 | | | | | 875 | | | | | 880 | |
| gaa | gat | gtc | aga | cgc | aca | cgg | ctc | cta | atc | cag | cag | gtc | cgg | gac | ttc | 2808 |
| Glu | Asp | Val | Arg | Arg | Thr | Arg | Leu | Leu | Ile | Gln | Gln | Val | Arg | Asp | Phe | |
| | | | | 885 | | | | | 890 | | | | | 895 | | |
| cta | aca | gac | ccc | gac | act | gat | gca | gcc | act | atc | cag | gag | gtc | agc | gag | 2856 |
| Leu | Thr | Asp | Pro | Asp | Thr | Asp | Ala | Ala | Thr | Ile | Gln | Glu | Val | Ser | Glu | |
| | | | 900 | | | | | 905 | | | | | 910 | | | |
| gcc | gtg | ctg | gcc | ctg | tgg | ctg | ccc | aca | gac | tca | gct | act | gtt | ctg | cag | 2904 |
| Ala | Val | Leu | Ala | Leu | Trp | Leu | Pro | Thr | Asp | Ser | Ala | Thr | Val | Leu | Gln | |

```
                915                 920                 925
aag atg aat gag atc cag gcc att gca gcc agg ctc ccc aac gtg gac      2952
Lys Met Asn Glu Ile Gln Ala Ile Ala Ala Arg Leu Pro Asn Val Asp
        930                 935                 940 ttg gtg ctg tcc cag acc aag cag gac att gcg cgt gcc cgc cgg ttg      3000
Leu Val Leu Ser Gln Thr Lys Gln Asp Ile Ala Arg Ala Arg Arg Leu
945                 950                 955                 960 cag gct gag gct gag gaa gcc agg agc cga gcc cat gca gtg gag ggc      3048
Gln Ala Glu Ala Glu Glu Ala Arg Ser Arg Ala His Ala Val Glu Gly
                965                 970                 975 cag gtg gag gat gtg gtt ggg aac ctg cgg cag ggg aca gtg gca ctg      3096
Gln Val Glu Asp Val Val Gly Asn Leu Arg Gln Gly Thr Val Ala Leu
            980                 985                 990 cag gaa gct cag gac acc atg caa ggc acc agc cgg tcc ctt cgg ctt      3144
Gln Glu Ala Gln Asp Thr Met Gln Gly Thr Ser Arg Ser Leu Arg Leu
        995                 1000                1005 atc cag gac agg gtt gct gag gtt cag cag gta ctg cgg cca gca gaa      3192
Ile Gln Asp Arg Val Ala Glu Val Gln Gln Val Leu Arg Pro Ala Glu
    1010                1015                1020 aag ctg gtg aca agc atg acc aag cag ctg ggt gac ttc tgg aca cgg      3240
Lys Leu Val Thr Ser Met Thr Lys Gln Leu Gly Asp Phe Trp Thr Arg
1025                1030                1035                1040 atg gag gag ctc cgc cac caa gcc cgg cag cag ggg gca gag gca gtc      3288
Met Glu Glu Leu Arg His Gln Ala Arg Gln Gln Gly Ala Glu Ala Val
                1045                1050                1055 cag gcc cag cag ctt gcg gaa ggt gcc agc gag cag gca ttg agt gcc      3336
Gln Ala Gln Gln Leu Ala Glu Gly Ala Ser Glu Gln Ala Leu Ser Ala
            1060                1065                1070 caa gag gga ttt gag aga ata aaa caa aag tat gct gag ttg aag gac      3384
Gln Glu Gly Phe Glu Arg Ile Lys Gln Lys Tyr Ala Glu Leu Lys Asp
        1075                1080                1085 cgg ttg ggt cag agt tcc atg ctg ggt gag cag ggt gcc cgg atc cag      3432
Arg Leu Gly Gln Ser Ser Met Leu Gly Glu Gln Gly Ala Arg Ile Gln
    1090                1095                1100 agt gtg aag aca gag gca gag gag ctg ttt ggg gag acc atg gag atg      3480
Ser Val Lys Thr Glu Ala Glu Glu Leu Phe Gly Glu Thr Met Glu Met
1105                1110                1115                1120 atg gac agg atg aaa gac atg gag ttg gag ctg ctg cgg ggc agc cag      3528
Met Asp Arg Met Lys Asp Met Glu Leu Glu Leu Leu Arg Gly Ser Gln
                1125                1130                1135 gcc atc atg ctg cgc tca gcg gac ctg aca gga ctg gag aag cgt gtg      3576
Ala Ile Met Leu Arg Ser Ala Asp Leu Thr Gly Leu Glu Lys Arg Val
            1140                1145                1150 gag cag atc cgt gac cac atc aat ggg cgc gtg ctc tac tat gcc acc      3624
Glu Gln Ile Arg Asp His Ile Asn Gly Arg Val Leu Tyr Tyr Ala Thr
        1155                1160                1165 tgc aag tgatgctaca cgttccagcc cgttgcccca ctcatctgcg cgctttgctt      3680
Cys Lys
    1170 ttggttgggg ggcagattgg gttggaatgc tttccatctc caggagactt tcatgtagcc      3740 caaagtacag cctggaccac ccctggtgtg tgtagctagt aagattaccc tgagctgcag      3800 ctgagcctga gccaatggga cagttacact tgacagacaa agatggtgga gattggcatg      3860 ccattgaaac taagagctct caagtcaagg aagctgggct gggcagtatc cccgcctttt      3920 agttctccac                                                             3930

<210> SEQ ID NO 14
<211> LENGTH: 1170
```

```
<212> TYPE: PRT
<213> ORGANISM: Homo sapiens

<400> SEQUENCE: 14

Met Arg Pro Phe Phe Leu Leu Cys Phe Ala Leu Pro Gly Leu Leu His
 1               5                  10                  15

Ala Gln Gln Ala Cys Ser Arg Gly Ala Cys Tyr Pro Pro Val Gly Asp
            20                  25                  30

Leu Leu Val Gly Arg Thr Arg Phe Leu Arg Ala Ser Ser Thr Cys Gly
        35                  40                  45

Leu Thr Lys Pro Glu Thr Tyr Cys Thr Gln Tyr Gly Glu Trp Gln Met
    50                  55                  60

Lys Cys Cys Lys Cys Asp Ser Arg Gln Pro His Asn Tyr Tyr Ser His
65                  70                  75                  80

Arg Val Glu Asn Val Ala Ser Ser Gly Pro Met Arg Trp Trp Gln
                85                  90                  95

Ser Gln Asn Asp Val Asn Pro Val Ser Leu Gln Leu Asp Leu Asp Arg
                100                 105                 110

Arg Phe Gln Leu Gln Glu Val Met Met Glu Phe Arg Gly Pro Met Pro
            115                 120                 125

Ala Gly Met Leu Ile Glu Arg Ser Ser Asp Phe Gly Lys Thr Trp Arg
        130                 135                 140

Val Tyr Gln Tyr Leu Ala Ala Asp Cys Thr Ser Thr Phe Pro Arg Val
145                 150                 155                 160

Arg Gln Gly Arg Pro Gln Ser Trp Gln Asp Val Arg Cys Gln Ser Leu
                165                 170                 175

Pro Gln Arg Pro Asn Ala Arg Leu Asn Gly Gly Lys Val Gln Leu Asn
            180                 185                 190

Leu Met Asp Leu Val Ser Gly Ile Pro Ala Thr Gln Ser Gln Lys Ile
        195                 200                 205

Gln Glu Val Gly Glu Ile Thr Asn Leu Arg Val Asn Phe Thr Arg Leu
    210                 215                 220

Ala Pro Val Pro Gln Arg Gly Tyr His Pro Pro Ser Ala Tyr Tyr Ala
225                 230                 235                 240

Val Ser Gln Leu Arg Leu Gln Gly Ser Cys Phe Cys His Gly His Ala
                245                 250                 255

Asp Arg Cys Ala Pro Lys Pro Gly Ala Ser Ala Gly Ser Thr Ala Val
            260                 265                 270

Gln Val His Asp Val Cys Val Cys Gln His Asn Thr Ala Gly Pro Asn
        275                 280                 285

Cys Glu Arg Cys Ala Pro Phe Tyr Asn Asn Arg Pro Trp Arg Pro Ala
    290                 295                 300

Glu Gly Gln Asp Ala His Glu Cys Gln Arg Cys Asp Cys Asn Gly His
305                 310                 315                 320

Ser Glu Thr Cys His Phe Asp Pro Ala Val Phe Ala Ala Ser Gln Gly
                325                 330                 335

Ala Tyr Gly Gly Val Cys Asp Asn Cys Arg Asp His Thr Glu Gly Lys
            340                 345                 350

Asn Cys Glu Arg Cys Gln Leu His Tyr Phe Arg Asn Arg Arg Pro Gly
        355                 360                 365

Ala Ser Ile Gln Glu Thr Cys Ile Ser Cys Glu Cys Asp Pro Asp Gly
    370                 375                 380

Ala Val Ala Gly Ala Pro Cys Asp Pro Val Thr Gly Gln Cys Val Cys
385                 390                 395                 400
```

-continued

```
Lys Glu His Val Gln Gly Glu Arg Cys Asp Leu Cys Lys Pro Gly Phe
                405                 410                 415
Thr Gly Leu Thr Tyr Ala Asn Pro Arg Arg Cys His Arg Cys Asp Cys
                420                 425                 430
Asn Ile Leu Gly Ser Arg Glu Met Pro Cys Asp Glu Ser Gly Arg
                435                 440                 445
Cys Leu Cys Leu Pro Asn Val Val Gly Pro Lys Cys Asp Gln Cys Ala
        450                 455                 460
Pro Tyr His Trp Lys Leu Ala Ser Gly Gln Gly Cys Glu Pro Cys Ala
465                 470                 475                 480
Cys Asp Pro His Asn Ser Leu Ser Pro Gln Cys Asn Gln Phe Thr Gly
                485                 490                 495
Gln Cys Pro Cys Arg Glu Gly Phe Gly Gly Leu Met Cys Ser Ala Ala
                500                 505                 510
Ala Ile Arg Gln Cys Pro Asp Arg Thr Tyr Gly Asp Val Ala Thr Gly
                515                 520                 525
Cys Arg Ala Cys Asp Cys Asp Phe Arg Gly Thr Glu Gly Pro Gly Cys
        530                 535                 540
Asp Lys Ala Ser Gly Arg Cys Leu Cys Arg Pro Gly Leu Thr Gly Pro
545                 550                 555                 560
Arg Cys Asp Gln Cys Gln Arg Gly Tyr Cys Asn Arg Tyr Pro Val Cys
                565                 570                 575
Val Ala Cys His Pro Cys Phe Gln Thr Tyr Asp Ala Asp Leu Arg Glu
                580                 585                 590
Gln Ala Leu Arg Phe Gly Arg Leu Pro Asn Ala Thr Ala Ser Leu Trp
                595                 600                 605
Ser Gly Pro Gly Leu Glu Asp Arg Gly Leu Ala Ser Arg Ile Leu Asp
        610                 615                 620
Ala Lys Ser Lys Ile Glu Gln Ile Arg Ala Val Leu Ser Ser Pro Ala
625                 630                 635                 640
Val Thr Glu Gln Glu Val Ala Gln Val Ala Ser Ala Ile Leu Ser Leu
                645                 650                 655
Arg Arg Thr Leu Gln Gly Leu Gln Leu Asp Leu Pro Leu Glu Glu Glu
                660                 665                 670
Thr Leu Ser Leu Pro Arg Asp Leu Glu Ser Leu Asp Arg Ser Phe Asn
                675                 680                 685
Gly Leu Leu Thr Met Tyr Gln Arg Lys Arg Glu Gln Phe Glu Lys Ile
        690                 695                 700
Ser Ser Ala Asp Pro Ser Gly Ala Phe Arg Met Leu Ser Thr Ala Tyr
705                 710                 715                 720
Glu Gln Ser Ala Gln Ala Ala Gln Gln Val Ser Asp Ser Ser Arg Leu
                725                 730                 735
Leu Asp Gln Leu Arg Asp Ser Arg Arg Glu Ala Glu Arg Leu Val Arg
                740                 745                 750
Gln Ala Gly Gly Gly Gly Thr Gly Ser Pro Lys Leu Val Ala Leu
                755                 760                 765
Arg Leu Glu Met Ser Ser Leu Pro Asp Leu Thr Pro Thr Phe Asn Lys
        770                 775                 780
Leu Cys Gly Asn Ser Arg Gln Met Ala Cys Thr Pro Ile Ser Cys Pro
785                 790                 795                 800
Gly Glu Leu Cys Pro Gln Asp Asn Gly Thr Ala Cys Ala Ser Arg Cys
                805                 810                 815
```

```
Arg Gly Val Leu Pro Arg Ala Gly Ala Phe Leu Met Ala Gly Gln
            820                 825                 830

Val Ala Glu Gln Leu Arg Gly Phe Asn Ala Gln Leu Gln Arg Thr Arg
        835                 840                 845

Gln Met Ile Arg Ala Ala Glu Glu Ser Ala Ser Gln Ile Gln Ser Ser
        850                 855                 860

Ala Gln Arg Leu Glu Thr Gln Val Ser Ala Ser Arg Ser Gln Met Glu
865                 870                 875                 880

Glu Asp Val Arg Arg Thr Arg Leu Leu Ile Gln Gln Val Arg Asp Phe
                885                 890                 895

Leu Thr Asp Pro Asp Thr Asp Ala Ala Thr Ile Gln Glu Val Ser Glu
                900                 905                 910

Ala Val Leu Ala Leu Trp Leu Pro Thr Asp Ser Ala Thr Val Leu Gln
        915                 920                 925

Lys Met Asn Glu Ile Gln Ala Ile Ala Ala Arg Leu Pro Asn Val Asp
        930                 935                 940

Leu Val Leu Ser Gln Thr Lys Gln Asp Ile Ala Arg Ala Arg Arg Leu
945                 950                 955                 960

Gln Ala Glu Ala Glu Glu Ala Arg Ser Arg Ala His Ala Val Glu Gly
                965                 970                 975

Gln Val Glu Asp Val Val Gly Asn Leu Arg Gln Gly Thr Val Ala Leu
            980                 985                 990

Gln Glu Ala Gln Asp Thr Met Gln Gly Thr Ser Arg Ser Leu Arg Leu
        995                 1000                1005

Ile Gln Asp Arg Val Ala Glu Val Gln Val Leu Arg Pro Ala Glu
    1010                1015                1020

Lys Leu Val Thr Ser Met Thr Lys Gln Leu Gly Asp Phe Trp Thr Arg
1025                1030                1035                1040

Met Glu Glu Leu Arg His Gln Ala Arg Gln Gln Gly Ala Glu Ala Val
                1045                1050                1055

Gln Ala Gln Gln Leu Ala Glu Gly Ala Ser Glu Gln Ala Leu Ser Ala
            1060                1065                1070

Gln Glu Gly Phe Glu Arg Ile Lys Gln Lys Tyr Ala Glu Leu Lys Asp
        1075                1080                1085

Arg Leu Gly Gln Ser Ser Met Leu Gly Glu Gln Gly Ala Arg Ile Gln
    1090                1095                1100

Ser Val Lys Thr Glu Ala Glu Glu Leu Phe Gly Glu Thr Met Glu Met
1105                1110                1115                1120

Met Asp Arg Met Lys Asp Met Glu Leu Glu Leu Leu Arg Gly Ser Gln
                1125                1130                1135

Ala Ile Met Leu Arg Ser Ala Asp Leu Thr Gly Leu Glu Lys Arg Val
            1140                1145                1150
Glu Gln Ile Arg Asp His Ile Asn Gly Arg Val Leu Tyr Tyr Ala Thr
        1155                1160                1165

Cys Lys
    1170

<210> SEQ ID NO 15
<211> LENGTH: 3759
<212> TYPE: DNA
<213> ORGANISM: Homo sapiens
<220> FEATURE:
<221> NAME/KEY: CDS
<222> LOCATION: (1)..(3459)

<400> SEQUENCE: 15
```

```
caa caa gcc tgc tcc cgt ggg gcc tgc tat cca cct gtt ggg gac ctg    48
Gln Gln Ala Cys Ser Arg Gly Ala Cys Tyr Pro Pro Val Gly Asp Leu
  1               5                  10                  15 ctt gtt ggg agg acc cgg ttt ctc cga gct tca tct acc tgt gga ctg    96
Leu Val Gly Arg Thr Arg Phe Leu Arg Ala Ser Ser Thr Cys Gly Leu
         20                  25                  30 acc aag cct gag acc tac tgc acc cag tat ggc gag tgg cag atg aaa   144
Thr Lys Pro Glu Thr Tyr Cys Thr Gln Tyr Gly Glu Trp Gln Met Lys
     35                  40                  45 tgc tgc aag tgt gac tcc agg cag cct cac aac tac tac agt cac cga   192
Cys Cys Lys Cys Asp Ser Arg Gln Pro His Asn Tyr Tyr Ser His Arg
 50                  55                  60 gta gag aat gtg gct tca tcc tcc ggc ccc atg cgc tgg tgg cag tcc   240
Val Glu Asn Val Ala Ser Ser Ser Gly Pro Met Arg Trp Trp Gln Ser
 65                  70                  75                  80 cag aat gat gtg aac cct gtc tct ctg cag ctg gac ctg gac agg aga   288
Gln Asn Asp Val Asn Pro Val Ser Leu Gln Leu Asp Leu Asp Arg Arg
                 85                  90                  95 ttc cag ctt caa gaa gtc atg atg gag ttc cga ggg ccc atg cct gcc   336
Phe Gln Leu Gln Glu Val Met Met Glu Phe Arg Gly Pro Met Pro Ala
            100                 105                 110 ggc atg ctg att gag cgc tcc tca gac ttc ggt aag acc tgg cga gtg   384
Gly Met Leu Ile Glu Arg Ser Ser Asp Phe Gly Lys Thr Trp Arg Val
        115                 120                 125 tac cag tac ctg gct gcc gac tgc acc tcc acc ttc cct cgg gtc cgc   432
Tyr Gln Tyr Leu Ala Ala Asp Cys Thr Ser Thr Phe Pro Arg Val Arg
    130                 135                 140 cag ggt cgg cct cag agc tgg cag gat gtt cgg tgc cag tcc ctg cct   480
Gln Gly Arg Pro Gln Ser Trp Gln Asp Val Arg Cys Gln Ser Leu Pro
145                 150                 155                 160 cag agg cct aat gca cgc cta aat ggg ggg aag gtc caa ctt aac ctt   528
Gln Arg Pro Asn Ala Arg Leu Asn Gly Gly Lys Val Gln Leu Asn Leu
                165                 170                 175 atg gat tta gtg tct ggg att cca gca act caa agt caa aaa att caa   576
Met Asp Leu Val Ser Gly Ile Pro Ala Thr Gln Ser Gln Lys Ile Gln
            180                 185                 190 gag gtg ggg gag atc aca aac ttg aga gtc aat ttc acc agg ctg gcc   624
Glu Val Gly Glu Ile Thr Asn Leu Arg Val Asn Phe Thr Arg Leu Ala
        195                 200                 205 cct gtg ccc caa agg ggc tac cac cct ccc agc gcc tac tat gct gtg   672
Pro Val Pro Gln Arg Gly Tyr His Pro Pro Ser Ala Tyr Tyr Ala Val
    210                 215                 220 tcc cag ctc cgt ctg cag ggg agc tgc ttc tgt cac ggc cat gct gat   720
Ser Gln Leu Arg Leu Gln Gly Ser Cys Phe Cys His Gly His Ala Asp
225                 230                 235                 240 cgc tgc gca ccc aag cct ggg gcc tct gca ggc tcc acc gct gtg cag   768
Arg Cys Ala Pro Lys Pro Gly Ala Ser Ala Gly Ser Thr Ala Val Gln
                245                 250                 255 gtc cac gat gtc tgc gtc tgc cag cac aac act gcc ggc cca aat tgt   816
Val His Asp Val Cys Val Cys Gln His Asn Thr Ala Gly Pro Asn Cys
            260                 265                 270 gag cgc tgt gca ccc ttc tac aac aac cgg ccc tgg aga ccg gcg gag   864
Glu Arg Cys Ala Pro Phe Tyr Asn Asn Arg Pro Trp Arg Pro Ala Glu
        275                 280                 285 ggc cag gac gcc cat gaa tgc caa agg tgc gac tgc aat ggg cac tca   912
Gly Gln Asp Ala His Glu Cys Gln Arg Cys Asp Cys Asn Gly His Ser
    290                 295                 300 gag aca tgt cac ttt gac ccc gct gtg ttt gcc gcc agc cag ggg gca   960
Glu Thr Cys His Phe Asp Pro Ala Val Phe Ala Ala Ser Gln Gly Ala
305                 310                 315                 320
```

```
tat gga ggt gtg tgt gac aat tgc cgg gac cac acc gaa ggc aag aac    1008
Tyr Gly Gly Val Cys Asp Asn Cys Arg Asp His Thr Glu Gly Lys Asn
                325                 330                 335 tgt gag cgg tgt cag ctg cac tat ttc cgg aac cgc cgc ccg gga gct    1056
Cys Glu Arg Cys Gln Leu His Tyr Phe Arg Asn Arg Arg Pro Gly Ala
            340                 345                 350 tcc att cag gag acc tgc atc tcc tgc gag tgt gat ccg gat ggg gca    1104
Ser Ile Gln Glu Thr Cys Ile Ser Cys Glu Cys Asp Pro Asp Gly Ala
        355                 360                 365 gtc gca ggg gct ccc tgt gac cca gtg acc ggg cag tgt gtg tgc aag    1152
Val Ala Gly Ala Pro Cys Asp Pro Val Thr Gly Gln Cys Val Cys Lys
    370                 375                 380 gag cat gtg cag gga gag cgc tgt gac cta tgc aag ccg ggc ttc act    1200
Glu His Val Gln Gly Glu Arg Cys Asp Leu Cys Lys Pro Gly Phe Thr
385                 390                 395                 400 gga ctc acc tac gcc aac ccg cga cgg tgc cac cgc tgt gac tgc aac    1248
Gly Leu Thr Tyr Ala Asn Pro Arg Arg Cys His Arg Cys Asp Cys Asn
                405                 410                 415 atc ctg ggg tcc cgg gag atg ccg tgt gac gag gag agt ggg cgc tgc    1296
Ile Leu Gly Ser Arg Glu Met Pro Cys Asp Glu Glu Ser Gly Arg Cys
            420                 425                 430 ctt tgt ctg ccc aac gtg gtg ggt ccc aaa tgt gac cag tgt gct ccc    1344
Leu Cys Leu Pro Asn Val Val Gly Pro Lys Cys Asp Gln Cys Ala Pro
        435                 440                 445 tac cac tgg aag ctg gcc agt ggc cag ggc tgt gaa ccg tgt gcc tgc    1392
Tyr His Trp Lys Leu Ala Ser Gly Gln Gly Cys Glu Pro Cys Ala Cys
    450                 455                 460 gac ccg cac aac tcc ctc agc cca cag tgc aac cag ttc aca ggg cag    1440
Asp Pro His Asn Ser Leu Ser Pro Gln Cys Asn Gln Phe Thr Gly Gln
465                 470                 475                 480 tgc ccc tgt cgg gaa ggc ttt ggt ggc ctg atg tgc agc gct gca gcc    1488
Cys Pro Cys Arg Glu Gly Phe Gly Gly Leu Met Cys Ser Ala Ala Ala
                485                 490                 495 atc cgc cag tgt cca gac cgg acc tat gga gac gtg gcc aca gga tgc    1536
Ile Arg Gln Cys Pro Asp Arg Thr Tyr Gly Asp Val Ala Thr Gly Cys
            500                 505                 510 cga gcc tgt gac tgt gat ttc cgg gga aca gag ggc ccg ggc tgc gac    1584
Arg Ala Cys Asp Cys Asp Phe Arg Gly Thr Glu Gly Pro Gly Cys Asp
        515                 520                 525 aag gca tca ggc cgc tgc ctc tgc cgc cct ggc ttg acc ggg ccc cgc    1632
Lys Ala Ser Gly Arg Cys Leu Cys Arg Pro Gly Leu Thr Gly Pro Arg
    530                 535                 540 tgt gac cag tgc cag cga ggc tac tgc aat cgc tac ccg gtg tgc gtg    1680
Cys Asp Gln Cys Gln Arg Gly Tyr Cys Asn Arg Tyr Pro Val Cys Val
545                 550                 555                 560 gcc tgc cac cct tgc ttc cag acc tat gat gcg gac ctc cgg gag cag    1728
Ala Cys His Pro Cys Phe Gln Thr Tyr Asp Ala Asp Leu Arg Glu Gln
                565                 570                 575 gcc ctg cgc ttt ggt aga ctc ccg aat gcc acc gcc agc ctg tgg tca    1776
Ala Leu Arg Phe Gly Arg Leu Pro Asn Ala Thr Ala Ser Leu Trp Ser
            580                 585                 590 ggg cct ggg ctg gag gac cgt ggc ctg gcc tcc cgg atc cta gat gca    1824
Gly Pro Gly Leu Glu Asp Arg Gly Leu Ala Ser Arg Ile Leu Asp Ala
        595                 600                 605 aag agt aag att gag cag atc cga gca gtt ctc agc agc ccc gca gtc    1872
Lys Ser Lys Ile Glu Gln Ile Arg Ala Val Leu Ser Ser Pro Ala Val
    610                 615                 620 aca gag cag gag gtg gct cag gtg gcc agt gcc atc ctc tcc ctc agg    1920
Thr Glu Gln Glu Val Ala Gln Val Ala Ser Ala Ile Leu Ser Leu Arg
```

```
                625                 630                 635                 640
cga act ctc cag ggc ctg cag ctg gat ctg ccc ctg gag gag gag acg           1968
Arg Thr Leu Gln Gly Leu Gln Leu Asp Leu Pro Leu Glu Glu Glu Thr
                    645                 650                 655 ttg tcc ctt ccg aga gac ctg gag agt ctt gac aga agc ttc aat ggt           2016
Leu Ser Leu Pro Arg Asp Leu Glu Ser Leu Asp Arg Ser Phe Asn Gly
                660                 665                 670 ctc ctt act atg tat cag agg aag agg gag cag ttt gaa aaa ata agc           2064
Leu Leu Thr Met Tyr Gln Arg Lys Arg Glu Gln Phe Glu Lys Ile Ser
            675                 680                 685 agt gct gat cct tca gga gcc ttc cgg atg ctg agc aca gcc tac gag           2112
Ser Ala Asp Pro Ser Gly Ala Phe Arg Met Leu Ser Thr Ala Tyr Glu
        690                 695                 700 cag tca gcc cag gct gct cag cag gtc tcc gac agc tcg cgc ctt ttg           2160
Gln Ser Ala Gln Ala Ala Gln Gln Val Ser Asp Ser Ser Arg Leu Leu
705                 710                 715                 720 gac cag ctc agg gac agc cgg aga gag gca gag agg ctg gtg cgg cag           2208
Asp Gln Leu Arg Asp Ser Arg Arg Glu Ala Glu Arg Leu Val Arg Gln
                725                 730                 735 gcg gga gga gga gga ggc acc ggc agc ccc aag ctt gtg gcc ctg agg           2256
Ala Gly Gly Gly Gly Gly Thr Gly Ser Pro Lys Leu Val Ala Leu Arg
                740                 745                 750 ttg gag atg tct tcg ttg cct gac ctg aca ccc acc ttc aac aag ctc           2304
Leu Glu Met Ser Ser Leu Pro Asp Leu Thr Pro Thr Phe Asn Lys Leu
            755                 760                 765 tgt ggc aac tcc agg cag atg gct tgc acc cca ata tca tgc cct ggt           2352
Cys Gly Asn Ser Arg Gln Met Ala Cys Thr Pro Ile Ser Cys Pro Gly
        770                 775                 780 gag cta tgt ccc caa gac aat ggc aca gcc tgt gcg tcc cgc tgc agg           2400
Glu Leu Cys Pro Gln Asp Asn Gly Thr Ala Cys Ala Ser Arg Cys Arg
785                 790                 795                 800 ggt gtc ctt ccc agg gcc ggt ggg gcc ttc ttg atg gcg ggg cag gtg           2448
Gly Val Leu Pro Arg Ala Gly Gly Ala Phe Leu Met Ala Gly Gln Val
                805                 810                 815 gct gag cag ctg cgg ggc ttc aat gcc cag ctc cag cgg acc agg cag           2496
Ala Glu Gln Leu Arg Gly Phe Asn Ala Gln Leu Gln Arg Thr Arg Gln
                820                 825                 830 atg att agg gca gcc gag gaa tct gcc tca cag att caa tcc agt gcc           2544
Met Ile Arg Ala Ala Glu Glu Ser Ala Ser Gln Ile Gln Ser Ser Ala
            835                 840                 845 cag cgc ttg gag acc cag gtg agc gcc agc cgc tcc cag atg gag gaa           2592
Gln Arg Leu Glu Thr Gln Val Ser Ala Ser Arg Ser Gln Met Glu Glu
        850                 855                 860 gat gtc aga cgc aca cgg ctc cta atc cag cag gtc cgg gac ttc cta           2640
Asp Val Arg Arg Thr Arg Leu Leu Ile Gln Gln Val Arg Asp Phe Leu
865                 870                 875                 880 aca gac ccc gac act gat gca gcc act atc cag gag gtc agc gag gcc           2688
Thr Asp Pro Asp Thr Asp Ala Ala Thr Ile Gln Glu Val Ser Glu Ala
                885                 890                 895 gtg ctg gcc ctg tgg ctg ccc aca gac tca gct act gtt ctg cag aag           2736
Val Leu Ala Leu Trp Leu Pro Thr Asp Ser Ala Thr Val Leu Gln Lys
                900                 905                 910 atg aat gag atc cag gcc att gca gcc agg ctc ccc aac gtg gac ttg           2784
Met Asn Glu Ile Gln Ala Ile Ala Ala Arg Leu Pro Asn Val Asp Leu
            915                 920                 925 gtg ctg tcc cag acc aag cag gac att gcg cgt gcc cgc agg ttg cag           2832
Val Leu Ser Gln Thr Lys Gln Asp Ile Ala Arg Ala Arg Arg Leu Gln
        930                 935                 940 gct gag gct gag gaa gcc agg agc cga gcc cat gca gtg gag ggc cag           2880
```

```
Ala Glu Ala Glu Glu Ala Arg Ser Arg Ala His Ala Val Glu Gly Gln
945                 950                 955                 960 gtg gag gat gtg gtt ggg aac ctg cgg cag ggg aca gtg gca ctg cag    2928
Val Glu Asp Val Val Gly Asn Leu Arg Gln Gly Thr Val Ala Leu Gln
                965                 970                 975 gaa gct cag gac acc atg caa ggc acc agc cgg tcc ctt cgg ctt atc    2976
Glu Ala Gln Asp Thr Met Gln Gly Thr Ser Arg Ser Leu Arg Leu Ile
            980                 985                 990 cag gac agg gtt gct gag gtt cag cag gta ctg cgg cca gca gaa aag    3024
Gln Asp Arg Val Ala Glu Val Gln Gln Val Leu Arg Pro Ala Glu Lys
        995                 1000                1005 ctg gtg aca agc atg acc aag cag ctg ggt gac ttc tgg aca cgg atg    3072
Leu Val Thr Ser Met Thr Lys Gln Leu Gly Asp Phe Trp Thr Arg Met
    1010                1015                1020 gag gag ctc cgc cac caa gcc cgg cag cag ggg gca gag gca gtc cag    3120
Glu Glu Leu Arg His Gln Ala Arg Gln Gln Gly Ala Glu Ala Val Gln
1025                1030                1035                1040 gcc cag cag ctt gcg gaa ggt gcc agc gag cag gca ttg agt gcc caa    3168
Ala Gln Gln Leu Ala Glu Gly Ala Ser Glu Gln Ala Leu Ser Ala Gln
                1045                1050                1055 gag gga ttt gag aga ata aaa caa aag tat gct gag ttg aag gac cgg    3216
Glu Gly Phe Glu Arg Ile Lys Gln Lys Tyr Ala Glu Leu Lys Asp Arg
            1060                1065                1070 ttg ggt cag agt tcc atg ctg ggt gag cag ggt gcc cgg atc cag agt    3264
Leu Gly Gln Ser Ser Met Leu Gly Glu Gln Gly Ala Arg Ile Gln Ser
        1075                1080                1085 gtg aag aca gag gca gag gag ctg ttt ggg gag acc atg gag atg atg    3312
Val Lys Thr Glu Ala Glu Glu Leu Phe Gly Glu Thr Met Glu Met Met
    1090                1095                1100 gac agg atg aaa gac atg gag ttg gag ctg ctg cgg ggc agc cag gcc    3360
Asp Arg Met Lys Asp Met Glu Leu Glu Leu Leu Arg Gly Ser Gln Ala
1105                1110                1115                1120 atc atg ctg cgc tca gcg gac ctg aca gga ctg gag aag cgt gtg gag    3408
Ile Met Leu Arg Ser Ala Asp Leu Thr Gly Leu Glu Lys Arg Val Glu
                1125                1130                1135 cag atc cgt gac cac atc aat ggg cgc gtg ctc tac tat gcc acc tgc    3456
Gln Ile Arg Asp His Ile Asn Gly Arg Val Leu Tyr Tyr Ala Thr Cys
            1140                1145                1150 aag tgatgctaca cgttccagcc cgttgcccca ctcatctgcg cgctttgctt         3509
Lys ttggttgggg ggcagattgg gttggaatgc tttccatctc caggagactt tcatgtagcc  3569
caaagtacag cctggaccac ccctggtgtg tgtagctagt aagattaccc tgagctgcag  3629
ctgagcctga gccaatggga cagttacact tgacagacaa agatggtgga gattggcatg  3689
ccattgaaac taagagctct caagtcaagg aagctgggct gggcagtatc ccccgccttt  3749
agttctccac                                                        3759

<210> SEQ ID NO 16
<211> LENGTH: 1153
<212> TYPE: PRT
<213> ORGANISM: Homo sapiens

<400> SEQUENCE: 16

Gln Gln Ala Cys Ser Arg Gly Ala Cys Tyr Pro Pro Val Gly Asp Leu
 1               5                   10                  15

Leu Val Gly Arg Thr Arg Phe Leu Arg Ala Ser Ser Thr Cys Gly Leu
            20                  25                  30

Thr Lys Pro Glu Thr Tyr Cys Thr Gln Tyr Gly Glu Trp Gln Met Lys
```

```
                    35                  40                  45
Cys Cys Lys Cys Asp Ser Arg Gln Pro His Asn Tyr Tyr Ser His Arg
         50                  55                  60

Val Glu Asn Val Ala Ser Ser Gly Pro Met Arg Trp Trp Gln Ser
 65                  70                  75                  80

Gln Asn Asp Val Asn Pro Val Ser Leu Gln Leu Asp Leu Asp Arg Arg
                     85                  90                  95

Phe Gln Leu Gln Glu Val Met Met Glu Phe Arg Gly Pro Met Pro Ala
             100                 105                 110

Gly Met Leu Ile Glu Arg Ser Ser Asp Phe Gly Lys Thr Trp Arg Val
             115                 120                 125

Tyr Gln Tyr Leu Ala Ala Asp Cys Thr Ser Thr Phe Pro Arg Val Arg
         130                 135                 140

Gln Gly Arg Pro Gln Ser Trp Gln Asp Val Arg Cys Gln Ser Leu Pro
145                 150                 155                 160

Gln Arg Pro Asn Ala Arg Leu Asn Gly Gly Lys Val Gln Leu Asn Leu
                 165                 170                 175

Met Asp Leu Val Ser Gly Ile Pro Ala Thr Gln Ser Gln Lys Ile Gln
             180                 185                 190

Glu Val Gly Glu Ile Thr Asn Leu Arg Val Asn Phe Thr Arg Leu Ala
         195                 200                 205

Pro Val Pro Gln Arg Gly Tyr His Pro Pro Ser Ala Tyr Tyr Ala Val
 210                 215                 220

Ser Gln Leu Arg Leu Gln Gly Ser Cys Phe Cys His Gly His Ala Asp
225                 230                 235                 240

Arg Cys Ala Pro Lys Pro Gly Ala Ser Ala Gly Ser Thr Ala Val Gln
                 245                 250                 255

Val His Asp Val Cys Val Cys Gln His Asn Thr Ala Gly Pro Asn Cys
             260                 265                 270

Glu Arg Cys Ala Pro Phe Tyr Asn Asn Arg Pro Trp Arg Pro Ala Glu
         275                 280                 285

Gly Gln Asp Ala His Glu Cys Gln Arg Cys Asp Cys Asn Gly His Ser
 290                 295                 300

Glu Thr Cys His Phe Asp Pro Ala Val Phe Ala Ala Ser Gln Gly Ala
305                 310                 315                 320

Tyr Gly Gly Val Cys Asp Asn Cys Arg Asp His Thr Glu Gly Lys Asn
                 325                 330                 335

Cys Glu Arg Cys Gln Leu His Tyr Phe Arg Asn Arg Arg Pro Gly Ala
             340                 345                 350

Ser Ile Gln Glu Thr Cys Ile Ser Cys Glu Cys Asp Pro Asp Gly Ala
         355                 360                 365

Val Ala Gly Ala Pro Cys Asp Pro Val Thr Gly Gln Cys Val Cys Lys
 370                 375                 380

Glu His Val Gln Gly Glu Arg Cys Asp Leu Cys Lys Pro Gly Phe Thr
385                 390                 395                 400

Gly Leu Thr Tyr Ala Asn Pro Arg Arg Cys His Arg Cys Asp Cys Asn
                 405                 410                 415

Ile Leu Gly Ser Arg Glu Met Pro Cys Asp Glu Glu Ser Gly Arg Cys
             420                 425                 430

Leu Cys Leu Pro Asn Val Val Gly Pro Lys Cys Asp Gln Cys Ala Pro
         435                 440                 445

Tyr His Trp Lys Leu Ala Ser Gly Gln Gly Cys Glu Pro Cys Ala Cys
 450                 455                 460
```

-continued

```
Asp Pro His Asn Ser Leu Ser Pro Gln Cys Asn Gln Phe Thr Gly Gln
465                 470                 475                 480

Cys Pro Cys Arg Glu Gly Phe Gly Gly Leu Met Cys Ser Ala Ala Ala
                485                 490                 495

Ile Arg Gln Cys Pro Asp Arg Thr Tyr Gly Asp Val Ala Thr Gly Cys
                500                 505                 510

Arg Ala Cys Asp Cys Asp Phe Arg Gly Thr Glu Gly Pro Gly Cys Asp
                515                 520                 525

Lys Ala Ser Gly Arg Cys Leu Cys Arg Pro Gly Leu Thr Gly Pro Arg
530                 535                 540

Cys Asp Gln Cys Gln Arg Gly Tyr Cys Asn Arg Tyr Pro Val Cys Val
545                 550                 555                 560

Ala Cys His Pro Cys Phe Gln Thr Tyr Asp Ala Asp Leu Arg Glu Gln
                565                 570                 575

Ala Leu Arg Phe Gly Arg Leu Pro Asn Ala Thr Ala Ser Leu Trp Ser
                580                 585                 590

Gly Pro Gly Leu Glu Asp Arg Gly Leu Ala Ser Arg Ile Leu Asp Ala
                595                 600                 605

Lys Ser Lys Ile Glu Gln Ile Arg Ala Val Leu Ser Ser Pro Ala Val
610                 615                 620

Thr Glu Gln Glu Val Ala Gln Val Ala Ser Ala Ile Leu Ser Leu Arg
625                 630                 635                 640

Arg Thr Leu Gln Gly Leu Gln Leu Asp Leu Pro Leu Glu Glu Glu Thr
                645                 650                 655

Leu Ser Leu Pro Arg Asp Leu Glu Ser Leu Asp Arg Ser Phe Asn Gly
                660                 665                 670

Leu Leu Thr Met Tyr Gln Arg Lys Arg Glu Gln Phe Glu Lys Ile Ser
                675                 680                 685

Ser Ala Asp Pro Ser Gly Ala Phe Arg Met Leu Ser Thr Ala Tyr Glu
                690                 695                 700

Gln Ser Ala Gln Ala Ala Gln Gln Val Ser Asp Ser Ser Arg Leu Leu
705                 710                 715                 720

Asp Gln Leu Arg Asp Ser Arg Arg Glu Ala Glu Arg Leu Val Arg Gln
                725                 730                 735

Ala Gly Gly Gly Gly Gly Thr Gly Ser Pro Lys Leu Val Ala Leu Arg
                740                 745                 750

Leu Glu Met Ser Ser Leu Pro Asp Leu Thr Pro Thr Phe Asn Lys Leu
                755                 760                 765

Cys Gly Asn Ser Arg Gln Met Ala Cys Thr Pro Ile Ser Cys Pro Gly
770                 775                 780

Glu Leu Cys Pro Gln Asp Asn Gly Thr Ala Cys Ala Ser Arg Cys Arg
785                 790                 795                 800

Gly Val Leu Pro Arg Ala Gly Gly Ala Phe Leu Met Ala Gly Gln Val
                805                 810                 815

Ala Glu Gln Leu Arg Gly Phe Asn Ala Gln Leu Gln Arg Thr Arg Gln
                820                 825                 830

Met Ile Arg Ala Ala Glu Glu Ser Ala Ser Gln Ile Gln Ser Ser Ala
                835                 840                 845

Gln Arg Leu Glu Thr Gln Val Ser Ala Ser Arg Ser Gln Met Glu Glu
                850                 855                 860

Asp Val Arg Arg Thr Arg Leu Leu Ile Gln Gln Val Arg Asp Phe Leu
865                 870                 875                 880
```

```
Thr Asp Pro Asp Thr Asp Ala Ala Thr Ile Gln Glu Val Ser Glu Ala
            885                 890                 895

Val Leu Ala Leu Trp Leu Pro Thr Asp Ser Ala Thr Val Leu Gln Lys
        900                 905                 910

Met Asn Glu Ile Gln Ala Ile Ala Ala Arg Leu Pro Asn Val Asp Leu
    915                 920                 925

Val Leu Ser Gln Thr Lys Gln Asp Ile Ala Arg Ala Arg Arg Leu Gln
    930                 935                 940

Ala Glu Ala Glu Ala Arg Ser Arg Ala His Ala Val Glu Gly Gln
945                 950                 955                 960

Val Glu Asp Val Val Gly Asn Leu Arg Gln Gly Thr Val Ala Leu Gln
            965                 970                 975

Glu Ala Gln Asp Thr Met Gln Gly Thr Ser Arg Ser Leu Arg Leu Ile
        980                 985                 990

Gln Asp Arg Val Ala Glu Val Gln Gln Val Leu Arg Pro Ala Glu Lys
    995                 1000                1005

Leu Val Thr Ser Met Thr Lys Gln Leu Gly Asp Phe Trp Thr Arg Met
    1010                1015                1020

Glu Glu Leu Arg His Gln Ala Arg Gln Gln Gly Ala Glu Ala Val Gln
1025                1030                1035                1040

Ala Gln Gln Leu Ala Glu Gly Ala Ser Glu Gln Ala Leu Ser Ala Gln
            1045                1050                1055

Glu Gly Phe Glu Arg Ile Lys Gln Lys Tyr Ala Glu Leu Lys Asp Arg
        1060                1065                1070

Leu Gly Gln Ser Ser Met Leu Gly Glu Gln Gly Ala Arg Ile Gln Ser
    1075                1080                1085

Val Lys Thr Glu Ala Glu Glu Leu Phe Gly Glu Thr Met Glu Met Met
    1090                1095                1100

Asp Arg Met Lys Asp Met Glu Leu Glu Leu Leu Arg Gly Ser Gln Ala
1105                1110                1115                1120

Ile Met Leu Arg Ser Ala Asp Leu Thr Gly Leu Glu Lys Arg Val Glu
            1125                1130                1135

Gln Ile Arg Asp His Ile Asn Gly Arg Val Leu Tyr Tyr Ala Thr Cys
        1140                1145                1150

Lys

<210> SEQ ID NO 17
<211> LENGTH: 3621
<212> TYPE: DNA
<213> ORGANISM: Homo sapiens
<220> FEATURE:
<221> NAME/KEY: CDS
<222> LOCATION: (60)..(3617)
<221> NAME/KEY: sig_peptide
<222> LOCATION: (60)..(110)
<221> NAME/KEY: misc_feature
<222> LOCATION: (123)..(146)

<400> SEQUENCE: 17
gtttaaactt aagcttctgc ctgccgcctg cctgcctgcc actgagggtt cccagcacc      59 atg agg gcc tgg atc ttc ttt ctc ctt tgc ctg gcc ggg agg gct ctg     107
Met Arg Ala Trp Ile Phe Phe Leu Leu Cys Leu Ala Gly Arg Ala Leu
  1               5                  10                  15 gca gcc cca cta gcc gac tac aag gac gac gat gac aag cta gcc caa     155
Ala Ala Pro Leu Ala Asp Tyr Lys Asp Asp Asp Asp Lys Leu Ala Gln
             20                  25                  30 caa gcc tgc tcc cgt ggg gcc tgc tat cca cct gtt ggg gac ctg ctt     203
```

```
                  -continued

Gln Ala Cys Ser Arg Gly Ala Cys Tyr Pro Pro Val Gly Asp Leu Leu
         35                  40                  45 gtt ggg agg acc cgg ttt ctc cga gct tca tct acc tgt gga ctg acc        251
Val Gly Arg Thr Arg Phe Leu Arg Ala Ser Ser Thr Cys Gly Leu Thr
 50                  55                  60 aag cct gag acc tac tgc acc cag tat ggc gag tgg cag atg aaa tgc        299
Lys Pro Glu Thr Tyr Cys Thr Gln Tyr Gly Glu Trp Gln Met Lys Cys
 65                  70                  75                  80 tgc aag tgt gac tcc agg cag cct cac aac tac tac agt cac cga gta        347
Cys Lys Cys Asp Ser Arg Gln Pro His Asn Tyr Tyr Ser His Arg Val
                 85                  90                  95 gag aat gtg gct tca tcc tcc ggc ccc atg cgc tgg tgg cag tcc cag        395
Glu Asn Val Ala Ser Ser Ser Gly Pro Met Arg Trp Trp Gln Ser Gln
                100                 105                 110 aat gat gtg aac cct gtc tct ctg cag ctg gac ctg gac agg aga ttc        443
Asn Asp Val Asn Pro Val Ser Leu Gln Leu Asp Leu Asp Arg Arg Phe
            115                 120                 125 cag ctt caa gaa gtc atg atg gag ttc cag ggg ccc atg cct gcc ggc        491
Gln Leu Gln Glu Val Met Met Glu Phe Gln Gly Pro Met Pro Ala Gly
130                 135                 140 atg ctg att gag cgc tcc tca gac ttc ggt aag acc tgg cga gtg tac        539
Met Leu Ile Glu Arg Ser Ser Asp Phe Gly Lys Thr Trp Arg Val Tyr
145                 150                 155                 160 cag tac ctg gct gcc gac tgc acc tcc acc ttc cct cgg gtc cgc cag        587
Gln Tyr Leu Ala Ala Asp Cys Thr Ser Thr Phe Pro Arg Val Arg Gln
                165                 170                 175 ggt cgg cct cag agc tgg cag gat gtt cgg tgc cag tcc ctg cct cag        635
Gly Arg Pro Gln Ser Trp Gln Asp Val Arg Cys Gln Ser Leu Pro Gln
                180                 185                 190 agg cct aat gca cgc cta aat ggg ggg aag gtc caa ctt aac ctt atg        683
Arg Pro Asn Ala Arg Leu Asn Gly Gly Lys Val Gln Leu Asn Leu Met
            195                 200                 205 gat tta gtg tct ggg att cca gca act caa agt caa aaa att caa gag        731
Asp Leu Val Ser Gly Ile Pro Ala Thr Gln Ser Gln Lys Ile Gln Glu
210                 215                 220 gtg ggg gag atc aca aac ttg aga gtc aat ttc acc agg ctg gcc cct        779
Val Gly Glu Ile Thr Asn Leu Arg Val Asn Phe Thr Arg Leu Ala Pro
225                 230                 235                 240 gtg ccc caa agg ggc tac cac cct ccc agc gcc tac tat gct gtg tcc        827
Val Pro Gln Arg Gly Tyr His Pro Pro Ser Ala Tyr Tyr Ala Val Ser
                245                 250                 255 cag ctc cgt ctg cag ggg agc tgc ttc tgt cac ggc cat gct gat cgc        875
Gln Leu Arg Leu Gln Gly Ser Cys Phe Cys His Gly His Ala Asp Arg
                260                 265                 270 tgc gca ccc aag cct ggg gcc tct gca ggc ccc tcc acc gct gtg cag        923
Cys Ala Pro Lys Pro Gly Ala Ser Ala Gly Pro Ser Thr Ala Val Gln
            275                 280                 285 gtc cac gat gtc tgc gtc tgc cag cac aac act gcc ggc cca aat tgt        971
Val His Asp Val Cys Val Cys Gln His Asn Thr Ala Gly Pro Asn Cys
290                 295                 300 gag cgc tgt gca ccc ttc tac aac aac cgg ccc tgg aga ccg gcg gag       1019
Glu Arg Cys Ala Pro Phe Tyr Asn Asn Arg Pro Trp Arg Pro Ala Glu
305                 310                 315                 320 ggc cag gac gcc cat gaa tgc caa agg tgc gac tgc aat ggg cac tca       1067
Gly Gln Asp Ala His Glu Cys Gln Arg Cys Asp Cys Asn Gly His Ser
                325                 330                 335 gag aca tgt cac ttt gac ccc gct gtg ttt gcc gcc agc cag ggg gca       1115
Glu Thr Cys His Phe Asp Pro Ala Val Phe Ala Ala Ser Gln Gly Ala
                340                 345                 350
```

-continued

| | |
|---|---|
| tat gga ggt gtg tgt gac aat tgc cgg gac cac acc gaa ggc aag aac<br>Tyr Gly Gly Val Cys Asp Asn Cys Arg Asp His Thr Glu Gly Lys Asn<br>355                360                365 | 1163 |
| tgt gag cgg tgt cag ctg cac tat ttc cgg aac cgg cgc ccg gga gct<br>Cys Glu Arg Cys Gln Leu His Tyr Phe Arg Asn Arg Arg Pro Gly Ala<br>370               375               380 | 1211 |
| tcc att cag gag acc tgc atc tcc tgc gag tgt gat ccg gat ggg gca<br>Ser Ile Gln Glu Thr Cys Ile Ser Cys Glu Cys Asp Pro Asp Gly Ala<br>385                390              395             400 | 1259 |
| gtg cca ggg gct ccc tgt gac cca gtg acc ggg cag tgt gtg tgc aag<br>Val Pro Gly Ala Pro Cys Asp Pro Val Thr Gly Gln Cys Val Cys Lys<br>              405              410              415 | 1307 |
| gag cat gtg cag gga gag cgc tgt gac cta tgc aag ccg ggc ttc act<br>Glu His Val Gln Gly Glu Arg Cys Asp Leu Cys Lys Pro Gly Phe Thr<br>              420              425              430 | 1355 |
| gga ctc acc tac gcc aac ccg cag ggc tgc cac cgc tgt gac tgc aac<br>Gly Leu Thr Tyr Ala Asn Pro Gln Gly Cys His Arg Cys Asp Cys Asn<br>              435              440              445 | 1403 |
| atc ctg ggg tcc cgg agg gac atg ccg tgt gac gag gag agt ggg cgc<br>Ile Leu Gly Ser Arg Arg Asp Met Pro Cys Asp Glu Glu Ser Gly Arg<br>450                455               460 | 1451 |
| tgc ctt tgt ctg ccc aac gtg gtg ggt ccc aaa tgt gac cag tgt gct<br>Cys Leu Cys Leu Pro Asn Val Val Gly Pro Lys Cys Asp Gln Cys Ala<br>465                470              475             480 | 1499 |
| ccc tac cac tgg aag ctg gcc agt ggc cag ggc tgt gaa ccg tgt gcc<br>Pro Tyr His Trp Lys Leu Ala Ser Gly Gln Gly Cys Glu Pro Cys Ala<br>              485              490              495 | 1547 |
| tgc gac ccg cac aac tcc ctc agc cca cag tgc aac cag ttc aca ggg<br>Cys Asp Pro His Asn Ser Leu Ser Pro Gln Cys Asn Gln Phe Thr Gly<br>              500              505              510 | 1595 |
| cag tgc ccc tgt cgg gaa ggc ttt ggt ggc ctg atg tgc agc gct gca<br>Gln Cys Pro Cys Arg Glu Gly Phe Gly Gly Leu Met Cys Ser Ala Ala<br>              515              520              525 | 1643 |
| gcc atc cgc cag tgt cca gac cgg acc tat gga gac gtg gcc aca gga<br>Ala Ile Arg Gln Cys Pro Asp Arg Thr Tyr Gly Asp Val Ala Thr Gly<br>530                535               540 | 1691 |
| tgc cga gcc tgt gac tgt gat ttc cgg gga aca gag ggc ccg ggc tgc<br>Cys Arg Ala Cys Asp Cys Asp Phe Arg Gly Thr Glu Gly Pro Gly Cys<br>545                550              555             560 | 1739 |
| gac aag gca tca ggc cgc tgc ctc tgc cgc cct ggc ttg acc ggg ccc<br>Asp Lys Ala Ser Gly Arg Cys Leu Cys Arg Pro Gly Leu Thr Gly Pro<br>              565              570              575 | 1787 |
| cgc tgt gac cag tgc cag cga ggc tac tgc aat cgc tac ccg gtg tgc<br>Arg Cys Asp Gln Cys Gln Arg Gly Tyr Cys Asn Arg Tyr Pro Val Cys<br>              580              585              590 | 1835 |
| gtg gcc tgc cac cct tgc ttc cag acc tat gat gcg gac ctc cgg gag<br>Val Ala Cys His Pro Cys Phe Gln Thr Tyr Asp Ala Asp Leu Arg Glu<br>              595              600              605 | 1883 |
| cag gcc ctg cgc ttt ggt aga ctc cgg aat gcc acc gcc agc ctg tgg<br>Gln Ala Leu Arg Phe Gly Arg Leu Arg Asn Ala Thr Ala Ser Leu Trp<br>610                615              620 | 1931 |
| tca ggg cct ggg ctg gag gac cgt ggc ctg gcc tcc cgg atc cta gat<br>Ser Gly Pro Gly Leu Glu Asp Arg Gly Leu Ala Ser Arg Ile Leu Asp<br>625                630              635             640 | 1979 |
| gca aag agt aag att gag cag atc cga gca gtt ctc agc agc ccc gca<br>Ala Lys Ser Lys Ile Glu Gln Ile Arg Ala Val Leu Ser Ser Pro Ala<br>              645              650              655 | 2027 |
| gtc aca gag cag gag gtg gct cag gtg gcc agt gcc atc ctc tcc ctc<br>Val Thr Glu Gln Glu Val Ala Gln Val Ala Ser Ala Ile Leu Ser Leu<br>              660              665              670 | 2075 |

```
agg cga act ctc cag ggc ctg cag ctg gat ctg ccc ctg gag gag gag      2123
Arg Arg Thr Leu Gln Gly Leu Gln Leu Asp Leu Pro Leu Glu Glu Glu
        675                 680                 685 acg ttg tcc ctt ccg aga gac ctg gag agt ctt gac aga agc ttc aat      2171
Thr Leu Ser Leu Pro Arg Asp Leu Glu Ser Leu Asp Arg Ser Phe Asn
        690                 695                 700 ggt ctc ctt act atg tat cag agg aag agg gag cag ttt gaa aaa ata      2219
Gly Leu Leu Thr Met Tyr Gln Arg Lys Arg Glu Gln Phe Glu Lys Ile
705                 710                 715                 720 agc agt gct gat cct tca gga gcc ttc cgg atg ctg agc aca gcc tac      2267
Ser Ser Ala Asp Pro Ser Gly Ala Phe Arg Met Leu Ser Thr Ala Tyr
                725                 730                 735 gag cag tca gcc cag gct gct cag cag gtc tcc gac agc tcg cgc ctt      2315
Glu Gln Ser Ala Gln Ala Ala Gln Gln Val Ser Asp Ser Ser Arg Leu
        740                 745                 750 ttg gac cag ctc agg gac agc cgg aga gag gca gag agg ctg gtg cgg      2363
Leu Asp Gln Leu Arg Asp Ser Arg Arg Glu Ala Glu Arg Leu Val Arg
        755                 760                 765 cag gcg gga gga gga gga ggc acc ggc agc ccc aag ctt gtg gcc ctg      2411
Gln Ala Gly Gly Gly Gly Gly Thr Gly Ser Pro Lys Leu Val Ala Leu
770                 775                 780 agg ctg gag atg tct tcg ttg cct gac ctg aca ccc acc ttc aac aag      2459
Arg Leu Glu Met Ser Ser Leu Pro Asp Leu Thr Pro Thr Phe Asn Lys
785                 790                 795                 800 ctc tgt ggc aac tcc agg cag atg gct tgc acc cca ata tca tgc cct      2507
Leu Cys Gly Asn Ser Arg Gln Met Ala Cys Thr Pro Ile Ser Cys Pro
                805                 810                 815 ggt gag cta tgt ccc caa gac aat ggc aca gcc tgt ggc tcc cgc tgc      2555
Gly Glu Leu Cys Pro Gln Asp Asn Gly Thr Ala Cys Gly Ser Arg Cys
                820                 825                 830 agg ggt gtc ctt ccc agg gcc ggt ggg gcc ttc ttg atg gcg ggg cag      2603
Arg Gly Val Leu Pro Arg Ala Gly Gly Ala Phe Leu Met Ala Gly Gln
        835                 840                 845 gtg gct gag cag ctg cgg ggc ttc aat gcc cag ctc cag cgg acc agg      2651
Val Ala Glu Gln Leu Arg Gly Phe Asn Ala Gln Leu Gln Arg Thr Arg
850                 855                 860 cag atg att agg gca gcc gag gaa tct gcc tca cag att caa tcc agt      2699
Gln Met Ile Arg Ala Ala Glu Glu Ser Ala Ser Gln Ile Gln Ser Ser
865                 870                 875                 880 gcc cag cgc ttg gag acc cag gtg agc gcc agc cgc tcc cag atg gag      2747
Ala Gln Arg Leu Glu Thr Gln Val Ser Ala Ser Arg Ser Gln Met Glu
                885                 890                 895 gaa gat gtc aga cgc aca cgg ctc cta atc cag cag gtc cgg gac ttc      2795
Glu Asp Val Arg Arg Thr Arg Leu Leu Ile Gln Gln Val Arg Asp Phe
                900                 905                 910 cta aca gac ccc gac act gat gca gcc act atc cag gag gtc agc gag      2843
Leu Thr Asp Pro Asp Thr Asp Ala Ala Thr Ile Gln Glu Val Ser Glu
        915                 920                 925 gcc gtg ctg gcc ctg tgg ctg ccc aca gac tca gct act gtt ctg cag      2891
Ala Val Leu Ala Leu Trp Leu Pro Thr Asp Ser Ala Thr Val Leu Gln
        930                 935                 940 aag atg aat gag atc cag gcc att gca gcc agg ctc ccc aac gtg gac      2939
Lys Met Asn Glu Ile Gln Ala Ile Ala Ala Arg Leu Pro Asn Val Asp
945                 950                 955                 960 ttg gtg ctg tcc cag acc aag cag gac att gcg cgt gcc cgc cgg ttg      2987
Leu Val Leu Ser Gln Thr Lys Gln Asp Ile Ala Arg Ala Arg Arg Leu
                965                 970                 975 cag gct gag gct gag gaa gcc agg agc cga gcc cat gca gtg gag ggc      3035
Gln Ala Glu Ala Glu Glu Ala Arg Ser Arg Ala His Ala Val Glu Gly
```

```
                    980             985             990
cag gtg aaa gat gtg gtt ggg aac ctg cgg cag ggg aca gtg gca ctg    3083
Gln Val Glu Asp Val Val Gly Asn Leu Arg Gln Gly Thr Val Ala Leu
        995             1000            1005 cag gaa gct cag gac acc atg caa ggc acc agc cgc tcc ctt cgg ctt    3131
Gln Glu Ala Gln Asp Thr Met Gln Gly Thr Ser Arg Ser Leu Arg Leu
    1010            1015            1020 atc cag gac agg gtt gct gag gtt cag cag gta ctg cgg cca gca gaa    3179
Ile Gln Asp Arg Val Ala Glu Val Gln Gln Val Leu Arg Pro Ala Glu
1025            1030            1035            1040 aag ctg gtg aca agc atg acc aag cag ctg ggt gac ttc tgg aca cgg    3227
Lys Leu Val Thr Ser Met Thr Lys Gln Leu Gly Asp Phe Trp Thr Arg
            1045            1050            1055 atg gag gag ctc cgc cac caa gcc cgg cag cag ggg gca gag gca gtc    3275
Met Glu Glu Leu Arg His Gln Ala Arg Gln Gln Gly Ala Glu Ala Val
        1060            1065            1070 cag gcc cag cag ctt gcg gaa ggt gcc agc gag cag gca ttg agt gcc    3323
Gln Ala Gln Gln Leu Ala Glu Gly Ala Ser Glu Gln Ala Leu Ser Ala
    1075            1080            1085 caa gag gga ttt gag aga ata aaa caa aag tat gct gag ttg aag gac    3371
Gln Glu Gly Phe Glu Arg Ile Lys Gln Lys Tyr Ala Glu Leu Lys Asp
1090            1095            1100 cgg ttg ggt cag agt tcc atg ctg ggt gag cag ggt gcc cgg atc cag    3419
Arg Leu Gly Gln Ser Ser Met Leu Gly Glu Gln Gly Ala Arg Ile Gln
1105            1110            1115            1120 agt gtg aag aca gag gca gag gag ctg ttt ggg gag acc atg gag atg    3467
Ser Val Lys Thr Glu Ala Glu Glu Leu Phe Gly Glu Thr Met Glu Met
            1125            1130            1135 atg gac agg atg aaa gac atg gag ttg gag ctg ctg cgg ggc agc cag    3515
Met Asp Arg Met Lys Asp Met Glu Leu Glu Leu Leu Arg Gly Ser Gln
        1140            1145            1150 gcc atc atg ctg cgc tca gcg gac ctg aca gga ctg gag aag cgt gtg    3563
Ala Ile Met Leu Arg Ser Ala Asp Leu Thr Gly Leu Glu Lys Arg Val
    1155            1160            1165 gag cag atc cgt gac cac atc aat ggg cgc gtg ctc tac tat gcc acc    3611
Glu Gln Ile Arg Asp His Ile Asn Gly Arg Val Leu Tyr Tyr Ala Thr
1170            1175            1180 tgc aag tgat                                                       3621
Cys Lys
1185

<210> SEQ ID NO 18
<211> LENGTH: 1186
<212> TYPE: PRT
<213> ORGANISM: Homo sapiens

<400> SEQUENCE: 18

Met Arg Ala Trp Ile Phe Phe Leu Leu Cys Leu Ala Gly Arg Ala Leu
1               5                   10                  15

Ala Ala Pro Leu Ala Asp Tyr Lys Asp Asp Asp Lys Leu Ala Gln
            20                  25                  30

Gln Ala Cys Ser Arg Gly Ala Cys Tyr Pro Pro Val Gly Asp Leu Leu
        35                  40                  45

Val Gly Arg Thr Arg Phe Leu Arg Ala Ser Ser Thr Cys Gly Leu Thr
    50                  55                  60

Lys Pro Glu Thr Tyr Cys Thr Gln Tyr Gly Glu Trp Gln Met Lys Cys
65                  70                  75                  80

Cys Lys Cys Asp Ser Arg Gln Pro His Asn Tyr Tyr Ser His Arg Val
                85                  90                  95
```

-continued

```
Glu Asn Val Ala Ser Ser Gly Pro Met Arg Trp Trp Gln Ser Gln
                100                 105                 110
Asn Asp Val Asn Pro Val Ser Leu Gln Leu Asp Leu Asp Arg Arg Phe
            115                 120                 125
Gln Leu Gln Glu Val Met Met Glu Phe Gln Gly Pro Met Pro Ala Gly
        130                 135                 140
Met Leu Ile Glu Arg Ser Ser Asp Phe Gly Lys Thr Trp Arg Val Tyr
145                 150                 155                 160
Gln Tyr Leu Ala Ala Asp Cys Thr Ser Thr Phe Pro Arg Val Arg Gln
                165                 170                 175
Gly Arg Pro Gln Ser Trp Gln Asp Val Arg Cys Gln Ser Leu Pro Gln
            180                 185                 190
Arg Pro Asn Ala Arg Leu Asn Gly Gly Lys Val Gln Leu Asn Leu Met
        195                 200                 205
Asp Leu Val Ser Gly Ile Pro Ala Thr Gln Ser Gln Lys Ile Gln Glu
210                 215                 220
Val Gly Glu Ile Thr Asn Leu Arg Val Asn Phe Thr Arg Leu Ala Pro
225                 230                 235                 240
Val Pro Gln Arg Gly Tyr His Pro Pro Ser Ala Tyr Tyr Ala Val Ser
                245                 250                 255
Gln Leu Arg Leu Gln Gly Ser Cys Phe Cys His Gly His Ala Asp Arg
            260                 265                 270
Cys Ala Pro Lys Pro Gly Ala Ser Ala Gly Pro Ser Thr Ala Val Gln
        275                 280                 285
Val His Asp Val Cys Val Cys Gln His Asn Thr Ala Gly Pro Asn Cys
290                 295                 300
Glu Arg Cys Ala Pro Phe Tyr Asn Asn Arg Pro Trp Arg Pro Ala Glu
305                 310                 315                 320
Gly Gln Asp Ala His Glu Cys Gln Arg Cys Asp Cys Asn Gly His Ser
                325                 330                 335
Glu Thr Cys His Phe Asp Pro Ala Val Phe Ala Ala Ser Gln Gly Ala
            340                 345                 350
Tyr Gly Gly Val Cys Asp Asn Cys Arg Asp His Thr Glu Gly Lys Asn
        355                 360                 365
Cys Glu Arg Cys Gln Leu His Tyr Phe Arg Asn Arg Arg Pro Gly Ala
370                 375                 380
Ser Ile Gln Glu Thr Cys Ile Ser Cys Glu Cys Asp Pro Asp Gly Ala
385                 390                 395                 400
Val Pro Gly Ala Pro Cys Asp Pro Val Thr Gly Gln Cys Val Cys Lys
                405                 410                 415
Glu His Val Gln Gly Glu Arg Cys Asp Leu Cys Lys Pro Gly Phe Thr
            420                 425                 430
Gly Leu Thr Tyr Ala Asn Pro Gln Gly Cys His Arg Cys Asp Cys Asn
        435                 440                 445
Ile Leu Gly Ser Arg Arg Asp Met Pro Cys Asp Glu Glu Ser Gly Arg
450                 455                 460
Cys Leu Cys Leu Pro Asn Val Val Gly Pro Lys Cys Asp Gln Cys Ala
465                 470                 475                 480
Pro Tyr His Trp Lys Leu Ala Ser Gly Gln Gly Cys Glu Pro Cys Ala
                485                 490                 495
Cys Asp Pro His Asn Ser Leu Ser Pro Gln Cys Asn Gln Phe Thr Gly
            500                 505                 510
```

-continued

```
Gln Cys Pro Cys Arg Glu Gly Phe Gly Gly Leu Met Cys Ser Ala Ala
        515                 520                 525

Ala Ile Arg Gln Cys Pro Asp Arg Thr Tyr Gly Asp Val Ala Thr Gly
    530                 535                 540

Cys Arg Ala Cys Asp Cys Asp Phe Arg Gly Thr Glu Gly Pro Gly Cys
545                 550                 555                 560

Asp Lys Ala Ser Gly Arg Cys Leu Cys Arg Pro Gly Leu Thr Gly Pro
                565                 570                 575

Arg Cys Asp Gln Cys Gln Arg Gly Tyr Cys Asn Arg Tyr Pro Val Cys
            580                 585                 590

Val Ala Cys His Pro Cys Phe Gln Thr Tyr Asp Ala Asp Leu Arg Glu
        595                 600                 605

Gln Ala Leu Arg Phe Gly Arg Leu Arg Asn Ala Thr Ala Ser Leu Trp
    610                 615                 620

Ser Gly Pro Gly Leu Glu Asp Arg Gly Leu Ala Ser Arg Ile Leu Asp
625                 630                 635                 640

Ala Lys Ser Lys Ile Glu Gln Ile Arg Ala Val Leu Ser Ser Pro Ala
                645                 650                 655

Val Thr Glu Gln Glu Val Ala Gln Val Ala Ser Ala Ile Leu Ser Leu
            660                 665                 670

Arg Arg Thr Leu Gln Gly Leu Gln Leu Asp Leu Pro Leu Glu Glu
    675                 680                 685

Thr Leu Ser Leu Pro Arg Asp Leu Glu Ser Leu Asp Arg Ser Phe Asn
690                 695                 700

Gly Leu Leu Thr Met Tyr Gln Arg Lys Arg Glu Gln Phe Glu Lys Ile
705                 710                 715                 720

Ser Ser Ala Asp Pro Ser Gly Ala Phe Arg Met Leu Ser Thr Ala Tyr
                725                 730                 735

Glu Gln Ser Ala Gln Ala Ala Gln Gln Val Ser Asp Ser Ser Arg Leu
            740                 745                 750

Leu Asp Gln Leu Arg Asp Ser Arg Arg Glu Ala Glu Arg Leu Val Arg
        755                 760                 765

Gln Ala Gly Gly Gly Gly Thr Gly Ser Pro Lys Leu Val Ala Leu
    770                 775                 780

Arg Leu Glu Met Ser Ser Leu Pro Asp Leu Thr Pro Thr Phe Asn Lys
785                 790                 795                 800

Leu Cys Gly Asn Ser Arg Gln Met Ala Cys Thr Pro Ile Ser Cys Pro
                805                 810                 815

Gly Glu Leu Cys Pro Gln Asp Asn Gly Thr Ala Cys Gly Ser Arg Cys
            820                 825                 830

Arg Gly Val Leu Pro Arg Ala Gly Gly Ala Phe Leu Met Ala Gly Gln
        835                 840                 845

Val Ala Glu Gln Leu Arg Gly Phe Asn Ala Gln Leu Gln Arg Thr Arg
    850                 855                 860

Gln Met Ile Arg Ala Ala Glu Glu Ser Ala Ser Gln Ile Gln Ser Ser
865                 870                 875                 880

Ala Gln Arg Leu Glu Thr Gln Val Ser Ala Ser Arg Ser Gln Met Glu
                885                 890                 895

Glu Asp Val Arg Arg Thr Arg Leu Leu Ile Gln Gln Val Arg Asp Phe
            900                 905                 910

Leu Thr Asp Pro Asp Thr Asp Ala Ala Thr Ile Gln Glu Val Ser Glu
        915                 920                 925

Ala Val Leu Ala Leu Trp Leu Pro Thr Asp Ser Ala Thr Val Leu Gln
```

-continued

```
                    930                 935                 940
Lys Met Asn Glu Ile Gln Ala Ile Ala Ala Arg Leu Pro Asn Val Asp
945                 950                 955                 960

Leu Val Leu Ser Gln Thr Lys Gln Asp Ile Ala Arg Ala Arg Arg Leu
                965                 970                 975

Gln Ala Glu Ala Glu Glu Ala Arg Ser Arg Ala His Ala Val Glu Gly
            980                 985                 990

Gln Val Glu Asp Val Val Gly Asn Leu Arg Gln Gly Thr Val Ala Leu
            995                 1000                1005

Gln Glu Ala Gln Asp Thr Met Gln Gly Thr Ser Arg Ser Leu Arg Leu
    1010                1015                1020

Ile Gln Asp Arg Val Ala Glu Val Gln Gln Val Leu Arg Pro Ala Glu
1025                1030                1035                1040

Lys Leu Val Thr Ser Met Thr Lys Gln Leu Gly Asp Phe Trp Thr Arg
                1045                1050                1055

Met Glu Glu Leu Arg His Gln Ala Arg Gln Gln Gly Ala Glu Ala Val
            1060                1065                1070

Gln Ala Gln Gln Leu Ala Glu Gly Ala Ser Glu Gln Ala Leu Ser Ala
        1075                1080                1085

Gln Glu Gly Phe Glu Arg Ile Lys Gln Lys Tyr Ala Glu Leu Lys Asp
    1090                1095                1100

Arg Leu Gly Gln Ser Ser Met Leu Gly Glu Gln Gly Ala Arg Ile Gln
1105                1110                1115                1120

Ser Val Lys Thr Glu Ala Glu Glu Leu Phe Gly Glu Thr Met Glu Met
                1125                1130                1135

Met Asp Arg Met Lys Asp Met Glu Leu Glu Leu Leu Arg Gly Ser Gln
            1140                1145                1150

Ala Ile Met Leu Arg Ser Ala Asp Leu Thr Gly Leu Glu Lys Arg Val
        1155                1160                1165

Glu Gln Ile Arg Asp His Ile Asn Gly Arg Val Leu Tyr Tyr Ala Thr
    1170                1175                1180

Cys Lys
1185

<210> SEQ ID NO 19
<211> LENGTH: 3511
<212> TYPE: DNA
<213> ORGANISM: Homo sapiens
<220> FEATURE:
<221> NAME/KEY: CDS
<222> LOCATION: (7)..(3507)
<221> NAME/KEY: misc_feature
<222> LOCATION: (13)..(36)

<400> SEQUENCE: 19 gcccca cta gcc gac tac aag gac gac gat gac aag cta gcc caa caa         48
       Leu Ala Asp Tyr Lys Asp Asp Asp Asp Lys Leu Ala Gln Gln
         1               5                   10 gcc tgc tcc cgt ggg gcc tgc tat cca cct gtt ggg gac ctg ctt gtt       96
Ala Cys Ser Arg Gly Ala Cys Tyr Pro Pro Val Gly Asp Leu Leu Val
 15                  20                  25                  30 ggg agg acc cgg ttt ctc cga gct tca tct acc tgt gga ctg acc aag      144
Gly Arg Thr Arg Phe Leu Arg Ala Ser Ser Thr Cys Gly Leu Thr Lys
                 35                  40                  45 cct gag acc tac tgc acc cag tat ggc gag tgg cag atg aaa tgc tgc      192
Pro Glu Thr Tyr Cys Thr Gln Tyr Gly Glu Trp Gln Met Lys Cys Cys
             50                  55                  60
```

-continued

```
aag tgt gac tcc agg cag cct cac aac tac tac agt cac cga gta gag      240
Lys Cys Asp Ser Arg Gln Pro His Asn Tyr Tyr Ser His Arg Val Glu
         65                  70                  75 aat gtg gct tca tcc tcc ggc ccc atg cgc tgg tgg cag tcc cag aat      288
Asn Val Ala Ser Ser Ser Gly Pro Met Arg Trp Trp Gln Ser Gln Asn
 80                  85                  90 gat gtg aac cct gtc tct ctg cag ctg gac ctg gac agg aga ttc cag      336
Asp Val Asn Pro Val Ser Leu Gln Leu Asp Leu Asp Arg Arg Phe Gln
 95                 100                 105                 110 ctt caa gaa gtc atg atg gag ttc cag ggg ccc atg cct gcc ggc atg      384
Leu Gln Glu Val Met Met Glu Phe Gln Gly Pro Met Pro Ala Gly Met
                115                 120                 125 ctg att gag cgc tcc tca gac ttc ggt aag acc tgg cga gtg tac cag      432
Leu Ile Glu Arg Ser Ser Asp Phe Gly Lys Thr Trp Arg Val Tyr Gln
            130                 135                 140 tac ctg gct gcc gac tgc acc tcc acc ttc cct cgg gtc cgc cag ggt      480
Tyr Leu Ala Ala Asp Cys Thr Ser Thr Phe Pro Arg Val Arg Gln Gly
        145                 150                 155 cgg cct cag agc tgg cag gat gtt cgg tgc cag tcc ctg cct cag agg      528
Arg Pro Gln Ser Trp Gln Asp Val Arg Cys Gln Ser Leu Pro Gln Arg
    160                 165                 170 cct aat gca cgc cta aat ggg ggg aag gtc caa ctt aac ctt atg gat      576
Pro Asn Ala Arg Leu Asn Gly Gly Lys Val Gln Leu Asn Leu Met Asp
175                 180                 185                 190 tta gtg tct ggg att cca gca act caa agt caa aaa att caa gag gtg      624
Leu Val Ser Gly Ile Pro Ala Thr Gln Ser Gln Lys Ile Gln Glu Val
                195                 200                 205 ggg gag atc aca aac ttg aga gtc aat ttc acc agg ctg gcc cct gtg      672
Gly Glu Ile Thr Asn Leu Arg Val Asn Phe Thr Arg Leu Ala Pro Val
            210                 215                 220 ccc caa agg ggc tac cac cct ccc agc gcc tac tat gct gtg tcc cag      720
Pro Gln Arg Gly Tyr His Pro Pro Ser Ala Tyr Tyr Ala Val Ser Gln
        225                 230                 235 ctc cgt ctg cag ggg agc tgc ttc tgt cac ggc cat gct gat cgc tgc      768
Leu Arg Leu Gln Gly Ser Cys Phe Cys His Gly His Ala Asp Arg Cys
    240                 245                 250 gca ccc aag cct ggg gcc tct gca ggc ccc tcc acc gct gtg cag gtc      816
Ala Pro Lys Pro Gly Ala Ser Ala Gly Pro Ser Thr Ala Val Gln Val
255                 260                 265                 270 cac gat gtc tgc gtc tgc cag cac aac act gcc ggc cca aat tgt gag      864
His Asp Val Cys Val Cys Gln His Asn Thr Ala Gly Pro Asn Cys Glu
                275                 280                 285 cgc tgt gca ccc ttc tac aac aac cgg ccc tgg aga ccg gcg gag ggc      912
Arg Cys Ala Pro Phe Tyr Asn Asn Arg Pro Trp Arg Pro Ala Glu Gly
            290                 295                 300 cag gac gcc cat gaa tgc caa agg tgc gac tgc aat ggg cac tca gag      960
Gln Asp Ala His Glu Cys Gln Arg Cys Asp Cys Asn Gly His Ser Glu
        305                 310                 315 aca tgt cac ttt gac ccc gct gtg ttt gcc gcc agc cag ggg gca tat     1008
Thr Cys His Phe Asp Pro Ala Val Phe Ala Ala Ser Gln Gly Ala Tyr
    320                 325                 330 gga ggt gtg tgt gac aat tgc cgg gac cac acc gaa ggc aag aac tgt     1056
Gly Gly Val Cys Asp Asn Cys Arg Asp His Thr Glu Gly Lys Asn Cys
335                 340                 345                 350 gag cgg tgt cag ctg cac tat ttc cgg aac cgg cgc ccg gga gct tcc     1104
Glu Arg Cys Gln Leu His Tyr Phe Arg Asn Arg Arg Pro Gly Ala Ser
                355                 360                 365 att cag gag acc tgc atc tcc tgc gag tgt gat ccg gat ggg gca gtg     1152
Ile Gln Glu Thr Cys Ile Ser Cys Glu Cys Asp Pro Asp Gly Ala Val
            370                 375                 380
```

```
cca ggg gct ccc tgt gac cca gtg acc ggg cag tgt gtg tgc aag gag      1200
Pro Gly Ala Pro Cys Asp Pro Val Thr Gly Gln Cys Val Cys Lys Glu
            385                 390                 395 cat gtg cag gga gag cgc tgt gac cta tgc aag ccg ggc ttc act gga      1248
His Val Gln Gly Glu Arg Cys Asp Leu Cys Lys Pro Gly Phe Thr Gly
        400                 405                 410 ctc acc tac gcc aac ccg cag ggc tgc cac cgc tgt gac tgc aac atc      1296
Leu Thr Tyr Ala Asn Pro Gln Gly Cys His Arg Cys Asp Cys Asn Ile
415                 420                 425                 430 ctg ggg tcc cgg agg gac atg ccg tgt gac gag gag agt ggg cgc tgc      1344
Leu Gly Ser Arg Arg Asp Met Pro Cys Asp Glu Glu Ser Gly Arg Cys
                435                 440                 445 ctt tgt ctg ccc aac gtg gtg ggt ccc aaa tgt gac cag tgt gct ccc      1392
Leu Cys Leu Pro Asn Val Val Gly Pro Lys Cys Asp Gln Cys Ala Pro
            450                 455                 460 tac cac tgg aag ctg gcc agt ggc cag ggc tgt gaa ccg tgt gcc tgc      1440
Tyr His Trp Lys Leu Ala Ser Gly Gln Gly Cys Glu Pro Cys Ala Cys
        465                 470                 475 gac ccg cac aac tcc ctc agc cca cag tgc aac cag ttc aca ggg cag      1488
Asp Pro His Asn Ser Leu Ser Pro Gln Cys Asn Gln Phe Thr Gly Gln
480                 485                 490 tgc ccc tgt cgg gaa ggc ttt ggt ggc ctg atg tgc agc gct gca gcc      1536
Cys Pro Cys Arg Glu Gly Phe Gly Gly Leu Met Cys Ser Ala Ala Ala
495                 500                 505                 510 atc cgc cag tgt cca gac cgg acc tat gga gac gtg gcc aca gga tgc      1584
Ile Arg Gln Cys Pro Asp Arg Thr Tyr Gly Asp Val Ala Thr Gly Cys
                515                 520                 525 cga gcc tgt gac tgt gat ttc cgg gga aca gag ggc ccg ggc tgc gac      1632
Arg Ala Cys Asp Cys Asp Phe Arg Gly Thr Glu Gly Pro Gly Cys Asp
            530                 535                 540 aag gca tca ggc cgc tgc ctc tgc cgc cct ggc ttg acc ggg ccc cgc      1680
Lys Ala Ser Gly Arg Cys Leu Cys Arg Pro Gly Leu Thr Gly Pro Arg
        545                 550                 555 tgt gac cag tgc cag cga ggc tac tgc aat cgc tac ccg gtg tgc gtg      1728
Cys Asp Gln Cys Gln Arg Gly Tyr Cys Asn Arg Tyr Pro Val Cys Val
560                 565                 570 gcc tgc cac cct tgc ttc cag acc tat gat gcg gac ctc cgg gag cag      1776
Ala Cys His Pro Cys Phe Gln Thr Tyr Asp Ala Asp Leu Arg Glu Gln
575                 580                 585                 590 gcc ctg cgc ttt ggt aga ctc cgg aat gcc acc gcc agc ctg tgg tca      1824
Ala Leu Arg Phe Gly Arg Leu Arg Asn Ala Thr Ala Ser Leu Trp Ser
                595                 600                 605 ggg cct ggg ctg gag gac cgt ggc ctg gcc tcc cgg atc cta gat gca      1872
Gly Pro Gly Leu Glu Asp Arg Gly Leu Ala Ser Arg Ile Leu Asp Ala
            610                 615                 620 aag agt aag att gag cag atc cga gca gtt ctc agc agc ccc gca gtc      1920
Lys Ser Lys Ile Glu Gln Ile Arg Ala Val Leu Ser Ser Pro Ala Val
        625                 630                 635 aca gag cag gag gtg gct cag gtg gcc agt gcc atc ctc tcc ctc agg      1968
Thr Glu Gln Glu Val Ala Gln Val Ala Ser Ala Ile Leu Ser Leu Arg
640                 645                 650 cga act ctc cag ggc ctg cag ctg gat ctg ccc ctg gag gag gag acg      2016
Arg Thr Leu Gln Gly Leu Gln Leu Asp Leu Pro Leu Glu Glu Glu Thr
655                 660                 665                 670 ttg tcc ctt ccg aga gac ctg gag agt ctt gac aga agc ttc aat ggt      2064
Leu Ser Leu Pro Arg Asp Leu Glu Ser Leu Asp Arg Ser Phe Asn Gly
                675                 680                 685 ctc ctt act atg tat cag agg aag agg gag cag ttt gaa aaa ata agc      2112
Leu Leu Thr Met Tyr Gln Arg Lys Arg Glu Gln Phe Glu Lys Ile Ser
```

```
                    690                    695                    700
agt gct gat cct tca gga gcc ttc cgg atg ctg agc aca gcc tac gag        2160
Ser Ala Asp Pro Ser Gly Ala Phe Arg Met Leu Ser Thr Ala Tyr Glu
            705                    710                    715 cag tca gcc cag gct gct cag cag gtc tcc gac agc tcg cgc ctt ttg        2208
Gln Ser Ala Gln Ala Ala Gln Gln Val Ser Asp Ser Ser Arg Leu Leu
    720                    725                    730 gac cag ctc agg gac agc cgg aga gag gca gag agg ctg gtg cgg cag        2256
Asp Gln Leu Arg Asp Ser Arg Arg Glu Ala Glu Arg Leu Val Arg Gln
735                    740                    745                    750 gcg gga gga gga gga ggc acc ggc agc ccc aag ctt gtg gcc ctg agg        2304
Ala Gly Gly Gly Gly Gly Thr Gly Ser Pro Lys Leu Val Ala Leu Arg
                755                    760                    765 ctg gag atg tct tcg ttg cct gac ctg aca ccc acc ttc aac aag ctc        2352
Leu Glu Met Ser Ser Leu Pro Asp Leu Thr Pro Thr Phe Asn Lys Leu
            770                    775                    780 tgt ggc aac tcc agg cag atg gct tgc acc cca ata tca tgc cct ggt        2400
Cys Gly Asn Ser Arg Gln Met Ala Cys Thr Pro Ile Ser Cys Pro Gly
        785                    790                    795 gag cta tgt ccc caa gac aat ggc aca gcc tgt ggc tcc cgc tgc agg        2448
Glu Leu Cys Pro Gln Asp Asn Gly Thr Ala Cys Gly Ser Arg Cys Arg
    800                    805                    810 ggt gtc ctt ccc agg gcc ggt ggg gcc ttc ttg atg gcg ggg cag gtg        2496
Gly Val Leu Pro Arg Ala Gly Gly Ala Phe Leu Met Ala Gly Gln Val
815                    820                    825                    830 gct gag cag ctg cgg ggc ttc aat gcc cag ctc cag cgg acc agg cag        2544
Ala Glu Gln Leu Arg Gly Phe Asn Ala Gln Leu Gln Arg Thr Arg Gln
                835                    840                    845 atg att agg gca gcc gag gaa tct gcc tca cag att caa tcc agt gcc        2592
Met Ile Arg Ala Ala Glu Glu Ser Ala Ser Gln Ile Gln Ser Ser Ala
            850                    855                    860 cag cgc ttg gag acc cag gtg agc gcc agc cgc tcc cag atg gag gaa        2640
Gln Arg Leu Glu Thr Gln Val Ser Ala Ser Arg Ser Gln Met Glu Glu
        865                    870                    875 gat gtc aga cgc aca cgg ctc cta atc cag cag gtc cgg gac ttc cta        2688
Asp Val Arg Arg Thr Arg Leu Leu Ile Gln Gln Val Arg Asp Phe Leu
    880                    885                    890 aca gac ccc gac act gat gca gcc act atc cag gag gtc agc gag gcc        2736
Thr Asp Pro Asp Thr Asp Ala Ala Thr Ile Gln Glu Val Ser Glu Ala
895                    900                    905                    910 gtg ctg gcc ctg tgg ctg ccc aca gac tca gct act gtt ctg cag aag        2784
Val Leu Ala Leu Trp Leu Pro Thr Asp Ser Ala Thr Val Leu Gln Lys
                915                    920                    925 atg aat gag atc cag gcc att gca gcc agg ctc ccc aac gtg gac ttg        2832
Met Asn Glu Ile Gln Ala Ile Ala Ala Arg Leu Pro Asn Val Asp Leu
            930                    935                    940 gtg ctg tcc cag acc aag cag gac att gcg cgt gcc cgc cgg ttg cag        2880
Val Leu Ser Gln Thr Lys Gln Asp Ile Ala Arg Ala Arg Arg Leu Gln
        945                    950                    955 gct gag gct gag gaa gcc agg agc cga gcc cat gca gtg gag ggc cag        2928
Ala Glu Ala Glu Glu Ala Arg Ser Arg Ala His Ala Val Glu Gly Gln
    960                    965                    970 gtg gaa gat gtg gtt ggg aac ctg cgg cag ggg aca gtg gca ctg cag        2976
Val Glu Asp Val Val Gly Asn Leu Arg Gln Gly Thr Val Ala Leu Gln
975                    980                    985                    990 gaa gct cag gac acc atg caa ggc acc agc cgc tcc ctt cgg ctt atc        3024
Glu Ala Gln Asp Thr Met Gln Gly Thr Ser Arg Ser Leu Arg Leu Ile
                995                    1000                   1005 cag gac agg gtt gct gag gtt cag cag gta ctg cgg cca gca gaa aag        3072
```

-continued

```
Gln Asp Arg Val Ala Glu Val Gln Gln Val Leu Arg Pro Ala Glu Lys
        1010                1015                1020 ctg gtg aca agc atg acc aag cag ctg ggt gac ttc tgg aca cgg atg    3120
Leu Val Thr Ser Met Thr Lys Gln Leu Gly Asp Phe Trp Thr Arg Met
    1025                1030                1035 gag gag ctc cgc cac caa gcc cgg cag cag ggg gca gag gca gtc cag    3168
Glu Glu Leu Arg His Gln Ala Arg Gln Gln Gly Ala Glu Ala Val Gln
1040                1045                1050 gcc cag cag ctt gcg gaa ggt gcc agc gag cag gca ttg agt gcc caa    3216
Ala Gln Gln Leu Ala Glu Gly Ala Ser Glu Gln Ala Leu Ser Ala Gln
1055                1060                1065                1070 gag gga ttt gag aga ata aaa caa aag tat gct gag ttg aag gac cgg    3264
Glu Gly Phe Glu Arg Ile Lys Gln Lys Tyr Ala Glu Leu Lys Asp Arg
            1075                1080                1085 ttg ggt cag agt tcc atg ctg ggt gag cag ggt gcc cgg atc cag agt    3312
Leu Gly Gln Ser Ser Met Leu Gly Glu Gln Gly Ala Arg Ile Gln Ser
        1090                1095                1100 gtg aag aca gag gca gag gag ctg ttt ggg gag acc atg gag atg atg    3360
Val Lys Thr Glu Ala Glu Glu Leu Phe Gly Glu Thr Met Glu Met Met
    1105                1110                1115 gac agg atg aaa gac atg gag ttg gag ctg ctg cgg ggc agc cag gcc    3408
Asp Arg Met Lys Asp Met Glu Leu Glu Leu Leu Arg Gly Ser Gln Ala
1120                1125                1130 atc atg ctg cgc tca gcg gac ctg aca gga ctg gag aag cgt gtg gag    3456
Ile Met Leu Arg Ser Ala Asp Leu Thr Gly Leu Glu Lys Arg Val Glu
1135                1140                1145                1150 cag atc cgt gac cac atc aat ggg cgc gtg ctc tac tat gcc acc tgc    3504
Gln Ile Arg Asp His Ile Asn Gly Arg Val Leu Tyr Tyr Ala Thr Cys
            1155                1160                1165 aag tgat                                                            3511
Lys

<210> SEQ ID NO 20
<211> LENGTH: 1167
<212> TYPE: PRT
<213> ORGANISM: Homo sapiens

<400> SEQUENCE: 20

Leu Ala Asp Tyr Lys Asp Asp Asp Lys Leu Ala Gln Gln Ala Cys
1               5                   10                  15

Ser Arg Gly Ala Cys Tyr Pro Val Gly Asp Leu Leu Val Gly Arg
                20                  25                  30

Thr Arg Phe Leu Arg Ala Ser Ser Thr Cys Gly Leu Thr Lys Pro Glu
            35                  40                  45

Thr Tyr Cys Thr Gln Tyr Gly Glu Trp Gln Met Lys Cys Cys Lys Cys
        50                  55                  60

Asp Ser Arg Gln Pro His Asn Tyr Tyr Ser His Arg Val Glu Asn Val
65                  70                  75                  80

Ala Ser Ser Ser Gly Pro Met Arg Trp Trp Gln Ser Gln Asn Asp Val
                85                  90                  95

Asn Pro Val Ser Leu Gln Leu Asp Leu Asp Arg Arg Phe Gln Leu Gln
                100                 105                 110

Glu Val Met Met Glu Phe Gln Gly Pro Met Pro Ala Gly Met Leu Ile
            115                 120                 125

Glu Arg Ser Ser Asp Phe Gly Lys Thr Trp Arg Val Tyr Gln Tyr Leu
        130                 135                 140

Ala Ala Asp Cys Thr Ser Thr Phe Pro Arg Val Arg Gln Gly Arg Pro
145                 150                 155                 160
```

```
Gln Ser Trp Gln Asp Val Arg Cys Gln Ser Leu Pro Gln Arg Pro Asn
                165                 170                 175
Ala Arg Leu Asn Gly Gly Lys Val Gln Leu Asn Leu Met Asp Leu Val
            180                 185                 190
Ser Gly Ile Pro Ala Thr Gln Ser Gln Lys Ile Gln Glu Val Gly Glu
        195                 200                 205
Ile Thr Asn Leu Arg Val Asn Phe Thr Arg Leu Ala Pro Val Pro Gln
    210                 215                 220
Arg Gly Tyr His Pro Pro Ser Ala Tyr Tyr Ala Val Ser Gln Leu Arg
225                 230                 235                 240
Leu Gln Gly Ser Cys Phe Cys His Gly His Ala Asp Arg Cys Ala Pro
                245                 250                 255
Lys Pro Gly Ala Ser Ala Gly Pro Ser Thr Ala Val Gln Val His Asp
            260                 265                 270
Val Cys Val Cys Gln His Asn Thr Ala Gly Pro Asn Cys Glu Arg Cys
        275                 280                 285
Ala Pro Phe Tyr Asn Asn Arg Pro Trp Arg Pro Ala Glu Gly Gln Asp
    290                 295                 300
Ala His Glu Cys Gln Arg Cys Asp Cys Asn Gly His Ser Glu Thr Cys
305                 310                 315                 320
His Phe Asp Pro Ala Val Phe Ala Ala Ser Gln Gly Ala Tyr Gly Gly
                325                 330                 335
Val Cys Asp Asn Cys Arg Asp His Thr Glu Gly Lys Asn Cys Glu Arg
            340                 345                 350
Cys Gln Leu His Tyr Phe Arg Asn Arg Arg Pro Gly Ala Ser Ile Gln
        355                 360                 365
Glu Thr Cys Ile Ser Cys Glu Cys Asp Pro Asp Gly Ala Val Pro Gly
    370                 375                 380
Ala Pro Cys Asp Pro Val Thr Gly Gln Cys Val Cys Lys Glu His Val
385                 390                 395                 400
Gln Gly Glu Arg Cys Asp Leu Cys Lys Pro Gly Phe Thr Gly Leu Thr
                405                 410                 415
Tyr Ala Asn Pro Gln Gly Cys His Arg Cys Asp Cys Asn Ile Leu Gly
            420                 425                 430
Ser Arg Arg Asp Met Pro Cys Asp Glu Glu Ser Gly Arg Cys Leu Cys
        435                 440                 445
Leu Pro Asn Val Val Gly Pro Lys Cys Asp Gln Cys Ala Pro Tyr His
    450                 455                 460
Trp Lys Leu Ala Ser Gly Gln Gly Cys Glu Pro Cys Ala Cys Asp Pro
465                 470                 475                 480
His Asn Ser Leu Ser Pro Gln Cys Asn Gln Phe Thr Gly Gln Cys Pro
                485                 490                 495
Cys Arg Glu Gly Phe Gly Gly Leu Met Cys Ser Ala Ala Ile Arg
            500                 505                 510
Gln Cys Pro Asp Arg Thr Tyr Gly Asp Val Ala Thr Gly Cys Arg Ala
        515                 520                 525
Cys Asp Cys Asp Phe Arg Gly Thr Glu Gly Pro Gly Cys Asp Lys Ala
    530                 535                 540
Ser Gly Arg Cys Leu Cys Arg Pro Gly Leu Thr Gly Pro Arg Cys Asp
545                 550                 555                 560
Gln Cys Gln Arg Gly Tyr Cys Asn Arg Tyr Pro Val Cys Val Ala Cys
                565                 570                 575
```

-continued

```
His Pro Cys Phe Gln Thr Tyr Asp Ala Asp Leu Arg Glu Gln Ala Leu
            580                 585                 590

Arg Phe Gly Arg Leu Arg Asn Ala Thr Ala Ser Leu Trp Ser Gly Pro
            595                 600                 605

Gly Leu Glu Asp Arg Gly Leu Ala Ser Arg Ile Leu Asp Ala Lys Ser
            610                 615                 620

Lys Ile Glu Gln Ile Arg Ala Val Leu Ser Ser Pro Ala Val Thr Glu
625                 630                 635                 640

Gln Glu Val Ala Gln Val Ala Ser Ala Ile Leu Ser Leu Arg Arg Thr
                645                 650                 655

Leu Gln Gly Leu Gln Leu Asp Leu Pro Leu Glu Glu Thr Leu Ser
            660                 665                 670

Leu Pro Arg Asp Leu Glu Ser Leu Asp Arg Ser Phe Asn Gly Leu Leu
            675                 680                 685

Thr Met Tyr Gln Arg Lys Arg Glu Gln Phe Glu Lys Ile Ser Ser Ala
            690                 695                 700

Asp Pro Ser Gly Ala Phe Arg Met Leu Ser Thr Ala Tyr Glu Gln Ser
705                 710                 715                 720

Ala Gln Ala Ala Gln Val Ser Asp Ser Ser Arg Leu Leu Asp Gln
                725                 730                 735

Leu Arg Asp Ser Arg Arg Glu Ala Glu Arg Leu Val Arg Gln Ala Gly
            740                 745                 750

Gly Gly Gly Gly Thr Gly Ser Pro Lys Leu Val Ala Leu Arg Leu Glu
            755                 760                 765

Met Ser Ser Leu Pro Asp Leu Thr Pro Thr Phe Asn Lys Leu Cys Gly
            770                 775                 780

Asn Ser Arg Gln Met Ala Cys Thr Pro Ile Ser Cys Pro Gly Glu Leu
785                 790                 795                 800

Cys Pro Gln Asp Asn Gly Thr Ala Cys Gly Ser Arg Cys Arg Gly Val
                805                 810                 815

Leu Pro Arg Ala Gly Gly Ala Phe Leu Met Ala Gly Gln Val Ala Glu
            820                 825                 830

Gln Leu Arg Gly Phe Asn Ala Gln Leu Gln Arg Thr Arg Gln Met Ile
            835                 840                 845

Arg Ala Ala Glu Glu Ser Ala Ser Gln Ile Gln Ser Ser Ala Gln Arg
            850                 855                 860

Leu Glu Thr Gln Val Ser Ala Ser Arg Ser Gln Met Glu Glu Asp Val
865                 870                 875                 880

Arg Arg Thr Arg Leu Leu Ile Gln Gln Val Arg Asp Phe Leu Thr Asp
                885                 890                 895

Pro Asp Thr Asp Ala Ala Thr Ile Gln Glu Val Ser Glu Ala Val Leu
            900                 905                 910

Ala Leu Trp Leu Pro Thr Asp Ser Ala Thr Val Leu Gln Lys Met Asn
            915                 920                 925

Glu Ile Gln Ala Ile Ala Ala Arg Leu Pro Asn Val Asp Leu Val Leu
            930                 935                 940

Ser Gln Thr Lys Gln Asp Ile Ala Arg Ala Arg Arg Leu Gln Ala Glu
945                 950                 955                 960

Ala Glu Glu Ala Arg Ser Arg Ala His Ala Val Glu Gly Gln Val Glu
                965                 970                 975

Asp Val Val Gly Asn Leu Arg Gln Gly Thr Val Ala Leu Gln Glu Ala
            980                 985                 990

Gln Asp Thr Met Gln Gly Thr Ser Arg Ser Leu Arg Leu Ile Gln Asp
```

-continued

```
                   995               1000               1005
     Arg Val Ala Glu Val Gln Gln Val Leu Arg Pro Ala Glu Lys Leu Val
         1010               1015               1020

Thr Ser Met Thr Lys Gln Leu Gly Asp Phe Trp Thr Arg Met Glu Glu
     1025               1030               1035               1040

Leu Arg His Gln Ala Arg Gln Gln Gly Ala Glu Ala Val Gln Ala Gln
                    1045               1050               1055

Gln Leu Ala Glu Gly Ala Ser Glu Gln Ala Leu Ser Ala Gln Glu Gly
                1060               1065               1070

Phe Glu Arg Ile Lys Gln Lys Tyr Ala Glu Leu Lys Asp Arg Leu Gly
             1075               1080               1085

Gln Ser Ser Met Leu Gly Glu Gln Gly Ala Arg Ile Gln Ser Val Lys
         1090               1095               1100

Thr Glu Ala Glu Glu Leu Phe Gly Glu Thr Met Glu Met Met Asp Arg
     1105               1110               1115               1120

Met Lys Asp Met Glu Leu Glu Leu Leu Arg Gly Ser Gln Ala Ile Met
                    1125               1130               1135

Leu Arg Ser Ala Asp Leu Thr Gly Leu Glu Lys Arg Val Glu Gln Ile
                1140               1145               1150

Arg Asp His Ile Asn Gly Arg Val Leu Tyr Tyr Ala Thr Cys Lys
             1155               1160               1165

<210> SEQ ID NO 21
<211> LENGTH: 3585
<212> TYPE: DNA
<213> ORGANISM: Homo sapiens
<220> FEATURE:
<221> NAME/KEY: CDS
<222> LOCATION: (60)..(3581)
<221> NAME/KEY: sig_peptide
<222> LOCATION: (60)..(116)

<400> SEQUENCE: 21
gtttaaactt aagcttctgc ctgccgcctg cctgcctgcc actgagggtt cccagcacc        59 atg agg gcc tgg atc ttc ttt ctc ctt tgc ctg gcc ggg agg gct ctg      107
Met Arg Ala Trp Ile Phe Phe Leu Leu Cys Leu Ala Gly Arg Ala Leu
  1               5                  10                  15 gca gcc cca caa caa gcc tgc tcc cgt ggg gcc tgc tat cca cct gtt      155
Ala Ala Pro Gln Gln Ala Cys Ser Arg Gly Ala Cys Tyr Pro Pro Val
             20                  25                  30 ggg gac ctg ctt gtt ggg agg acc cgg ttt ctc cga gct tca tct acc      203
Gly Asp Leu Leu Val Gly Arg Thr Arg Phe Leu Arg Ala Ser Ser Thr
         35                  40                  45 tgt gga ctg acc aag cct gag acc tac tgc acc cag tat ggc gag tgg      251
Cys Gly Leu Thr Lys Pro Glu Thr Tyr Cys Thr Gln Tyr Gly Glu Trp
     50                  55                  60 cag atg aaa tgc tgc aag tgt gac tcc agg cag cct cac aac tac tac      299
Gln Met Lys Cys Cys Lys Cys Asp Ser Arg Gln Pro His Asn Tyr Tyr
 65                  70                  75                  80 agt cac cga gta gag aat gtg gct tca tcc tcc ggc ccc atg cgc tgg      347
Ser His Arg Val Glu Asn Val Ala Ser Ser Ser Gly Pro Met Arg Trp
                 85                  90                  95 tgg cag tcc cag aat gat gtg aac cct gtc tct ctg cag ctg gac ctg      395
Trp Gln Ser Gln Asn Asp Val Asn Pro Val Ser Leu Gln Leu Asp Leu
            100                 105                 110 gac agg aga ttc cag ctt caa gaa gtc atg atg gag ttc cag ggg ccc      443
Asp Arg Arg Phe Gln Leu Gln Glu Val Met Met Glu Phe Gln Gly Pro
        115                 120                 125
```

```
atg cct gcc ggc atg ctg att gag cgc tcc tca gac ttc ggt aag acc       491
Met Pro Ala Gly Met Leu Ile Glu Arg Ser Ser Asp Phe Gly Lys Thr
    130                 135                 140 tgg cga gtg tac cag tac ctg gct gcc gac tgc acc tcc acc ttc cct       539
Trp Arg Val Tyr Gln Tyr Leu Ala Ala Asp Cys Thr Ser Thr Phe Pro
145                 150                 155                 160 cgg gtc cgc cag ggt cgg cct cag agc tgg cag gat gtt cgg tgc cag       587
Arg Val Arg Gln Gly Arg Pro Gln Ser Trp Gln Asp Val Arg Cys Gln
                165                 170                 175 tcc ctg cct cag agg cct aat gca cgc cta aat ggg ggg aag gtc caa       635
Ser Leu Pro Gln Arg Pro Asn Ala Arg Leu Asn Gly Gly Lys Val Gln
            180                 185                 190 ctt aac ctt atg gat tta gtg tct ggg att cca gca act caa agt caa       683
Leu Asn Leu Met Asp Leu Val Ser Gly Ile Pro Ala Thr Gln Ser Gln
        195                 200                 205 aaa att caa gag gtg ggg gag atc aca aac ttg aga gtc aat ttc acc       731
Lys Ile Gln Glu Val Gly Glu Ile Thr Asn Leu Arg Val Asn Phe Thr
    210                 215                 220 agg ctg gcc cct gtg ccc caa agg ggc tac cac cct ccc agc gcc tac       779
Arg Leu Ala Pro Val Pro Gln Arg Gly Tyr His Pro Pro Ser Ala Tyr
225                 230                 235                 240 tat gct gtg tcc cag ctc cgt ctg cag ggg agc tgc ttc tgt cac ggc       827
Tyr Ala Val Ser Gln Leu Arg Leu Gln Gly Ser Cys Phe Cys His Gly
                245                 250                 255 cat gct gat cgc tgc gca ccc aag cct ggg gcc tct gca ggc ccc tcc       875
His Ala Asp Arg Cys Ala Pro Lys Pro Gly Ala Ser Ala Gly Pro Ser
            260                 265                 270 acc gct gtg cag gtc cac gat gtc tgc gtc tgc cag cac aac act gcc       923
Thr Ala Val Gln Val His Asp Val Cys Val Cys Gln His Asn Thr Ala
        275                 280                 285 ggc cca aat tgt gag cgc tgt gca ccc ttc tac aac aac cgg ccc tgg       971
Gly Pro Asn Cys Glu Arg Cys Ala Pro Phe Tyr Asn Asn Arg Pro Trp
    290                 295                 300 aga ccg gcg gag ggc cag gac gcc cat gaa tgc caa agg tgc gac tgc       1019
Arg Pro Ala Glu Gly Gln Asp Ala His Glu Cys Gln Arg Cys Asp Cys
305                 310                 315                 320 aat ggg cac tca gag aca tgt cac ttt gac ccc gct gtg ttt gcc gcc       1067
Asn Gly His Ser Glu Thr Cys His Phe Asp Pro Ala Val Phe Ala Ala
                325                 330                 335 agc cag ggg gca tat gga ggt gtg tgt gac aat tgc cgg gac cac acc       1115
Ser Gln Gly Ala Tyr Gly Gly Val Cys Asp Asn Cys Arg Asp His Thr
            340                 345                 350 gaa ggc aag aac tgt gag cgg tgt cag ctg cac tat ttc cgg aac cgg       1163
Glu Gly Lys Asn Cys Glu Arg Cys Gln Leu His Tyr Phe Arg Asn Arg
        355                 360                 365 cgc ccg gga gct tcc att cag gag acc tgc atc tcc tgc gag tgt gat       1211
Arg Pro Gly Ala Ser Ile Gln Glu Thr Cys Ile Ser Cys Glu Cys Asp
    370                 375                 380 ccg gat ggg gca gtg cca ggg gct ccc tgt gac cca gtg acc ggg cag       1259
Pro Asp Gly Ala Val Pro Gly Ala Pro Cys Asp Pro Val Thr Gly Gln
385                 390                 395                 400 tgt gtg tgc aag gag cat gtg cag gga gag cgc tgt gac cta tgc aag       1307
Cys Val Cys Lys Glu His Val Gln Gly Glu Arg Cys Asp Leu Cys Lys
                405                 410                 415 ccg ggc ttc act gga ctc acc tac gcc aac cca cag ggc tgc cac cgc       1355
Pro Gly Phe Thr Gly Leu Thr Tyr Ala Asn Pro Gln Gly Cys His Arg
            420                 425                 430 tgt gac tgc aac atc ctg ggg tcc cgg agg gac atg ccg tgt gac gag       1403
Cys Asp Cys Asn Ile Leu Gly Ser Arg Arg Asp Met Pro Cys Asp Glu
        435                 440                 445
```

```
gag agt ggg cgc tgc ctt tgt ctg ccc aac gtg gtg ggt ccc aaa tgt    1451
Glu Ser Gly Arg Cys Leu Cys Leu Pro Asn Val Val Gly Pro Lys Cys
    450                 455                 460 gac cag tgt gct ccc tac cac tgg aag ctg gcc agt ggc cag ggc tgt    1499
Asp Gln Cys Ala Pro Tyr His Trp Lys Leu Ala Ser Gly Gln Gly Cys
465                 470                 475                 480 gaa ccg tgt gcc tgc gac ccg cac aac tcc ctc agc cca cag tgc aac    1547
Glu Pro Cys Ala Cys Asp Pro His Asn Ser Leu Ser Pro Gln Cys Asn
                485                 490                 495 cag ttc aca ggg cag tgc ccc tgt cgg gaa ggc ttt ggt ggc ctg atg    1595
Gln Phe Thr Gly Gln Cys Pro Cys Arg Glu Gly Phe Gly Gly Leu Met
            500                 505                 510 tgc agc gct gca gcc atc cgc cag tgt cca gac cgg acc tat gga gac    1643
Cys Ser Ala Ala Ala Ile Arg Gln Cys Pro Asp Arg Thr Tyr Gly Asp
        515                 520                 525 gtg gcc aca gga tgc cga gcc tgt gac tgt gat ttc cgg gga aca gag    1691
Val Ala Thr Gly Cys Arg Ala Cys Asp Cys Asp Phe Arg Gly Thr Glu
    530                 535                 540 ggc ccg ggc tgc gac aag gca tca ggc cgc tgc ctc tgc cgc cct ggc    1739
Gly Pro Gly Cys Asp Lys Ala Ser Gly Arg Cys Leu Cys Arg Pro Gly
545                 550                 555                 560 ttg acc ggg ccc cgc tgt gac cag tgc cag cga ggc tac tgc aat cgc    1787
Leu Thr Gly Pro Arg Cys Asp Gln Cys Gln Arg Gly Tyr Cys Asn Arg
                565                 570                 575 tac ccg gtg tgc gtg gcc tgc cac cct tgc ttc cag acc tat gat gcg    1835
Tyr Pro Val Cys Val Ala Cys His Pro Cys Phe Gln Thr Tyr Asp Ala
            580                 585                 590 gac ctc cgg gag cag gcc ctg cgc ttt ggt aga ctc cgg aat gcc acc    1883
Asp Leu Arg Glu Gln Ala Leu Arg Phe Gly Arg Leu Arg Asn Ala Thr
        595                 600                 605 gcc agc ctg tgg tca ggg cct ggg ctg gag gac cgt ggc ctg gcc tcc    1931
Ala Ser Leu Trp Ser Gly Pro Gly Leu Glu Asp Arg Gly Leu Ala Ser
    610                 615                 620 cgg atc cta gat gca aag agt aag att gag cag atc cga gca gtt ctc    1979
Arg Ile Leu Asp Ala Lys Ser Lys Ile Glu Gln Ile Arg Ala Val Leu
625                 630                 635                 640 agc agc ccc gca gtc aca gag cag gag gtg gct cag gtg gcc agt gcc    2027
Ser Ser Pro Ala Val Thr Glu Gln Glu Val Ala Gln Val Ala Ser Ala
                645                 650                 655 atc ctc tcc ctc agg cga act ctc cag ggc ctg cag ctg gat ctg ccc    2075
Ile Leu Ser Leu Arg Arg Thr Leu Gln Gly Leu Gln Leu Asp Leu Pro
            660                 665                 670 ctg gag gag gag acg ttg tcc ctt ccg aga gac ctg gag agt ctt gac    2123
Leu Glu Glu Glu Thr Leu Ser Leu Pro Arg Asp Leu Glu Ser Leu Asp
        675                 680                 685 aga agc ttc aat ggt ctc ctt act atg tat cag agg aag agg gag cag    2171
Arg Ser Phe Asn Gly Leu Leu Thr Met Tyr Gln Arg Lys Arg Glu Gln
    690                 695                 700 ttt gaa aaa ata agc agt gct gat cct tca gga gcc ttc cgg atg ctg    2219
Phe Glu Lys Ile Ser Ser Ala Asp Pro Ser Gly Ala Phe Arg Met Leu
705                 710                 715                 720 agc aca gcc tac gag cag tca gcc cag gct gct cag cag gtc tcc gac    2267
Ser Thr Ala Tyr Glu Gln Ser Ala Gln Ala Ala Gln Gln Val Ser Asp
                725                 730                 735 agc tcg cgc ctt ttg gac cag ctc agg gac agc cgg aga gag gca gag    2315
Ser Ser Arg Leu Leu Asp Gln Leu Arg Asp Ser Arg Arg Glu Ala Glu
            740                 745                 750 agg ctg gtg cgg cag gcg gga gga gga gga ggc acc ggc agc ccc aag    2363
Arg Leu Val Arg Gln Ala Gly Gly Gly Gly Gly Thr Gly Ser Pro Lys
```

```
                755                 760                 765
ctt gtg gcc ctg agg ctg gag atg tct tcg ttg cct gac ctg aca ccc      2411
Leu Val Ala Leu Arg Leu Glu Met Ser Ser Leu Pro Asp Leu Thr Pro
    770                 775                 780 acc ttc aac aag ctc tgt ggc aac tcc agg cag atg gct tgc acc cca      2459
Thr Phe Asn Lys Leu Cys Gly Asn Ser Arg Gln Met Ala Cys Thr Pro
785                 790                 795                 800 ata tca tgc cct ggt gag cta tgt ccc caa gac aat ggc aca gcc tgt      2507
Ile Ser Cys Pro Gly Glu Leu Cys Pro Gln Asp Asn Gly Thr Ala Cys
                805                 810                 815 ggc tcc cgc tgc agg ggt gtc ctt ccc agg gcc ggt ggg gcc ttc ttg      2555
Gly Ser Arg Cys Arg Gly Val Leu Pro Arg Ala Gly Gly Ala Phe Leu
            820                 825                 830 atg gcg ggg cag gtg gct gag cag ctg cgg ggc ttc aat gcc cag ctc      2603
Met Ala Gly Gln Val Ala Glu Gln Leu Arg Gly Phe Asn Ala Gln Leu
        835                 840                 845 cag cgg acc agg cag atg att agg gca gcc gag gaa tct gcc tca cag      2651
Gln Arg Thr Arg Gln Met Ile Arg Ala Ala Glu Glu Ser Ala Ser Gln
    850                 855                 860 att caa tcc agt gcc cag cgc ttg gag acc cag gtg agc gcc agc cgc      2699
Ile Gln Ser Ser Ala Gln Arg Leu Glu Thr Gln Val Ser Ala Ser Arg
865                 870                 875                 880 tcc cag atg gag gaa gat gtc aga cgc aca cgg ctc cta atc cag cag      2747
Ser Gln Met Glu Glu Asp Val Arg Arg Thr Arg Leu Leu Ile Gln Gln
                885                 890                 895 gtc cgg gac ttc cta aca gac ccc gac act gat gca gcc act atc cag      2795
Val Arg Asp Phe Leu Thr Asp Pro Asp Thr Asp Ala Ala Thr Ile Gln
            900                 905                 910 gag gtc agc gag gcc gtg ctg gcc ctg tgg ctg ccc aca gac tca gct      2843
Glu Val Ser Glu Ala Val Leu Ala Leu Trp Leu Pro Thr Asp Ser Ala
        915                 920                 925 act gtt ctg cag aag atg aat gag atc cag gcc att gca gcc agg ctc      2891
Thr Val Leu Gln Lys Met Asn Glu Ile Gln Ala Ile Ala Ala Arg Leu
    930                 935                 940 ccc aac gtg gac ttg gtg ctg tcc cag acc aag cag gac att gcg cgt      2939
Pro Asn Val Asp Leu Val Leu Ser Gln Thr Lys Gln Asp Ile Ala Arg
945                 950                 955                 960 gcc cgc cgg ttg cag gct gag gct gag gaa gcc agg agc cga gcc cat      2987
Ala Arg Arg Leu Gln Ala Glu Ala Glu Glu Ala Arg Ser Arg Ala His
                965                 970                 975 gca gtg gag ggc cag gtg gaa gat gtg gtt ggg aac ctg cgg cag ggg      3035
Ala Val Glu Gly Gln Val Glu Asp Val Val Gly Asn Leu Arg Gln Gly
            980                 985                 990 aca gtg gca ctg cag gaa gct cag gac acc atg caa ggc acc agc cgc      3083
Thr Val Ala Leu Gln Glu Ala Gln Asp Thr Met Gln Gly Thr Ser Arg
        995                 1000                1005 tcc ctt cgg ctt atc cag gac agg gtt gct gag gtt cag cag gta ctg      3131
Ser Leu Arg Leu Ile Gln Asp Arg Val Ala Glu Val Gln Gln Val Leu
    1010                1015                1020 cgg cca gca gaa aag ctg gtg aca agc atg acc aag cag ctg ggt gac      3179
Arg Pro Ala Glu Lys Leu Val Thr Ser Met Thr Lys Gln Leu Gly Asp
1025                1030                1035                1040 ttc tgg aca cgg atg gag gag ctc cgc cac caa gcc cgg cag cag ggg      3227
Phe Trp Thr Arg Met Glu Glu Leu Arg His Gln Ala Arg Gln Gln Gly
                1045                1050                1055 gca gag gca gtc cag gcc cag cag ctt gcg gaa ggt gcc agc gag cag      3275
Ala Glu Ala Val Gln Ala Gln Gln Leu Ala Glu Gly Ala Ser Glu Gln
            1060                1065                1070 gca ttg agt gcc caa gag gga ttt gag aga ata aaa caa aag tat gct      3323
```

-continued

```
Ala Leu Ser Ala Gln Glu Gly Phe Glu Arg Ile Lys Gln Lys Tyr Ala
    1075                1080                1085 gag ttg aag gac cgg ttg ggt cag agt tcc atg ctg ggt gag cag ggt        3371
Glu Leu Lys Asp Arg Leu Gly Gln Ser Ser Met Leu Gly Glu Gln Gly
1090                1095                1100 gcc cgg atc cag agt gtg aag aca gag gca gag gag ctg ttt ggg gag        3419
Ala Arg Ile Gln Ser Val Lys Thr Glu Ala Glu Glu Leu Phe Gly Glu
1105                1110                1115                1120 acc atg gag atg atg gac agg atg aaa gac atg gag ttg gag ctg ctg        3467
Thr Met Glu Met Met Asp Arg Met Lys Asp Met Glu Leu Glu Leu Leu
            1125                1130                1135 cgg ggc agc cag gcc atc atg ctg cgc tca gcg gac ctg aca gga ctg        3515
Arg Gly Ser Gln Ala Ile Met Leu Arg Ser Ala Asp Leu Thr Gly Leu
        1140                1145                1150 gag aag cgt gtg gag cag atc cgt gac cac atc aat ggg cgc gtg ctc        3563
Glu Lys Arg Val Glu Gln Ile Arg Asp His Ile Asn Gly Arg Val Leu
    1155                1160                1165 tac tat gcc acc tgc aag tgat                                           3585
Tyr Tyr Ala Thr Cys Lys
    1170
```

<210> SEQ ID NO 22
<211> LENGTH: 1174
<212> TYPE: PRT
<213> ORGANISM: Homo sapiens

<400> SEQUENCE: 22

```
Met Arg Ala Trp Ile Phe Phe Leu Leu Cys Leu Ala Gly Arg Ala Leu
1               5                   10                  15

Ala Ala Pro Gln Gln Ala Cys Ser Arg Gly Ala Cys Tyr Pro Pro Val
            20                  25                  30

Gly Asp Leu Leu Val Gly Arg Thr Arg Phe Leu Arg Ala Ser Ser Thr
        35                  40                  45

Cys Gly Leu Thr Lys Pro Glu Thr Tyr Cys Thr Gln Tyr Gly Glu Trp
    50                  55                  60

Gln Met Lys Cys Cys Lys Cys Asp Ser Arg Gln Pro His Asn Tyr Tyr
65                  70                  75                  80

Ser His Arg Val Glu Asn Val Ala Ser Ser Gly Pro Met Arg Trp
                85                  90                  95

Trp Gln Ser Gln Asn Asp Val Asn Pro Val Ser Leu Gln Leu Asp Leu
            100                 105                 110

Asp Arg Arg Phe Gln Leu Gln Glu Val Met Met Glu Phe Gln Gly Pro
        115                 120                 125

Met Pro Ala Gly Met Leu Ile Glu Arg Ser Ser Asp Phe Gly Lys Thr
    130                 135                 140

Trp Arg Val Tyr Gln Tyr Leu Ala Ala Asp Cys Thr Ser Thr Phe Pro
145                 150                 155                 160

Arg Val Arg Gln Gly Arg Pro Gln Ser Trp Gln Asp Val Arg Cys Gln
                165                 170                 175

Ser Leu Pro Gln Arg Pro Asn Ala Arg Leu Asn Gly Gly Lys Val Gln
            180                 185                 190

Leu Asn Leu Met Asp Leu Val Ser Gly Ile Pro Ala Thr Gln Ser Gln
        195                 200                 205

Lys Ile Gln Glu Val Gly Glu Ile Thr Asn Leu Arg Val Asn Phe Thr
    210                 215                 220

Arg Leu Ala Pro Val Pro Gln Arg Gly Tyr His Pro Pro Ser Ala Tyr
225                 230                 235                 240
```

-continued

```
Tyr Ala Val Ser Gln Leu Arg Leu Gln Gly Ser Cys Phe Cys His Gly
            245                 250                 255

His Ala Asp Arg Cys Ala Pro Lys Pro Gly Ala Ser Ala Gly Pro Ser
            260                 265                 270

Thr Ala Val Gln Val His Asp Val Cys Val Cys Gln His Asn Thr Ala
            275                 280                 285

Gly Pro Asn Cys Glu Arg Cys Ala Pro Phe Tyr Asn Asn Arg Pro Trp
            290                 295                 300

Arg Pro Ala Glu Gly Gln Asp Ala His Glu Cys Gln Arg Cys Asp Cys
305                 310                 315                 320

Asn Gly His Ser Glu Thr Cys His Phe Asp Pro Ala Val Phe Ala Ala
                325                 330                 335

Ser Gln Gly Ala Tyr Gly Gly Val Cys Asp Asn Cys Arg Asp His Thr
                340                 345                 350

Glu Gly Lys Asn Cys Glu Arg Cys Gln Leu His Tyr Phe Arg Asn Arg
            355                 360                 365

Arg Pro Gly Ala Ser Ile Gln Glu Thr Cys Ile Ser Cys Glu Cys Asp
    370                 375                 380

Pro Asp Gly Ala Val Pro Gly Ala Pro Cys Asp Pro Val Thr Gly Gln
385                 390                 395                 400

Cys Val Cys Lys Glu His Val Gln Gly Glu Arg Cys Asp Leu Cys Lys
            405                 410                 415

Pro Gly Phe Thr Gly Leu Thr Tyr Ala Asn Pro Gln Gly Cys His Arg
            420                 425                 430

Cys Asp Cys Asn Ile Leu Gly Ser Arg Arg Asp Met Pro Cys Asp Glu
            435                 440                 445

Glu Ser Gly Arg Cys Leu Cys Leu Pro Asn Val Val Gly Pro Lys Cys
    450                 455                 460

Asp Gln Cys Ala Pro Tyr His Trp Lys Leu Ala Ser Gly Gln Gly Cys
465                 470                 475                 480

Glu Pro Cys Ala Cys Asp Pro His Asn Ser Leu Ser Pro Gln Cys Asn
                485                 490                 495

Gln Phe Thr Gly Gln Cys Pro Cys Arg Glu Gly Phe Gly Gly Leu Met
                500                 505                 510

Cys Ser Ala Ala Ala Ile Arg Gln Cys Pro Asp Arg Thr Tyr Gly Asp
            515                 520                 525

Val Ala Thr Gly Cys Arg Ala Cys Asp Cys Asp Phe Arg Gly Thr Glu
            530                 535                 540

Gly Pro Gly Cys Asp Lys Ala Ser Gly Arg Cys Leu Cys Arg Pro Gly
545                 550                 555                 560

Leu Thr Gly Pro Arg Cys Asp Gln Cys Gln Arg Gly Tyr Cys Asn Arg
                565                 570                 575

Tyr Pro Val Cys Val Ala Cys His Pro Cys Phe Gln Thr Tyr Asp Ala
                580                 585                 590

Asp Leu Arg Glu Gln Ala Leu Arg Phe Gly Arg Leu Arg Asn Ala Thr
            595                 600                 605

Ala Ser Leu Trp Ser Gly Pro Gly Leu Glu Asp Arg Gly Leu Ala Ser
    610                 615                 620

Arg Ile Leu Asp Ala Lys Ser Lys Ile Glu Gln Ile Arg Ala Val Leu
625                 630                 635                 640

Ser Ser Pro Ala Val Thr Glu Gln Glu Val Ala Gln Val Ala Ser Ala
                645                 650                 655
```

-continued

```
Ile Leu Ser Leu Arg Arg Thr Leu Gln Gly Leu Gln Leu Asp Leu Pro
            660                 665                 670

Leu Glu Glu Glu Thr Leu Ser Leu Pro Arg Asp Leu Glu Ser Leu Asp
            675                 680                 685

Arg Ser Phe Asn Gly Leu Leu Thr Met Tyr Gln Arg Lys Arg Glu Gln
            690                 695                 700

Phe Glu Lys Ile Ser Ser Ala Asp Pro Ser Gly Ala Phe Arg Met Leu
705                 710                 715                 720

Ser Thr Ala Tyr Glu Gln Ser Ala Gln Ala Gln Val Ser Asp
                725                 730                 735

Ser Ser Arg Leu Leu Asp Gln Leu Arg Asp Ser Arg Glu Ala Glu
            740                 745                 750

Arg Leu Val Arg Gln Ala Gly Gly Gly Gly Thr Gly Ser Pro Lys
            755                 760                 765

Leu Val Ala Leu Arg Leu Glu Met Ser Ser Leu Pro Asp Leu Thr Pro
            770                 775                 780

Thr Phe Asn Lys Leu Cys Gly Asn Ser Arg Gln Met Ala Cys Thr Pro
785                 790                 795                 800

Ile Ser Cys Pro Gly Glu Leu Cys Pro Gln Asp Asn Gly Thr Ala Cys
                805                 810                 815

Gly Ser Arg Cys Arg Gly Val Leu Pro Arg Ala Gly Ala Phe Leu
            820                 825                 830

Met Ala Gly Gln Val Ala Glu Gln Leu Arg Gly Phe Asn Ala Gln Leu
            835                 840                 845

Gln Arg Thr Arg Gln Met Ile Arg Ala Ala Glu Glu Ser Ala Ser Gln
            850                 855                 860

Ile Gln Ser Ser Ala Gln Arg Leu Glu Thr Gln Val Ser Ala Ser Arg
865                 870                 875                 880

Ser Gln Met Glu Glu Asp Val Arg Arg Thr Arg Leu Leu Ile Gln Gln
                885                 890                 895

Val Arg Asp Phe Leu Thr Asp Pro Asp Thr Asp Ala Ala Thr Ile Gln
                900                 905                 910

Glu Val Ser Glu Ala Val Leu Ala Leu Trp Leu Pro Thr Asp Ser Ala
            915                 920                 925

Thr Val Leu Gln Lys Met Asn Glu Ile Gln Ala Ile Ala Ala Arg Leu
            930                 935                 940

Pro Asn Val Asp Leu Val Leu Ser Gln Thr Lys Gln Asp Ile Ala Arg
945                 950                 955                 960

Ala Arg Arg Leu Gln Ala Glu Ala Glu Ala Arg Ser Arg Ala His
                965                 970                 975

Ala Val Glu Gly Gln Val Glu Asp Val Val Gly Asn Leu Arg Gln Gly
            980                 985                 990

Thr Val Ala Leu Gln Glu Ala Gln Asp Thr Met Gln Gly Thr Ser Arg
            995                1000                1005

Ser Leu Arg Leu Ile Gln Asp Arg Val Ala Glu Val Gln Gln Val Leu
        1010                1015                1020

Arg Pro Ala Glu Lys Leu Val Thr Ser Met Thr Lys Gln Leu Gly Asp
1025               1030                1035                1040

Phe Trp Thr Arg Met Glu Glu Leu Arg His Gln Ala Arg Gln Gln Gly
                1045                1050                1055

Ala Glu Ala Val Gln Ala Gln Leu Ala Glu Gly Ala Ser Glu Gln
            1060                1065                1070

Ala Leu Ser Ala Gln Glu Gly Phe Glu Arg Ile Lys Gln Lys Tyr Ala
```

```
                1075                1080                1085
Glu Leu Lys Asp Arg Leu Gly Gln Ser Ser Met Leu Gly Glu Gln Gly
    1090                1095                1100

Ala Arg Ile Gln Ser Val Lys Thr Glu Ala Glu Leu Phe Gly Glu
1105                1110                1115                1120

Thr Met Glu Met Met Asp Arg Met Lys Asp Met Glu Leu Glu Leu Leu
                1125                1130                1135

Arg Gly Ser Gln Ala Ile Met Leu Arg Ser Ala Asp Leu Thr Gly Leu
        1140                1145                1150

Glu Lys Arg Val Glu Gln Ile Arg Asp His Ile Asn Gly Arg Val Leu
            1155                1160                1165

Tyr Tyr Ala Thr Cys Lys
    1170

<210> SEQ ID NO 23
<211> LENGTH: 3469
<212> TYPE: DNA
<213> ORGANISM: Homo sapiens
<220> FEATURE:
<221> NAME/KEY: CDS
<222> LOCATION: (1)..(3465)

<400> SEQUENCE: 23 caa caa gcc tgc tcc cgt ggg gcc tgc tat cca cct gtt ggg gac ctg      48
Gln Gln Ala Cys Ser Arg Gly Ala Cys Tyr Pro Pro Val Gly Asp Leu
  1               5                  10                  15 ctt gtt ggg agg acc cgg ttt ctc cga gct tca tct acc tgt gga ctg      96
Leu Val Gly Arg Thr Arg Phe Leu Arg Ala Ser Ser Thr Cys Gly Leu
                 20                  25                  30 acc aag cct gag acc tac tgc acc cag tat ggc gag tgg cag atg aaa     144
Thr Lys Pro Glu Thr Tyr Cys Thr Gln Tyr Gly Glu Trp Gln Met Lys
             35                  40                  45 tgc tgc aag tgt gac tcc agg cag cct cac aac tac tac agt cac cga     192
Cys Cys Lys Cys Asp Ser Arg Gln Pro His Asn Tyr Tyr Ser His Arg
         50                  55                  60 gta gag aat gtg gct tca tcc tcc ggc ccc atg cgc tgg tgg cag tcc     240
Val Glu Asn Val Ala Ser Ser Ser Gly Pro Met Arg Trp Trp Gln Ser
 65                  70                  75                  80 cag aat gat gtg aac cct gtc tct ctg cag ctg gac ctg gac agg aga     288
Gln Asn Asp Val Asn Pro Val Ser Leu Gln Leu Asp Leu Asp Arg Arg
                 85                  90                  95 ttc cag ctt caa gaa gtc atg atg gag ttc cag ggg ccc atg cct gcc     336
Phe Gln Leu Gln Glu Val Met Met Glu Phe Gln Gly Pro Met Pro Ala
                100                 105                 110 ggc atg ctg att gag cgc tcc tca gac ttc ggt aag acc tgg cga gtg     384
Gly Met Leu Ile Glu Arg Ser Ser Asp Phe Gly Lys Thr Trp Arg Val
            115                 120                 125 tac cag tac ctg gct gcc gac tgc acc tcc acc ttc cct cgg gtc cgc     432
Tyr Gln Tyr Leu Ala Ala Asp Cys Thr Ser Thr Phe Pro Arg Val Arg
        130                 135                 140 cag ggt cgg cct cag agc tgg cag gat gtt cgg tgc cag tcc ctg cct     480
Gln Gly Arg Pro Gln Ser Trp Gln Asp Val Arg Cys Gln Ser Leu Pro
145                 150                 155                 160 cag agg cct aat gca cgc cta aat ggg ggg aag gtc caa ctt aac ctt     528
Gln Arg Pro Asn Ala Arg Leu Asn Gly Gly Lys Val Gln Leu Asn Leu
                165                 170                 175 atg gat tta gtg tct ggg att cca gca act caa agt caa aaa att caa     576
Met Asp Leu Val Ser Gly Ile Pro Ala Thr Gln Ser Gln Lys Ile Gln
                180                 185                 190
```

-continued

```
gag gtg ggg gag atc aca aac ttg aga gtc aat ttc acc agg ctg gcc      624
Glu Val Gly Glu Ile Thr Asn Leu Arg Val Asn Phe Thr Arg Leu Ala
        195                 200                 205 cct gtg ccc caa agg ggc tac cac cct ccc agc gcc tac tat gct gtg      672
Pro Val Pro Gln Arg Gly Tyr His Pro Pro Ser Ala Tyr Tyr Ala Val
    210                 215                 220 tcc cag ctc cgt ctg cag ggg agc tgc ttc tgt cac ggc cat gct gat      720
Ser Gln Leu Arg Leu Gln Gly Ser Cys Phe Cys His Gly His Ala Asp
225                 230                 235                 240 cgc tgc gca ccc aag cct ggg gcc tct gca ggc ccc tcc acc gct gtg      768
Arg Cys Ala Pro Lys Pro Gly Ala Ser Ala Gly Pro Ser Thr Ala Val
                245                 250                 255 cag gtc cac gat gtc tgc gtc tgc cag cac aac act gcc ggc cca aat      816
Gln Val His Asp Val Cys Val Cys Gln His Asn Thr Ala Gly Pro Asn
            260                 265                 270 tgt gag cgc tgt gca ccc ttc tac aac aac cgg ccc tgg aga ccg gcg      864
Cys Glu Arg Cys Ala Pro Phe Tyr Asn Asn Arg Pro Trp Arg Pro Ala
        275                 280                 285 gag ggc cag gac gcc cat gaa tgc caa agg tgc gac tgc aat ggg cac      912
Glu Gly Gln Asp Ala His Glu Cys Gln Arg Cys Asp Cys Asn Gly His
    290                 295                 300 tca gag aca tgt cac ttt gac ccc gct gtg ttt gcc gcc agc cag ggg      960
Ser Glu Thr Cys His Phe Asp Pro Ala Val Phe Ala Ala Ser Gln Gly
305                 310                 315                 320 gca tat gga ggt gtg tgt gac aat tgc cgg gac cac acc gaa ggc aag     1008
Ala Tyr Gly Gly Val Cys Asp Asn Cys Arg Asp His Thr Glu Gly Lys
                325                 330                 335 aac tgt gag cgg tgt cag ctg cac tat ttc cgg aac cgc cgc ccg gga     1056
Asn Cys Glu Arg Cys Gln Leu His Tyr Phe Arg Asn Arg Arg Pro Gly
            340                 345                 350 gct tcc att cag gag acc tgc atc tcc tgc gag tgt gat ccg gat ggg     1104
Ala Ser Ile Gln Glu Thr Cys Ile Ser Cys Glu Cys Asp Pro Asp Gly
        355                 360                 365 gca gtg cca ggg gct ccc tgt gac cca gtg acc ggg cag tgt gtg tgc     1152
Ala Val Pro Gly Ala Pro Cys Asp Pro Val Thr Gly Gln Cys Val Cys
    370                 375                 380 aag gag cat gtg cag gga gag cgc tgt gac cta tgc aag ccg ggc ttc     1200
Lys Glu His Val Gln Gly Glu Arg Cys Asp Leu Cys Lys Pro Gly Phe
385                 390                 395                 400 act gga ctc acc tac gcc aac ccg cag ggc tgc cac cgc tgt gac tgc     1248
Thr Gly Leu Thr Tyr Ala Asn Pro Gln Gly Cys His Arg Cys Asp Cys
                405                 410                 415 aac atc ctg ggg tcc cgg agg gac atg ccg tgt gac gag gag agt ggg     1296
Asn Ile Leu Gly Ser Arg Arg Asp Met Pro Cys Asp Glu Glu Ser Gly
            420                 425                 430 cgc tgc ctt tgt ctg ccc aac gtg gtg ggt ccc aaa tgt gac cag tgt     1344
Arg Cys Leu Cys Leu Pro Asn Val Val Gly Pro Lys Cys Asp Gln Cys
        435                 440                 445 gct ccc tac cac tgg aag ctg gcc agt ggc cag ggc tgt gaa ccg tgt     1392
Ala Pro Tyr His Trp Lys Leu Ala Ser Gly Gln Gly Cys Glu Pro Cys
    450                 455                 460 gcc tgc gac ccg cac aac tcc ctc agc cca cag tgc aac cag ttc aca     1440
Ala Cys Asp Pro His Asn Ser Leu Ser Pro Gln Cys Asn Gln Phe Thr
465                 470                 475                 480 ggg cag tgc ccc tgt cgg gaa ggc ttt ggt ggc ctg atg tgc agc gct     1488
Gly Gln Cys Pro Cys Arg Glu Gly Phe Gly Gly Leu Met Cys Ser Ala
                485                 490                 495 gca gcc atc cgc cag tgt cca gac cgg acc tat gga gac gtg gcc aca     1536
Ala Ala Ile Arg Gln Cys Pro Asp Arg Thr Tyr Gly Asp Val Ala Thr
            500                 505                 510
```

```
gga tgc cga gcc tgt gac tgt gat ttc cgg gga aca gag ggc ccg ggc    1584
Gly Cys Arg Ala Cys Asp Cys Asp Phe Arg Gly Thr Glu Gly Pro Gly
            515                 520                 525 tgc gac aag gca tca ggc cgc tgc ctc tgc cgc cct ggc ttg acc ggg    1632
Cys Asp Lys Ala Ser Gly Arg Cys Leu Cys Arg Pro Gly Leu Thr Gly
        530                 535                 540 ccc cgc tgt gac cag tgc cag cga ggc tac tgc aat cgc tac ccg gtg    1680
Pro Arg Cys Asp Gln Cys Gln Arg Gly Tyr Cys Asn Arg Tyr Pro Val
545                 550                 555                 560 tgc gtg gcc tgc cac cct tgc ttc cag acc tat gat gcg gac ctc cgg    1728
Cys Val Ala Cys His Pro Cys Phe Gln Thr Tyr Asp Ala Asp Leu Arg
                565                 570                 575 gag cag gcc ctg cgc ttt ggt aga ctc cgg aat gcc acc gcc agc ctg    1776
Glu Gln Ala Leu Arg Phe Gly Arg Leu Arg Asn Ala Thr Ala Ser Leu
            580                 585                 590 tgg tca ggg cct ggg ctg gag gac cgt ggc ctg gcc tcc cgg atc cta    1824
Trp Ser Gly Pro Gly Leu Glu Asp Arg Gly Leu Ala Ser Arg Ile Leu
        595                 600                 605 gat gca aag agt aag att gag cag atc cga gca gtt ctc agc agc ccc    1872
Asp Ala Lys Ser Lys Ile Glu Gln Ile Arg Ala Val Leu Ser Ser Pro
610                 615                 620 gca gtc aca gag cag gag gtg gct cag gtg gcc agt gcc atc ctc tcc    1920
Ala Val Thr Glu Gln Glu Val Ala Gln Val Ala Ser Ala Ile Leu Ser
625                 630                 635                 640 ctc agg cga act ctc cag ggc ctg cag ctg gat ctg ccc ctg gag gag    1968
Leu Arg Arg Thr Leu Gln Gly Leu Gln Leu Asp Leu Pro Leu Glu Glu
                645                 650                 655 gag acg ttg tcc ctt ccg aga gac ctg gag agt ctt gac aga agc ttc    2016
Glu Thr Leu Ser Leu Pro Arg Asp Leu Glu Ser Leu Asp Arg Ser Phe
            660                 665                 670 aat ggt ctc ctt act atg tat cag agg aag agg gag cag ttt gaa aaa    2064
Asn Gly Leu Leu Thr Met Tyr Gln Arg Lys Arg Glu Gln Phe Glu Lys
        675                 680                 685 ata agc agt gct gat cct tca gga gcc ttc cgg atg ctg agc aca gcc    2112
Ile Ser Ser Ala Asp Pro Ser Gly Ala Phe Arg Met Leu Ser Thr Ala
    690                 695                 700 tac gag cag tca gcc cag gct gct cag cag gtc tcc gac agc tcg cgc    2160
Tyr Glu Gln Ser Ala Gln Ala Ala Gln Gln Val Ser Asp Ser Ser Arg
705                 710                 715                 720 ctt ttg gac cag ctc agg gac agc cgg aga gag gca gag agg ctg gtg    2208
Leu Leu Asp Gln Leu Arg Asp Ser Arg Arg Glu Ala Glu Arg Leu Val
                725                 730                 735 cgg cag gcg gga gga gga gga ggc acc ggc agc ccc aag ctt gtg gcc    2256
Arg Gln Ala Gly Gly Gly Gly Gly Thr Gly Ser Pro Lys Leu Val Ala
            740                 745                 750 ctg agg ctg gag atg tct tcg ttg cct gac ctg aca ccc acc ttc aac    2304
Leu Arg Leu Glu Met Ser Ser Leu Pro Asp Leu Thr Pro Thr Phe Asn
        755                 760                 765 aag ctc tgt ggc aac tcc agg cag atg gct tgc acc cca ata tca tgc    2352
Lys Leu Cys Gly Asn Ser Arg Gln Met Ala Cys Thr Pro Ile Ser Cys
    770                 775                 780 cct ggt gag cta tgt ccc caa gac aat ggc aca gcc tgt ggc tcc cgc    2400
Pro Gly Glu Leu Cys Pro Gln Asp Asn Gly Thr Ala Cys Gly Ser Arg
785                 790                 795                 800 tgc agg ggt gtc ctt ccc agg gcc ggt ggg gcc ttc ttg atg gcg ggg    2448
Cys Arg Gly Val Leu Pro Arg Ala Gly Gly Ala Phe Leu Met Ala Gly
                805                 810                 815 cag gtg gct gag cag ctg cgg ggc ttc aat gcc cag ctc cag cgg acc    2496
Gln Val Ala Glu Gln Leu Arg Gly Phe Asn Ala Gln Leu Gln Arg Thr
```

```
                820                 825                 830
agg cag atg att agg gca gcc gag gaa tct gcc tca cag att caa tcc    2544
Arg Gln Met Ile Arg Ala Ala Glu Glu Ser Ala Ser Gln Ile Gln Ser
            835                 840                 845 agt gcc cag cgc ttg gag acc cag gtg agc gcc agc cgc tcc cag atg    2592
Ser Ala Gln Arg Leu Glu Thr Gln Val Ser Ala Ser Arg Ser Gln Met
        850                 855                 860 gag gaa gat gtc aga cgc aca cgg ctc cta atc cag cag gtc cgg gac    2640
Glu Glu Asp Val Arg Arg Thr Arg Leu Leu Ile Gln Gln Val Arg Asp
865                 870                 875                 880 ttc cta aca gac ccc gac act gat gca gcc act atc cag gag gtc agc    2688
Phe Leu Thr Asp Pro Asp Thr Asp Ala Ala Thr Ile Gln Glu Val Ser
                885                 890                 895 gag gcc gtg ctg gcc ctg tgg ctg ccc aca gac tca gct act gtt ctg    2736
Glu Ala Val Leu Ala Leu Trp Leu Pro Thr Asp Ser Ala Thr Val Leu
            900                 905                 910 cag aag atg aat gag atc cag gcc att gca gcc agg ctc ccc aac gtg    2784
Gln Lys Met Asn Glu Ile Gln Ala Ile Ala Ala Arg Leu Pro Asn Val
        915                 920                 925 gac ttg gtg ctg tcc cag acc aag cag gac att gcg cgt gcc cgc cgg    2832
Asp Leu Val Leu Ser Gln Thr Lys Gln Asp Ile Ala Arg Ala Arg Arg
930                 935                 940 ttg cag gct gag gct gag gaa gcc agg agc cga gcc cat gca gtg gag    2880
Leu Gln Ala Glu Ala Glu Glu Ala Arg Ser Arg Ala His Ala Val Glu
945                 950                 955                 960 ggc cag gtg gaa gat gtg gtt ggg aac ctg cgg cag ggg aca gtg gca    2928
Gly Gln Val Glu Asp Val Val Gly Asn Leu Arg Gln Gly Thr Val Ala
                965                 970                 975 ctg cag gaa gct cag gac acc atg caa ggc acc agc cgc tcc ctt cgg    2976
Leu Gln Glu Ala Gln Asp Thr Met Gln Gly Thr Ser Arg Ser Leu Arg
            980                 985                 990 ctt atc cag gac agg gtt gct gag gtt cag cag gta ctg cgg cca gca    3024
Leu Ile Gln Asp Arg Val Ala Glu Val Gln Gln Val Leu Arg Pro Ala
        995                 1000                1005 gaa aag ctg gtg aca agc atg acc aag cag ctg ggt gac ttc tgg aca    3072
Glu Lys Leu Val Thr Ser Met Thr Lys Gln Leu Gly Asp Phe Trp Thr
    1010                1015                1020 cgg atg gag gag ctc cgc cac caa gcc cgg cag cag ggg gca gag gca    3120
Arg Met Glu Glu Leu Arg His Gln Ala Arg Gln Gln Gly Ala Glu Ala
1025                1030                1035                1040 gtc cag gcc cag cag ctt gcg gaa ggt gcc agc gag cag gca ttg agt    3168
Val Gln Ala Gln Gln Leu Ala Glu Gly Ala Ser Glu Gln Ala Leu Ser
                1045                1050                1055 gcc caa gag gga ttt gag aga ata aaa caa aag tat gct gag ttg aag    3216
Ala Gln Glu Gly Phe Glu Arg Ile Lys Gln Lys Tyr Ala Glu Leu Lys
            1060                1065                1070 gac cgg ttg ggt cag agt tcc atg ctg ggt gag cag ggt gcc cgg atc    3264
Asp Arg Leu Gly Gln Ser Ser Met Leu Gly Glu Gln Gly Ala Arg Ile
        1075                1080                1085 cag agt gtg aag aca gag gca gag gag ctg ttt ggg gag acc atg gag    3312
Gln Ser Val Lys Thr Glu Ala Glu Glu Leu Phe Gly Glu Thr Met Glu
    1090                1095                1100 atg atg gac agg atg aaa gac atg gag ttg gag ctg ctg cgg ggc agc    3360
Met Met Asp Arg Met Lys Asp Met Glu Leu Glu Leu Leu Arg Gly Ser
1105                1110                1115                1120 cag gcc atc atg ctg cgc tca gcg gac ctg aca gga ctg gag aag cgt    3408
Gln Ala Ile Met Leu Arg Ser Ala Asp Leu Thr Gly Leu Glu Lys Arg
                1125                1130                1135 gtg gag cag atc cgt gac cac atc aat ggg cgc gtg ctc tac tat gcc    3456
```

```
Val Glu Gln Ile Arg Asp His Ile Asn Gly Arg Val Leu Tyr Tyr Ala
        1140                1145                1150 acc tgc aag tgat                                                        3469
Thr Cys Lys
        1155
```

<210> SEQ ID NO 24
<211> LENGTH: 1155
<212> TYPE: PRT
<213> ORGANISM: Homo sapiens

<400> SEQUENCE: 24

```
Gln Gln Ala Cys Ser Arg Gly Ala Cys Tyr Pro Pro Val Gly Asp Leu
  1               5                  10                  15

Leu Val Gly Arg Thr Arg Phe Leu Arg Ala Ser Ser Thr Cys Gly Leu
                 20                  25                  30

Thr Lys Pro Glu Thr Tyr Cys Thr Gln Tyr Gly Glu Trp Gln Met Lys
             35                  40                  45

Cys Cys Lys Cys Asp Ser Arg Gln Pro His Asn Tyr Tyr Ser His Arg
 50                  55                  60

Val Glu Asn Val Ala Ser Ser Gly Pro Met Arg Trp Trp Gln Ser
 65                  70                  75                  80

Gln Asn Asp Val Asn Pro Val Ser Leu Gln Leu Asp Leu Asp Arg Arg
                 85                  90                  95

Phe Gln Leu Gln Glu Val Met Met Glu Phe Gln Gly Pro Met Pro Ala
                100                 105                 110

Gly Met Leu Ile Glu Arg Ser Ser Asp Phe Gly Lys Thr Trp Arg Val
            115                 120                 125

Tyr Gln Tyr Leu Ala Ala Asp Cys Thr Ser Thr Phe Pro Arg Val Arg
130                 135                 140

Gln Gly Arg Pro Gln Ser Trp Gln Asp Val Arg Cys Gln Ser Leu Pro
145                 150                 155                 160

Gln Arg Pro Asn Ala Arg Leu Asn Gly Gly Lys Val Gln Leu Asn Leu
                165                 170                 175

Met Asp Leu Val Ser Gly Ile Pro Ala Thr Gln Ser Gln Lys Ile Gln
            180                 185                 190

Glu Val Gly Glu Ile Thr Asn Leu Arg Val Asn Phe Thr Arg Leu Ala
        195                 200                 205

Pro Val Pro Gln Arg Gly Tyr His Pro Pro Ser Ala Tyr Tyr Ala Val
210                 215                 220

Ser Gln Leu Arg Leu Gln Gly Ser Cys Phe Cys His Gly His Ala Asp
225                 230                 235                 240

Arg Cys Ala Pro Lys Pro Gly Ala Ser Ala Gly Pro Ser Thr Ala Val
                245                 250                 255

Gln Val His Asp Val Cys Val Cys Gln His Asn Thr Ala Gly Pro Asn
            260                 265                 270

Cys Glu Arg Cys Ala Pro Phe Tyr Asn Asn Arg Pro Trp Arg Pro Ala
        275                 280                 285

Glu Gly Gln Asp Ala His Glu Cys Gln Arg Cys Asp Cys Asn Gly His
290                 295                 300

Ser Glu Thr Cys His Phe Asp Pro Ala Val Phe Ala Ala Ser Gln Gly
305                 310                 315                 320

Ala Tyr Gly Gly Val Cys Asp Asn Cys Arg Asp His Thr Glu Gly Lys
                325                 330                 335

Asn Cys Glu Arg Cys Gln Leu His Tyr Phe Arg Asn Arg Arg Pro Gly
```

-continued

```
                340                 345                 350
Ala Ser Ile Gln Glu Thr Cys Ile Ser Cys Glu Cys Asp Pro Asp Gly
            355                 360                 365
Ala Val Pro Gly Ala Pro Cys Asp Pro Val Thr Gly Gln Cys Val Cys
370                 375                 380
Lys Glu His Val Gln Gly Glu Arg Cys Asp Leu Cys Lys Pro Gly Phe
385                 390                 395                 400
Thr Gly Leu Thr Tyr Ala Asn Pro Gln Gly Cys His Arg Cys Asp Cys
                405                 410                 415
Asn Ile Leu Gly Ser Arg Arg Asp Met Pro Cys Asp Glu Glu Ser Gly
            420                 425                 430
Arg Cys Leu Cys Leu Pro Asn Val Val Gly Pro Lys Cys Asp Gln Cys
            435                 440                 445
Ala Pro Tyr His Trp Lys Leu Ala Ser Gly Gln Gly Cys Glu Pro Cys
            450                 455                 460
Ala Cys Asp Pro His Asn Ser Leu Ser Pro Gln Cys Asn Gln Phe Thr
465                 470                 475                 480
Gly Gln Cys Pro Cys Arg Glu Gly Phe Gly Gly Leu Met Cys Ser Ala
                485                 490                 495
Ala Ala Ile Arg Gln Cys Pro Asp Arg Thr Tyr Gly Asp Val Ala Thr
                500                 505                 510
Gly Cys Arg Ala Cys Asp Cys Asp Phe Arg Gly Thr Glu Gly Pro Gly
            515                 520                 525
Cys Asp Lys Ala Ser Gly Arg Cys Leu Cys Arg Pro Gly Leu Thr Gly
            530                 535                 540
Pro Arg Cys Asp Gln Cys Gln Arg Gly Tyr Cys Asn Arg Tyr Pro Val
545                 550                 555                 560
Cys Val Ala Cys His Pro Cys Phe Gln Thr Tyr Asp Ala Asp Leu Arg
                565                 570                 575
Glu Gln Ala Leu Arg Phe Gly Arg Leu Arg Asn Ala Thr Ala Ser Leu
            580                 585                 590
Trp Ser Gly Pro Gly Leu Glu Asp Arg Gly Leu Ala Ser Arg Ile Leu
            595                 600                 605
Asp Ala Lys Ser Lys Ile Glu Gln Ile Arg Ala Val Leu Ser Ser Pro
610                 615                 620
Ala Val Thr Glu Gln Glu Val Ala Gln Val Ala Ser Ala Ile Leu Ser
625                 630                 635                 640
Leu Arg Arg Thr Leu Gln Gly Leu Gln Leu Asp Leu Pro Leu Glu Glu
                645                 650                 655
Glu Thr Leu Ser Leu Pro Arg Asp Leu Glu Ser Leu Asp Arg Ser Phe
            660                 665                 670
Asn Gly Leu Leu Thr Met Tyr Gln Arg Lys Arg Glu Gln Phe Glu Lys
            675                 680                 685
Ile Ser Ser Ala Asp Pro Ser Gly Ala Phe Arg Met Leu Ser Thr Ala
690                 695                 700
Tyr Glu Gln Ser Ala Gln Ala Ala Gln Gln Val Ser Asp Ser Ser Arg
705                 710                 715                 720
Leu Leu Asp Gln Leu Arg Asp Ser Arg Arg Glu Ala Glu Arg Leu Val
                725                 730                 735
Arg Gln Ala Gly Gly Gly Gly Thr Gly Ser Pro Lys Leu Val Ala
            740                 745                 750
Leu Arg Leu Glu Met Ser Ser Leu Pro Asp Leu Thr Pro Thr Phe Asn
            755                 760                 765
```

-continued

```
Lys Leu Cys Gly Asn Ser Arg Gln Met Ala Cys Thr Pro Ile Ser Cys
    770                 775                 780
Pro Gly Glu Leu Cys Pro Gln Asp Asn Gly Thr Ala Cys Gly Ser Arg
785                 790                 795                 800
Cys Arg Gly Val Leu Pro Arg Ala Gly Ala Phe Leu Met Ala Gly
                805                 810                 815
Gln Val Ala Glu Gln Leu Arg Gly Phe Asn Ala Gln Leu Gln Arg Thr
                820                 825                 830
Arg Gln Met Ile Arg Ala Ala Glu Glu Ser Ala Ser Gln Ile Gln Ser
            835                 840                 845
Ser Ala Gln Arg Leu Glu Thr Gln Val Ser Ala Ser Arg Ser Gln Met
    850                 855                 860
Glu Glu Asp Val Arg Arg Thr Arg Leu Leu Ile Gln Gln Val Arg Asp
865                 870                 875                 880
Phe Leu Thr Asp Pro Asp Thr Asp Ala Ala Thr Ile Gln Glu Val Ser
                885                 890                 895
Glu Ala Val Leu Ala Leu Trp Leu Pro Thr Asp Ser Ala Thr Val Leu
                900                 905                 910
Gln Lys Met Asn Glu Ile Gln Ala Ile Ala Ala Arg Leu Pro Asn Val
            915                 920                 925
Asp Leu Val Leu Ser Gln Thr Lys Gln Asp Ile Ala Arg Ala Arg Arg
    930                 935                 940
Leu Gln Ala Glu Ala Glu Glu Ala Arg Ser Arg Ala His Ala Val Glu
945                 950                 955                 960
Gly Gln Val Glu Asp Val Val Gly Asn Leu Arg Gln Gly Thr Val Ala
                965                 970                 975
Leu Gln Glu Ala Gln Asp Thr Met Gln Gly Thr Ser Arg Ser Leu Arg
                980                 985                 990
Leu Ile Gln Asp Arg Val Ala Glu Val Gln Gln Val Leu Arg Pro Ala
            995                 1000                1005
Glu Lys Leu Val Thr Ser Met Thr Lys Gln Leu Gly Asp Phe Trp Thr
    1010                1015                1020
Arg Met Glu Glu Leu Arg His Gln Ala Arg Gln Gln Gly Ala Glu Ala
1025                1030                1035                1040
Val Gln Ala Gln Gln Leu Ala Glu Gly Ala Ser Glu Gln Ala Leu Ser
                1045                1050                1055
Ala Gln Glu Gly Phe Glu Arg Ile Lys Gln Lys Tyr Ala Glu Leu Lys
                1060                1065                1070
Asp Arg Leu Gly Gln Ser Ser Met Leu Gly Glu Gln Gly Ala Arg Ile
                1075                1080                1085
Gln Ser Val Lys Thr Glu Ala Glu Glu Leu Phe Gly Glu Thr Met Glu
    1090                1095                1100
Met Met Asp Arg Met Lys Asp Met Glu Leu Glu Leu Leu Arg Gly Ser
1105                1110                1115                1120
Gln Ala Ile Met Leu Arg Ser Ala Asp Leu Thr Gly Leu Glu Lys Arg
                1125                1130                1135
Val Glu Gln Ile Arg Asp His Ile Asn Gly Arg Val Leu Tyr Tyr Ala
                1140                1145                1150
Thr Cys Lys
    1155

<210> SEQ ID NO 25
<211> LENGTH: 5200
```

```
<212> TYPE: DNA
<213> ORGANISM: Homo sapiens
<220> FEATURE:
<221> NAME/KEY: CDS
<222> LOCATION: (118)..(3696)
<221> NAME/KEY: sig_peptide
<222> LOCATION: (118)..(180)

<400> SEQUENCE: 25
gaccacctga tcgaaggaaa aggaaggcac agcggagcgc agagtgagaa ccaccaaccg      60
aggcgccggg cagcgacccc tgcagcggag acagagactg agcggcccgg caccgcc       117 atg cct gcg ctc tgg ctg ggc tgc tgc ctc tgc ttc tcg ctc ctc ctg      165
Met Pro Ala Leu Trp Leu Gly Cys Cys Leu Cys Phe Ser Leu Leu Leu
 1               5                  10                  15 ccc gca gcc cgg gcc acc tcc agg agg gaa gtc tgt gat tgc aat ggg      213
Pro Ala Ala Arg Ala Thr Ser Arg Arg Glu Val Cys Asp Cys Asn Gly
             20                  25                  30 aag tcc agg cag tgt atc ttt gat cgg gaa ctt cac aga caa act ggt      261
Lys Ser Arg Gln Cys Ile Phe Asp Arg Glu Leu His Arg Gln Thr Gly
         35                  40                  45 aat gga ttc cgc tgc ctc aac tgc aat gac aac act gat ggc att cac      309
Asn Gly Phe Arg Cys Leu Asn Cys Asn Asp Asn Thr Asp Gly Ile His
     50                  55                  60 tgc gag aag tgc aag aat ggc ttt tac cgg cac aga gaa agg gac cgc      357
Cys Glu Lys Cys Lys Asn Gly Phe Tyr Arg His Arg Glu Arg Asp Arg
 65                  70                  75                  80 tgt ttg ccc tgc aat tgt aac tcc aaa ggt tct ctt agt gct cga tgt      405
Cys Leu Pro Cys Asn Cys Asn Ser Lys Gly Ser Leu Ser Ala Arg Cys
                 85                  90                  95 gac aac tct gga cgg tgc agc tgt aaa cca ggt gtg aca gga gcc aga      453
Asp Asn Ser Gly Arg Cys Ser Cys Lys Pro Gly Val Thr Gly Ala Arg
            100                 105                 110 tgc gac cga tgt ctg cca ggc ttc cac atg ctc acg gat gcg ggg tgc      501
Cys Asp Arg Cys Leu Pro Gly Phe His Met Leu Thr Asp Ala Gly Cys
        115                 120                 125 acc caa gac cag aga ctg cta gac tcc aag tgt gac tgt gac cca gct      549
Thr Gln Asp Gln Arg Leu Leu Asp Ser Lys Cys Asp Cys Asp Pro Ala
    130                 135                 140 ggc atc gca ggg ccc tgt gac gcg ggc cgc tgt gtc tgc aag cca gct      597
Gly Ile Ala Gly Pro Cys Asp Ala Gly Arg Cys Val Cys Lys Pro Ala
145                 150                 155                 160 gtt act gga gaa cgc tgt gat agg tgt cga tca ggt tac tat aat ctg      645
Val Thr Gly Glu Arg Cys Asp Arg Cys Arg Ser Gly Tyr Tyr Asn Leu
                165                 170                 175 gat ggg ggg aac cct gag ggc tgt acc cag tgt ttc tgc tat ggg cat      693
Asp Gly Gly Asn Pro Glu Gly Cys Thr Gln Cys Phe Cys Tyr Gly His
            180                 185                 190 tca gcc agc tgc cgc agc tct gca gaa tac agt gtc cat aag atc acc      741
Ser Ala Ser Cys Arg Ser Ser Ala Glu Tyr Ser Val His Lys Ile Thr
        195                 200                 205 tct acc ttt cat caa gat gtt gat ggc tgg aag gct gtc caa cga aat      789
Ser Thr Phe His Gln Asp Val Asp Gly Trp Lys Ala Val Gln Arg Asn
    210                 215                 220 ggg tct cct gca aag ctc caa tgg tca cag cgc cat caa gat gtg ttt      837
Gly Ser Pro Ala Lys Leu Gln Trp Ser Gln Arg His Gln Asp Val Phe
225                 230                 235                 240 agc tca gcc caa cga cta gat cct gtc tat ttt gtg gct cct gcc aaa      885
Ser Ser Ala Gln Arg Leu Asp Pro Val Tyr Phe Val Ala Pro Ala Lys
                245                 250                 255 ttt ctt ggg aat caa cag gtg agc tat ggg caa agc ctg tcc ttt gac      933
```

```
                    -continued

Phe Leu Gly Asn Gln Gln Val Ser Tyr Gly Gln Ser Leu Ser Phe Asp
            260                 265                 270 tac cgt gtg gac aga gga ggc aga cac cca tct gcc cat gat gtg atc      981
Tyr Arg Val Asp Arg Gly Gly Arg His Pro Ser Ala His Asp Val Ile
        275                 280                 285 ctg gaa ggt gct ggt cta cgg atc aca gct ccc ttg atg cca ctt ggc     1029
Leu Glu Gly Ala Gly Leu Arg Ile Thr Ala Pro Leu Met Pro Leu Gly
    290                 295                 300 aag aca ctg cct tgt ggg ctc acc aag act tac aca ttc agg tta aat     1077
Lys Thr Leu Pro Cys Gly Leu Thr Lys Thr Tyr Thr Phe Arg Leu Asn
305                 310                 315                 320 gag cat cca agc aat aat tgg agc ccc cag ctg agt tac ttt gag tat     1125
Glu His Pro Ser Asn Asn Trp Ser Pro Gln Leu Ser Tyr Phe Glu Tyr
                325                 330                 335 cga agg tta ctg cgg aat ctc aca gcc ctc cgc atc cga gct aca tat     1173
Arg Arg Leu Leu Arg Asn Leu Thr Ala Leu Arg Ile Arg Ala Thr Tyr
            340                 345                 350 gga gaa tac agt act ggg tac att gac aat gtg acc ctg att tca gcc     1221
Gly Glu Tyr Ser Thr Gly Tyr Ile Asp Asn Val Thr Leu Ile Ser Ala
        355                 360                 365 cgc cct gtc tct gga gcc cca gca ccc tgg gtt gaa cag tgt ata tgt     1269
Arg Pro Val Ser Gly Ala Pro Ala Pro Trp Val Glu Gln Cys Ile Cys
    370                 375                 380 cct gtt ggg tac aag ggg caa ttc tgc cag gat tgt gct tct ggc tac     1317
Pro Val Gly Tyr Lys Gly Gln Phe Cys Gln Asp Cys Ala Ser Gly Tyr
385                 390                 395                 400 aag aga gat tca gcg aga ctg ggg cct ttt ggc acc tgt att cct tgt     1365
Lys Arg Asp Ser Ala Arg Leu Gly Pro Phe Gly Thr Cys Ile Pro Cys
                405                 410                 415 aac tgt caa ggg gga ggg gcc tgt gat cca gac aca gga gat tgt tat     1413
Asn Cys Gln Gly Gly Gly Ala Cys Asp Pro Asp Thr Gly Asp Cys Tyr
            420                 425                 430 tca ggg gat gag aat cct gac att gag tgt gct gac tgc cca att ggt     1461
Ser Gly Asp Glu Asn Pro Asp Ile Glu Cys Ala Asp Cys Pro Ile Gly
        435                 440                 445 ttc tac aac gat ccg cac gac ccc cgc agc tgc aag cca tgt ccc tgt     1509
Phe Tyr Asn Asp Pro His Asp Pro Arg Ser Cys Lys Pro Cys Pro Cys
    450                 455                 460 cat aac ggg ttc agc tgc tca gtg att ccg gag acg gag gag gtg gtg     1557
His Asn Gly Phe Ser Cys Ser Val Ile Pro Glu Thr Glu Glu Val Val
465                 470                 475                 480 tgc aat aac tgc cct ccc ggg gtc acc ggt gcc cgc tgt gag ctc tgt     1605
Cys Asn Asn Cys Pro Pro Gly Val Thr Gly Ala Arg Cys Glu Leu Cys
                485                 490                 495 gct gat ggc tac ttt ggg gac ccc ttt ggt gaa cat ggc cca gtg agg     1653
Ala Asp Gly Tyr Phe Gly Asp Pro Phe Gly Glu His Gly Pro Val Arg
            500                 505                 510 cct tgt cag ccc tgt caa tgc aac agc aat gtg gac ccc agt gcc tct     1701
Pro Cys Gln Pro Cys Gln Cys Asn Ser Asn Val Asp Pro Ser Ala Ser
        515                 520                 525 ggg aat tgt gac cgg ctg aca ggc agg tgt ttg aag tgt atc cac aac     1749
Gly Asn Cys Asp Arg Leu Thr Gly Arg Cys Leu Lys Cys Ile His Asn
    530                 535                 540 aca gcc ggc atc tac tgc gac cag tgc aaa gca ggc tac ttc ggg gac     1797
Thr Ala Gly Ile Tyr Cys Asp Gln Cys Lys Ala Gly Tyr Phe Gly Asp
545                 550                 555                 560 cca ttg gct ccc aac cca gca gac aag tgt cga gct tgc aac tgt aac     1845
Pro Leu Ala Pro Asn Pro Ala Asp Lys Cys Arg Ala Cys Asn Cys Asn
                565                 570                 575
```

-continued

| | |
|---|---|
| ccc atg ggc tca gag cct gta gga tgt cga agt gat ggc acc tgt gtt<br>Pro Met Gly Ser Glu Pro Val Gly Cys Arg Ser Asp Gly Thr Cys Val<br>580 585 590 | 1893 |
| tgc aag cca gga ttt ggt ggc ccc aac tgt gag cat gga gca ttc agc<br>Cys Lys Pro Gly Phe Gly Gly Pro Asn Cys Glu His Gly Ala Phe Ser<br>595 600 605 | 1941 |
| tgt cca gct tgc tat aat caa gtg aag att cag atg gat cag ttt atg<br>Cys Pro Ala Cys Tyr Asn Gln Val Lys Ile Gln Met Asp Gln Phe Met<br>610 615 620 | 1989 |
| cag cag ctt cag aga atg gag gcc ctg att tca aag gct cag ggt ggt<br>Gln Gln Leu Gln Arg Met Glu Ala Leu Ile Ser Lys Ala Gln Gly Gly<br>625 630 635 640 | 2037 |
| gat gga gta gta cct gat aca gag ctg gaa ggc agg atg cag cag gct<br>Asp Gly Val Val Pro Asp Thr Glu Leu Glu Gly Arg Met Gln Gln Ala<br>645 650 655 | 2085 |
| gag cag gcc ctt cag gac att ctg aga gat gcc cag att tca gaa ggt<br>Glu Gln Ala Leu Gln Asp Ile Leu Arg Asp Ala Gln Ile Ser Glu Gly<br>660 665 670 | 2133 |
| gct agc aga tcc ctt ggt ctc cag ttg gcc aag gtg agg agc caa gag<br>Ala Ser Arg Ser Leu Gly Leu Gln Leu Ala Lys Val Arg Ser Gln Glu<br>675 680 685 | 2181 |
| aac agc tac cag agc cgc ctg gat gac ctc aag atg act gtg gaa aga<br>Asn Ser Tyr Gln Ser Arg Leu Asp Asp Leu Lys Met Thr Val Glu Arg<br>690 695 700 | 2229 |
| gtt cgg gct ctg gga agt cag tac cag aac cga gtt cgg gat act cac<br>Val Arg Ala Leu Gly Ser Gln Tyr Gln Asn Arg Val Arg Asp Thr His<br>705 710 715 720 | 2277 |
| agg ctc atc act cag atg cag ctg agc ctg gca gaa agt gaa gct tcc<br>Arg Leu Ile Thr Gln Met Gln Leu Ser Leu Ala Glu Ser Glu Ala Ser<br>725 730 735 | 2325 |
| ttg gga aac act aac att cct gcc tca gac cac tac gtg ggg cca aat<br>Leu Gly Asn Thr Asn Ile Pro Ala Ser Asp His Tyr Val Gly Pro Asn<br>740 745 750 | 2373 |
| ggc ttt aaa agt ctg gct cag gag gcc aca aga tta gca gaa agc cac<br>Gly Phe Lys Ser Leu Ala Gln Glu Ala Thr Arg Leu Ala Glu Ser His<br>755 760 765 | 2421 |
| gtt gag tca gcc agt aac atg gag caa ctg aca agg gaa act gag gac<br>Val Glu Ser Ala Ser Asn Met Glu Gln Leu Thr Arg Glu Thr Glu Asp<br>770 775 780 | 2469 |
| tat tcc aaa caa gcc ctc tca ctg gtg cgc aag gcc ctg cat gaa gga<br>Tyr Ser Lys Gln Ala Leu Ser Leu Val Arg Lys Ala Leu His Glu Gly<br>785 790 795 800 | 2517 |
| gtc gga agc gga agc ggt agc ccg gac ggt gct gtg gtg caa ggg ctt<br>Val Gly Ser Gly Ser Gly Ser Pro Asp Gly Ala Val Val Gln Gly Leu<br>805 810 815 | 2565 |
| gtg gaa aaa ttg gag aaa acc aag tcc ctg gcc cag cag ttg aca agg<br>Val Glu Lys Leu Glu Lys Thr Lys Ser Leu Ala Gln Gln Leu Thr Arg<br>820 825 830 | 2613 |
| gag gcc act caa gcg gaa att gaa gca gat agg tct tat cag cac agt<br>Glu Ala Thr Gln Ala Glu Ile Glu Ala Asp Arg Ser Tyr Gln His Ser<br>835 840 845 | 2661 |
| ctc cgc ctc ctg gat tca gtg tct ccg ctt cag gga gtc agt gat cag<br>Leu Arg Leu Leu Asp Ser Val Ser Pro Leu Gln Gly Val Ser Asp Gln<br>850 855 860 | 2709 |
| tcc ttt cag gtg gaa gaa gca aag agg atc aaa caa aaa gcg gat tca<br>Ser Phe Gln Val Glu Glu Ala Lys Arg Ile Lys Gln Lys Ala Asp Ser<br>865 870 875 880 | 2757 |
| ctc tca agc ctg gta acc agg cat atg gat gag ttc aag cgt aca caa<br>Leu Ser Ser Leu Val Thr Arg His Met Asp Glu Phe Lys Arg Thr Gln<br>885 890 895 | 2805 |

```
aag aat ctg gga aac tgg aaa gaa gaa gca cag cag ctc tta cag aat      2853
Lys Asn Leu Gly Asn Trp Lys Glu Glu Ala Gln Gln Leu Leu Gln Asn
            900                 905                 910 gga aaa agt ggg aga gag aaa tca gat cag ctg ctt tcc cgt gcc aat      2901
Gly Lys Ser Gly Arg Glu Lys Ser Asp Gln Leu Leu Ser Arg Ala Asn
        915                 920                 925 ctt gct aaa agc aga gca caa gaa gca ctg agt atg ggc aat gcc act      2949
Leu Ala Lys Ser Arg Ala Gln Glu Ala Leu Ser Met Gly Asn Ala Thr
    930                 935                 940 ttt tat gaa gtt gag agc atc ctt aaa aac ctc aga gag ttt gac ctg      2997
Phe Tyr Glu Val Glu Ser Ile Leu Lys Asn Leu Arg Glu Phe Asp Leu
945                 950                 955                 960 cag gtg gac aac aga aaa gca gaa gct gaa gaa gcc atg aag aga ctc      3045
Gln Val Asp Asn Arg Lys Ala Glu Ala Glu Glu Ala Met Lys Arg Leu
                965                 970                 975 tcc tac atc agc cag aag gtt tca gat gcc agt gac aag acc cag caa      3093
Ser Tyr Ile Ser Gln Lys Val Ser Asp Ala Ser Asp Lys Thr Gln Gln
            980                 985                 990 gca gaa aga gcc ctg ggg agc gct gct gct gat gca cag agg gca aag      3141
Ala Glu Arg Ala Leu Gly Ser Ala Ala Ala Asp Ala Gln Arg Ala Lys
        995                 1000                1005 aat ggg gcc ggg gag gcc ctg gaa atc tcc agt gag att gaa cag gag      3189
Asn Gly Ala Gly Glu Ala Leu Glu Ile Ser Ser Glu Ile Glu Gln Glu
    1010                1015                1020 att ggg agt ctg aac ttg gaa gcc aat gtg aca gca gat gga gcc ttg      3237
Ile Gly Ser Leu Asn Leu Glu Ala Asn Val Thr Ala Asp Gly Ala Leu
1025                1030                1035                1040 gcc atg gaa aag gga ctg gcc tct ctg aag agt gag atg agg gaa gtg      3285
Ala Met Glu Lys Gly Leu Ala Ser Leu Lys Ser Glu Met Arg Glu Val
                1045                1050                1055 gaa gga gag ctg gaa agg aag gag ctg gag ttt gac acg aat atg gat      3333
Glu Gly Glu Leu Glu Arg Lys Glu Leu Glu Phe Asp Thr Asn Met Asp
            1060                1065                1070 gca gta cag atg gtg att aca gaa gcc cag aag gtt gat acc aga gcc      3381
Ala Val Gln Met Val Ile Thr Glu Ala Gln Lys Val Asp Thr Arg Ala
        1075                1080                1085 aag aac gct ggg gtt aca atc caa gac aca ctc aac aca tta gac ggc      3429
Lys Asn Ala Gly Val Thr Ile Gln Asp Thr Leu Asn Thr Leu Asp Gly
    1090                1095                1100 ctc ctg cat ctg atg gac cag cct ctc agt gta gat gaa gag ggg ctg      3477
Leu Leu His Leu Met Asp Gln Pro Leu Ser Val Asp Glu Glu Gly Leu
1105                1110                1115                1120 gtc tta ctg gag cag aag ctt tcc cga gcc aag acc cag atc aac agc      3525
Val Leu Leu Glu Gln Lys Leu Ser Arg Ala Lys Thr Gln Ile Asn Ser
                1125                1130                1135 caa ctg cgg ccc atg atg tca gag ctg gaa gag agg gca cgt cag cag      3573
Gln Leu Arg Pro Met Met Ser Glu Leu Glu Glu Arg Ala Arg Gln Gln
            1140                1145                1150 agg ggc cac ctc cat ttg ctg gag aca agc ata gat ggg att ctg gct      3621
Arg Gly His Leu His Leu Leu Glu Thr Ser Ile Asp Gly Ile Leu Ala
        1155                1160                1165 gat gtg aag aac ttg gag aac att agg gac aac ctg ccc cca ggc tgc      3669
Asp Val Lys Asn Leu Glu Asn Ile Arg Asp Asn Leu Pro Pro Gly Cys
    1170                1175                1180 tac aat acc cag gct ctt gag caa cag tgaagctgcc ataaatattt            3716
Tyr Asn Thr Gln Ala Leu Glu Gln Gln
1185                1190 ctcaactgag gttcttggga tacagatctc agggctcggg agccatgtca tgtgagtggg   3776
```

-continued

```
tgggatgggg acatttgaac atgtttaatg ggtatgctca ggtcaactga cctgacccca    3836
ttcctgatcc catggccagg tggttgtctt attgcaccat actccttgct tcctgatgct    3896
gggcatgagg cagataggca ctggtgtgag aatgatcaag gatctggacc ccaaagatag    3956
actggatgga agacaaact gcacaggcag atgtttgcct cataatagtc gtaagtggag     4016
tcctggaatt tggacaagtg ctgttgggat atagtcaact tattctttga gtaatgtgac    4076
taaaggaaaa aactttgact ttgcccaggc atgaaattct tcctaatgtc agaacagagt    4136
gcaacccagt cacactgtgg ccagtaaaat actattgcct catattgtcc tctgcaagct    4196
tcttgctgat cagagttcct cctacttaca acccagggtg tgaacatgtt ctccattttc    4256
aagctggaag aagtgagcag tgttggagtg aggacctgta aggcaggccc attcagagct    4316
atggtgcttg ctggtgcctg ccaccttcaa gttctggacc tgggcatgac atcctttctt    4376
ttaatgatgc catggcaact tagagattgc attttatta aagcatttcc taccagcaaa     4436
gcaaatgttg ggaaagtatt tacttttcg gtttcaaagt gatagaaaag tgtggcttgg     4496
gcattgaaag aggtaaaatt ctctagattt attagtccta attcaatcct acttttcgaa    4556
caccaaaaat gatgcgcatc aatgtatttt atcttatttt ctcaatctcc tctctctttc    4616
ctccacccat aataagagaa tgttcctact cacacttcag ctgggtcaca tccatccctc    4676
cattcatcct tccatccatc tttccatcca ttacctccat ccatccttcc aacatatatt    4736
tattgagtac ctactgtgtg ccaggggctg gtgggacagt ggtgacatag tctctgccct    4796
catagagttg attgtctagt gaggaagaca agcatttta aaaaataaat ttaaacttac     4856
aaactttgtt tgtcacaagt ggtgtttatt gcaataaccg cttggtttgc aacctctttg    4916
ctcaacagaa catatgttgc aagaccctcc catgggcact gagtttggca aggatgacag    4976
agctctgggt tgtgcacatt tctttgcatt ccagcgtcac tctgtgcctt ctacaactga    5036
ttgcaacaga ctgttgagtt atgataacac cagtgggaat gctggagga accagaggca    5096 cttccacctt ggctgggaag actatggtgc tgccttgctt ctgtatttcc ttggattttc    5156
ctgaaagtgt ttttaaataa agaacaattg ttagatgcca aaaa                    5200
```

<210> SEQ ID NO 26
<211> LENGTH: 1193
<212> TYPE: PRT
<213> ORGANISM: Homo sapiens

<400> SEQUENCE: 26

```
Met Pro Ala Leu Trp Leu Gly Cys Cys Leu Cys Phe Ser Leu Leu Leu
 1               5                  10                  15

Pro Ala Ala Arg Ala Thr Ser Arg Arg Glu Val Cys Asp Cys Asn Gly
            20                  25                  30

Lys Ser Arg Gln Cys Ile Phe Asp Arg Glu Leu His Arg Gln Thr Gly
        35                  40                  45

Asn Gly Phe Arg Cys Leu Asn Cys Asn Asp Asn Thr Asp Gly Ile His
    50                  55                  60

Cys Glu Lys Cys Lys Asn Gly Phe Tyr Arg His Arg Glu Arg Asp Arg
65                  70                  75                  80

Cys Leu Pro Cys Asn Cys Asn Ser Lys Gly Ser Leu Ser Ala Arg Cys
                85                  90                  95

Asp Asn Ser Gly Arg Cys Ser Cys Lys Pro Gly Val Thr Gly Ala Arg
            100                 105                 110

Cys Asp Arg Cys Leu Pro Gly Phe His Met Leu Thr Asp Ala Gly Cys
        115                 120                 125
```

```
Thr Gln Asp Gln Arg Leu Leu Asp Ser Lys Cys Asp Cys Asp Pro Ala
    130                 135                 140

Gly Ile Ala Gly Pro Cys Asp Ala Gly Arg Cys Val Cys Lys Pro Ala
145                 150                 155                 160

Val Thr Gly Glu Arg Cys Asp Arg Cys Arg Ser Gly Tyr Tyr Asn Leu
                165                 170                 175

Asp Gly Gly Asn Pro Glu Gly Cys Thr Gln Cys Phe Cys Tyr Gly His
                180                 185                 190

Ser Ala Ser Cys Arg Ser Ser Ala Glu Tyr Ser Val His Lys Ile Thr
            195                 200                 205

Ser Thr Phe His Gln Asp Val Asp Gly Trp Lys Ala Val Gln Arg Asn
    210                 215                 220

Gly Ser Pro Ala Lys Leu Gln Trp Ser Gln Arg His Gln Asp Val Phe
225                 230                 235                 240

Ser Ser Ala Gln Arg Leu Asp Pro Val Tyr Phe Val Ala Pro Ala Lys
                245                 250                 255

Phe Leu Gly Asn Gln Gln Val Ser Tyr Gly Gln Ser Leu Ser Phe Asp
                260                 265                 270

Tyr Arg Val Asp Arg Gly Gly Arg His Pro Ser Ala His Asp Val Ile
    275                 280                 285

Leu Glu Gly Ala Gly Leu Arg Ile Thr Ala Pro Leu Met Pro Leu Gly
    290                 295                 300

Lys Thr Leu Pro Cys Gly Leu Thr Lys Thr Tyr Thr Phe Arg Leu Asn
305                 310                 315                 320

Glu His Pro Ser Asn Asn Trp Ser Pro Gln Leu Ser Tyr Phe Glu Tyr
                325                 330                 335

Arg Arg Leu Leu Arg Asn Leu Thr Ala Leu Arg Ile Arg Ala Thr Tyr
            340                 345                 350

Gly Glu Tyr Ser Thr Gly Tyr Ile Asp Asn Val Thr Leu Ile Ser Ala
            355                 360                 365

Arg Pro Val Ser Gly Ala Pro Ala Pro Trp Val Glu Gln Cys Ile Cys
    370                 375                 380

Pro Val Gly Tyr Lys Gly Gln Phe Cys Gln Asp Cys Ala Ser Gly Tyr
385                 390                 395                 400

Lys Arg Asp Ser Ala Arg Leu Gly Pro Phe Gly Thr Cys Ile Pro Cys
                405                 410                 415

Asn Cys Gln Gly Gly Ala Cys Asp Pro Asp Thr Gly Asp Cys Tyr
                420                 425                 430

Ser Gly Asp Glu Asn Pro Asp Ile Glu Cys Ala Asp Cys Pro Ile Gly
            435                 440                 445

Phe Tyr Asn Asp Pro His Asp Pro Arg Ser Cys Lys Pro Cys Pro Cys
    450                 455                 460

His Asn Gly Phe Ser Cys Ser Val Ile Pro Glu Thr Glu Val Val
465                 470                 475                 480

Cys Asn Asn Cys Pro Pro Gly Val Thr Gly Ala Arg Cys Glu Leu Cys
                485                 490                 495

Ala Asp Gly Tyr Phe Gly Asp Pro Phe Gly Glu His Gly Pro Val Arg
            500                 505                 510

Pro Cys Gln Pro Cys Gln Cys Asn Ser Asn Val Asp Pro Ser Ala Ser
    515                 520                 525

Gly Asn Cys Asp Arg Leu Thr Gly Arg Cys Leu Lys Cys Ile His Asn
530                 535                 540
```

-continued

```
Thr Ala Gly Ile Tyr Cys Asp Gln Cys Lys Ala Gly Tyr Phe Gly Asp
545                 550                 555                 560

Pro Leu Ala Pro Asn Pro Ala Asp Lys Cys Arg Ala Cys Asn Cys Asn
                565                 570                 575

Pro Met Gly Ser Glu Pro Val Gly Cys Arg Ser Asp Gly Thr Cys Val
                580                 585                 590

Cys Lys Pro Gly Phe Gly Gly Pro Asn Cys Glu His Gly Ala Phe Ser
            595                 600                 605

Cys Pro Ala Cys Tyr Asn Gln Val Lys Ile Gln Met Asp Gln Phe Met
        610                 615                 620

Gln Gln Leu Gln Arg Met Glu Ala Leu Ile Ser Lys Ala Gln Gly Gly
625                 630                 635                 640

Asp Gly Val Val Pro Asp Thr Glu Leu Glu Gly Arg Met Gln Gln Ala
                645                 650                 655

Glu Gln Ala Leu Gln Asp Ile Leu Arg Asp Ala Gln Ile Ser Glu Gly
                660                 665                 670

Ala Ser Arg Ser Leu Gly Leu Gln Leu Ala Lys Val Arg Ser Gln Glu
            675                 680                 685

Asn Ser Tyr Gln Ser Arg Leu Asp Asp Leu Lys Met Thr Val Glu Arg
690                 695                 700

Val Arg Ala Leu Gly Ser Gln Tyr Gln Asn Arg Val Arg Asp Thr His
705                 710                 715                 720

Arg Leu Ile Thr Gln Met Gln Leu Ser Leu Ala Glu Ser Glu Ala Ser
                725                 730                 735

Leu Gly Asn Thr Asn Ile Pro Ala Ser Asp His Tyr Val Gly Pro Asn
                740                 745                 750

Gly Phe Lys Ser Leu Ala Gln Glu Ala Thr Arg Leu Ala Glu Ser His
            755                 760                 765

Val Glu Ser Ala Ser Asn Met Glu Gln Leu Thr Arg Glu Thr Glu Asp
        770                 775                 780

Tyr Ser Lys Gln Ala Leu Ser Leu Val Arg Lys Ala Leu His Glu Gly
785                 790                 795                 800

Val Gly Ser Gly Ser Gly Ser Pro Asp Gly Ala Val Val Gln Gly Leu
                805                 810                 815

Val Glu Lys Leu Glu Lys Thr Lys Ser Leu Ala Gln Gln Leu Thr Arg
                820                 825                 830

Glu Ala Thr Gln Ala Glu Ile Glu Ala Asp Arg Ser Tyr Gln His Ser
            835                 840                 845

Leu Arg Leu Leu Asp Ser Val Ser Pro Leu Gln Gly Val Ser Asp Gln
850                 855                 860

Ser Phe Gln Val Glu Glu Ala Lys Arg Ile Lys Gln Lys Ala Asp Ser
865                 870                 875                 880

Leu Ser Ser Leu Val Thr Arg His Met Asp Glu Phe Lys Arg Thr Gln
                885                 890                 895

Lys Asn Leu Gly Asn Trp Lys Glu Ala Gln Gln Leu Leu Gln Asn
                900                 905                 910

Gly Lys Ser Gly Arg Glu Lys Ser Asp Gln Leu Leu Ser Arg Ala Asn
            915                 920                 925

Leu Ala Lys Ser Arg Ala Gln Glu Ala Leu Ser Met Gly Asn Ala Thr
        930                 935                 940

Phe Tyr Glu Val Glu Ser Ile Leu Lys Asn Leu Arg Glu Phe Asp Leu
945                 950                 955                 960

Gln Val Asp Asn Arg Lys Ala Glu Ala Glu Glu Ala Met Lys Arg Leu
```

```
                      965                 970                 975
Ser Tyr Ile Ser Gln Lys Val Ser Asp Ala Ser Asp Lys Thr Gln Gln
            980                 985                 990

Ala Glu Arg Ala Leu Gly Ser Ala Ala Asp Ala Gln Arg Ala Lys
        995                 1000                1005

Asn Gly Ala Gly Glu Ala Leu Glu Ile Ser Ser Glu Ile Glu Gln Glu
    1010                1015                1020

Ile Gly Ser Leu Asn Leu Glu Ala Asn Val Thr Ala Asp Gly Ala Leu
1025                1030                1035                1040

Ala Met Glu Lys Gly Leu Ala Ser Leu Lys Ser Glu Met Arg Glu Val
                1045                1050                1055

Glu Gly Glu Leu Glu Arg Lys Glu Leu Glu Phe Asp Thr Asn Met Asp
            1060                1065                1070

Ala Val Gln Met Val Ile Thr Glu Ala Gln Lys Val Asp Thr Arg Ala
        1075                1080                1085

Lys Asn Ala Gly Val Thr Ile Gln Asp Thr Leu Asn Thr Leu Asp Gly
    1090                1095                1100

Leu Leu His Leu Met Asp Gln Pro Leu Ser Val Asp Glu Glu Gly Leu
1105                1110                1115                1120

Val Leu Leu Glu Gln Lys Leu Ser Arg Ala Lys Thr Gln Ile Asn Ser
                1125                1130                1135

Gln Leu Arg Pro Met Met Ser Glu Leu Glu Glu Arg Ala Arg Gln Gln
            1140                1145                1150

Arg Gly His Leu His Leu Leu Glu Thr Ser Ile Asp Gly Ile Leu Ala
        1155                1160                1165

Asp Val Lys Asn Leu Glu Asn Ile Arg Asp Asn Leu Pro Pro Gly Cys
    1170                1175                1180

Tyr Asn Thr Gln Ala Leu Glu Gln Gln
1185                1190

<210> SEQ ID NO 27
<211> LENGTH: 5020
<212> TYPE: DNA
<213> ORGANISM: Homo sapiens
<220> FEATURE:
<221> NAME/KEY: CDS
<222> LOCATION: (1)..(3516)

<400> SEQUENCE: 27 acc tcc agg agg gaa gtc tgt gat tgc aat ggg aag tcc agg cag tgt      48
Thr Ser Arg Arg Glu Val Cys Asp Cys Asn Gly Lys Ser Arg Gln Cys
  1               5                  10                  15 atc ttt gat cgg gaa ctt cac aga caa act ggt aat gga ttc cgc tgc     96
Ile Phe Asp Arg Glu Leu His Arg Gln Thr Gly Asn Gly Phe Arg Cys
             20                  25                  30 ctc aac tgc aat gac aac act gat ggc att cac tgc gag aag tgc aag    144
Leu Asn Cys Asn Asp Asn Thr Asp Gly Ile His Cys Glu Lys Cys Lys
         35                  40                  45 aat ggc ttt tac cgg cac aga gaa agg gac cgc tgt ttg ccc tgc aat    192
Asn Gly Phe Tyr Arg His Arg Glu Arg Asp Arg Cys Leu Pro Cys Asn
     50                  55                  60 tgt aac tcc aaa ggt tct ctt agt gct cga tgt gac aac tct gga cgg    240
Cys Asn Ser Lys Gly Ser Leu Ser Ala Arg Cys Asp Asn Ser Gly Arg
 65                  70                  75                  80 tgc agc tgt aaa cca ggt gtg aca gga gcc aga tgc gac cga tgt ctg    288
Cys Ser Cys Lys Pro Gly Val Thr Gly Ala Arg Cys Asp Arg Cys Leu
                 85                  90                  95
```

```
cca ggc ttc cac atg ctc acg gat gcg ggg tgc acc caa gac cag aga       336
Pro Gly Phe His Met Leu Thr Asp Ala Gly Cys Thr Gln Asp Gln Arg
        100                 105                 110 ctg cta gac tcc aag tgt gac tgt gac cca gct ggc atc gca ggg ccc       384
Leu Leu Asp Ser Lys Cys Asp Cys Asp Pro Ala Gly Ile Ala Gly Pro
            115                 120                 125 tgt gac gcg ggc cgc tgt gtc tgc aag cca gct gtt act gga gaa cgc       432
Cys Asp Ala Gly Arg Cys Val Cys Lys Pro Ala Val Thr Gly Glu Arg
130                 135                 140 tgt gat agg tgt cga tca ggt tac tat aat ctg gat ggg ggg aac cct       480
Cys Asp Arg Cys Arg Ser Gly Tyr Tyr Asn Leu Asp Gly Gly Asn Pro
145                 150                 155                 160 gag ggc tgt acc cag tgt ttc tgc tat ggg cat tca gcc agc tgc cgc       528
Glu Gly Cys Thr Gln Cys Phe Cys Tyr Gly His Ser Ala Ser Cys Arg
                165                 170                 175 agc tct gca gaa tac agt gtc cat aag atc acc tct acc ttt cat caa       576
Ser Ser Ala Glu Tyr Ser Val His Lys Ile Thr Ser Thr Phe His Gln
            180                 185                 190 gat gtt gat ggc tgg aag gct gtc caa cga aat ggg tct cct gca aag       624
Asp Val Asp Gly Trp Lys Ala Val Gln Arg Asn Gly Ser Pro Ala Lys
        195                 200                 205 ctc caa tgg tca cag cgc cat caa gat gtg ttt agc tca gcc caa cga       672
Leu Gln Trp Ser Gln Arg His Gln Asp Val Phe Ser Ser Ala Gln Arg
    210                 215                 220 cta gat cct gtc tat ttt gtg gct cct gcc aaa ttt ctt ggg aat caa       720
Leu Asp Pro Val Tyr Phe Val Ala Pro Ala Lys Phe Leu Gly Asn Gln
225                 230                 235                 240 cag gtg agc tat ggg caa agc ctg tcc ttt gac tac cgt gtg gac aga       768
Gln Val Ser Tyr Gly Gln Ser Leu Ser Phe Asp Tyr Arg Val Asp Arg
                245                 250                 255 gga ggc aga cac cca tct gcc cat gat gtg atc ctg gaa ggt gct ggt       816
Gly Gly Arg His Pro Ser Ala His Asp Val Ile Leu Glu Gly Ala Gly
            260                 265                 270 cta cgg atc aca gct ccc ttg atg cca ctt ggc aag aca ctg cct tgt       864
Leu Arg Ile Thr Ala Pro Leu Met Pro Leu Gly Lys Thr Leu Pro Cys
        275                 280                 285 ggg ctc acc aag act tac aca ttc agg tta aat gag cat cca agc aat       912
Gly Leu Thr Lys Thr Tyr Thr Phe Arg Leu Asn Glu His Pro Ser Asn
    290                 295                 300 aat tgg agc ccc cag ctg agt tac ttt gag tat cga agg tta ctg cgg       960
Asn Trp Ser Pro Gln Leu Ser Tyr Phe Glu Tyr Arg Arg Leu Leu Arg
305                 310                 315                 320 aat ctc aca gcc ctc cgc atc cga gct aca tat gga gaa tac agt act      1008
Asn Leu Thr Ala Leu Arg Ile Arg Ala Thr Tyr Gly Glu Tyr Ser Thr
                325                 330                 335 ggg tac att gac aat gtg acc ctg att tca gcc cgc cct gtc tct gga      1056
Gly Tyr Ile Asp Asn Val Thr Leu Ile Ser Ala Arg Pro Val Ser Gly
            340                 345                 350 gcc cca gca ccc tgg gtt gaa cag tgt ata tgt cct gtt ggg tac aag      1104
Ala Pro Ala Pro Trp Val Glu Gln Cys Ile Cys Pro Val Gly Tyr Lys
        355                 360                 365 ggg caa ttc tgc cag gat tgt gct tct ggc tac aag aga gat tca gcg      1152
Gly Gln Phe Cys Gln Asp Cys Ala Ser Gly Tyr Lys Arg Asp Ser Ala
    370                 375                 380 aga ctg ggg cct ttt ggc acc tgt att cct tgt aac tgt caa ggg gga      1200
Arg Leu Gly Pro Phe Gly Thr Cys Ile Pro Cys Asn Cys Gln Gly Gly
385                 390                 395                 400 ggg gcc tgt gat cca gac aca gga gat tgt tat tca ggg gat gag aat      1248
Gly Ala Cys Asp Pro Asp Thr Gly Asp Cys Tyr Ser Gly Asp Glu Asn
                405                 410                 415
```

```
cct gac att gag tgt gct gac tgc cca att ggt ttc tac aac gat ccg    1296
Pro Asp Ile Glu Cys Ala Asp Cys Pro Ile Gly Phe Tyr Asn Asp Pro
            420                 425                 430 cac gac ccc cgc agc tgc aag cca tgt ccc tgt cat aac ggg ttc agc    1344
His Asp Pro Arg Ser Cys Lys Pro Cys Pro Cys His Asn Gly Phe Ser
        435                 440                 445 tgc tca gtg att ccg gag acg gag gag gtg gtg tgc aat aac tgc cct    1392
Cys Ser Val Ile Pro Glu Thr Glu Glu Val Val Cys Asn Asn Cys Pro
450                 455                 460 ccc ggg gtc acc ggt gcc cgc tgt gag ctc tgt gct gat ggc tac ttt    1440
Pro Gly Val Thr Gly Ala Arg Cys Glu Leu Cys Ala Asp Gly Tyr Phe
465                 470                 475                 480 ggg gac ccc ttt ggt gaa cat ggc cca gtg agg cct tgt cag ccc tgt    1488
Gly Asp Pro Phe Gly Glu His Gly Pro Val Arg Pro Cys Gln Pro Cys
                485                 490                 495 caa tgc aac agc aat gtg gac ccc agt gcc tct ggg aat tgt gac cgg    1536
Gln Cys Asn Ser Asn Val Asp Pro Ser Ala Ser Gly Asn Cys Asp Arg
            500                 505                 510 ctg aca ggc agg tgt ttg aag tgt atc cac aac aca gcc ggc atc tac    1584
Leu Thr Gly Arg Cys Leu Lys Cys Ile His Asn Thr Ala Gly Ile Tyr
        515                 520                 525 tgc gac cag tgc aaa gca ggc tac ttc ggg gac cca ttg gct ccc aac    1632
Cys Asp Gln Cys Lys Ala Gly Tyr Phe Gly Asp Pro Leu Ala Pro Asn
530                 535                 540 cca gca gac aag tgt cga gct tgc aac tgt aac ccc atg ggc tca gag    1680
Pro Ala Asp Lys Cys Arg Ala Cys Asn Cys Asn Pro Met Gly Ser Glu
545                 550                 555                 560 cct gta gga tgt cga agt gat ggc acc tgt gtt tgc aag cca gga ttt    1728
Pro Val Gly Cys Arg Ser Asp Gly Thr Cys Val Cys Lys Pro Gly Phe
                565                 570                 575 ggt ggc ccc aac tgt gag cat gga gca ttc agc tgt cca gct tgc tat    1776
Gly Gly Pro Asn Cys Glu His Gly Ala Phe Ser Cys Pro Ala Cys Tyr
            580                 585                 590 aat caa gtg aag att cag atg gat cag ttt atg cag cag ctt cag aga    1824
Asn Gln Val Lys Ile Gln Met Asp Gln Phe Met Gln Gln Leu Gln Arg
        595                 600                 605 atg gag gcc ctg att tca aag gct cag ggt ggt gat gga gta gta cct    1872
Met Glu Ala Leu Ile Ser Lys Ala Gln Gly Gly Asp Gly Val Val Pro
610                 615                 620 gat aca gag ctg gaa ggc agg atg cag cag gct gag cag gcc ctt cag    1920
Asp Thr Glu Leu Glu Gly Arg Met Gln Gln Ala Glu Gln Ala Leu Gln
625                 630                 635                 640 gac att ctg aga gat gcc cag att tca gaa ggt gct agc aga tcc ctt    1968
Asp Ile Leu Arg Asp Ala Gln Ile Ser Glu Gly Ala Ser Arg Ser Leu
                645                 650                 655 ggt ctc cag ttg gcc aag gtg agg agc caa gag aac agc tac cag agc    2016
Gly Leu Gln Leu Ala Lys Val Arg Ser Gln Glu Asn Ser Tyr Gln Ser
            660                 665                 670 cgc ctg gat gac ctc aag atg act gtg aaa aga gtt cgg gct ctg gga    2064
Arg Leu Asp Asp Leu Lys Met Thr Val Glu Arg Val Arg Ala Leu Gly
        675                 680                 685 agt cag tac cag aac cga gtt cgg gat act cac agg ctc atc act cag    2112
Ser Gln Tyr Gln Asn Arg Val Arg Asp Thr His Arg Leu Ile Thr Gln
690                 695                 700 atg cag ctg agc ctg gca gaa agt gaa gct tcc ttg gga aac act aac    2160
Met Gln Leu Ser Leu Ala Glu Ser Glu Ala Ser Leu Gly Asn Thr Asn
705                 710                 715                 720 att cct gcc tca gac cac tac gtg ggg cca aat ggc ttt aaa agt ctg    2208
Ile Pro Ala Ser Asp His Tyr Val Gly Pro Asn Gly Phe Lys Ser Leu
```

```
                725                 730                 735
gct cag gag gcc aca aga tta gca gaa agc cac gtt gag tca gcc agt    2256
Ala Gln Glu Ala Thr Arg Leu Ala Glu Ser His Val Glu Ser Ala Ser
            740                 745                 750 aac atg gag caa ctg aca agg gaa act gag gac tat tcc aaa caa gcc    2304
Asn Met Glu Gln Leu Thr Arg Glu Thr Glu Asp Tyr Ser Lys Gln Ala
        755                 760                 765 ctc tca ctg gtg cgc aag gcc ctg cat gaa gga gtc gga agc gga agc    2352
Leu Ser Leu Val Arg Lys Ala Leu His Glu Gly Val Gly Ser Gly Ser
    770                 775                 780 ggt agc ccg gac ggt gct gtg gtg caa ggg ctt gtg gaa aaa ttg gag    2400
Gly Ser Pro Asp Gly Ala Val Val Gln Gly Leu Val Glu Lys Leu Glu
785                 790                 795                 800 aaa acc aag tcc ctg gcc cag cag ttg aca agg gag gcc act caa gcg    2448
Lys Thr Lys Ser Leu Ala Gln Gln Leu Thr Arg Glu Ala Thr Gln Ala
            805                 810                 815 gaa att gaa gca gat agg tct tat cag cac agt ctc cgc ctc ctg gat    2496
Glu Ile Glu Ala Asp Arg Ser Tyr Gln His Ser Leu Arg Leu Leu Asp
        820                 825                 830 tca gtg tct ccg ctt cag gga gtc agt gat cag tcc ttt cag gtg gaa    2544
Ser Val Ser Pro Leu Gln Gly Val Ser Asp Gln Ser Phe Gln Val Glu
    835                 840                 845 gaa gca aag agg atc aaa caa aaa gcg gat tca ctc tca agc ctg gta    2592
Glu Ala Lys Arg Ile Lys Gln Lys Ala Asp Ser Leu Ser Ser Leu Val
850                 855                 860 acc agg cat atg gat gag ttc aag cgt aca caa aag aat ctg gga aac    2640
Thr Arg His Met Asp Glu Phe Lys Arg Thr Gln Lys Asn Leu Gly Asn
865                 870                 875                 880 tgg aaa gaa gaa gca cag cag ctc tta cag aat gga aaa agt ggg aga    2688
Trp Lys Glu Glu Ala Gln Gln Leu Leu Gln Asn Gly Lys Ser Gly Arg
            885                 890                 895 gag aaa tca gat cag ctg ctt tcc cgt gcc aat ctt gct aaa agc aga    2736
Glu Lys Ser Asp Gln Leu Leu Ser Arg Ala Asn Leu Ala Lys Ser Arg
        900                 905                 910 gca caa gaa gca ctg agt atg ggc aat gcc act ttt tat gaa gtt gag    2784
Ala Gln Glu Ala Leu Ser Met Gly Asn Ala Thr Phe Tyr Glu Val Glu
    915                 920                 925 agc atc ctt aaa aac ctc aga gag ttt gac ctg cag gtg gac aac aga    2832
Ser Ile Leu Lys Asn Leu Arg Glu Phe Asp Leu Gln Val Asp Asn Arg
930                 935                 940 aaa gca gaa gct gaa gaa gcc atg aag aga ctc tcc tac atc agc cag    2880
Lys Ala Glu Ala Glu Glu Ala Met Lys Arg Leu Ser Tyr Ile Ser Gln
945                 950                 955                 960 aag gtt tca gat gcc agt gac aag acc cag caa gca gaa aga gcc ctg    2928
Lys Val Ser Asp Ala Ser Asp Lys Thr Gln Gln Ala Glu Arg Ala Leu
            965                 970                 975 ggg agc gct gct gct gat gca cag agg gca aag aat ggg gcc ggg gag    2976
Gly Ser Ala Ala Ala Asp Ala Gln Arg Ala Lys Asn Gly Ala Gly Glu
        980                 985                 990 gcc ctg gaa atc tcc agt gag att gaa cag gag att ggg agt ctg aac    3024
Ala Leu Glu Ile Ser Ser Glu Ile Glu Gln Glu Ile Gly Ser Leu Asn
    995                 1000                1005 ttg gaa gcc aat gtg aca gca gat gga gcc ttg gcc atg gaa aag gga    3072
Leu Glu Ala Asn Val Thr Ala Asp Gly Ala Leu Ala Met Glu Lys Gly
    1010                1015                1020 ctg gcc tct ctg aag agt gag atg agg gaa gtg gaa gga gag ctg gaa    3120
Leu Ala Ser Leu Lys Ser Glu Met Arg Glu Val Glu Gly Glu Leu Glu
1025                1030                1035                1040 agg aag gag ctg gag ttt gac acg aat atg gat gca gta cag atg gtg    3168
```

-continued

```
Arg Lys Glu Leu Glu Phe Asp Thr Asn Met Asp Ala Val Gln Met Val
            1045                1050                1055
att aca gaa gcc cag aag gtt gat acc aga gcc aag aac gct ggg gtt      3216
Ile Thr Glu Ala Gln Lys Val Asp Thr Arg Ala Lys Asn Ala Gly Val
        1060                1065                1070
aca atc caa gac aca ctc aac aca tta gac ggc ctc ctg cat ctg atg      3264
Thr Ile Gln Asp Thr Leu Asn Thr Leu Asp Gly Leu Leu His Leu Met
    1075                1080                1085
gac cag cct ctc agt gta gat gaa gag ggg ctg gtc tta ctg gag cag      3312
Asp Gln Pro Leu Ser Val Asp Glu Glu Gly Leu Val Leu Leu Glu Gln
1090                1095                1100
aag ctt tcc cga gcc aag acc cag atc aac agc caa ctg cgg ccc atg      3360
Lys Leu Ser Arg Ala Lys Thr Gln Ile Asn Ser Gln Leu Arg Pro Met
1105                1110                1115                1120
atg tca gag ctg gaa gag agg gca cgt cag cag agg ggc cac ctc cat      3408
Met Ser Glu Leu Glu Glu Arg Ala Arg Gln Gln Arg Gly His Leu His
            1125                1130                1135
ttg ctg gag aca agc ata gat ggg att ctg gct gat gtg aag aac ttg      3456
Leu Leu Glu Thr Ser Ile Asp Gly Ile Leu Ala Asp Val Lys Asn Leu
        1140                1145                1150
gag aac att agg gac aac ctg ccc cca ggc tgc tac aat acc cag gct      3504
Glu Asn Ile Arg Asp Asn Leu Pro Pro Gly Cys Tyr Asn Thr Gln Ala
    1155                1160                1165
ctt gag caa cag tgaagctgcc ataaatattt ctcaactgag gttcttggga         3556
Leu Glu Gln Gln
    1170
tacagatctc agggctcggg agccatgtca tgtgagtggg tgggatgggg acatttgaac    3616
atgtttaatg ggtatgctca ggtcaactga cctgacccca ttcctgatcc catggccagg    3676
tggttgtctt attgcaccat actccttgct tcctgatgct gggcatgagg cagataggca    3736
ctggtgtgag aatgatcaag gatctggacc ccaaagatag actggatgga agacaaact     3796
gcacaggcag atgtttgcct cataatagtc gtaagtggag tcctggaatt tggacaagtg    3856
ctgtgggat atagtcaact tattctttga gtaatgtgac taaaggaaaa aactttgact     3916
ttgcccaggc atgaaattct tcctaatgtc agaacagagt gcaacccagt cacactgtgg    3976
ccagtaaaat actattgcct catattgtcc tctgcaagct tcttgctgat cagagttcct    4036
cctacttaca acccagggtg tgaacatgtt ctccattttc aagctggaag aagtgagcag    4096
tgttggagtg aggacctgta aggcaggccc attcagagct atggtgcttg ctggtgcctg    4156
ccaccttcaa gttctggacc tgggcatgac atcctttctt ttaatgatgc catggcaact    4216
tagagattgc attttatta aagcatttcc taccagcaaa gcaatgttg ggaaagtatt      4276
tacttttcg gtttcaaagt gatagaaaag tgtggcttgg gcattgaaag aggtaaaatt     4336
ctctagattt attagtccta attcaatcct acttttcgaa caccaaaat gatgcgcatc     4396
aatgtatttt atcttatttt ctcaatctcc tctctctttc ctccacccat aataagagaa    4456
tgttcctact cacacttcag ctgggtcaca tccatccctc cattcatcct tccatccatc    4516
tttccatcca ttacctccat ccatccttcc aacatatatt tattgagtac ctactgtgtg    4576
ccagggggtg gtgggacagt ggtgacatag tctctgccct catagagttg attgtctagt    4636
gaggaagaca agcattttta aaaataaat ttaaacttac aaactttgtt tgtcacaagt     4696
ggtgtttatt gcaataaccg cttggtttgc aacctctttg ctcaacagaa catatgttgc    4756
aagaccctcc catgggcact gagtttggca aggatgacag agctctgggt tgtgcacatt    4816
tctttgcatt ccagcgtcac tctgtgcctt ctacaactga ttgcaacaga ctgttgagtt    4876
```

```
atgataacac cagtgggaat tgctggagga accagaggca cttccacctt ggctgggaag   4936
actatggtgc tgccttgctt ctgtatttcc ttggattttc ctgaaagtgt ttttaaataa   4996
agaacaattg ttagatgcca aaaa                                          5020
```

<210> SEQ ID NO 28
<211> LENGTH: 1172
<212> TYPE: PRT
<213> ORGANISM: Homo sapiens

<400> SEQUENCE: 28

```
Thr Ser Arg Arg Glu Val Cys Asp Cys Asn Gly Lys Ser Arg Gln Cys
 1               5                  10                  15

Ile Phe Asp Arg Glu Leu His Arg Gln Thr Gly Asn Gly Phe Arg Cys
            20                  25                  30

Leu Asn Cys Asn Asp Asn Thr Asp Gly Ile His Cys Glu Lys Cys Lys
        35                  40                  45

Asn Gly Phe Tyr Arg His Arg Glu Arg Asp Arg Cys Leu Pro Cys Asn
    50                  55                  60

Cys Asn Ser Lys Gly Ser Leu Ser Ala Arg Cys Asp Asn Ser Gly Arg
 65                  70                  75                  80

Cys Ser Cys Lys Pro Gly Val Thr Gly Ala Arg Cys Asp Arg Cys Leu
                85                  90                  95

Pro Gly Phe His Met Leu Thr Asp Ala Gly Cys Thr Gln Asp Gln Arg
            100                 105                 110

Leu Leu Asp Ser Lys Cys Asp Cys Asp Pro Ala Gly Ile Ala Gly Pro
        115                 120                 125

Cys Asp Ala Gly Arg Cys Val Cys Lys Pro Ala Val Thr Gly Glu Arg
    130                 135                 140

Cys Asp Arg Cys Arg Ser Gly Tyr Tyr Asn Leu Asp Gly Gly Asn Pro
145                 150                 155                 160

Glu Gly Cys Thr Gln Cys Phe Cys Tyr Gly His Ser Ala Ser Cys Arg
                165                 170                 175

Ser Ser Ala Glu Tyr Ser Val His Lys Ile Thr Ser Thr Phe His Gln
            180                 185                 190

Asp Val Asp Gly Trp Lys Ala Val Gln Arg Asn Gly Ser Pro Ala Lys
        195                 200                 205

Leu Gln Trp Ser Gln Arg His Gln Asp Val Phe Ser Ala Gln Arg
    210                 215                 220

Leu Asp Pro Val Tyr Phe Val Ala Pro Ala Lys Phe Leu Gly Asn Gln
225                 230                 235                 240

Gln Val Ser Tyr Gly Gln Ser Leu Ser Phe Asp Tyr Arg Val Asp Arg
                245                 250                 255

Gly Gly Arg His Pro Ser Ala His Asp Val Ile Leu Glu Gly Ala Gly
            260                 265                 270

Leu Arg Ile Thr Ala Pro Leu Met Pro Leu Gly Lys Thr Leu Pro Cys
        275                 280                 285

Gly Leu Thr Lys Thr Tyr Thr Phe Arg Leu Asn Glu His Pro Ser Asn
    290                 295                 300

Asn Trp Ser Pro Gln Leu Ser Tyr Phe Glu Tyr Arg Arg Leu Leu Arg
305                 310                 315                 320

Asn Leu Thr Ala Leu Arg Ile Arg Ala Thr Tyr Gly Glu Tyr Ser Thr
                325                 330                 335

Gly Tyr Ile Asp Asn Val Thr Leu Ile Ser Ala Arg Pro Val Ser Gly
            340                 345                 350
```

```
Ala Pro Ala Pro Trp Val Glu Gln Cys Ile Cys Pro Val Gly Tyr Lys
        355                 360                 365
Gly Gln Phe Cys Gln Asp Cys Ala Ser Gly Tyr Lys Arg Asp Ser Ala
    370                 375                 380
Arg Leu Gly Pro Phe Gly Thr Cys Ile Pro Cys Asn Cys Gln Gly Gly
385                 390                 395                 400
Gly Ala Cys Asp Pro Asp Thr Gly Asp Cys Tyr Ser Gly Asp Glu Asn
                405                 410                 415
Pro Asp Ile Glu Cys Ala Asp Cys Pro Ile Gly Phe Tyr Asn Asp Pro
            420                 425                 430
His Asp Pro Arg Ser Cys Lys Pro Cys Pro Cys His Asn Gly Phe Ser
        435                 440                 445
Cys Ser Val Ile Pro Glu Thr Glu Val Val Cys Asn Asn Cys Pro
    450                 455                 460
Pro Gly Val Thr Gly Ala Arg Cys Glu Leu Cys Ala Asp Gly Tyr Phe
465                 470                 475                 480
Gly Asp Pro Phe Gly Glu His Gly Pro Val Arg Pro Cys Gln Pro Cys
                485                 490                 495
Gln Cys Asn Ser Asn Val Asp Pro Ser Ala Ser Gly Asn Cys Asp Arg
        500                 505                 510
Leu Thr Gly Arg Cys Leu Lys Cys Ile His Asn Thr Ala Gly Ile Tyr
    515                 520                 525
Cys Asp Gln Cys Lys Ala Gly Tyr Phe Gly Asp Pro Leu Ala Pro Asn
    530                 535                 540
Pro Ala Asp Lys Cys Arg Ala Cys Asn Cys Asn Pro Met Gly Ser Glu
545                 550                 555                 560
Pro Val Gly Cys Arg Ser Asp Gly Thr Cys Val Cys Lys Pro Gly Phe
                565                 570                 575
Gly Gly Pro Asn Cys Glu His Gly Ala Phe Ser Cys Pro Ala Cys Tyr
            580                 585                 590
Asn Gln Val Lys Ile Gln Met Asp Gln Phe Met Gln Gln Leu Gln Arg
        595                 600                 605
Met Glu Ala Leu Ile Ser Lys Ala Gln Gly Gly Asp Gly Val Val Pro
    610                 615                 620
Asp Thr Glu Leu Glu Gly Arg Met Gln Gln Ala Glu Gln Ala Leu Gln
625                 630                 635                 640
Asp Ile Leu Arg Asp Ala Gln Ile Ser Glu Gly Ala Ser Arg Ser Leu
            645                 650                 655
Gly Leu Gln Leu Ala Lys Val Arg Ser Gln Glu Asn Ser Tyr Gln Ser
        660                 665                 670
Arg Leu Asp Asp Leu Lys Met Thr Val Glu Arg Val Arg Ala Leu Gly
        675                 680                 685
Ser Gln Tyr Gln Asn Arg Val Arg Asp Thr His Arg Leu Ile Thr Gln
        690                 695                 700
Met Gln Leu Ser Leu Ala Glu Ser Glu Ala Ser Leu Gly Asn Thr Asn
705                 710                 715                 720
Ile Pro Ala Ser Asp His Tyr Val Gly Pro Asn Gly Phe Lys Ser Leu
                725                 730                 735
Ala Gln Glu Ala Thr Arg Leu Ala Glu Ser His Val Glu Ser Ala Ser
                740                 745                 750
Asn Met Glu Gln Leu Thr Arg Glu Thr Glu Asp Tyr Ser Lys Gln Ala
        755                 760                 765
```

```
Leu Ser Leu Val Arg Lys Ala Leu His Glu Gly Val Gly Ser Gly Ser
    770                 775                 780

Gly Ser Pro Asp Gly Ala Val Gln Gly Leu Val Glu Lys Leu Glu
785                 790                 795                 800

Lys Thr Lys Ser Leu Ala Gln Gln Leu Thr Arg Glu Ala Thr Gln Ala
                805                 810                 815

Glu Ile Glu Ala Asp Arg Ser Tyr Gln His Ser Leu Arg Leu Leu Asp
            820                 825                 830

Ser Val Ser Pro Leu Gln Gly Val Ser Asp Gln Ser Phe Gln Val Glu
            835                 840                 845

Glu Ala Lys Arg Ile Lys Gln Lys Ala Asp Ser Leu Ser Ser Leu Val
        850                 855                 860

Thr Arg His Met Asp Glu Phe Lys Arg Thr Gln Lys Asn Leu Gly Asn
865                 870                 875                 880

Trp Lys Glu Glu Ala Gln Gln Leu Leu Gln Asn Gly Lys Ser Gly Arg
                885                 890                 895

Glu Lys Ser Asp Gln Leu Leu Ser Arg Ala Asn Leu Ala Lys Ser Arg
            900                 905                 910

Ala Gln Glu Ala Leu Ser Met Gly Asn Ala Thr Phe Tyr Glu Val Glu
        915                 920                 925

Ser Ile Leu Lys Asn Leu Arg Glu Phe Asp Leu Gln Val Asp Asn Arg
    930                 935                 940

Lys Ala Glu Ala Glu Glu Ala Met Lys Arg Leu Ser Tyr Ile Ser Gln
945                 950                 955                 960

Lys Val Ser Asp Ala Ser Asp Lys Thr Gln Gln Ala Glu Arg Ala Leu
                965                 970                 975

Gly Ser Ala Ala Ala Asp Ala Gln Arg Ala Lys Asn Gly Ala Gly Glu
            980                 985                 990

Ala Leu Glu Ile Ser Ser Glu Ile Glu Gln Glu Ile Gly Ser Leu Asn
        995                 1000                1005

Leu Glu Ala Asn Val Thr Ala Asp Gly Ala Leu Ala Met Glu Lys Gly
    1010                1015                1020

Leu Ala Ser Leu Lys Ser Glu Met Arg Glu Val Glu Gly Glu Leu Glu
1025                1030                1035                1040

Arg Lys Glu Leu Glu Phe Asp Thr Asn Met Asp Ala Val Gln Met Val
                1045                1050                1055

Ile Thr Glu Ala Gln Lys Val Asp Thr Arg Ala Lys Asn Ala Gly Val
            1060                1065                1070

Thr Ile Gln Asp Thr Leu Asn Thr Leu Asp Gly Leu Leu His Leu Met
        1075                1080                1085

Asp Gln Pro Leu Ser Val Asp Glu Glu Gly Leu Val Leu Leu Glu Gln
    1090                1095                1100

Lys Leu Ser Arg Ala Lys Thr Gln Ile Asn Ser Gln Leu Arg Pro Met
1105                1110                1115                1120

Met Ser Glu Leu Glu Glu Arg Ala Arg Gln Gln Arg Gly His Leu His
                1125                1130                1135

Leu Leu Glu Thr Ser Ile Asp Gly Ile Leu Ala Asp Val Lys Asn Leu
            1140                1145                1150

Glu Asn Ile Arg Asp Asn Leu Pro Pro Gly Cys Tyr Asn Thr Gln Ala
        1155                1160                1165

Leu Glu Gln Gln
    1170
```

```
<210> SEQ ID NO 29
<211> LENGTH: 3720
<212> TYPE: DNA
<213> ORGANISM: Homo sapiens
<220> FEATURE:
<221> NAME/KEY: CDS
<222> LOCATION: (38)..(3616)
<221> NAME/KEY: sig_peptide
<222> LOCATION: (38)..(100)

<400> SEQUENCE: 29
gtttaaactt aagcttggta ccgagctcgg atccgcc atg cct gcg ctc tgg ctg         55
                                        Met Pro Ala Leu Trp Leu
                                          1               5 ggc tgc tgc ctc tgc ttc tcg ctc ctg ccc gca gcc cgg gcc acc             103
Gly Cys Cys Leu Cys Phe Ser Leu Leu Pro Ala Ala Arg Ala Thr
             10                  15                  20 tcc agg agg gaa gtc tgt gat tgc aat ggg aag tcc agg cag tgt atc         151
Ser Arg Arg Glu Val Cys Asp Cys Asn Gly Lys Ser Arg Gln Cys Ile
         25                  30                  35 ttt gat cgg gaa ctt cac aga caa act ggt aat gga ttc cgc tgc ctc         199
Phe Asp Arg Glu Leu His Arg Gln Thr Gly Asn Gly Phe Arg Cys Leu
     40                  45                  50 aac tgc aat gac aac act gat ggc att cac tgc gag aag tgc aag aat         247
Asn Cys Asn Asp Asn Thr Asp Gly Ile His Cys Glu Lys Cys Lys Asn
 55                  60                  65                  70 ggc ttt tac cgg cac aga gaa agg gac cgc tgt ttg ccc tgc aat tgt         295
Gly Phe Tyr Arg His Arg Glu Arg Asp Arg Cys Leu Pro Cys Asn Cys
             75                  80                  85 aac tcc aaa ggt tct ctt agt gct cga tgt gac aac tct gga cgg tgc         343
Asn Ser Lys Gly Ser Leu Ser Ala Arg Cys Asp Asn Ser Gly Arg Cys
         90                  95                 100 agc tgt aaa cca ggt gtg aca gga gcc aga tgc gac cga tgt ctg cca         391
Ser Cys Lys Pro Gly Val Thr Gly Ala Arg Cys Asp Arg Cys Leu Pro
        105                 110                 115 ggc ttc cac atg ctc acg gat gcg ggg tgc acc caa gac cag aga ctg         439
Gly Phe His Met Leu Thr Asp Ala Gly Cys Thr Gln Asp Gln Arg Leu
    120                 125                 130 cta gac tcc aag tgt gac tgt gac cca gct ggc atc gca ggg ccc tgt         487
Leu Asp Ser Lys Cys Asp Cys Asp Pro Ala Gly Ile Ala Gly Pro Cys
135                 140                 145                 150 gac gcg ggc cgc tgt gtc tgc aag cca gct gtt act gga gaa cgc tgt         535
Asp Ala Gly Arg Cys Val Cys Lys Pro Ala Val Thr Gly Glu Arg Cys
                155                 160                 165 gat ggg tgt cga tca ggt tac tat aat ctg gat ggg gga aac cct gag         583
Asp Gly Cys Arg Ser Gly Tyr Tyr Asn Leu Asp Gly Gly Asn Pro Glu
            170                 175                 180 ggc tgt acc cag tgt ttc tgc tat ggg cat tca gcc agc tgc cgc agc         631
Gly Cys Thr Gln Cys Phe Cys Tyr Gly His Ser Ala Ser Cys Arg Ser
        185                 190                 195 tct gca gaa tac agt gtc cat aag atc acc tct acc ttt cat caa gat         679
Ser Ala Glu Tyr Ser Val His Lys Ile Thr Ser Thr Phe His Gln Asp
    200                 205                 210 gtt gat ggc tgg aag gct gtc caa cga aat ggg tct cct gca aag ctc         727
Val Asp Gly Trp Lys Ala Val Gln Arg Asn Gly Ser Pro Ala Lys Leu
215                 220                 225                 230 caa tgg tca cag cgc cat caa gat gtg ttt agc tca gcc caa cga cta         775
Gln Trp Ser Gln Arg His Gln Asp Val Phe Ser Ser Ala Gln Arg Leu
                235                 240                 245 gac cct gtc tat ttt gtg gct cct gcc aaa ttt ctt ggg aat caa cag         823
Asp Pro Val Tyr Phe Val Ala Pro Ala Lys Phe Leu Gly Asn Gln Gln
            250                 255                 260
```

```
gtg agc tat ggg caa agc ctg tcc ttt gac tac cgt gtg gac aga gga      871
Val Ser Tyr Gly Gln Ser Leu Ser Phe Asp Tyr Arg Val Asp Arg Gly
        265                 270                 275 ggc aga cac cca tct gcc cat gat gtg att ctg gaa ggt gct ggt cta      919
Gly Arg His Pro Ser Ala His Asp Val Ile Leu Glu Gly Ala Gly Leu
    280                 285                 290 cgg atc aca gct ccc ttg atg cca ctt ggc aag aca ctg cct tgt ggg      967
Arg Ile Thr Ala Pro Leu Met Pro Leu Gly Lys Thr Leu Pro Cys Gly
295                 300                 305                 310 ctc acc aag act tac aca ttc agg tta aat gag cat cca agc aat aat     1015
Leu Thr Lys Thr Tyr Thr Phe Arg Leu Asn Glu His Pro Ser Asn Asn
                315                 320                 325 tgg agc ccc cag ctg agt tac ttt gag tat cga agg tta ctg cgg aat     1063
Trp Ser Pro Gln Leu Ser Tyr Phe Glu Tyr Arg Arg Leu Leu Arg Asn
            330                 335                 340 ctc aca gcc ctc cgc atc cga gct aca tat gga gaa tac agt act ggg     1111
Leu Thr Ala Leu Arg Ile Arg Ala Thr Tyr Gly Glu Tyr Ser Thr Gly
        345                 350                 355 tac att gac aat gtg acc ctg att tca gcc cgc cct gtc tct gga gcc     1159
Tyr Ile Asp Asn Val Thr Leu Ile Ser Ala Arg Pro Val Ser Gly Ala
    360                 365                 370 cca gca ccc tgg gtt gaa cag tgt ata tgt cct gtt ggg tac aag ggg     1207
Pro Ala Pro Trp Val Glu Gln Cys Ile Cys Pro Val Gly Tyr Lys Gly
375                 380                 385                 390 caa ttc tgc cag gat tgt gct tct ggc tac aag aga gat tca gcg aga     1255
Gln Phe Cys Gln Asp Cys Ala Ser Gly Tyr Lys Arg Asp Ser Ala Arg
                395                 400                 405 ctg ggg cct ttt ggc acc tgt att cct tgt aac tgt caa ggg gga ggg     1303
Leu Gly Pro Phe Gly Thr Cys Ile Pro Cys Asn Cys Gln Gly Gly Gly
            410                 415                 420 gcc tgt gat cca gac aca gga gat tgt tat tca ggg gat gag aat cct     1351
Ala Cys Asp Pro Asp Thr Gly Asp Cys Tyr Ser Gly Asp Glu Asn Pro
        425                 430                 435 gac att gag tgt gct gac tgc cca att ggt ttc tac aac gat ccg cac     1399
Asp Ile Glu Cys Ala Asp Cys Pro Ile Gly Phe Tyr Asn Asp Pro His
    440                 445                 450 gac ccc cgc agc tgc aag cca tgt ccc tgt cat aac ggg ttc agc tgc     1447
Asp Pro Arg Ser Cys Lys Pro Cys Pro Cys His Asn Gly Phe Ser Cys
455                 460                 465                 470 tca gtg atg ccg gag acg gag gag gtg gtg tgc aat aac tgc cct ccc     1495
Ser Val Met Pro Glu Thr Glu Glu Val Val Cys Asn Asn Cys Pro Pro
                475                 480                 485 ggg gtc acc ggt gcc cgc tgt gag ctc tgt gct gat ggc tac ttt ggg     1543
Gly Val Thr Gly Ala Arg Cys Glu Leu Cys Ala Asp Gly Tyr Phe Gly
            490                 495                 500 gac ccc ttt ggt gaa cat ggc cca gtg agg cct tgt cag ccc tgt caa     1591
Asp Pro Phe Gly Glu His Gly Pro Val Arg Pro Cys Gln Pro Cys Gln
        505                 510                 515 tgc aac aac aat gtg gac ccc agt gcc tct ggg aat tgt gac cgg ctg     1639
Cys Asn Asn Asn Val Asp Pro Ser Ala Ser Gly Asn Cys Asp Arg Leu
    520                 525                 530 aca ggc agg tgt ttg aag tgt atc cac aac aca gcc ggc atc tac tgc     1687
Thr Gly Arg Cys Leu Lys Cys Ile His Asn Thr Ala Gly Ile Tyr Cys
535                 540                 545                 550 gac cag tgc aaa gca ggc tac ttc ggg gac cca ttg gct ccc aac cca     1735
Asp Gln Cys Lys Ala Gly Tyr Phe Gly Asp Pro Leu Ala Pro Asn Pro
                555                 560                 565 gca gac aag tgt cga gct tgc aac tgt aac ccc atg ggc tca gag cct     1783
Ala Asp Lys Cys Arg Ala Cys Asn Cys Asn Pro Met Gly Ser Glu Pro
```

```
                570                     575                     580
gta gga tgt cga agt gat ggc acc tgt gtt tgc aag cca gga ttt ggt      1831
Val Gly Cys Arg Ser Asp Gly Thr Cys Val Cys Lys Pro Gly Phe Gly
            585                     590                     595 ggc ccc aac tgt gag cat gga gca ttc agc tgt cca gct tgc tat aat      1879
Gly Pro Asn Cys Glu His Gly Ala Phe Ser Cys Pro Ala Cys Tyr Asn
600                     605                     610 caa gtg aag att cag atg gat cag ttt atg cag cag ctt cag aga atg      1927
Gln Val Lys Ile Gln Met Asp Gln Phe Met Gln Gln Leu Gln Arg Met
615                     620                     625                     630 gag gcc ctg att tca aag gct cag ggt ggt gat gga gta gta cct gat      1975
Glu Ala Leu Ile Ser Lys Ala Gln Gly Gly Asp Gly Val Val Pro Asp
            635                     640                     645 aca gag ctg gaa ggc agg atg cag cag gct gag cag gcc ctt cag gac      2023
Thr Glu Leu Glu Gly Arg Met Gln Gln Ala Glu Gln Ala Leu Gln Asp
            650                     655                     660 att ctg aga gat gcc cag att tca gaa ggt gct agc aga tcc ctt ggt      2071
Ile Leu Arg Asp Ala Gln Ile Ser Glu Gly Ala Ser Arg Ser Leu Gly
            665                     670                     675 ctc cag ttg gcc aag gtg agg agc caa gag aac agc tac cag agc cgc      2119
Leu Gln Leu Ala Lys Val Arg Ser Gln Glu Asn Ser Tyr Gln Ser Arg
            680                     685                     690 ctg gat gac ctc aag atg act gtg gaa aga gtt cgg gct ctg gga agt      2167
Leu Asp Asp Leu Lys Met Thr Val Glu Arg Val Arg Ala Leu Gly Ser
695                     700                     705                     710 cag tac cag aac cga gtt cgg gat act cac agg ctc atc act cag atg      2215
Gln Tyr Gln Asn Arg Val Arg Asp Thr His Arg Leu Ile Thr Gln Met
            715                     720                     725 cag ctg agc ctg gca gaa agt gaa gct tcc ttg gga aac act aac att      2263
Gln Leu Ser Leu Ala Glu Ser Glu Ala Ser Leu Gly Asn Thr Asn Ile
            730                     735                     740 cct gcc tca gac cac tac gtg ggg cca aat ggc ttt aaa agt ctg gct      2311
Pro Ala Ser Asp His Tyr Val Gly Pro Asn Gly Phe Lys Ser Leu Ala
            745                     750                     755 cag gag gcc aca aga tta gca gaa agc cac gtt gag tca gcc agt aac      2359
Gln Glu Ala Thr Arg Leu Ala Glu Ser His Val Glu Ser Ala Ser Asn
760                     765                     770 atg gag caa ctg aca agg gaa act gag gac tat tcc aaa caa gcc ctc      2407
Met Glu Gln Leu Thr Arg Glu Thr Glu Asp Tyr Ser Lys Gln Ala Leu
775                     780                     785                     790 tca ctg gtg cgc aag gcc ctg cat gaa gga gtc gga agc gga agc ggt      2455
Ser Leu Val Arg Lys Ala Leu His Glu Gly Val Gly Ser Gly Ser Gly
            795                     800                     805 agc ccg gac ggt gct gtg gtg caa ggg ctt gtg gaa aaa ttg gag aaa      2503
Ser Pro Asp Gly Ala Val Val Gln Gly Leu Val Glu Lys Leu Glu Lys
            810                     815                     820 acc aag tcc ctg gcc cag cag ttg aca agg gag gcc act caa gcg gaa      2551
Thr Lys Ser Leu Ala Gln Gln Leu Thr Arg Glu Ala Thr Gln Ala Glu
            825                     830                     835 att gaa gca gat agg tct tat cag cac agt ctc cgc ctc ctg gat tca      2599
Ile Glu Ala Asp Arg Ser Tyr Gln His Ser Leu Arg Leu Leu Asp Ser
840                     845                     850 gtg tct ccg ctt cag gga gtc agt gat cag tcc ttt cag gtg gaa gaa      2647
Val Ser Pro Leu Gln Gly Val Ser Asp Gln Ser Phe Gln Val Glu Glu
855                     860                     865                     870 gca aag agg atc aaa caa aaa gcg gat tca ctc tca agc ctg gta acc      2695
Ala Lys Arg Ile Lys Gln Lys Ala Asp Ser Leu Ser Ser Leu Val Thr
            875                     880                     885 agg cat atg gat gag ttc aag cgt aca caa aag aat ctg gga aac tgg      2743
```

```
                                                         -continued

Arg His Met Asp Glu Phe Lys Arg Thr Gln Lys Asn Leu Gly Asn Trp
            890                 895                 900 aaa gaa gaa gca cag cag ctc tta cag aat gga aaa agt ggg aga gag     2791
Lys Glu Glu Ala Gln Gln Leu Leu Gln Asn Gly Lys Ser Gly Arg Glu
        905                 910                 915 aaa tca gat cag ctg ctt tcc cgt gcc aat ctt gct aaa agc aga gca     2839
Lys Ser Asp Gln Leu Leu Ser Arg Ala Asn Leu Ala Lys Ser Arg Ala
    920                 925                 930 caa gaa gca ctg agt atg ggc aat gcc act ttt tat gaa gtt gag agc     2887
Gln Glu Ala Leu Ser Met Gly Asn Ala Thr Phe Tyr Glu Val Glu Ser
935                 940                 945                 950 atc ctt aaa aac ctc aga gag ttt gac ctg cag gtg gac aac aga aaa     2935
Ile Leu Lys Asn Leu Arg Glu Phe Asp Leu Gln Val Asp Asn Arg Lys
                955                 960                 965 gca gaa gct gaa gaa gcc atg aag aga ctc tcc tac atc agc cag aag     2983
Ala Glu Ala Glu Glu Ala Met Lys Arg Leu Ser Tyr Ile Ser Gln Lys
            970                 975                 980 gtt tca gat gcc agt gac aag acc cag caa gca gaa aga gcc ctg ggg     3031
Val Ser Asp Ala Ser Asp Lys Thr Gln Gln Ala Glu Arg Ala Leu Gly
        985                 990                 995 agc gct gct gct gat gca cag agg gca aag aat ggg gcc ggg gag gcc     3079
Ser Ala Ala Ala Asp Ala Gln Arg Ala Lys Asn Gly Ala Gly Glu Ala
    1000                1005                1010 ctg gaa atc tcc agt gag att gaa cag gag att ggg agt ctg aac ttg     3127
Leu Glu Ile Ser Ser Glu Ile Glu Gln Glu Ile Gly Ser Leu Asn Leu
1015                1020                1025                1030 gaa gcc aat gtg aca gca gat gga gcc ttg gcc atg gaa aag gga ctg     3175
Glu Ala Asn Val Thr Ala Asp Gly Ala Leu Ala Met Glu Lys Gly Leu
                1035                1040                1045 gcc tct ctg aag agt gag atg agg gaa gtg gaa gga gag ctg gaa agg     3223
Ala Ser Leu Lys Ser Glu Met Arg Glu Val Glu Gly Glu Leu Glu Arg
            1050                1055                1060 aag gag ctg gag ttt gac acg aat atg gat gca gta cag atg gtg att     3271
Lys Glu Leu Glu Phe Asp Thr Asn Met Asp Ala Val Gln Met Val Ile
        1065                1070                1075 aca gaa gcc cag aag gtt gat acc aga gcc aag aac gct ggg gtt aca     3319
Thr Glu Ala Gln Lys Val Asp Thr Arg Ala Lys Asn Ala Gly Val Thr
    1080                1085                1090 atc caa gac aca ctc aac aca tta gac ggc ctc ctg cat ctg atg gac     3367
Ile Gln Asp Thr Leu Asn Thr Leu Asp Gly Leu Leu His Leu Met Asp
1095                1100                1105                1110 cag cct ctc agt gta gat gaa gag ggg ctg gtc tta ctg gag cag aag     3415
Gln Pro Leu Ser Val Asp Glu Glu Gly Leu Val Leu Leu Glu Gln Lys
                1115                1120                1125 ctt tcc cga gcc aag acc cag atc aac agc caa ctg cgg ccc atg atg     3463
Leu Ser Arg Ala Lys Thr Gln Ile Asn Ser Gln Leu Arg Pro Met Met
            1130                1135                1140 tca gag ctg gaa gag agg gca cgt cag cag agg ggc cac ctc cat ttg     3511
Ser Glu Leu Glu Glu Arg Ala Arg Gln Gln Arg Gly His Leu His Leu
        1145                1150                1155 ctg gag aca agc ata gat ggg att ctg gct gat gtg aag aac ttg gag     3559
Leu Glu Thr Ser Ile Asp Gly Ile Leu Ala Asp Val Lys Asn Leu Glu
    1160                1165                1170 aac att agg gac aac ctg ccc cca ggc tgc tac aat acc cag gct ctt     3607
Asn Ile Arg Asp Asn Leu Pro Pro Gly Cys Tyr Asn Thr Gln Ala Leu
1175                1180                1185                1190 gag caa cag tgaagctgcc ataaatattt ctcaactgag gttcttggga             3656
Glu Gln Gln tacagatctc agggctcggg agccatgtca tgtgagtggg tgggatgggg acatttgaac   3716
``` atgt                                                                                        3720

<210> SEQ ID NO 30
<211> LENGTH: 1193
<212> TYPE: PRT
<213> ORGANISM: Homo sapiens

<400> SEQUENCE: 30

```
Met Pro Ala Leu Trp Leu Gly Cys Cys Leu Cys Phe Ser Leu Leu Leu
 1               5                  10                  15

Pro Ala Ala Arg Ala Thr Ser Arg Arg Glu Val Cys Asp Cys Asn Gly
            20                  25                  30

Lys Ser Arg Gln Cys Ile Phe Asp Arg Glu Leu His Arg Gln Thr Gly
    35                  40                  45

Asn Gly Phe Arg Cys Leu Asn Cys Asn Asp Thr Asp Gly Ile His
50                  55                  60

Cys Glu Lys Cys Lys Asn Gly Phe Tyr Arg His Arg Glu Arg Asp Arg
65                  70                  75                  80

Cys Leu Pro Cys Asn Cys Asn Ser Lys Gly Ser Leu Ser Ala Arg Cys
                85                  90                  95

Asp Asn Ser Gly Arg Cys Ser Cys Lys Pro Gly Val Thr Gly Ala Arg
            100                 105                 110

Cys Asp Arg Cys Leu Pro Gly Phe His Met Leu Thr Asp Ala Gly Cys
        115                 120                 125

Thr Gln Asp Gln Arg Leu Leu Asp Ser Lys Cys Asp Cys Asp Pro Ala
    130                 135                 140

Gly Ile Ala Gly Pro Cys Asp Ala Gly Arg Cys Val Cys Lys Pro Ala
145                 150                 155                 160

Val Thr Gly Glu Arg Cys Asp Gly Cys Arg Ser Gly Tyr Tyr Asn Leu
                165                 170                 175

Asp Gly Gly Asn Pro Glu Gly Cys Thr Gln Cys Phe Cys Tyr Gly His
            180                 185                 190

Ser Ala Ser Cys Arg Ser Ser Ala Glu Tyr Ser Val His Lys Ile Thr
        195                 200                 205

Ser Thr Phe His Gln Asp Val Asp Gly Trp Lys Ala Val Gln Arg Asn
    210                 215                 220

Gly Ser Pro Ala Lys Leu Gln Trp Ser Gln Arg His Gln Asp Val Phe
225                 230                 235                 240

Ser Ser Ala Gln Arg Leu Asp Pro Val Tyr Phe Val Ala Pro Ala Lys
                245                 250                 255

Phe Leu Gly Asn Gln Gln Val Ser Tyr Gly Gln Ser Leu Ser Phe Asp
            260                 265                 270

Tyr Arg Val Asp Arg Gly Gly Arg His Pro Ser Ala His Asp Val Ile
        275                 280                 285

Leu Glu Gly Ala Gly Leu Arg Ile Thr Ala Pro Leu Met Pro Leu Gly
    290                 295                 300

Lys Thr Leu Pro Cys Gly Leu Thr Lys Thr Tyr Thr Phe Arg Leu Asn
305                 310                 315                 320

Glu His Pro Ser Asn Asn Trp Ser Pro Gln Leu Ser Tyr Phe Glu Tyr
                325                 330                 335

Arg Arg Leu Leu Arg Asn Leu Thr Ala Leu Arg Ile Arg Ala Thr Tyr
            340                 345                 350

Gly Glu Tyr Ser Thr Gly Tyr Ile Asp Asn Val Thr Leu Ile Ser Ala
        355                 360                 365
```

```
Arg Pro Val Ser Gly Ala Pro Ala Pro Trp Val Glu Gln Cys Ile Cys
    370                 375                 380
Pro Val Gly Tyr Lys Gly Gln Phe Cys Gln Asp Cys Ala Ser Gly Tyr
385                 390                 395                 400
Lys Arg Asp Ser Ala Arg Leu Gly Pro Phe Gly Thr Cys Ile Pro Cys
                405                 410                 415
Asn Cys Gln Gly Gly Ala Cys Asp Pro Asp Thr Gly Asp Cys Tyr
                420                 425                 430
Ser Gly Asp Glu Asn Pro Asp Ile Glu Cys Ala Asp Cys Pro Ile Gly
            435                 440                 445
Phe Tyr Asn Asp Pro His Asp Pro Arg Ser Cys Lys Pro Cys Pro Cys
        450                 455                 460
His Asn Gly Phe Ser Cys Ser Val Met Pro Glu Thr Glu Val Val
465                 470                 475                 480
Cys Asn Asn Cys Pro Pro Gly Val Thr Gly Ala Arg Cys Glu Leu Cys
                485                 490                 495
Ala Asp Gly Tyr Phe Gly Asp Pro Phe Gly Glu His Gly Pro Val Arg
            500                 505                 510
Pro Cys Gln Pro Cys Gln Cys Asn Asn Asn Val Asp Pro Ser Ala Ser
        515                 520                 525
Gly Asn Cys Asp Arg Leu Thr Gly Arg Cys Leu Lys Cys Ile His Asn
    530                 535                 540
Thr Ala Gly Ile Tyr Cys Asp Gln Cys Lys Ala Gly Tyr Phe Gly Asp
545                 550                 555                 560
Pro Leu Ala Pro Asn Pro Ala Asp Lys Cys Arg Ala Cys Asn Cys Asn
                565                 570                 575
Pro Met Gly Ser Glu Pro Val Gly Cys Arg Ser Asp Gly Thr Cys Val
            580                 585                 590
Cys Lys Pro Gly Phe Gly Gly Pro Asn Cys Glu His Gly Ala Phe Ser
        595                 600                 605
Cys Pro Ala Cys Tyr Asn Gln Val Lys Ile Gln Met Asp Gln Phe Met
    610                 615                 620
Gln Gln Leu Gln Arg Met Glu Ala Leu Ile Ser Lys Ala Gln Gly Gly
625                 630                 635                 640
Asp Gly Val Val Pro Asp Thr Glu Leu Glu Gly Arg Met Gln Gln Ala
                645                 650                 655
Glu Gln Ala Leu Gln Asp Ile Leu Arg Asp Ala Gln Ile Ser Glu Gly
            660                 665                 670
Ala Ser Arg Ser Leu Gly Leu Gln Leu Ala Lys Val Arg Ser Gln Glu
        675                 680                 685
Asn Ser Tyr Gln Ser Arg Leu Asp Asp Leu Lys Met Thr Val Glu Arg
    690                 695                 700
Val Arg Ala Leu Gly Ser Gln Tyr Gln Asn Arg Val Arg Asp Thr His
705                 710                 715                 720
Arg Leu Ile Thr Gln Met Gln Leu Ser Leu Ala Glu Ser Glu Ala Ser
                725                 730                 735
Leu Gly Asn Thr Asn Ile Pro Ala Ser Asp His Tyr Val Gly Pro Asn
            740                 745                 750
Gly Phe Lys Ser Leu Ala Gln Glu Ala Thr Arg Leu Ala Glu Ser His
        755                 760                 765
Val Glu Ser Ala Ser Asn Met Glu Gln Leu Thr Arg Glu Thr Glu Asp
770                 775                 780
```

-continued

```
Tyr Ser Lys Gln Ala Leu Ser Leu Val Arg Lys Ala Leu His Glu Gly
785                 790                 795                 800

Val Gly Ser Gly Ser Gly Ser Pro Asp Gly Ala Val Val Gln Gly Leu
            805                 810                 815

Val Glu Lys Leu Glu Lys Thr Lys Ser Leu Ala Gln Gln Leu Thr Arg
            820                 825                 830

Glu Ala Thr Gln Ala Glu Ile Glu Ala Asp Arg Ser Tyr Gln His Ser
            835                 840                 845

Leu Arg Leu Leu Asp Ser Val Ser Pro Leu Gln Gly Val Ser Asp Gln
850                 855                 860

Ser Phe Gln Val Glu Glu Ala Lys Arg Ile Lys Gln Lys Ala Asp Ser
865                 870                 875                 880

Leu Ser Ser Leu Val Thr Arg His Met Asp Glu Phe Lys Arg Thr Gln
                885                 890                 895

Lys Asn Leu Gly Asn Trp Lys Glu Glu Ala Gln Gln Leu Leu Gln Asn
            900                 905                 910

Gly Lys Ser Gly Arg Glu Lys Ser Asp Gln Leu Leu Ser Arg Ala Asn
            915                 920                 925

Leu Ala Lys Ser Arg Ala Gln Glu Ala Leu Ser Met Gly Asn Ala Thr
930                 935                 940

Phe Tyr Glu Val Glu Ser Ile Leu Lys Asn Leu Arg Glu Phe Asp Leu
945                 950                 955                 960

Gln Val Asp Asn Arg Lys Ala Glu Ala Glu Ala Met Lys Arg Leu
                965                 970                 975

Ser Tyr Ile Ser Gln Lys Val Ser Asp Ala Ser Asp Lys Thr Gln Gln
            980                 985                 990

Ala Glu Arg Ala Leu Gly Ser Ala Ala Asp Ala Gln Arg Ala Lys
            995                 1000                1005

Asn Gly Ala Gly Glu Ala Leu Gly Ile Ser Ser Glu Ile Glu Gln Glu
        1010                1015                1020

Ile Gly Ser Leu Asn Leu Glu Ala Asn Val Thr Ala Asp Gly Ala Leu
1025                1030                1035                1040

Ala Met Glu Lys Gly Leu Ala Ser Leu Lys Ser Glu Met Arg Glu Val
                1045                1050                1055

Glu Gly Glu Leu Glu Arg Lys Leu Glu Phe Asp Thr Asn Met Asp
            1060                1065                1070

Ala Val Gln Met Val Ile Thr Glu Ala Gln Lys Val Asp Thr Arg Ala
        1075                1080                1085

Lys Asn Ala Gly Val Thr Ile Gln Asp Thr Leu Asn Thr Leu Asp Gly
    1090                1095                1100

Leu Leu His Leu Met Asp Gln Pro Leu Ser Val Asp Glu Glu Gly Leu
1105                1110                1115                1120

Val Leu Leu Glu Gln Lys Leu Ser Arg Ala Lys Thr Gln Ile Asn Ser
                1125                1130                1135

Gln Leu Arg Pro Met Met Ser Glu Leu Glu Glu Arg Ala Arg Gln Gln
            1140                1145                1150

Arg Gly His Leu His Leu Leu Glu Thr Ser Ile Asp Gly Ile Leu Ala
        1155                1160                1165

Asp Val Lys Asn Leu Glu Asn Ile Arg Asp Asn Leu Pro Pro Gly Cys
    1170                1175                1180

Tyr Asn Thr Gln Ala Leu Glu Gln Gln
1185                1190
```

```
<210> SEQ ID NO 31
<211> LENGTH: 3620
<212> TYPE: DNA
<213> ORGANISM: Homo sapiens
<220> FEATURE:
<221> NAME/KEY: CDS
<222> LOCATION: (1)..(3516)

<400> SEQUENCE: 31
```

| | | | | | | | | | | | | | | | | |
|---|---|---|---|---|---|---|---|---|---|---|---|---|---|---|---|---|
| acc | tcc | agg | agg | gaa | gtc | tgt | gat | tgc | aat | ggg | aag | tcc | agg | cag | tgt | 48 |
| Thr | Ser | Arg | Arg | Glu | Val | Cys | Asp | Cys | Asn | Gly | Lys | Ser | Arg | Gln | Cys | |
| 1 | | | | 5 | | | | | 10 | | | | | 15 | | |
| atc | ttt | gat | cgg | gaa | ctt | cac | aga | caa | act | ggt | aat | gga | ttc | cgc | tgc | 96 |
| Ile | Phe | Asp | Arg | Glu | Leu | His | Arg | Gln | Thr | Gly | Asn | Gly | Phe | Arg | Cys | |
| | | | 20 | | | | | 25 | | | | | 30 | | | |
| ctc | aac | tgc | aat | gac | aac | act | gat | ggc | att | cac | tgc | gag | aag | tgc | aag | 144 |
| Leu | Asn | Cys | Asn | Asp | Asn | Thr | Asp | Gly | Ile | His | Cys | Glu | Lys | Cys | Lys | |
| | | 35 | | | | | 40 | | | | | 45 | | | | |
| aat | ggc | ttt | tac | cgg | cac | aga | gaa | agg | gac | cgc | tgt | ttg | ccc | tgc | aat | 192 |
| Asn | Gly | Phe | Tyr | Arg | His | Arg | Glu | Arg | Asp | Arg | Cys | Leu | Pro | Cys | Asn | |
| | 50 | | | | | 55 | | | | | 60 | | | | | |
| tgt | aac | tcc | aaa | ggt | tct | ctt | agt | gct | cga | tgt | gac | aac | tct | gga | cgg | 240 |
| Cys | Asn | Ser | Lys | Gly | Ser | Leu | Ser | Ala | Arg | Cys | Asp | Asn | Ser | Gly | Arg | |
| 65 | | | | | 70 | | | | | 75 | | | | | 80 | |
| tgc | agc | tgt | aaa | cca | ggt | gtg | aca | gga | gcc | aga | tgc | gac | cga | tgt | ctg | 288 |
| Cys | Ser | Cys | Lys | Pro | Gly | Val | Thr | Gly | Ala | Arg | Cys | Asp | Arg | Cys | Leu | |
| | | | | 85 | | | | | 90 | | | | | 95 | | |
| cca | ggc | ttc | cac | atg | ctc | acg | gat | gcg | ggg | tgc | acc | caa | gac | cag | aga | 336 |
| Pro | Gly | Phe | His | Met | Leu | Thr | Asp | Ala | Gly | Cys | Thr | Gln | Asp | Gln | Arg | |
| | | | 100 | | | | | 105 | | | | | 110 | | | |
| ctg | cta | gac | tcc | aag | tgt | gac | tgt | gac | cca | gct | ggc | atc | gca | ggg | ccc | 384 |
| Leu | Leu | Asp | Ser | Lys | Cys | Asp | Cys | Asp | Pro | Ala | Gly | Ile | Ala | Gly | Pro | |
| | | 115 | | | | | 120 | | | | | 125 | | | | |
| tgt | gac | gcg | ggc | cgc | tgt | gtc | tgc | aag | cca | gct | gtt | act | gga | gaa | cgc | 432 |
| Cys | Asp | Ala | Gly | Arg | Cys | Val | Cys | Lys | Pro | Ala | Val | Thr | Gly | Glu | Arg | |
| | 130 | | | | | 135 | | | | | 140 | | | | | |
| tgt | gat | ggg | tgt | cga | tca | ggt | tac | tat | aat | ctg | gat | ggg | ggg | aac | cct | 480 |
| Cys | Asp | Gly | Cys | Arg | Ser | Gly | Tyr | Tyr | Asn | Leu | Asp | Gly | Gly | Asn | Pro | |
| 145 | | | | | 150 | | | | | 155 | | | | | 160 | |
| gag | ggc | tgt | acc | cag | tgt | ttc | tgc | tat | ggg | cat | tca | gcc | agc | tgc | cgc | 528 |
| Glu | Gly | Cys | Thr | Gln | Cys | Phe | Cys | Tyr | Gly | His | Ser | Ala | Ser | Cys | Arg | |
| | | | | 165 | | | | | 170 | | | | | 175 | | |
| agc | tct | gca | gaa | tac | agt | gtc | cat | aag | atc | acc | tct | acc | ttt | cat | caa | 576 |
| Ser | Ser | Ala | Glu | Tyr | Ser | Val | His | Lys | Ile | Thr | Ser | Thr | Phe | His | Gln | |
| | | | 180 | | | | | 185 | | | | | 190 | | | |
| gat | gtt | gat | ggc | tgg | aag | gct | gtc | caa | cga | aat | ggg | tct | cct | gca | aag | 624 |
| Asp | Val | Asp | Gly | Trp | Lys | Ala | Val | Gln | Arg | Asn | Gly | Ser | Pro | Ala | Lys | |
| | | 195 | | | | | 200 | | | | | 205 | | | | |
| ctc | caa | tgg | tca | cag | cgc | cat | caa | gat | gtg | ttt | agc | tca | gcc | caa | cga | 672 |
| Leu | Gln | Trp | Ser | Gln | Arg | His | Gln | Asp | Val | Phe | Ser | Ser | Ala | Gln | Arg | |
| | 210 | | | | | 215 | | | | | 220 | | | | | |
| cta | gac | cct | gtc | tat | ttt | gtg | gct | cct | gcc | aaa | ttt | ctt | ggg | aat | caa | 720 |
| Leu | Asp | Pro | Val | Tyr | Phe | Val | Ala | Pro | Ala | Lys | Phe | Leu | Gly | Asn | Gln | |
| 225 | | | | | 230 | | | | | 235 | | | | | 240 | |
| cag | gtg | agc | tat | ggg | caa | agc | ctg | tcc | ttt | gac | tac | cgt | gtg | gac | aga | 768 |
| Gln | Val | Ser | Tyr | Gly | Gln | Ser | Leu | Ser | Phe | Asp | Tyr | Arg | Val | Asp | Arg | |
| | | | | 245 | | | | | 250 | | | | | 255 | | |
| gga | ggc | aga | cac | cca | tct | gcc | cat | gat | gtg | att | ctg | gaa | ggt | gct | ggt | 816 |
| Gly | Gly | Arg | His | Pro | Ser | Ala | His | Asp | Val | Ile | Leu | Glu | Gly | Ala | Gly | |
| | | | 260 | | | | | 265 | | | | | 270 | | | |
| cta | cgg | atc | aca | gct | ccc | ttg | atg | cca | ctt | ggc | aag | aca | ctg | cct | tgt | 864 |

```
                        -continued

Leu Arg Ile Thr Ala Pro Leu Met Pro Leu Gly Lys Thr Leu Pro Cys
        275                 280                 285 ggg ctc acc aag act tac aca ttc agg tta aat gag cat cca agc aat       912
Gly Leu Thr Lys Thr Tyr Thr Phe Arg Leu Asn Glu His Pro Ser Asn
        290                 295                 300 aat tgg agc ccc cag ctg agt tac ttt gag tat cga agg tta ctg cgg       960
Asn Trp Ser Pro Gln Leu Ser Tyr Phe Glu Tyr Arg Arg Leu Leu Arg
305                 310                 315                 320 aat ctc aca gcc ctc cgc atc cga gct aca tat gga gaa tac agt act      1008
Asn Leu Thr Ala Leu Arg Ile Arg Ala Thr Tyr Gly Glu Tyr Ser Thr
                325                 330                 335 ggg tac att gac aat gtg acc ctg att tca gcc cgc cct gtc tct gga      1056
Gly Tyr Ile Asp Asn Val Thr Leu Ile Ser Ala Arg Pro Val Ser Gly
                340                 345                 350 gcc cca gca ccc tgg gtt gaa cag tgt ata tgt cct gtt ggg tac aag      1104
Ala Pro Ala Pro Trp Val Glu Gln Cys Ile Cys Pro Val Gly Tyr Lys
                355                 360                 365 ggg caa ttc tgc cag gat tgt gct tct ggc tac aag aga gat tca gcg      1152
Gly Gln Phe Cys Gln Asp Cys Ala Ser Gly Tyr Lys Arg Asp Ser Ala
        370                 375                 380 aga ctg ggg cct ttt ggc acc tgt att cct tgt aac tgt caa ggg gga      1200
Arg Leu Gly Pro Phe Gly Thr Cys Ile Pro Cys Asn Cys Gln Gly Gly
385                 390                 395                 400 ggg gcc tgt gat cca gac aca gga gat tgt tat tca ggg gat gag aat      1248
Gly Ala Cys Asp Pro Asp Thr Gly Asp Cys Tyr Ser Gly Asp Glu Asn
                405                 410                 415 cct gac att gag tgt gct gac tgc cca att ggt ttc tac aac gat ccg      1296
Pro Asp Ile Glu Cys Ala Asp Cys Pro Ile Gly Phe Tyr Asn Asp Pro
                420                 425                 430 cac gac ccc cgc agc tgc aag cca tgt ccc tgt cat aac ggg ttc agc      1344
His Asp Pro Arg Ser Cys Lys Pro Cys Pro Cys His Asn Gly Phe Ser
                435                 440                 445 tgc tca gtg atg ccg gag acg gag gag gtg gtg tgc aat aac tgc cct      1392
Cys Ser Val Met Pro Glu Thr Glu Glu Val Val Cys Asn Asn Cys Pro
        450                 455                 460 ccc ggg gtc acc ggt gcc cgc tgt gag ctc tgt gct gat ggc tac ttt      1440
Pro Gly Val Thr Gly Ala Arg Cys Glu Leu Cys Ala Asp Gly Tyr Phe
465                 470                 475                 480 ggg gac ccc ttt ggt gaa cat ggc cca gtg agg cct tgt cag ccc tgt      1488
Gly Asp Pro Phe Gly Glu His Gly Pro Val Arg Pro Cys Gln Pro Cys
                485                 490                 495 caa tgc aac aac aat gtg gac ccc agt gcc tct ggg aat tgt gac cgg      1536
Gln Cys Asn Asn Asn Val Asp Pro Ser Ala Ser Gly Asn Cys Asp Arg
                500                 505                 510 ctg aca ggc agg tgt ttg aag tgt atc cac aac aca gcc ggc atc tac      1584
Leu Thr Gly Arg Cys Leu Lys Cys Ile His Asn Thr Ala Gly Ile Tyr
                515                 520                 525 tgc gac cag tgc aaa gca ggc tac ttc ggg gac cca ttg gct ccc aac      1632
Cys Asp Gln Cys Lys Ala Gly Tyr Phe Gly Asp Pro Leu Ala Pro Asn
        530                 535                 540 cca gca gac aag tgt cga gct tgc aac tgt aac ccc atg ggc tca gag      1680
Pro Ala Asp Lys Cys Arg Ala Cys Asn Cys Asn Pro Met Gly Ser Glu
545                 550                 555                 560 cct gta gga tgt cga agt gat ggc acc tgt gtt tgc aag cca gga ttt      1728
Pro Val Gly Cys Arg Ser Asp Gly Thr Cys Val Cys Lys Pro Gly Phe
                565                 570                 575 ggt ggc ccc aac tgt gag cat gga gca ttc agc tgt cca gct tgc tat      1776
Gly Gly Pro Asn Cys Glu His Gly Ala Phe Ser Cys Pro Ala Cys Tyr
                580                 585                 590
```

-continued

| | |
|---|---|
| aat caa gtg aag att cag atg gat cag ttt atg cag cag ctt cag aga<br>Asn Gln Val Lys Ile Gln Met Asp Gln Phe Met Gln Gln Leu Gln Arg<br>595 600 605 | 1824 |
| atg gag gcc ctg att tca aag gct cag ggt ggt gat gga gta gta cct<br>Met Glu Ala Leu Ile Ser Lys Ala Gln Gly Gly Asp Gly Val Val Pro<br>610 615 620 | 1872 |
| gat aca gag ctg gaa ggc agg atg cag cag gct gag cag gcc ctt cag<br>Asp Thr Glu Leu Glu Gly Arg Met Gln Gln Ala Glu Gln Ala Leu Gln<br>625 630 635 640 | 1920 |
| gac att ctg aga gat gcc cag att tca gaa ggt gct agc aga tcc ctt<br>Asp Ile Leu Arg Asp Ala Gln Ile Ser Glu Gly Ala Ser Arg Ser Leu<br>645 650 655 | 1968 |
| ggt ctc cag ttg gcc aag gtg agg agc caa gag aac agc tac cag agc<br>Gly Leu Gln Leu Ala Lys Val Arg Ser Gln Glu Asn Ser Tyr Gln Ser<br>660 665 670 | 2016 |
| cgc ctg gat gac ctc aag atg act gtg gaa aga gtt cgg gct ctg gga<br>Arg Leu Asp Asp Leu Lys Met Thr Val Glu Arg Val Arg Ala Leu Gly<br>675 680 685 | 2064 |
| agt cag tac cag aac cga gtt cgg gat act cac agg ctc atc act cag<br>Ser Gln Tyr Gln Asn Arg Val Arg Asp Thr His Arg Leu Ile Thr Gln<br>690 695 700 | 2112 |
| atg cag ctg agc ctg gca gaa agt gaa gct tcc ttg gga aac act aac<br>Met Gln Leu Ser Leu Ala Glu Ser Glu Ala Ser Leu Gly Asn Thr Asn<br>705 710 715 720 | 2160 |
| att cct gcc tca gac cac tac gtg ggg cca aat ggc ttt aaa agt ctg<br>Ile Pro Ala Ser Asp His Tyr Val Gly Pro Asn Gly Phe Lys Ser Leu<br>725 730 735 | 2208 |
| gct cag gag gcc aca aga tta gca gaa agc cac gtt gag tca gcc agt<br>Ala Gln Glu Ala Thr Arg Leu Ala Glu Ser His Val Glu Ser Ala Ser<br>740 745 750 | 2256 |
| aac atg gag caa ctg aca agg gaa act gag gac tat tcc aaa caa gcc<br>Asn Met Glu Gln Leu Thr Arg Glu Thr Glu Asp Tyr Ser Lys Gln Ala<br>755 760 765 | 2304 |
| ctc tca ctg gtg cgc aag gcc ctg cat gaa gga gtc gga agc gga agc<br>Leu Ser Leu Val Arg Lys Ala Leu His Glu Gly Val Gly Ser Gly Ser<br>770 775 780 | 2352 |
| ggt agc ccg gac ggt gct gtg gtg caa ggg ctt gtg gaa aaa ttg gag<br>Gly Ser Pro Asp Gly Ala Val Val Gln Gly Leu Val Glu Lys Leu Glu<br>785 790 795 800 | 2400 |
| aaa acc aag tcc ctg gcc cag cag ttg aca agg gag gcc act caa gcg<br>Lys Thr Lys Ser Leu Ala Gln Gln Leu Thr Arg Glu Ala Thr Gln Ala<br>805 810 815 | 2448 |
| gaa att gaa gca gat agg tct tat cag cac agt ctc cgc ctc ctg gat<br>Glu Ile Glu Ala Asp Arg Ser Tyr Gln His Ser Leu Arg Leu Leu Asp<br>820 825 830 | 2496 |
| tca gtg tct ccg ctt cag gga gtc agt gat cag tcc ttt cag gtg gaa<br>Ser Val Ser Pro Leu Gln Gly Val Ser Asp Gln Ser Phe Gln Val Glu<br>835 840 845 | 2544 |
| gaa gca aag agg atc aaa caa aaa gcg gat tca ctc tca agc ctg gta<br>Glu Ala Lys Arg Ile Lys Gln Lys Ala Asp Ser Leu Ser Ser Leu Val<br>850 855 860 | 2592 |
| acc agg cat atg gat gag ttc aag cgt aca caa aag aat ctg gga aac<br>Thr Arg His Met Asp Glu Phe Lys Arg Thr Gln Lys Asn Leu Gly Asn<br>865 870 875 880 | 2640 |
| tgg aaa gaa gaa gca cag cag ctc tta cag aat gga aaa agt ggg aga<br>Trp Lys Glu Glu Ala Gln Gln Leu Leu Gln Asn Gly Lys Ser Gly Arg<br>885 890 895 | 2688 |
| gag aaa tca gat cag ctg ctt tcc cgt gcc aat ctt gct aaa agc aga<br>Glu Lys Ser Asp Gln Leu Leu Ser Arg Ala Asn Leu Ala Lys Ser Arg<br>900 905 910 | 2736 |

```
gca caa gaa gca ctg agt atg ggc aat gcc act ttt tat gaa gtt gag    2784
Ala Gln Glu Ala Leu Ser Met Gly Asn Ala Thr Phe Tyr Glu Val Glu
            915                 920                 925 agc atc ctt aaa aac ctc aga gag ttt gac ctg cag gtg gac aac aga    2832
Ser Ile Leu Lys Asn Leu Arg Glu Phe Asp Leu Gln Val Asp Asn Arg
        930                 935                 940 aaa gca gaa gct gaa gaa gcc atg aag aga ctc tcc tac atc agc cag    2880
Lys Ala Glu Ala Glu Glu Ala Met Lys Arg Leu Ser Tyr Ile Ser Gln
945                 950                 955                 960 aag gtt tca gat gcc agt gac aag acc cag caa gca gaa aga gcc ctg    2928
Lys Val Ser Asp Ala Ser Asp Lys Thr Gln Gln Ala Glu Arg Ala Leu
                965                 970                 975 ggg agc gct gct gct gat gca cag agg gca aag aat ggg gcc ggg gag    2976
Gly Ser Ala Ala Ala Asp Ala Gln Arg Ala Lys Asn Gly Ala Gly Glu
            980                 985                 990 gcc ctg gaa atc tcc agt gag att gaa cag gag att ggg agt ctg aac    3024
Ala Leu Glu Ile Ser Ser Glu Ile Glu Gln Glu Ile Gly Ser Leu Asn
        995                 1000                1005 ttg gaa gcc aat gtg aca gca gat gga gcc ttg gcc atg gaa aag gga    3072
Leu Glu Ala Asn Val Thr Ala Asp Gly Ala Leu Ala Met Glu Lys Gly
    1010                1015                1020 ctg gcc tct ctg aag agt gag atg agg gaa gtg gaa gga gag ctg gaa    3120
Leu Ala Ser Leu Lys Ser Glu Met Arg Glu Val Glu Gly Glu Leu Glu
1025                1030                1035                1040 agg aag gag ctg gag ttt gac acg aat atg gat gca gta cag atg gtg    3168
Arg Lys Glu Leu Glu Phe Asp Thr Asn Met Asp Ala Val Gln Met Val
                1045                1050                1055 att aca gaa gcc cag aag gtt gat acc aga gcc aag aac gct ggg gtt    3216
Ile Thr Glu Ala Gln Lys Val Asp Thr Arg Ala Lys Asn Ala Gly Val
            1060                1065                1070 aca atc caa gac aca ctc aac aca tta gac ggc ctc ctg cat ctg atg    3264
Thr Ile Gln Asp Thr Leu Asn Thr Leu Asp Gly Leu Leu His Leu Met
        1075                1080                1085 gac cag cct ctc agt gta gat gaa gag ggg ctg gtc tta ctg gag cag    3312
Asp Gln Pro Leu Ser Val Asp Glu Glu Gly Leu Val Leu Leu Glu Gln
    1090                1095                1100 aag ctt tcc cga gcc aag acc cag atc aac agc caa ctg cgg ccc atg    3360
Lys Leu Ser Arg Ala Lys Thr Gln Ile Asn Ser Gln Leu Arg Pro Met
1105                1110                1115                1120 atg tca gag ctg gaa gag agg gca cgt cag cag agg ggc cac ctc cat    3408
Met Ser Glu Leu Glu Glu Arg Ala Arg Gln Gln Arg Gly His Leu His
                1125                1130                1135 ttg ctg gag aca agc ata gat ggg att ctg gct gat gtg aag aac ttg    3456
Leu Leu Glu Thr Ser Ile Asp Gly Ile Leu Ala Asp Val Lys Asn Leu
            1140                1145                1150 gag aac att agg gac aac ctg ccc cca ggc tgc tac aat acc cag gct    3504
Glu Asn Ile Arg Asp Asn Leu Pro Pro Gly Cys Tyr Asn Thr Gln Ala
        1155                1160                1165 ctt gag caa cag tgaagctgcc ataaatattt ctcaactgag gttcttggga       3556
Leu Glu Gln Gln
    1170 tacagatctc agggctcggg agccatgtca tgtgagtggg tgggatgggg acatttgaac 3616 atgt                                                              3620

<210> SEQ ID NO 32
<211> LENGTH: 1172
<212> TYPE: PRT
<213> ORGANISM: Homo sapiens
```

```
<400> SEQUENCE: 32

Thr Ser Arg Arg Glu Val Cys Asp Cys Asn Gly Lys Ser Arg Gln Cys
 1               5                  10                  15

Ile Phe Asp Arg Glu Leu His Arg Gln Thr Gly Asn Gly Phe Arg Cys
            20                  25                  30

Leu Asn Cys Asn Asp Asn Thr Asp Gly Ile His Cys Glu Lys Cys Lys
        35                  40                  45

Asn Gly Phe Tyr Arg His Arg Glu Arg Asp Arg Cys Leu Pro Cys Asn
    50                  55                  60

Cys Asn Ser Lys Gly Ser Leu Ser Ala Arg Cys Asp Asn Ser Gly Arg
65              70                  75                  80

Cys Ser Cys Lys Pro Gly Val Thr Gly Ala Arg Cys Asp Arg Cys Leu
                85                  90                  95

Pro Gly Phe His Met Leu Thr Asp Ala Gly Cys Thr Gln Asp Gln Arg
            100                 105                 110

Leu Leu Asp Ser Lys Cys Asp Cys Asp Pro Ala Gly Ile Ala Gly Pro
        115                 120                 125

Cys Asp Ala Gly Arg Cys Val Cys Lys Pro Ala Val Thr Gly Glu Arg
130                 135                 140

Cys Asp Gly Cys Arg Ser Gly Tyr Tyr Asn Leu Asp Gly Gly Asn Pro
145                 150                 155                 160

Glu Gly Cys Thr Gln Cys Phe Cys Tyr Gly His Ser Ala Ser Cys Arg
                165                 170                 175

Ser Ser Ala Glu Tyr Ser Val His Lys Ile Thr Ser Thr Phe His Gln
            180                 185                 190

Asp Val Asp Gly Trp Lys Ala Val Gln Arg Asn Gly Ser Pro Ala Lys
        195                 200                 205

Leu Gln Trp Ser Gln Arg His Gln Asp Val Phe Ser Ser Ala Gln Arg
    210                 215                 220

Leu Asp Pro Val Tyr Phe Val Ala Pro Ala Lys Phe Leu Gly Asn Gln
225                 230                 235                 240

Gln Val Ser Tyr Gly Gln Ser Leu Ser Phe Asp Tyr Arg Val Asp Arg
                245                 250                 255

Gly Gly Arg His Pro Ser Ala His Asp Val Ile Leu Glu Gly Ala Gly
            260                 265                 270

Leu Arg Ile Thr Ala Pro Leu Met Pro Leu Gly Lys Thr Leu Pro Cys
        275                 280                 285

Gly Leu Thr Lys Thr Tyr Thr Phe Arg Leu Asn Glu His Pro Ser Asn
    290                 295                 300

Asn Trp Ser Pro Gln Leu Ser Tyr Phe Glu Tyr Arg Arg Leu Leu Arg
305                 310                 315                 320

Asn Leu Thr Ala Leu Arg Ile Arg Ala Thr Tyr Gly Glu Tyr Ser Thr
                325                 330                 335

Gly Tyr Ile Asp Asn Val Thr Leu Ile Ser Ala Arg Pro Val Ser Gly
            340                 345                 350

Ala Pro Ala Pro Trp Val Glu Gln Cys Ile Cys Pro Val Gly Tyr Lys
        355                 360                 365

Gly Gln Phe Cys Gln Asp Cys Ala Ser Gly Tyr Lys Arg Asp Ser Ala
    370                 375                 380

Arg Leu Gly Pro Phe Gly Thr Cys Ile Pro Cys Asn Cys Gln Gly Gly
385                 390                 395                 400

Gly Ala Cys Asp Pro Asp Thr Gly Asp Cys Tyr Ser Gly Asp Glu Asn
                405                 410                 415
```

```
Pro Asp Ile Glu Cys Ala Asp Cys Pro Ile Gly Phe Tyr Asn Asp Pro
            420                 425                 430

His Asp Pro Arg Ser Cys Lys Pro Cys Pro Cys His Asn Gly Phe Ser
        435                 440                 445

Cys Ser Val Met Pro Glu Thr Glu Val Val Cys Asn Asn Cys Pro
    450                 455                 460

Pro Gly Val Thr Gly Ala Arg Cys Glu Leu Cys Ala Asp Gly Tyr Phe
465                 470                 475                 480

Gly Asp Pro Phe Gly Glu His Gly Pro Val Arg Pro Cys Gln Pro Cys
                485                 490                 495

Gln Cys Asn Asn Asn Val Asp Pro Ser Ala Ser Gly Asn Cys Asp Arg
            500                 505                 510

Leu Thr Gly Arg Cys Leu Lys Cys Ile His Asn Thr Ala Gly Ile Tyr
        515                 520                 525

Cys Asp Gln Cys Lys Ala Gly Tyr Phe Gly Asp Pro Leu Ala Pro Asn
    530                 535                 540

Pro Ala Asp Lys Cys Arg Ala Cys Asn Cys Asn Pro Met Gly Ser Glu
545                 550                 555                 560

Pro Val Gly Cys Arg Ser Asp Gly Thr Cys Val Cys Lys Pro Gly Phe
                565                 570                 575

Gly Gly Pro Asn Cys Glu His Gly Ala Phe Ser Cys Pro Ala Cys Tyr
            580                 585                 590

Asn Gln Val Lys Ile Gln Met Asp Gln Phe Met Gln Gln Leu Gln Arg
        595                 600                 605

Met Glu Ala Leu Ile Ser Lys Ala Gln Gly Gly Asp Gly Val Val Pro
    610                 615                 620

Asp Thr Glu Leu Glu Gly Arg Met Gln Gln Ala Glu Gln Ala Leu Gln
625                 630                 635                 640

Asp Ile Leu Arg Asp Ala Gln Ile Ser Glu Gly Ala Ser Arg Ser Leu
                645                 650                 655

Gly Leu Gln Leu Ala Lys Val Arg Ser Gln Glu Asn Ser Tyr Gln Ser
            660                 665                 670

Arg Leu Asp Asp Leu Lys Met Thr Val Glu Arg Val Arg Ala Leu Gly
        675                 680                 685

Ser Gln Tyr Gln Asn Arg Val Arg Asp Thr His Arg Leu Ile Thr Gln
    690                 695                 700

Met Gln Leu Ser Leu Ala Glu Ser Glu Ala Ser Leu Gly Asn Thr Asn
705                 710                 715                 720

Ile Pro Ala Ser Asp His Tyr Val Gly Pro Asn Gly Phe Lys Ser Leu
                725                 730                 735

Ala Gln Glu Ala Thr Arg Leu Ala Glu Ser His Val Glu Ser Ala Ser
            740                 745                 750

Asn Met Glu Gln Leu Thr Arg Glu Thr Glu Asp Tyr Ser Lys Gln Ala
        755                 760                 765

Leu Ser Leu Val Arg Lys Ala Leu His Glu Gly Val Gly Ser Gly Ser
    770                 775                 780

Gly Ser Pro Asp Gly Ala Val Val Gln Gly Leu Val Glu Lys Leu Glu
785                 790                 795                 800

Lys Thr Lys Ser Leu Ala Gln Gln Leu Thr Arg Glu Ala Thr Gln Ala
                805                 810                 815

Glu Ile Glu Ala Asp Arg Ser Tyr Gln His Ser Leu Arg Leu Leu Asp
            820                 825                 830
```

```
Ser Val Ser Pro Leu Gln Gly Val Ser Asp Gln Ser Phe Gln Val Glu
        835                 840                 845

Glu Ala Lys Arg Ile Lys Gln Lys Ala Asp Ser Leu Ser Ser Leu Val
        850                 855                 860

Thr Arg His Met Asp Glu Phe Lys Arg Thr Gln Lys Asn Leu Gly Asn
865                 870                 875                 880

Trp Lys Glu Glu Ala Gln Gln Leu Leu Gln Asn Gly Lys Ser Gly Arg
                885                 890                 895

Glu Lys Ser Asp Gln Leu Leu Ser Arg Ala Asn Leu Ala Lys Ser Arg
            900                 905                 910

Ala Gln Glu Ala Leu Ser Met Gly Asn Ala Thr Phe Tyr Glu Val Glu
        915                 920                 925

Ser Ile Leu Lys Asn Leu Arg Glu Phe Asp Leu Gln Val Asp Asn Arg
    930                 935                 940

Lys Ala Glu Ala Glu Ala Met Lys Arg Leu Ser Tyr Ile Ser Gln
945                 950                 955                 960

Lys Val Ser Asp Ala Ser Asp Lys Thr Gln Gln Ala Glu Arg Ala Leu
                965                 970                 975

Gly Ser Ala Ala Asp Ala Gln Arg Ala Lys Asn Gly Ala Gly Glu
            980                 985                 990

Ala Leu Glu Ile Ser Ser Glu Ile Glu Gln Glu Ile Gly Ser Leu Asn
        995                1000                1005

Leu Glu Ala Asn Val Thr Ala Asp Gly Ala Leu Ala Met Glu Lys Gly
    1010                1015                1020

Leu Ala Ser Leu Lys Ser Glu Met Arg Glu Val Glu Gly Leu Glu
1025                1030                1035                1040

Arg Lys Glu Leu Glu Phe Asp Thr Asn Met Asp Ala Val Gln Met Val
                1045                1050                1055

Ile Thr Glu Ala Gln Lys Val Asp Thr Arg Ala Lys Asn Ala Gly Val
            1060                1065                1070

Thr Ile Gln Asp Thr Leu Asn Thr Leu Asp Gly Leu Leu His Leu Met
        1075                1080                1085

Asp Gln Pro Leu Ser Val Asp Glu Glu Gly Leu Val Leu Leu Glu Gln
    1090                1095                1100

Lys Leu Ser Arg Ala Lys Thr Gln Ile Asn Ser Gln Leu Arg Pro Met
1105                1110                1115                1120

Met Ser Glu Leu Glu Glu Arg Ala Arg Gln Gln Arg Gly His Leu His
                1125                1130                1135

Leu Leu Glu Thr Ser Ile Asp Gly Ile Leu Ala Asp Val Lys Asn Leu
            1140                1145                1150

Glu Asn Ile Arg Asp Asn Leu Pro Pro Gly Cys Tyr Asn Thr Gln Ala
        1155                1160                1165

Leu Glu Gln Gln
    1170

<210> SEQ ID NO 33
<211> LENGTH: 5159
<212> TYPE: DNA
<213> ORGANISM: Mus musculus
<220> FEATURE:
<221> NAME/KEY: CDS
<222> LOCATION: (40)..(3615)
<221> NAME/KEY: sig_peptide
<222> LOCATION: (40)..(102)
<221> NAME/KEY: unsure
<222> LOCATION: (3330)
<223> OTHER INFORMATION: "r" can be a or g
```

```
<400> SEQUENCE: 33
tcggcacgag ggcacccgca gcgggcaggc cgcccggcc atg cct gcg ctc tgg          54
                                           Met Pro Ala Leu Trp
                                            1               5 ctc agc tgc tgc ctc ggt gtc gcg ctc ctg ctg ccc gcc agc cag gcc        102
Leu Ser Cys Cys Leu Gly Val Ala Leu Leu Leu Pro Ala Ser Gln Ala
             10                  15                  20 acc tcc agg agg gaa gtc tgt gat tgc aat ggg aag tcc agg caa tgt        150
Thr Ser Arg Arg Glu Val Cys Asp Cys Asn Gly Lys Ser Arg Gln Cys
         25                  30                  35 gtc ttt gat cag gag ctc cat cga caa gca ggc agc ggg ttc cgt tgc        198
Val Phe Asp Gln Glu Leu His Arg Gln Ala Gly Ser Gly Phe Arg Cys
     40                  45                  50 ctc aac tgc aat gac aat aca gcg ggg gtt cac tgc gag cgg tcg agg        246
Leu Asn Cys Asn Asp Asn Thr Ala Gly Val His Cys Glu Arg Ser Arg
 55                  60                  65 gag ggg ttt tac cag cat cag agc aag agc cgc tgc cta ccc tgc aac        294
Glu Gly Phe Tyr Gln His Gln Ser Lys Ser Arg Cys Leu Pro Cys Asn
 70                  75                  80                  85 tgc cac tca aag ggt tcc ctc agt gct gga tgt gac aac tct gga caa        342
Cys His Ser Lys Gly Ser Leu Ser Ala Gly Cys Asp Asn Ser Gly Gln
                 90                  95                 100 tgc agg tgt aag cca ggt gtg aca gga caa aga tgt gac cag tgt cag        390
Cys Arg Cys Lys Pro Gly Val Thr Gly Gln Arg Cys Asp Gln Cys Gln
                105                 110                 115 cca ggc ttc cat atg ctc acc gat gct gga tgc acc cga gac cag ggg        438
Pro Gly Phe His Met Leu Thr Asp Ala Gly Cys Thr Arg Asp Gln Gly
            120                 125                 130 caa cta gat tcc aag tgt gac tgt gac cca gct ggc atc tct gga ccc        486
Gln Leu Asp Ser Lys Cys Asp Cys Asp Pro Ala Gly Ile Ser Gly Pro
    135                 140                 145 tgt gat tct ggc cga tgt gtc tgc aaa cca gcc gtc act gga gag cgc        534
Cys Asp Ser Gly Arg Cys Val Cys Lys Pro Ala Val Thr Gly Glu Arg
150                 155                 160                 165 tgt gat agg tgc cga cca cgt gac tat cat ctg gac cgg gca aac cct        582
Cys Asp Arg Cys Arg Pro Arg Asp Tyr His Leu Asp Arg Ala Asn Pro
                170                 175                 180 gag ggc tgt acc cag tgt ttc tgc tat ggg cat tca gcc agc tgc cac        630
Glu Gly Cys Thr Gln Cys Phe Cys Tyr Gly His Ser Ala Ser Cys His
            185                 190                 195 gcc tct gcc gac ttc agt gtc cac aaa atc act tca act ttc agt cag        678
Ala Ser Ala Asp Phe Ser Val His Lys Ile Thr Ser Thr Phe Ser Gln
        200                 205                 210 gat gtg gat ggt tgg aag gcg gtt cag aga aac ggg gca cct gca aaa        726
Asp Val Asp Gly Trp Lys Ala Val Gln Arg Asn Gly Ala Pro Ala Lys
    215                 220                 225 ctc cac tgg tca cag cgc cat cgg gac gtg ttt agt tct gcc gac aga        774
Leu His Trp Ser Gln Arg His Arg Asp Val Phe Ser Ser Ala Arg Arg
230                 235                 240                 245 tca gac ccc gtc tat ttc gtg gcc cct gcc aaa ttc ctc ggt aac cag        822
Ser Asp Pro Val Tyr Phe Val Ala Pro Ala Lys Phe Leu Gly Asn Gln
                250                 255                 260 caa gtg agt tac ggg cag agc ctg tct ttt gac tac cgc gtg gac aga        870
Gln Val Ser Tyr Gly Gln Ser Leu Ser Phe Asp Tyr Arg Val Asp Arg
            265                 270                 275 gga ggt aga cag ccg tct gcc tac gat gtg atc ctg gaa ggt gct ggt        918
Gly Gly Arg Gln Pro Ser Ala Tyr Asp Val Ile Leu Glu Gly Ala Gly
        280                 285                 290
```

-continued

| | | |
|---|---|---|
| cta cag atc aga gct cct ctg atg gct cca ggc aag aca ctt cct tgt<br>Leu Gln Ile Arg Ala Pro Leu Met Ala Pro Gly Lys Thr Leu Pro Cys<br>295                                     300                        305 | | 966 |

```
cta cag atc aga gct cct ctg atg gct cca ggc aag aca ctt cct tgt       966
Leu Gln Ile Arg Ala Pro Leu Met Ala Pro Gly Lys Thr Leu Pro Cys
        295                 300                 305 ggg atc aca aag act tac aca ttc aga ctg aat gaa cat cca agc agt      1014
Gly Ile Thr Lys Thr Tyr Thr Phe Arg Leu Asn Glu His Pro Ser Ser
310                 315                 320                 325 cac tgg agt ccc cag ctg agt tat ttc gaa tat cga agg tta ctg cgg      1062
His Trp Ser Pro Gln Leu Ser Tyr Phe Glu Tyr Arg Arg Leu Leu Arg
                330                 335                 340 aac ctc aca gcc ctc ctg atg atc cga gct acg tac gga gaa tat agt      1110
Asn Leu Thr Ala Leu Leu Met Ile Arg Ala Thr Tyr Gly Glu Tyr Ser
            345                 350                 355 aca ggg tac att gat aac gtg acc ctg gtt tca gcc cgc cct gtc ctt      1158
Thr Gly Tyr Ile Asp Asn Val Thr Leu Val Ser Ala Arg Pro Val Leu
        360                 365                 370 gga gcc cca gcc cct tgg gtt gaa cgt tgt gta tgc ctg ctg ggg tac      1206
Gly Ala Pro Ala Pro Trp Val Glu Arg Cys Val Cys Leu Leu Gly Tyr
    375                 380                 385 aag gga caa ttc tgc cag gaa tgt gct tct ggt tac aaa aga gat tcg      1254
Lys Gly Gln Phe Cys Gln Glu Cys Ala Ser Gly Tyr Lys Arg Asp Ser
390                 395                 400                 405 gca aga ttg ggc gct ttt ggc gcc tgt gtt ccc tgt aac tgc caa ggg      1302
Ala Arg Leu Gly Ala Phe Gly Ala Cys Val Pro Cys Asn Cys Gln Gly
                410                 415                 420 gag ggg gcc tgt gat cca gac acg gga gat tgc tac tcg ggg gac gag      1350
Glu Gly Ala Cys Asp Pro Asp Thr Gly Asp Cys Tyr Ser Gly Asp Glu
            425                 430                 435 aat cct gac att gag tgt gct gac tgt ccc atc ggt ttc tac aat gac      1398
Asn Pro Asp Ile Glu Cys Ala Asp Cys Pro Ile Gly Phe Tyr Asn Asp
        440                 445                 450 cca cat gac ccc cgc agc tgc aag cca tgt ccc tgt cac aat ggg ttc      1446
Pro His Asp Pro Arg Ser Cys Lys Pro Cys Pro Cys His Asn Gly Phe
    455                 460                 465 agc tgt tca gtg atg cct gag aca gag gag gtg gtg tgt aac aac tgt      1494
Ser Cys Ser Val Met Pro Glu Thr Glu Glu Val Val Cys Asn Asn Cys
470                 475                 480                 485 ccc cct ggg gtc aca ggt gcc cgc tgt gag ctc tgt gct gat ggc ttc      1542
Pro Pro Gly Val Thr Gly Ala Arg Cys Glu Leu Cys Ala Asp Gly Phe
                490                 495                 500 ttt ggg gat ccc ttt ggg gaa cat ggc cca gtg agg cct tgt caa cgc      1590
Phe Gly Asp Pro Phe Gly Glu His Gly Pro Val Arg Pro Cys Gln Arg
            505                 510                 515 tgc caa tgc aac aac aac gtg gac ccc aat gcc tct ggg aac tgt gac      1638
Cys Gln Cys Asn Asn Asn Val Asp Pro Asn Ala Ser Gly Asn Cys Asp
        520                 525                 530 cag ttg aca ggc aga tgc ttg aaa tgt atc tac aac acg gcc ggt gtc      1686
Gln Leu Thr Gly Arg Cys Leu Lys Cys Ile Tyr Asn Thr Ala Gly Val
    535                 540                 545 tac tgt gac cag tgc aaa gca ggt tac ttt gga gac cca ttg gct ccc      1734
Tyr Cys Asp Gln Cys Lys Ala Gly Tyr Phe Gly Asp Pro Leu Ala Pro
550                 555                 560                 565 aac cca gca gac aag tgt cga gct tgc aac tgc agc ccc atg ggt gcg      1782
Asn Pro Ala Asp Lys Cys Arg Ala Cys Asn Cys Ser Pro Met Gly Ala
                570                 575                 580 gag cct gga gag tgt cga ggt gat ggc agc tgt gtt tgc aag cca ggc      1830
Glu Pro Gly Glu Cys Arg Gly Asp Gly Ser Cys Val Cys Lys Pro Gly
            585                 590                 595 ttt ggc gcc ttc aac tgt gat cac gca gcc cta acc agt tgt cct gct      1878
Phe Gly Ala Phe Asn Cys Asp His Ala Ala Leu Thr Ser Cys Pro Ala
        600                 605                 610
```

```
tgc tac aat caa gtg aag att cag atg gac cag ttt acc cag cag ctc    1926
Cys Tyr Asn Gln Val Lys Ile Gln Met Asp Gln Phe Thr Gln Gln Leu
        615                 620                 625 cag agc ctg gag gcc ctg gtt tca aag gct cag ggt ggt ggt ggt ggt    1974
Gln Ser Leu Glu Ala Leu Val Ser Lys Ala Gln Gly Gly Gly Gly Gly
630                 635                 640                 645 ggt aca gtc cca gtg cag ctg gaa ggc agg atc gag cag gct gag cag    2022
Gly Thr Val Pro Val Gln Leu Glu Gly Arg Ile Glu Gln Ala Glu Gln
                650                 655                 660 gcc ctt cag gac att ctg gga gaa gct cag att tca gaa ggg gca atg    2070
Ala Leu Gln Asp Ile Leu Gly Glu Ala Gln Ile Ser Glu Gly Ala Met
            665                 670                 675 aga gcc gtt gct gtc cgg ctg gcc aag gca agg agc caa gag aac gac    2118
Arg Ala Val Ala Val Arg Leu Ala Lys Ala Arg Ser Gln Glu Asn Asp
        680                 685                 690 tac aag acc cgc ctg gat gac ctc aag atg act gca gaa agg atc cgg    2166
Tyr Lys Thr Arg Leu Asp Asp Leu Lys Met Thr Ala Glu Arg Ile Arg
    695                 700                 705 gcc ctg ggc agt cag cat cag aac aga gtt cag gat acg agc aga ctc    2214
Ala Leu Gly Ser Gln His Gln Asn Arg Val Gln Asp Thr Ser Arg Leu
710                 715                 720                 725 atc tct cag atg cgc ctg agt ctg gca gga agc gaa gct ctc ttg gaa    2262
Ile Ser Gln Met Arg Leu Ser Leu Ala Gly Ser Glu Ala Leu Leu Glu
                730                 735                 740 aac act aat atc cat tct tct gag cac tac gtg ggg ccg aat gat ttt    2310
Asn Thr Asn Ile His Ser Ser Glu His Tyr Val Gly Pro Asn Asp Phe
                745                 750                 755 aaa agt ctg gct cag gag gct aca aga aag gca gac agc cac gct gag    2358
Lys Ser Leu Ala Gln Glu Ala Thr Arg Lys Ala Asp Ser His Ala Glu
            760                 765                 770 tca gct aac gca atg aag caa cta gca agg gaa act gag gac tac tcc    2406
Ser Ala Asn Ala Met Lys Gln Leu Ala Arg Glu Thr Glu Asp Tyr Ser
        775                 780                 785 aaa caa gca ctt tca ttg gcc cgc aag ctc ttg agt gga gga ggc gga    2454
Lys Gln Ala Leu Ser Leu Ala Arg Lys Leu Leu Ser Gly Gly Gly Gly
790                 795                 800                 805 agt ggc tct tgg gac agc tcc gtg gta caa ggt ctt atg gga aaa tta    2502
Ser Gly Ser Trp Asp Ser Ser Val Val Gln Gly Leu Met Gly Lys Leu
                810                 815                 820 gag aaa acc aag tcc ctg agc cag cag ctg tca ttg gag ggc acc caa    2550
Glu Lys Thr Lys Ser Leu Ser Gln Gln Leu Ser Leu Glu Gly Thr Gln
            825                 830                 835 gcc gac att gaa gct gat agg tcg tat cag cac agt ctc cgc ctc ctg    2598
Ala Asp Ile Glu Ala Asp Arg Ser Tyr Gln His Ser Leu Arg Leu Leu
        840                 845                 850 gat tct gcc tct cag ctt cag gga gtc agt gat ctg tcc ttt cag gtg    2646
Asp Ser Ala Ser Gln Leu Gln Gly Val Ser Asp Leu Ser Phe Gln Val
    855                 860                 865 gaa gca aag agg atc aga caa aag gct gat tct ctc tca aac ctg gtg    2694
Glu Ala Lys Arg Ile Arg Gln Lys Ala Asp Ser Leu Ser Asn Leu Val
870                 875                 880                 885 acc aga caa acg gat gca ttc acg cgt gtg cga aac aat ctg ggg aac    2742
Thr Arg Gln Thr Asp Ala Phe Thr Arg Val Arg Asn Asn Leu Gly Asn
                890                 895                 900 tgg gaa aaa gaa aca cgg cag ctt tta cag act gga aag gat agg aga    2790
Trp Glu Lys Glu Thr Arg Gln Leu Leu Gln Thr Gly Lys Asp Arg Arg
            905                 910                 915 cag act tca gat cag ctg ctt tcc cgt gcc aac ctt gct aaa aac aga    2838
Gln Thr Ser Asp Gln Leu Leu Ser Arg Ala Asn Leu Ala Lys Asn Arg
```

```
                920              925              930
gcc caa gaa gcg cta agt atg ggc aat gcc act ttt tat gaa gtt gag    2886
Ala Gln Glu Ala Leu Ser Met Gly Asn Ala Thr Phe Tyr Glu Val Glu
    935              940              945 aac atc ctg aag aac ctc cga gag ttt gat ctg cag gtt gaa gac aga    2934
Asn Ile Leu Lys Asn Leu Arg Glu Phe Asp Leu Gln Val Glu Asp Arg
950              955              960              965 aaa gca gag gct gaa gag gcc atg aag aga ctc tcc tct att agc cag    2982
Lys Ala Glu Ala Glu Glu Ala Met Lys Arg Leu Ser Ser Ile Ser Gln
                970              975              980 aag gtt gcg gat gcc agt gac aag acc cag caa gca gaa acg gcc ctg    3030
Lys Val Ala Asp Ala Ser Asp Lys Thr Gln Gln Ala Glu Thr Ala Leu
            985              990              995 ggg agc gcc act gcc gac acc caa cgg gca aag aac gca gct agg gag    3078
Gly Ser Ala Thr Ala Asp Thr Gln Arg Ala Lys Asn Ala Ala Arg Glu
        1000             1005             1010 gcc ctg gag atc agc agc gag ata gag ctg gag ata ggg agt ctg aac    3126
Ala Leu Glu Ile Ser Ser Glu Ile Glu Leu Glu Ile Gly Ser Leu Asn
    1015             1020             1025 ttg gaa gct aat gtg aca gca gat ggg gcc ttg gcc atg gag aaa ggg    3174
Leu Glu Ala Asn Val Thr Ala Asp Gly Ala Leu Ala Met Glu Lys Gly
1030             1035             1040             1045 act gcc act ctg aag agc gag atg aga gag atg att gag ctg gcc aga    3222
Thr Ala Thr Leu Lys Ser Glu Met Arg Glu Met Ile Glu Leu Ala Arg
             1050             1055             1060 aag gag ctg gag ttt gac acg gat aag gac acg gtg cag ctg gtg att    3270
Lys Glu Leu Glu Phe Asp Thr Asp Lys Asp Thr Val Gln Leu Val Ile
         1065             1070             1075 act gaa gcc cag caa gct gat gcc aga gcc acg agt gcc gga gtt acc    3318
Thr Glu Ala Gln Gln Ala Asp Ala Arg Ala Thr Ser Ala Gly Val Thr
     1080             1085             1090 atc caa gac acr ctc aac aca ttg gac ggc atc cta cac ctc ata gac    3366
Ile Gln Asp Thr Leu Asn Thr Leu Asp Gly Ile Leu His Leu Ile Asp
    1095             1100             1105 cag cct ggc agt gtg gat gaa gaa ggg atg atg cta tta gaa caa ggg    3414
Gln Pro Gly Ser Val Asp Glu Glu Gly Met Met Leu Leu Glu Gln Gly
1110             1115             1120             1125 ctt ttc caa gcc aag acc cag atc aac agt cga ctt cgg ccc ttg atg    3462
Leu Phe Gln Ala Lys Thr Gln Ile Asn Ser Arg Leu Arg Pro Leu Met
             1130             1135             1140 tct gac ctg gag gag agg gtg cgt cgg cag agg aac cac ctc cat ctg    3510
Ser Asp Leu Glu Glu Arg Val Arg Arg Gln Arg Asn His Leu His Leu
         1145             1150             1155 ctg gag act agc ata gat gga att ctt gct gat gtg aag aac ctg gag    3558
Leu Glu Thr Ser Ile Asp Gly Ile Leu Ala Asp Val Lys Asn Leu Glu
     1160             1165             1170 aac att cga gac aac ctg ccc cca ggc tgc tac aat acc caa gct ctt    3606
Asn Ile Arg Asp Asn Leu Pro Pro Gly Cys Tyr Asn Thr Gln Ala Leu
    1175             1180             1185 gag caa cag tgaagttgtc atagagattt gtccactgtt gtgaaaggac             3655
Glu Gln Gln
1190 acagacctca gggtcagga gccatctcgt gtggatgggc tgtgctcagg ctatctgaac    3715 acatttaatg ggtttgttca ggtccaattc catccctgag accatgggct gtggatgtct   3775 tcctgtacca atataatact gtttgtactt cctgatgctg gcagtgaggc agatagcatt   3835 gagtatgaga ttgatcaagg aggacaaat cgtgcgctca gaacagtgac aaactgaatt    3895 ctgggcagtg aggcagatag cattgagtat gagattgatc aaggacctgg accccaaaga   3955
```

-continued

```
tagactggat ggaaagacaa actgcacagg cagatgtttg cctcataata gtcgtaagtg    4015
gagtcctgga atttggtcag aacagtgaaa aactggaatt ctgggatata gaaagatcct    4075
gctgctatgt caggacaaag tgagatctaa tcccgctgcg gccagcaaag tactcttgct    4135
tcacccacta gacgtttttt gtccaccaca tttcctccag tgcccaccca atacatgagt    4195
atgtcctcca cttcatgctg agtgcagaga gcagtgatgg tatagatctg gaaatctggc    4255
ccatgtggag cagtggtgcc cgcctgcacc cctaaccttc atgctctcgg cctgagtgtg    4315
acagcctttc tcctaatggt gcgaacaact tagaggctgt attttttttat gaaagcatct    4375 tttaccagcc aagcaatcat tgggaaagta tttctttgag tttcaaagtg atataagaaa    4435
tgtgtctggc actaaaggaa gtggagttat ctaaaagata tattcatcat aatccaatct    4495
tcctttggaa acactaaaac tcatatacat ctgtgtattg tatcttattt tctctttctc    4555
ctctctcttt cctccaccca taataagaga atgttcctac tcacacttca gctgggtcac    4615
atccatccct ccattcatcc ttccatccat cttttccatcc attacctcca tccagccttc    4675
taacatatat ttattgcgtc actactgtgt gccaggggtg agtggaacag tatggacagt    4735
ctctactctc atggagttga gtgtctagtg agagaacaac attagaataa gtaaatggaa    4795
actcccatgc cttgttcatc tcatgtgata tttattgcag tcacccaccc tttggtttga    4855
aacctctttt cttaataatg tgttgcaaga cattcccatg agggtacttg agttagagca    4915
aagttgagat cgctctgagt tgtacacatt tctctatgtt ccagccgtct ctccacccct    4975
tccacacaga ctgtgcacag actggtgcat cagggcaata ccagtgggaa ttgctgaagg    5035
aaccagaggc attgggacct cagtttggaa gactactgta ctgtctcacc tctgtacttc    5095
cttgtctttt catggatgtg ttattaaata aagaacgagt gttagatgct aaaaaaaaaa    5155
aaaa                                                                 5159
```

<210> SEQ ID NO 34
<211> LENGTH: 1192
<212> TYPE: PRT
<213> ORGANISM: Mus musculus

<400> SEQUENCE: 34

```
Met Pro Ala Leu Trp Leu Ser Cys Cys Leu Gly Val Ala Leu Leu Leu
 1               5                  10                  15

Pro Ala Ser Gln Ala Thr Ser Arg Arg Glu Val Cys Asp Cys Asn Gly
            20                  25                  30

Lys Ser Arg Gln Cys Val Phe Asp Gln Glu Leu His Arg Gln Ala Gly
        35                  40                  45

Ser Gly Phe Arg Cys Leu Asn Cys Asn Asp Asn Thr Ala Gly Val His
    50                  55                  60

Cys Glu Arg Ser Arg Glu Gly Phe Tyr Gln His Gln Ser Lys Ser Arg
65                  70                  75                  80

Cys Leu Pro Cys Asn Cys His Ser Lys Gly Ser Leu Ser Ala Gly Cys
                85                  90                  95

Asp Asn Ser Gly Gln Cys Arg Cys Lys Pro Gly Val Thr Gly Gln Arg
            100                 105                 110

Cys Asp Gln Cys Gln Pro Gly Phe His Met Leu Thr Asp Ala Gly Cys
        115                 120                 125

Thr Arg Asp Gln Gly Gln Leu Asp Ser Lys Cys Asp Cys Asp Pro Ala
    130                 135                 140

Gly Ile Ser Gly Pro Cys Asp Ser Gly Arg Cys Val Cys Lys Pro Ala
```

```
                    145                 150                 155                 160
Val Thr Gly Glu Arg Cys Asp Arg Cys Arg Pro Arg Asp Tyr His Leu
                165                 170                 175
Asp Arg Ala Asn Pro Glu Gly Cys Thr Gln Cys Phe Cys Tyr Gly His
            180                 185                 190
Ser Ala Ser Cys His Ala Ser Ala Asp Phe Ser Val His Lys Ile Thr
        195                 200                 205
Ser Thr Phe Ser Gln Asp Val Asp Gly Trp Lys Ala Val Gln Arg Asn
    210                 215                 220
Gly Ala Pro Ala Lys Leu His Trp Ser Gln Arg His Arg Asp Val Phe
225                 230                 235                 240
Ser Ser Ala Arg Arg Ser Asp Pro Val Tyr Phe Val Ala Pro Ala Lys
                245                 250                 255
Phe Leu Gly Asn Gln Gln Val Ser Tyr Gly Gln Ser Leu Ser Phe Asp
            260                 265                 270
Tyr Arg Val Asp Arg Gly Gly Arg Gln Pro Ser Ala Tyr Asp Val Ile
        275                 280                 285
Leu Glu Gly Ala Gly Leu Gln Ile Arg Ala Pro Leu Met Ala Pro Gly
    290                 295                 300
Lys Thr Leu Pro Cys Gly Ile Thr Lys Thr Tyr Thr Phe Arg Leu Asn
305                 310                 315                 320
Glu His Pro Ser Ser His Trp Ser Pro Gln Leu Ser Tyr Phe Glu Tyr
                325                 330                 335
Arg Arg Leu Leu Arg Asn Leu Thr Ala Leu Leu Met Ile Arg Ala Thr
            340                 345                 350
Tyr Gly Glu Tyr Ser Thr Gly Tyr Ile Asp Asn Val Thr Leu Val Ser
        355                 360                 365
Ala Arg Pro Val Leu Gly Ala Pro Ala Pro Trp Val Glu Arg Cys Val
    370                 375                 380
Cys Leu Leu Gly Tyr Lys Gly Gln Phe Cys Gln Glu Cys Ala Ser Gly
385                 390                 395                 400
Tyr Lys Arg Asp Ser Ala Arg Leu Gly Ala Phe Gly Ala Cys Val Pro
                405                 410                 415
Cys Asn Cys Gln Gly Glu Gly Ala Cys Asp Pro Asp Thr Gly Asp Cys
            420                 425                 430
Tyr Ser Gly Asp Glu Asn Pro Asp Ile Glu Cys Ala Asp Cys Pro Ile
        435                 440                 445
Gly Phe Tyr Asn Asp Pro His Asp Pro Arg Ser Cys Lys Pro Cys Pro
    450                 455                 460
Cys His Asn Gly Phe Ser Cys Ser Val Met Pro Glu Thr Glu Glu Val
465                 470                 475                 480
Val Cys Asn Asn Cys Pro Pro Gly Val Thr Gly Ala Arg Cys Glu Leu
                485                 490                 495
Cys Ala Asp Gly Phe Phe Gly Asp Pro Phe Gly Glu His Gly Pro Val
            500                 505                 510
Arg Pro Cys Gln Arg Cys Gln Cys Asn Asn Asn Val Asp Pro Asn Ala
        515                 520                 525
Ser Gly Asn Cys Asp Gln Leu Thr Gly Arg Cys Leu Lys Cys Ile Tyr
    530                 535                 540
Asn Thr Ala Gly Val Tyr Cys Asp Gln Cys Lys Ala Gly Tyr Phe Gly
545                 550                 555                 560
Asp Pro Leu Ala Pro Asn Pro Ala Asp Lys Cys Arg Ala Cys Asn Cys
                565                 570                 575
```

-continued

```
Ser Pro Met Gly Ala Glu Pro Gly Glu Cys Arg Gly Asp Gly Ser Cys
        580                 585                 590
Val Cys Lys Pro Gly Phe Gly Ala Phe Asn Cys Asp His Ala Ala Leu
        595                 600                 605
Thr Ser Cys Pro Ala Cys Tyr Asn Gln Val Lys Ile Gln Met Asp Gln
        610                 615                 620
Phe Thr Gln Gln Leu Gln Ser Leu Glu Ala Leu Val Ser Lys Ala Gln
625                 630                 635                 640
Gly Gly Gly Gly Gly Thr Val Pro Val Gln Leu Glu Gly Arg Ile
                645                 650                 655
Glu Gln Ala Glu Gln Ala Leu Gln Asp Ile Leu Gly Glu Ala Gln Ile
                660                 665                 670
Ser Glu Gly Ala Met Arg Ala Val Ala Val Arg Leu Ala Lys Ala Arg
                675                 680                 685
Ser Gln Glu Asn Asp Tyr Lys Thr Arg Leu Asp Asp Leu Lys Met Thr
                690                 695                 700
Ala Glu Arg Ile Arg Ala Leu Gly Ser Gln His Gln Asn Arg Val Gln
705                 710                 715                 720
Asp Thr Ser Arg Leu Ile Ser Gln Met Arg Leu Ser Leu Ala Gly Ser
                725                 730                 735
Glu Ala Leu Leu Glu Asn Thr Asn Ile His Ser Ser Glu His Tyr Val
                740                 745                 750
Gly Pro Asn Asp Phe Lys Ser Leu Ala Gln Glu Ala Thr Arg Lys Ala
                755                 760                 765
Asp Ser His Ala Glu Ser Ala Asn Ala Met Lys Gln Leu Ala Arg Glu
                770                 775                 780
Thr Glu Asp Tyr Ser Lys Gln Ala Leu Ser Leu Ala Arg Lys Leu Leu
785                 790                 795                 800
Ser Gly Gly Gly Ser Gly Ser Trp Asp Ser Ser Val Val Gln Gly
                805                 810                 815
Leu Met Gly Lys Leu Glu Lys Thr Lys Ser Leu Ser Gln Gln Leu Ser
                820                 825                 830
Leu Glu Gly Thr Gln Ala Asp Ile Glu Ala Asp Arg Ser Tyr Gln His
                835                 840                 845
Ser Leu Arg Leu Leu Asp Ser Ala Ser Gln Leu Gln Gly Val Ser Asp
850                 855                 860
Leu Ser Phe Gln Val Glu Ala Lys Arg Ile Arg Gln Lys Ala Asp Ser
865                 870                 875                 880
Leu Ser Asn Leu Val Thr Arg Gln Thr Asp Ala Phe Thr Arg Val Arg
                885                 890                 895
Asn Asn Leu Gly Asn Trp Glu Lys Glu Thr Arg Gln Leu Leu Gln Thr
                900                 905                 910
Gly Lys Asp Arg Arg Gln Thr Ser Asp Gln Leu Leu Ser Arg Ala Asn
                915                 920                 925
Leu Ala Lys Asn Arg Ala Gln Glu Ala Leu Ser Met Gly Asn Ala Thr
                930                 935                 940
Phe Tyr Glu Val Glu Asn Ile Leu Lys Asn Leu Arg Glu Phe Asp Leu
945                 950                 955                 960
Gln Val Glu Asp Arg Lys Ala Glu Ala Glu Ala Met Lys Arg Leu
                965                 970                 975
Ser Ser Ile Ser Gln Lys Val Ala Asp Ala Ser Asp Lys Thr Gln Gln
                980                 985                 990
```

-continued

```
Ala Glu Thr Ala Leu Gly Ser Ala Thr Ala Asp Thr Gln Arg Ala Lys
        995                 1000                1005
Asn Ala Ala Arg Glu Ala Leu Glu Ile Ser Ser Glu Ile Glu Leu Glu
    1010                1015                1020
Ile Gly Ser Leu Asn Leu Glu Ala Asn Val Thr Ala Asp Gly Ala Leu
1025                1030                1035                1040
Ala Met Glu Lys Gly Thr Ala Thr Leu Lys Ser Glu Met Arg Glu Met
                1045                1050                1055
Ile Glu Leu Ala Arg Lys Glu Leu Glu Phe Asp Thr Asp Lys Asp Thr
            1060                1065                1070
Val Gln Leu Val Ile Thr Glu Ala Gln Gln Ala Asp Ala Arg Ala Thr
        1075                1080                1085
Ser Ala Gly Val Thr Ile Gln Asp Thr Leu Asn Thr Leu Asp Gly Ile
    1090                1095                1100
Leu His Leu Ile Asp Gln Pro Gly Ser Val Asp Glu Glu Gly Met Met
1105                1110                1115                1120
Leu Leu Glu Gln Gly Leu Phe Gln Ala Lys Thr Gln Ile Asn Ser Arg
                1125                1130                1135
Leu Arg Pro Leu Met Ser Asp Leu Glu Glu Arg Val Arg Arg Gln Arg
            1140                1145                1150
Asn His Leu His Leu Leu Glu Thr Ser Ile Asp Gly Ile Leu Ala Asp
        1155                1160                1165
Val Lys Asn Leu Glu Asn Ile Arg Asp Asn Leu Pro Pro Gly Cys Tyr
    1170                1175                1180
Asn Thr Gln Ala Leu Glu Gln Gln
1185                1190

<210> SEQ ID NO 35
<211> LENGTH: 5057
<212> TYPE: DNA
<213> ORGANISM: Mus musculus
<220> FEATURE:
<221> NAME/KEY: CDS
<222> LOCATION: (1)..(3513)
<221> NAME/KEY: unsure
<222> LOCATION: (3228)
<223> OTHER INFORMATION: "r" can be a or g

<400> SEQUENCE: 35 acc tcc agg agg gaa gtc tgt gat tgc aat ggg aag tcc agg caa tgt      48
Thr Ser Arg Arg Glu Val Cys Asp Cys Asn Gly Lys Ser Arg Gln Cys
  1               5                  10                  15 gtc ttt gat cag gag ctc cat cga caa gca ggc agc ggg ttc cgt tgc      96
Val Phe Asp Gln Glu Leu His Arg Gln Ala Gly Ser Gly Phe Arg Cys
                20                  25                  30 ctc aac tgc aat gac aat aca gcg ggg gtt cac tgc gag cgg tcg agg     144
Leu Asn Cys Asn Asp Asn Thr Ala Gly Val His Cys Glu Arg Ser Arg
            35                  40                  45 gag ggg ttt tac cag cat cag agc aag agc cgc tgc cta ccc tgc aac     192
Glu Gly Phe Tyr Gln His Gln Ser Lys Ser Arg Cys Leu Pro Cys Asn
        50                  55                  60 tgc cac tca aag ggt tcc ctc agt gct gga tgt gac aac tct gga caa     240
Cys His Ser Lys Gly Ser Leu Ser Ala Gly Cys Asp Asn Ser Gly Gln
65                  70                  75                  80 tgc agg tgt aag cca ggt gtg aca gga caa aga tgt gac cag tgt cag     288
Cys Arg Cys Lys Pro Gly Val Thr Gly Gln Arg Cys Asp Gln Cys Gln
                85                  90                  95 cca ggc ttc cat atg ctc acc gat gct gga tgc acc cga gac cag ggg     336
Pro Gly Phe His Met Leu Thr Asp Ala Gly Cys Thr Arg Asp Gln Gly
```

```
              100                 105                 110
caa cta gat tcc aag tgt gac tgt gac cca gct ggc atc tct gga ccc       384
Gln Leu Asp Ser Lys Cys Asp Cys Asp Pro Ala Gly Ile Ser Gly Pro
            115                 120                 125 tgt gat tct ggc cga tgt gtc tgc aaa cca gcc gtc act gga gag cgc       432
Cys Asp Ser Gly Arg Cys Val Cys Lys Pro Ala Val Thr Gly Glu Arg
        130                 135                 140 tgt gat agg tgc cga cca cgt gac tat cat ctg gac cgg gca aac cct       480
Cys Asp Arg Cys Arg Pro Arg Asp Tyr His Leu Asp Arg Ala Asn Pro
145                 150                 155                 160 gag ggc tgt acc cag tgt ttc tgc tat ggg cat tca gcc agc tgc cac       528
Glu Gly Cys Thr Gln Cys Phe Cys Tyr Gly His Ser Ala Ser Cys His
                165                 170                 175 gcc tct gcc gac ttc agt gtc cac aaa atc act tca act ttc agt cag       576
Ala Ser Ala Asp Phe Ser Val His Lys Ile Thr Ser Thr Phe Ser Gln
            180                 185                 190 gat gtg gat ggt tgg aag gcg gtt cag aga aac ggg gca cct gca aaa       624
Asp Val Asp Gly Trp Lys Ala Val Gln Arg Asn Gly Ala Pro Ala Lys
        195                 200                 205 ctc cac tgg tca cag cgc cat cgg gac gtg ttt agt tct gcc cga aga       672
Leu His Trp Ser Gln Arg His Arg Asp Val Phe Ser Ser Ala Arg Arg
    210                 215                 220 tca gac ccc gtc tat ttc gtg gcc cct gcc aaa ttc ctc ggt aac cag       720
Ser Asp Pro Val Tyr Phe Val Ala Pro Ala Lys Phe Leu Gly Asn Gln
225                 230                 235                 240 caa gtg agt tac ggg cag agc ctg tct ttt gac tac cgc gtg gac aga       768
Gln Val Ser Tyr Gly Gln Ser Leu Ser Phe Asp Tyr Arg Val Asp Arg
                245                 250                 255 gga ggt aga cag ccg tct gcc tac gat gtg atc ctg gaa ggt gct ggt       816
Gly Gly Arg Gln Pro Ser Ala Tyr Asp Val Ile Leu Glu Gly Ala Gly
            260                 265                 270 cta cag atc aga gct cct ctg atg gct cca ggc aag aca ctt cct tgt       864
Leu Gln Ile Arg Ala Pro Leu Met Ala Pro Gly Lys Thr Leu Pro Cys
        275                 280                 285 ggg atc aca aag act tac aca ttc aga ctg aat gaa cat cca agc agt       912
Gly Ile Thr Lys Thr Tyr Thr Phe Arg Leu Asn Glu His Pro Ser Ser
    290                 295                 300 cac tgg agt ccc cag ctg agt tat ttc gaa tat cga agg tta ctg cgg       960
His Trp Ser Pro Gln Leu Ser Tyr Phe Glu Tyr Arg Arg Leu Leu Arg
305                 310                 315                 320 aac ctc aca gcc ctc ctg atg atc cga gct acg tac gga gaa tat agt      1008
Asn Leu Thr Ala Leu Leu Met Ile Arg Ala Thr Tyr Gly Glu Tyr Ser
                325                 330                 335 aca ggg tac att gat aac gtg acc ctg gtt tca gcc cgc cct gtc ctt      1056
Thr Gly Tyr Ile Asp Asn Val Thr Leu Val Ser Ala Arg Pro Val Leu
            340                 345                 350 gga gcc cca gcc cct tgg gtt gaa cgt tgt gta tgc ctg ctg ggg tac      1104
Gly Ala Pro Ala Pro Trp Val Glu Arg Cys Val Cys Leu Leu Gly Tyr
        355                 360                 365 aag gga caa ttc tgc cag gaa tgt gct tct ggt tac aaa aga gat tcg      1152
Lys Gly Gln Phe Cys Gln Glu Cys Ala Ser Gly Tyr Lys Arg Asp Ser
    370                 375                 380 gca aga ttg ggc gct ttt ggc gcc tgt gtt ccc tgt aac tgc caa ggg      1200
Ala Arg Leu Gly Ala Phe Gly Ala Cys Val Pro Cys Asn Cys Gln Gly
385                 390                 395                 400 gag ggg gcc tgt gat cca gac acg gga gat tgc tac tcg ggg gac gag      1248
Glu Gly Ala Cys Asp Pro Asp Thr Gly Asp Cys Tyr Ser Gly Asp Glu
                405                 410                 415 aat cct gac att gag tgt gct gac tgt ccc atc ggt ttc tac aat gac      1296
```

```
                                             -continued

Asn Pro Asp Ile Glu Cys Ala Asp Cys Pro Ile Gly Phe Tyr Asn Asp
            420                 425                 430 cca cat gac ccc cgc agc tgc aag cca tgt ccc tgt cac aat ggg ttc      1344
Pro His Asp Pro Arg Ser Cys Lys Pro Cys Pro Cys His Asn Gly Phe
            435                 440                 445 agc tgt tca gtg atg cct gag aca gag gag gtg gtg tgt aac aac tgt      1392
Ser Cys Ser Val Met Pro Glu Thr Glu Glu Val Val Cys Asn Asn Cys
450                 455                 460 ccc cct ggg gtc aca ggt gcc cgc tgt gag ctc tgt gct gat ggc ttc      1440
Pro Pro Gly Val Thr Gly Ala Arg Cys Glu Leu Cys Ala Asp Gly Phe
465                 470                 475                 480 ttt ggg gat ccc ttt ggg gaa cat ggc cca gtg agg cct tgt caa cgc      1488
Phe Gly Asp Pro Phe Gly Glu His Gly Pro Val Arg Pro Cys Gln Arg
            485                 490                 495 tgc caa tgc aac aac aac gtg gac ccc aat gcc tct ggg aac tgt gac      1536
Cys Gln Cys Asn Asn Asn Val Asp Pro Asn Ala Ser Gly Asn Cys Asp
            500                 505                 510 cag ttg aca ggc aga tgc ttg aaa tgt atc tac aac acg gcc ggt gtc      1584
Gln Leu Thr Gly Arg Cys Leu Lys Cys Ile Tyr Asn Thr Ala Gly Val
            515                 520                 525 tac tgt gac cag tgc aaa gca ggt tac ttt gga gac cca ttg gct ccc      1632
Tyr Cys Asp Gln Cys Lys Ala Gly Tyr Phe Gly Asp Pro Leu Ala Pro
530                 535                 540 aac cca gca gac aag tgt cga gct tgc aac tgc agc ccc atg ggt gcg      1680
Asn Pro Ala Asp Lys Cys Arg Ala Cys Asn Cys Ser Pro Met Gly Ala
545                 550                 555                 560 gag cct gga gag tgt cga ggt gat ggc agc tgt gtt tgc aag cca ggc      1728
Glu Pro Gly Glu Cys Arg Gly Asp Gly Ser Cys Val Cys Lys Pro Gly
            565                 570                 575 ttt ggc gcc ttc aac tgt gat cac gca gcc cta acc agt tgt cct gct      1776
Phe Gly Ala Phe Asn Cys Asp His Ala Ala Leu Thr Ser Cys Pro Ala
            580                 585                 590 tgc tac aat caa gtg aag att cag atg gac cag ttt acc cag cag ctc      1824
Cys Tyr Asn Gln Val Lys Ile Gln Met Asp Gln Phe Thr Gln Gln Leu
            595                 600                 605 cag agc ctg gag gcc ctg gtt tca aag gct cag ggt ggt ggt ggt ggt      1872
Gln Ser Leu Glu Ala Leu Val Ser Lys Ala Gln Gly Gly Gly Gly Gly
            610                 615                 620 ggt aca gtc cca gtg cag ctg gaa ggc agg atc gag cag gct gag cag      1920
Gly Thr Val Pro Val Gln Leu Glu Gly Arg Ile Glu Gln Ala Glu Gln
625                 630                 635                 640 gcc ctt cag gac att ctg gga gaa gct cag att tca gaa ggg gca atg      1968
Ala Leu Gln Asp Ile Leu Gly Glu Ala Gln Ile Ser Glu Gly Ala Met
            645                 650                 655 aga gcc gtt gct gtc cgg ctg gcc aag gca agg agc caa gag aac gac      2016
Arg Ala Val Ala Val Arg Leu Ala Lys Ala Arg Ser Gln Glu Asn Asp
            660                 665                 670 tac aag acc cgc ctg gat gac ctc aag atg act gca gaa agg atc cgg      2064
Tyr Lys Thr Arg Leu Asp Asp Leu Lys Met Thr Ala Glu Arg Ile Arg
            675                 680                 685 gcc ctg ggc agt cag cat cag aac aga gtt cag gat acg agc aga ctc      2112
Ala Leu Gly Ser Gln His Gln Asn Arg Val Gln Asp Thr Ser Arg Leu
            690                 695                 700 atc tct cag atg cgc ctg agt ctg gca gga agc gaa gct ctc ttg gaa      2160
Ile Ser Gln Met Arg Leu Ser Leu Ala Gly Ser Glu Ala Leu Leu Glu
705                 710                 715                 720 aac act aat atc cat tct tct gag cac tac gtg ggg ccg aat gat ttt      2208
Asn Thr Asn Ile His Ser Ser Glu His Tyr Val Gly Pro Asn Asp Phe
            725                 730                 735
```

```
-continued aaa agt ctg gct cag gag gct aca aga aag gca gac agc cac gct gag      2256
Lys Ser Leu Ala Gln Glu Ala Thr Arg Lys Ala Asp Ser His Ala Glu
        740                 745                 750 tca gct aac gca atg aag caa cta gca agg gaa act gag gac tac tcc      2304
Ser Ala Asn Ala Met Lys Gln Leu Ala Arg Glu Thr Glu Asp Tyr Ser
            755                 760                 765 aaa caa gca ctt tca ttg gcc cgc aag ctc ttg agt gga gga ggc gga      2352
Lys Gln Ala Leu Ser Leu Ala Arg Lys Leu Leu Ser Gly Gly Gly Gly
770                 775                 780 agt ggc tct tgg gac agc tcc gtg gta caa ggt ctt atg gga aaa tta      2400
Ser Gly Ser Trp Asp Ser Ser Val Val Gln Gly Leu Met Gly Lys Leu
785                 790                 795                 800 gag aaa acc aag tcc ctg agc cag cag ctg tca ttg gag ggc acc caa      2448
Glu Lys Thr Lys Ser Leu Ser Gln Gln Leu Ser Leu Glu Gly Thr Gln
        805                 810                 815 gcc gac att gaa gct gat agg tcg tat cag cac agt ctc cgc ctc ctg      2496
Ala Asp Ile Glu Ala Asp Arg Ser Tyr Gln His Ser Leu Arg Leu Leu
            820                 825                 830 gat tct gcc tct cag ctt cag gga gtc agt gat ctg tcc ttt cag gtg      2544
Asp Ser Ala Ser Gln Leu Gln Gly Val Ser Asp Leu Ser Phe Gln Val
835                 840                 845 gaa gca aag agg atc aga caa aag gct gat tct ctc tca aac ctg gtg      2592
Glu Ala Lys Arg Ile Arg Gln Lys Ala Asp Ser Leu Ser Asn Leu Val
850                 855                 860 acc aga caa acg gat gca ttc acg cgt gtg cga aac aat ctg ggg aac      2640
Thr Arg Gln Thr Asp Ala Phe Thr Arg Val Arg Asn Asn Leu Gly Asn
865                 870                 875                 880 tgg gaa aaa gaa aca cgg cag ctt tta cag act gga aag gat agg aga      2688
Trp Glu Lys Glu Thr Arg Gln Leu Leu Gln Thr Gly Lys Asp Arg Arg
        885                 890                 895 cag act tca gat cag ctg ctt tcc cgt gcc aac ctt gct aaa aac aga      2736
Gln Thr Ser Asp Gln Leu Leu Ser Arg Ala Asn Leu Ala Lys Asn Arg
            900                 905                 910 gcc caa gaa gcg cta agt atg ggc aat gcc act ttt tat gaa gtt gag      2784
Ala Gln Glu Ala Leu Ser Met Gly Asn Ala Thr Phe Tyr Glu Val Glu
915                 920                 925 aac atc ctg aag aac ctc cga gag ttt gat ctg cag gtt gaa gac aga      2832
Asn Ile Leu Lys Asn Leu Arg Glu Phe Asp Leu Gln Val Glu Asp Arg
930                 935                 940 aaa gca gag gct gaa gag gcc atg aag aga ctc tcc tct att agc cag      2880
Lys Ala Glu Ala Glu Glu Ala Met Lys Arg Leu Ser Ser Ile Ser Gln
945                 950                 955                 960 aag gtt gcg gat gcc agt gac aag acc cag caa gca gaa acg gcc ctg      2928
Lys Val Ala Asp Ala Ser Asp Lys Thr Gln Gln Ala Glu Thr Ala Leu
            965                 970                 975 ggg agc gcc act gcc gac acc caa cgg gca aag aac gca gct agg gag      2976
Gly Ser Ala Thr Ala Asp Thr Gln Arg Ala Lys Asn Ala Ala Arg Glu
        980                 985                 990 gcc ctg gag atc agc agc gag ata gag ctg gag ata ggg agt ctg aac      3024
Ala Leu Glu Ile Ser Ser Glu Ile Glu Leu Glu Ile Gly Ser Leu Asn
            995                 1000                1005 ttg gaa gct aat gtg aca gca gat ggg gcc ttg gcc atg gag aaa ggg      3072
Leu Glu Ala Asn Val Thr Ala Asp Gly Ala Leu Ala Met Glu Lys Gly
    1010                1015                1020 act gcc act ctg aag agc gag atg aga gag atg att gag ctg gcc aga      3120
Thr Ala Thr Leu Lys Ser Glu Met Arg Glu Met Ile Glu Leu Ala Arg
1025                1030                1035                1040 aag gag ctg gag ttt gac acg gat aag gac acg gtg cag ctg gtg att      3168
Lys Glu Leu Glu Phe Asp Thr Asp Lys Asp Thr Val Gln Leu Val Ile
            1045                1050                1055
```

```
act gaa gcc cag caa gct gat gcc aga gcc acg agt gcc gga gtt acc      3216
Thr Glu Ala Gln Gln Ala Asp Ala Arg Ala Thr Ser Ala Gly Val Thr
            1060                1065                1070 atc caa gac acr ctc aac aca ttg gac ggc atc cta cac ctc ata gac      3264
Ile Gln Asp Thr Leu Asn Thr Leu Asp Gly Ile Leu His Leu Ile Asp
        1075                1080                1085 cag cct ggc agt gtg gat gaa gaa ggg atg atg cta tta gaa caa ggg      3312
Gln Pro Gly Ser Val Asp Glu Glu Gly Met Met Leu Leu Glu Gln Gly
    1090                1095                1100 ctt ttc caa gcc aag acc cag atc aac agt cga ctt cgg ccc ttg atg      3360
Leu Phe Gln Ala Lys Thr Gln Ile Asn Ser Arg Leu Arg Pro Leu Met
1105                1110                1115                1120 tct gac ctg gag gag agg gtg cgt cgg cag agg aac cac ctc cat ctg      3408
Ser Asp Leu Glu Glu Arg Val Arg Arg Gln Arg Asn His Leu His Leu
            1125                1130                1135 ctg gag act agc ata gat gga att ctt gct gat gtg aag aac ctg gag      3456
Leu Glu Thr Ser Ile Asp Gly Ile Leu Ala Asp Val Lys Asn Leu Glu
        1140                1145                1150 aac att cga gac aac ctg ccc cca ggc tgc tac aat acc caa gct ctt      3504
Asn Ile Arg Asp Asn Leu Pro Pro Gly Cys Tyr Asn Thr Gln Ala Leu
    1155                1160                1165 gag caa cag tgaagttgtc atagagattt gtccactgtt gtgaaaggac              3553
Glu Gln Gln
    1170 acagacctca ggggtcagga gccatctcgt gtggatgggc tgtgctcagg ctatctgaac    3613 acatttaatg ggtttgttca ggtccaattc catccctgag accatgggct gtggatgtct    3673 tcctgtacca atataatact gtttgtactt cctgatgctg gcagtgaggc agatagcatt    3733 gagtatgaga ttgatcaagg agggacaaat cgtgcgctca aacagtgac aaactgaatt     3793 ctgggcagtg aggcagatag cattgagtat gagattgatc aaggacctgg accccaaaga   3853 tagactggat ggaaagacaa actgcacagg cagatgtttg cctcataata gtcgtaagtg    3913 gagtcctgga atttggtcag aacagtgaaa aactggaatt ctgggatata gaaagatcct    3973 gctgctatgt caggacaaag tgagatctaa tcccgctgcg gccagcaaag tactcttgct    4033 tcacccacta gacgttttt gtccaccaca tttcctccag tgcccaccca atacatgagt     4093 atgtcctcca cttcatgctg agtgcagaga gcagtgatgg tatagatctg gaaatctggc    4153 ccatgtggag cagtggtgcc cgcctgcacc cctaaccttc atgctctcgg cctgagtgtg    4213 acagcctttc tcctaatggt gcgaacaact tagaggctgt attttttat gaaagcatct     4273 tttaccagcc aagcaatcat tgggaaagta tttctttgag tttcaaagtg atataagaaa    4333 tgtgtctggc actaaaggaa gtggagttat ctaaaagata tattcatcat aatccaatct    4393 tcctttggaa acactaaaac tcatatacat ctgtgtattg tatcttattt tctctttctc    4453 ctctctcttt cctccaccca taataagaga atgttcctac tcacacttca gctgggtcac    4513 atccatccct ccattcatcc ttccatccat cttccatcc attacctcca tccagccttc     4573 taacatatat ttattgcgtc actactgtgt gccaggggtg agtggaacag tatggacagt    4633 ctctactctc atggagttga gtgtctagtg agagaacaac attagaataa gtaaatggaa    4693 actcccatgc cttgttcatc tcatgtgata tttattgcag tcacccaccc tttgtttga     4753 aacctctttt cttaataatg tgttgcaaga cattcccatg agggtacttg agttagagca    4813 aagttgagat cgctctgagt tgtacacatt tctctatgtt ccagccgtct ctccaccct     4873 tccacacaga ctgtgcacag actggtgcat cagggcaata ccagtgggaa ttgctgaagg    4933
```

-continued

```
aaccagaggc attgggacct cagtttggaa gactactgta ctgtctcacc tctgtacttc   4993
cttgtctttt catggatgtg ttattaaata aagaacgagt gttagatgct aaaaaaaaaa   5053
aaaa                                                                 5057
```

<210> SEQ ID NO 36
<211> LENGTH: 1171
<212> TYPE: PRT
<213> ORGANISM: Mus musculus

<400> SEQUENCE: 36

```
Thr Ser Arg Arg Glu Val Cys Asp Cys Asn Gly Lys Ser Arg Gln Cys
  1               5                  10                  15

Val Phe Asp Gln Glu Leu His Arg Gln Ala Gly Ser Gly Phe Arg Cys
             20                  25                  30

Leu Asn Cys Asn Asp Asn Thr Ala Gly Val His Cys Glu Arg Ser Arg
         35                  40                  45

Glu Gly Phe Tyr Gln His Gln Ser Lys Ser Arg Cys Leu Pro Cys Asn
     50                  55                  60

Cys His Ser Lys Gly Ser Leu Ser Ala Gly Cys Asp Asn Ser Gly Gln
 65                  70                  75                  80

Cys Arg Cys Lys Pro Gly Val Thr Gly Gln Arg Cys Asp Gln Cys Gln
                 85                  90                  95

Pro Gly Phe His Met Leu Thr Asp Ala Gly Cys Thr Arg Asp Gln Gly
            100                 105                 110

Gln Leu Asp Ser Lys Cys Asp Cys Asp Pro Ala Gly Ile Ser Gly Pro
        115                 120                 125

Cys Asp Ser Gly Arg Cys Val Cys Lys Pro Ala Val Thr Gly Glu Arg
    130                 135                 140

Cys Asp Arg Cys Arg Pro Arg Asp Tyr His Leu Asp Arg Ala Asn Pro
145                 150                 155                 160

Glu Gly Cys Thr Gln Cys Phe Cys Tyr Gly His Ser Ala Ser Cys His
                165                 170                 175

Ala Ser Ala Asp Phe Ser Val His Lys Ile Thr Ser Thr Phe Ser Gln
            180                 185                 190

Asp Val Asp Gly Trp Lys Ala Val Gln Arg Asn Gly Ala Pro Ala Lys
        195                 200                 205

Leu His Trp Ser Gln Arg His Arg Asp Val Phe Ser Ser Ala Arg Arg
    210                 215                 220

Ser Asp Pro Val Tyr Phe Val Ala Pro Ala Lys Phe Leu Gly Asn Gln
225                 230                 235                 240

Gln Val Ser Tyr Gly Gln Ser Leu Ser Phe Asp Tyr Arg Val Asp Arg
                245                 250                 255

Gly Gly Arg Gln Pro Ser Ala Tyr Asp Val Ile Leu Glu Gly Ala Gly
            260                 265                 270

Leu Gln Ile Arg Ala Pro Leu Met Ala Pro Gly Lys Thr Leu Pro Cys
        275                 280                 285

Gly Ile Thr Lys Thr Tyr Thr Phe Arg Leu Asn Glu His Pro Ser Ser
    290                 295                 300

His Trp Ser Pro Gln Leu Ser Tyr Phe Glu Tyr Arg Arg Leu Leu Arg
305                 310                 315                 320

Asn Leu Thr Ala Leu Leu Met Ile Arg Ala Thr Tyr Gly Glu Tyr Ser
                325                 330                 335

Thr Gly Tyr Ile Asp Asn Val Thr Leu Val Ser Ala Arg Pro Val Leu
            340                 345                 350
```

-continued

```
Gly Ala Pro Ala Pro Trp Val Glu Arg Cys Val Cys Leu Leu Gly Tyr
        355                 360                 365
Lys Gly Gln Phe Cys Gln Glu Cys Ala Ser Gly Tyr Lys Arg Asp Ser
    370                 375                 380
Ala Arg Leu Gly Ala Phe Gly Ala Cys Val Pro Cys Asn Cys Gln Gly
385                 390                 395                 400
Glu Gly Ala Cys Asp Pro Asp Thr Gly Asp Cys Tyr Ser Gly Asp Glu
                405                 410                 415
Asn Pro Asp Ile Glu Cys Ala Asp Cys Pro Ile Gly Phe Tyr Asn Asp
                420                 425                 430
Pro His Asp Pro Arg Ser Cys Lys Pro Cys Pro Cys His Asn Gly Phe
            435                 440                 445
Ser Cys Ser Val Met Pro Glu Thr Glu Val Val Cys Asn Asn Cys
    450                 455                 460
Pro Pro Gly Val Thr Gly Ala Arg Cys Glu Leu Cys Ala Asp Gly Phe
465                 470                 475                 480
Phe Gly Asp Pro Phe Gly Glu His Gly Pro Val Arg Pro Cys Gln Arg
                485                 490                 495
Cys Gln Cys Asn Asn Asn Val Asp Pro Asn Ala Ser Gly Asn Cys Asp
                500                 505                 510
Gln Leu Thr Gly Arg Cys Leu Lys Cys Ile Tyr Asn Thr Ala Gly Val
        515                 520                 525
Tyr Cys Asp Gln Cys Lys Ala Gly Tyr Phe Gly Asp Pro Leu Ala Pro
    530                 535                 540
Asn Pro Ala Asp Lys Cys Arg Ala Cys Asn Cys Ser Pro Met Gly Ala
545                 550                 555                 560
Glu Pro Gly Glu Cys Arg Gly Asp Gly Ser Cys Val Cys Lys Pro Gly
                565                 570                 575
Phe Gly Ala Phe Asn Cys Asp His Ala Ala Leu Thr Ser Cys Pro Ala
                580                 585                 590
Cys Tyr Asn Gln Val Lys Ile Gln Met Asp Gln Phe Thr Gln Gln Leu
    595                 600                 605
Gln Ser Leu Glu Ala Leu Val Ser Lys Ala Gln Gly Gly Gly Gly Gly
    610                 615                 620
Gly Thr Val Pro Val Gln Leu Glu Gly Arg Ile Glu Gln Ala Glu Gln
625                 630                 635                 640
Ala Leu Gln Asp Ile Leu Gly Glu Ala Gln Ile Ser Glu Gly Ala Met
                645                 650                 655
Arg Ala Val Ala Val Arg Leu Ala Lys Ala Arg Ser Gln Glu Asn Asp
                660                 665                 670
Tyr Lys Thr Arg Leu Asp Asp Leu Lys Met Thr Ala Glu Arg Ile Arg
        675                 680                 685
Ala Leu Gly Ser Gln His Gln Asn Arg Val Gln Asp Thr Ser Arg Leu
    690                 695                 700
Ile Ser Gln Met Arg Leu Ser Leu Ala Gly Ser Glu Ala Leu Leu Glu
705                 710                 715                 720
Asn Thr Asn Ile His Ser Ser Glu His Tyr Val Gly Pro Asn Asp Phe
                725                 730                 735
Lys Ser Leu Ala Gln Glu Ala Thr Arg Lys Ala Asp Ser His Ala Glu
                740                 745                 750
Ser Ala Asn Ala Met Lys Gln Leu Ala Arg Glu Thr Glu Asp Tyr Ser
    755                 760                 765
```

-continued

```
Lys Gln Ala Leu Ser Leu Ala Arg Lys Leu Leu Ser Gly Gly Gly
        770                 775                 780

Ser Gly Ser Trp Asp Ser Ser Val Val Gln Gly Leu Met Gly Lys Leu
785                 790                 795                 800

Glu Lys Thr Lys Ser Leu Ser Gln Gln Leu Ser Leu Glu Gly Thr Gln
                805                 810                 815

Ala Asp Ile Glu Ala Asp Arg Ser Tyr Gln His Ser Leu Arg Leu Leu
            820                 825                 830

Asp Ser Ala Ser Gln Leu Gln Gly Val Ser Asp Leu Ser Phe Gln Val
        835                 840                 845

Glu Ala Lys Arg Ile Arg Gln Lys Ala Asp Ser Leu Ser Asn Leu Val
850                 855                 860

Thr Arg Gln Thr Asp Ala Phe Thr Arg Val Arg Asn Asn Leu Gly Asn
865                 870                 875                 880

Trp Glu Lys Glu Thr Arg Gln Leu Leu Gln Thr Gly Lys Asp Arg Arg
                885                 890                 895

Gln Thr Ser Asp Gln Leu Leu Ser Arg Ala Asn Leu Ala Lys Asn Arg
            900                 905                 910

Ala Gln Glu Ala Leu Ser Met Gly Asn Ala Thr Phe Tyr Glu Val Glu
        915                 920                 925

Asn Ile Leu Lys Asn Leu Arg Glu Phe Asp Leu Gln Val Glu Asp Arg
        930                 935                 940

Lys Ala Glu Ala Glu Ala Met Lys Arg Leu Ser Ser Ile Ser Gln
945                 950                 955                 960

Lys Val Ala Asp Ala Ser Asp Lys Thr Gln Gln Ala Glu Thr Ala Leu
            965                 970                 975

Gly Ser Ala Thr Ala Asp Thr Gln Arg Ala Lys Asn Ala Ala Arg Glu
        980                 985                 990

Ala Leu Glu Ile Ser Ser Glu Ile Glu Leu Glu Ile Gly Ser Leu Asn
        995                 1000                1005

Leu Glu Ala Asn Val Thr Ala Asp Gly Ala Leu Ala Met Glu Lys Gly
    1010                1015                1020

Thr Ala Thr Leu Lys Ser Glu Met Arg Glu Met Ile Glu Leu Ala Arg
1025                1030                1035                1040

Lys Glu Leu Glu Phe Asp Thr Asp Lys Asp Thr Val Gln Leu Val Ile
            1045                1050                1055

Thr Glu Ala Gln Gln Ala Asp Ala Arg Ala Thr Ser Ala Gly Val Thr
        1060                1065                1070

Ile Gln Asp Thr Leu Asn Thr Leu Asp Gly Ile Leu His Leu Ile Asp
        1075                1080                1085

Gln Pro Gly Ser Val Asp Glu Glu Gly Met Met Leu Leu Glu Gln Gly
    1090                1095                1100

Leu Phe Gln Ala Lys Thr Gln Ile Asn Ser Arg Leu Arg Pro Leu Met
1105                1110                1115                1120

Ser Asp Leu Glu Glu Arg Val Arg Arg Gln Arg Asn His Leu His Leu
            1125                1130                1135

Leu Glu Thr Ser Ile Asp Gly Ile Leu Ala Asp Val Lys Asn Leu Glu
        1140                1145                1150

Asn Ile Arg Asp Asn Leu Pro Pro Gly Cys Tyr Asn Thr Gln Ala Leu
        1155                1160                1165

Glu Gln Gln
    1170
```